US012590090B2

(12) United States Patent
Arai et al.

(10) Patent No.: US 12,590,090 B2
(45) Date of Patent: Mar. 31, 2026

(54) PYRIMIDINE-AND NITROGEN-CONTAINING BICYCLIC COMPOUND

(71) Applicants: Asahi Kasei Pharma Corporation, Tokyo (JP); Vernalis (R&D) Limited, Cambridge (GB)

(72) Inventors: Koichiro Arai, Tokyo (JP); Kenichiro Takaba, Tokyo (JP); Masakazu Atobe, Tokyo (JP); Misato Takashima, Tokyo (JP); Naomi Aono, Tokyo (JP); Andrew John Potter, Cambridge (GB); Daniel Paul Maddox, Cambridge (GB)

(73) Assignees: ASAHI KASEI PHARMA CORPORATION, Tokyo (JP); VERNALIS (R&D) LIMITED, Cambridge (GB)

( * ) Notice: Subject to any disclaimer, the term of this patent is extended or adjusted under 35 U.S.C. 154(b) by 425 days.

(21) Appl. No.: 18/029,289

(22) PCT Filed: Sep. 30, 2020

(86) PCT No.: PCT/JP2020/037048

§ 371 (c)(1),
(2) Date: Mar. 29, 2023

(87) PCT Pub. No.: WO2022/070289

PCT Pub. Date: Apr. 7, 2022

(65) Prior Publication Data

US 2024/0025893 A1 Jan. 25, 2024

(51) Int. Cl.

| | |
|---|---|
| ***C07D 471/04*** | (2006.01) |
| ***A61P 19/02*** | (2006.01) |
| ***A61P 35/02*** | (2006.01) |
| ***C07D 417/08*** | (2006.01) |
| ***C07D 417/14*** | (2006.01) |
| ***C07D 491/107*** | (2006.01) |
| ***C07D 498/18*** | (2006.01) |

(52) U.S. Cl.

CPC ............ *C07D 471/04* (2013.01); *A61P 19/02* (2018.01); *A61P 35/02* (2018.01); *C07D 417/08* (2013.01); *C07D 417/14* (2013.01); *C07D 491/107* (2013.01); *C07D 498/18* (2013.01)

(58) Field of Classification Search

CPC .................................................... C07D 471/04

See application file for complete search history.

(56) References Cited

U.S. PATENT DOCUMENTS

| | | | |
|---|---|---|---|
| 2012/0252777 | A1 | 10/2012 | Hermann et al. |
| 2014/0194404 | A1 | 7/2014 | McElroy et al. |

FOREIGN PATENT DOCUMENTS

| | | | | |
|---|---|---|---|---|
| CN | 106946890 | A | 7/2017 | |
| CN | 108473498 | A | 8/2018 | |
| CN | 110003219 | A | 7/2019 | |
| RU | 2 548 363 | C2 | 4/2015 | |
| RU | 2 632 900 | C2 | 10/2017 | |
| WO | WO 2012/007375 | A1 | 1/2012 | |
| WO | WO 2012/068546 | A1 | 5/2012 | |
| WO | WO 2013/042137 | A1 | 3/2013 | |
| WO | WO 2013/104575 | A1 | 7/2013 | |
| WO | WO 2013/106614 | A1 | 7/2013 | |
| WO | WO 2015/048281 | A1 | 4/2015 | |
| WO | WO 2015/150995 | A1 | 10/2015 | |
| WO | WO 2016/053771 | A1 | 4/2016 | |
| WO | WO 2017/108723 | A2 | 6/2017 | |
| WO | WO 2016/144846 | A1 | 9/2018 | |
| WO | WO 2019/070093 | A1 | 4/2019 | |
| WO | WO-2022070288 | A1 * | 4/2022 | ........... C07D 471/04 |

OTHER PUBLICATIONS

Kim "PubChem in 2021: new data content and improved web interfaces" Nucleic Acids Research, 2021, vol. 49, Database issue Published online Nov. 5, 2020.*

Bartlett "Exploiting Chemical Diversity for Drug Discovery" Edited by Paul A Bartlett and Michael Entzeroth, The Royal Society of Chemistry, 2006, pp. 113-118.*

"Find ETDs Home » Thesis Resources » Find ETDs" Online: "https://ndltd.org/thesis-resources/find-etds/" Accessed Jan. 31, 2023.*

Irwin "Zinc—A Free Database of Commercially Available Compounds for Virtual Screening" J. Chem. Inf. Model. 2005, 45, 177-182.*

STN database Registry (CAS REGISTRYSM) Sep. 2016 2 pages.*

Bai et al., "The recent advance of Interleukin-1 receptor associated kinase 4 inhibitors for the treatment of inflammation and related diseases," European Journal of Medicinal Chemistry, vol. 258, 2023, pp. 1-21.

Saudi Arabian Office Action for Saudi Arabian Application No. 523440074, dated Nov. 1, 2024, with an English translation.

Canadian Office Action for Canadian Application No. 3,194,164, dated May 15, 2024.

Australian Office Action for corresponding Australian Application No. 2020471055, dated Aug. 16, 2023.

Russian Office Action for Russian Application No. 2023107549, dated Feb. 27, 2024, with English translation.

Chen et al., "Research progress of small molecule IRAK-4 inhibitors," Central South Pharmacy, vol. 13, No. 10, 2015, pp. 1017-1024, with an English abstract.

(Continued)

*Primary Examiner* — Nizal S Chandrakumar

(74) *Attorney, Agent, or Firm* — Birch, Stewart, Kolasch & Birch, LLP

(57) ABSTRACT

A compound represented by the general formula (1) or a salt thereof, which has a superior IRAK-4 inhibitory activity, and is useful as active ingredients of medicaments for prophylactic treatment and/or therapeutic treatment of diseases relating to IRAK-4 inhibition.

(1)

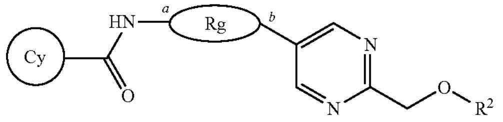

35 Claims, 1 Drawing Sheet

(56) References Cited

OTHER PUBLICATIONS

Chinese Office Action and Search Report for Chinese Application No. 202080105488.8, dated Mar. 30, 2024, with an English translation.
Extended European Search Report for European Application No. 20956217.2, dated May 21, 2024.
Flannery et al., "The interleukin-1 receptor-associated kinases: Critical regulators of innate immune signalling," Biochemical Pharmacology, vol. 80, 2010, pp. 1981-1991.
Heifetz et al., "Fragment Molecular Orbital Method Applied to Lead Optimization of Novel Interleukin-2 Inducible T-Cell Kinase (ITK) Inhibitors," Journal of Medicinal Chemistry, vol. 59, No. 9, Mar. 7, 2016, pp. 4352-4363.
International Preliminary Report on Patentability and English translation of the Written Opinion of the International Searching Authority for International Application No. PCT/JP2020/037048, dated Mar. 28, 2023.
International Search Report and Written Opinion of the International Searching Authority for International Application No. PCT/JP2020/037048, dated Nov. 24, 2020.
Jain et al., "IL-1 receptor-associated kinase signaling and its role in inflammation, cancer progression, and therapy resistance," Frontiers in Immunology, Nov. 17, 2014, vol. 5, Article 553, pp. 1-8.
Koziczak-Holbro et al., "The Critical Role of Kinase Activity of Interleukin-1 Receptor-Associated Kinase 4 in Animal Models of Joint Inflammation," Arthritis & Rheumatism, vol. 60, No. 6, Jun. 2009, pp. 1661-1671.
Nair et al., "Optimization of Nicotinamides as Potent and Selective IRAK4 Inhibitors with Efficacy in a Murine Model Psoriasis," Medicinal Chemistry Letters, vol. 11, Jun. 10, 2020, pp. 1402-1409.
Picard et al., "Pyogenic Bacterial Infections in Humans with IRAK-4 Deficiency," Science, vol. 299, Mar. 28, 2003, pp. 2076-2079 (5 pages total).
Suzuki et al., "Severe impairment of Interleukin-1 and Toll-like receptor signalling in mice lacking IRAK-4," Nature, vol. 416, Apr. 18, 2002, pp. 750-754.
Wan et al., "Interleukin-1 Receptor-associated Kinase 2 Is Critical for Lipopolysaccharide-mediated Post-transcriptional Control," The Journal of Biological Chemistry, vol. 284, No. 16, Apr. 17, 2009, pp. 10367-10375.
Russian Office Action and Search Report for Russian Application No. 2023107549/04, dated Oct. 25, 2023, with an English translation.
Indian Office Action and Search Report for Indian Application No. 202317021013, dated Dec. 30, 2025, with English translation.

* cited by examiner

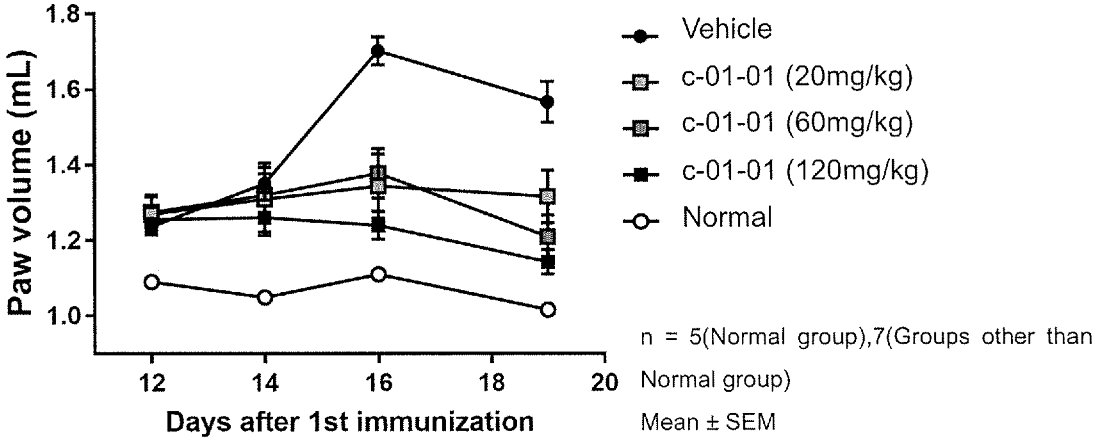
1.8
1.6
1.4
1.2
1.0
Paw volume (mL)
12
14
16
18
20
Days after 1st immunization
Vehicle
c-01-01 (20mg/kg)
c-01-01 (60mg/kg)
c-01-01 (120mg/kg)
Normal
n = 5(Normal group),7(Groups other than Normal group)
Mean ± SEM

PYRIMIDINE-AND NITROGEN-CONTAINING BICYCLIC COMPOUND

TECHNICAL FIELD

The present invention relates to a novel nitrogen-containing bicyclic compound, and a medicament containing it as an active ingredient.

BACKGROUND ART

Interleukin 1 receptor-associated kinase 4 (IRAK-4) is a protein-phosphorylating enzyme that plays an important role in downstream signaling of Toll-like receptors (TLRs), interleukin 1 receptor (IL-1R), IL-18R, and IL-33R (Non-patent document 1). Since the TLR/IL-1 receptor family has an important function for inflammation and biophylaxis, it is thought that the downstream signaling plays major roles in many diseases including inflammatory diseases and autoimmune diseases.

TLRs use pathogen-associated molecular patterns (PAMPs) derived from infectious microorganisms such as bacteria, fungi, parasites, and viruses as ligands. They also recognize damage-associated molecular patterns (DAMPs) released from damaged cells or apoptosizing cells, and are activated. If a ligand binds with TLRs or IL-1 receptor family members, an adaptor molecule, MyD88, is recruited in a common intracellular region called TIR (Toll/IL-1 receptor) region. It is thought that IRAK-4 is recruited to the receptors through the interaction with MyD88, and the downstream signaling is started (Non-patent document 2). IRAK-4 activates IRAK-1 and IRAK-2, and further controls the production of inflammatory mediators such as cytokines and chemokines via activation of signaling molecules in the downstream such as NF-kB and MAPK.

It has been reported that a human IRAK-4 gene-deficient cell does not react to agonists for TLRs other than TLR3, IL-1β and IL-18 (Non-patent document 3). An IRAK-4 gene-deficient mouse also does not react to agonists for TLRs other than TLR3, IL-1β and IL-18 (Non-patent document 4). On the other hand, in IRAK-1 gene-deficient mice and IRAK-2 gene-deficient mice, only a partial suppression of these signals is observed (Non-patent document 5). For this reason, it is thought that, among the IRAK family members, IRAK-4 bears the most important role in these signal transductions. It has been reported that, in kinase activity-deficient IRAK-4 knock-in mice, severities of arthritis, experimental autoallergic encephalomyelitis, and arteriosclerosis model are suppressed compared with those in wild-type mice (Non-patent document 6). Therefore, the kinase activity of IRAK-4 is indispensable for the signal transductions responsible for pathology, and IRAK-4 inhibitors may exhibit superior effectiveness for therapeutic treatment of autoimmune diseases such as acute and chronic inflammations, rheumatoid arthritis, and systemic erythematodes, metabolic disorders such as gout and diabetes, and such diseases as tumors.

As compounds having an IRAK-4 inhibitory activity, there are known, for example, the compounds described in Patent documents 1 to 6.

PRIOR ART REFERENCES

Patent Documents

Patent document 1: International Patent Publication WO2016/144846
Patent document 2: International Patent Publication WO2016/053771
Patent document 3: International Patent Publication WO2015/048281
Patent document 4: International Patent Publication WO2013/042137
Patent document 5: International Patent Publication WO2012/068546
Patent document 6: International Patent Publication WO2015/150995

Non-Patent Documents

Non-patent document 1: Flannery S. & Bowie A. G., Biochemical Pharmacology, 80 (2010) 1981-1991
Non-patent document 2: Jain A. et al., Froniters in Immunology, 5 (2014) Article 553
Non-patent document 3: Picad C. et al., Science, 299 (2003) 2076-2079
Non-patent document 4: Suzuki N. et al., Nature, 416 (2002) 750-754
Non-patent-document 5: Wan Y. et al., J. Biol. Chem., 284 (2009) 10367-10375
Non-patent-document 6: Koziczak-Holbro M. et al., Arthritis & Rheumatism, 60 (2009) 1661-1671

SUMMARY OF THE INVENTION

Object to be Achieved by the Invention

An object of the present invention is to provide a novel compound that has an IRAK-4 inhibitory activity. Another object of the present invention is to provide a novel compound useful as an active ingredient of a medicament for prophylactic and/or therapeutic treatment of a disease relating to IRAK-4 inhibition. Yet another object of the present invention is to provide a medicament containing the compound.

Means for Achieving the Objects

The inventors of the present invention conducted various researches in order to achieve the aforementioned objects. As a result, they found that the compounds of the present invention represented by the following formula (1) have a superior IRAK-4 inhibitory activity, and these compounds are useful for prophylactic and/or therapeutic treatment of a disease relating to IRAK-4 inhibition, and accomplished the present invention.

The present invention is thus embodied, for example, as follows.

[1] A compound represented by the following general formula (1):

[Formula 1]

(1)

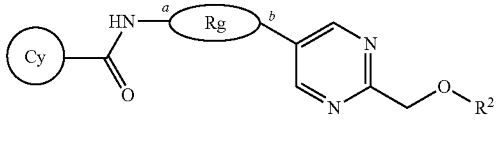

[in the formula (1),

Rg is a group represented by the following general formula (1-1):

[Formula 2]

(1-1)

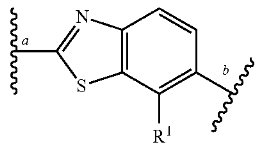

or the following general formula (1-2):

[Formula 3]

(1-2)

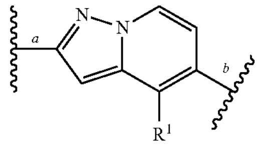

(a and b represent direction of bonding), $R^1$ is —H, —F, —Cl, methyl, or $C_{1-3}$ alkoxy, the $C_{1-3}$ alkoxy may be substituted with the same or different 1 to 3 substituents selected from the group $G^1$;

the group $G^1$ is a group consisting of —F, hydroxy, cyano, halogeno-$C_{1-6}$ alkyl, $C_{1-4}$ alkoxy, phenyl, 5- or 6-membered heteroaryl, and a 3- to 7-membered saturated ring group, the phenyl and 5- or 6-membered heteroaryl included in the group $G^1$ may be substituted with the same or different 1 to 3 substituents selected from the group $G^{Ar}$;

the group $G^{Ar}$ is a group consisting of —F, —Cl, hydroxy, cyano, $C_{1-6}$ alkyl, halogeno-$C_{1-6}$ alkyl, and —$NH_2$;

$R^2$ is $C_{1-6}$ alkyl, halogeno-$C_{1-6}$ alkyl, or a 3- to 7-membered saturated ring group, $R^2$ may be substituted with the same or different 1 to 3 substituents selected from the group $G^2$, the group $G^2$ is a group consisting of —F, hydroxy, halogeno-$C_{1-3}$ alkyl, and $C_{1-4}$ alkoxy;

Cy is a group represented by the following general formula (2-1):

[Formula 4]

(2-1)

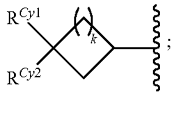

in the formula (2-1), k is an integer of 0 or 1;

$R^{Cy1}$ and $R^{Cy2}$ are independently —H, —F, hydroxy, cyano, $C_{1-6}$ alkyl, halogeno-$C_{16}$ alkyl, $C_{1-6}$ alkoxy, —$NR^{11}R^{12}$, phenyl, 5- or 6-membered heteroaryl, or a 3- to 7-membered saturated ring group, the phenyl and 5- or 6-membered heteroaryl as $R^{Cy1}$ or $R^{Cy2}$ may be substituted with the same or different 1 to 3 substituents selected from the group $G^{Ar}$, $R^{Cy1}$ and $R^{Cy2}$ may be substituted with the same or different 1 to 3 substituents selected from the group $G^1$;

$R^{11}$ and $R^{12}$ are independently —H, $C_{1-6}$ alkyl, halogeno-$C_{1-6}$ alkyl, hydroxy-$C_{1-6}$ alkyl, $C_{1-6}$ alkoxy-$C_{1-6}$ alkyl, a 3- to 7-membered saturated ring group, phenyl, or 5- or 6-membered heteroaryl, and $R^{11}$ and $R^{12}$ may be substituted with the same or different 1 to 3 substituents selected from the group $G^1$; or $R^{11}$ and $R^{12}$ combine to form a 4- to 10-membered saturated ring or a 7- to 11-membered spiro ring, the 4- to 10-membered saturated ring and 7- to 11-membered spiro ring may contain the same or different 1 or 2 heteroatoms selected from the group consisting of O and N, or —$S(O_2)$—, in addition to N, the 4- to 10-membered saturated ring and 7- to 11-membered spiro ring may be substituted with the same or different 1 to 3 substituents selected from the group $G^3$;

the group $G^3$ is a group consisting of —F, hydroxy, $C_{1-6}$ alkyl, halogeno-$C_{1-6}$ alkyl, hydroxy-$C_{16}$ alkyl, $C_{1-6}$ alkoxy, $C_{1-6}$ alkoxy-$C_{1-6}$ alkyl, halogeno-$C_{16}$ alkoxy, —$C(O)R^{14}$, —$NR^{13}C(O)R^{14}$, —$C(O)NR^{13}R^{14}$, —$C(O)NH_2$, —$NR^{13}S(O_2)R^{14}$, —$S(O_2)NR^{13}R^{14}$, —$S(O_2)NH_2$, —$S(O_2)R^{14}$, phenyl, 5- or 6-membered heteroaryl, and a 3- to 7-membered saturated ring group, the phenyl and 5- or 6-membered heteroaryl included in the group $G^3$ may be substituted with the same or different 1 to 3 substituents selected from the group $G^{Ar}$;

$R^{13}$ is —H, $C_{1-3}$ alkyl, halogeno-$C_{1-3}$ alkyl, $C_{1-3}$ alkoxy-$C_{1-3}$ alkyl, halogeno-$C_{1-3}$ alkoxy-$C_{1-3}$ alkyl, phenyl, 5- or 6-membered heteroaryl, or a 3- to 7-membered saturated ring group, the phenyl and 5- or 6-membered heteroaryl as $R^3$ may be substituted with the same or different 1 to 3 substituents selected from the group $G^{Ar}$;

$R^{14}$ is $C_{1-6}$ alkyl, halogeno-$C_{1-6}$ alkyl, $C_{1-6}$ alkoxy-$C_{1-6}$ alkyl, halogeno-$C_{1-6}$ alkoxy-$C_{1-6}$ alkyl, phenyl, 5- or 6-membered heteroaryl, or a 3- to 7-membered saturated ring group, and the phenyl and 5- or 6-membered heteroaryl as $R^{14}$ may be substituted with the same or different 1 to 3 substituents selected from the group $G^{Ar}$; or $R^{13}$ and $R^{14}$ combine to form a 4- to 7-membered saturated ring or a 7- to 11-membered spiro ring, and the 4- to 7-membered saturated ring and 7- to 11-membered spiro ring may contain the same or different 1 or 2 heteroatoms selected from the group consisting of O and N, or —$S(O_2)$—, in addition to N; or $R^{Cy1}$ and $R^{Cy2}$ combine to form a 4- to 7-membered saturated ring, the 4- to 7-membered saturated ring may contain the same or different 1 or 2 heteroatoms selected from the group consisting of O and N, or —$S(O_2)$—, and the 4- to 7-membered saturated ring may be substituted with the same or different 1 to 3 substituents selected from the group $G^1$], or a salt thereof.

[2] The compound or a salt thereof according to [1], wherein Rg is a group represented by the general formula (1-1).

[3] The compound or a salt thereof according to [2] mentioned above, wherein $R^1$ is —F, —Cl, methyl, or $C_{1-3}$ alkoxy.

[4] The compound or a salt thereof according to [2] mentioned above, wherein $R^1$ is $C_{1-3}$ alkoxy.

[4-2] The compound or a salt thereof according to [2] mentioned above, wherein $R^1$ is ethoxy, methoxy, or methoxyethoxy.

[4-3] The compound or a salt thereof according to [2] mentioned above, wherein $R^1$ is ethoxy or methoxy.

[5] The compound or a salt thereof according to [2] mentioned above, wherein $R^1$ is methoxy.

[6] The compound or a salt thereof according to any one of [2] to [5] mentioned above, wherein $R^1$ is —H; and Cy is a group represented by the following general formula (2-1-1):

[Formula 5]

(2-1-1)

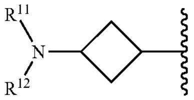

($R^1$ and $R^{12}$ have the same meanings as those defined above).

[6-2] The compound or a salt thereof according to any one of [2] to [5] mentioned above, wherein $R^{11}$ and $R^{22}$ are independently —H, $C_{1-6}$ alkyl, halogeno-$C_{1-6}$ alkyl, hydroxy-$C_{1-6}$alkyl, $C_{1-6}$ alkoxy-$C_{1-6}$ alkyl, a 3- to 7-membered saturated ring group, phenyl, or 5- or 6-membered heteroaryl, and $R^{11}$ and $R^{12}$ may be substituted with the same or different 1 to 3 substituents selected from the group $G^1$.

[6-3] The compound or a salt thereof according to any one of [2] to [5] mentioned above, wherein $R^{11}$ and $R^{22}$ are independently —H, $C_{1-6}$ alkyl, halogeno-$C_{1-6}$ alkyl, a 3- to 7-membered saturated ring group, or 5- or 6-membered heteroaryl, and $R^{11}$ and $R^{12}$ may be substituted with the same or different 1 to 3 substituents selected from the group G.

[6-4] The compound or a salt thereof according to any one of [2] to [5] mentioned above, wherein $R^{11}$ and $R^{22}$ are independently —H, $C_{1-6}$ alkyl, halogeno-$C_{1-6}$ alkyl, or a 3- to 5-membered saturated ring group, and $R^{11}$ and $R^{12}$ may be substituted with the same or different 1 to 3 substituents selected from the group $G^1$.

[6-5] The compound or a salt thereof according to any one of [2] to [5] mentioned above, wherein $R^{11}$ and $R^{12}$ combine to form a 4- to 10-membered saturated ring or a 7- to 11-membered spiro ring, the 4- to 10-membered saturated ring and 7- to 11-membered spiro ring may contain the same or different 1 or 2 heteroatoms selected from the group consisting of O and N, or —$S(O_2)$—, in addition to N, and the 4- to 10-membered saturated ring and 7- to 11-membered Spiro ring may be substituted with the same or different 1 to 3 substituents selected from the group $G^3$.

[6-6] The compound or a salt thereof according to any one of [2] to [5] mentioned above, wherein $R^{11}$ and $R^{12}$ combine to form a 4- to 10-membered saturated ring or a 7- to 11-membered spiro ring, the 4- to 10-membered saturated ring and 7- to 11-membered spiro ring may contain the same or different 1 or 2 heteroatoms selected from the group consisting of O and N, or —$S(O_2)$—, in addition to N, and the 4- to 10-membered saturated ring and 7- to 11-membered spiro ring may be substituted with the same or different 1 to 3 substituents selected from the group $G^3$.

[6-7] The compound or a salt thereof according to any one of [2] to [5] mentioned above, wherein $R^{11}$ and $R^{12}$ combine to form a saturated ring represented by any one of the following general formulas (2-1-1-a-1) to (2-1-1-a-7):

[Formula 6]

(2-1-1-a-1)

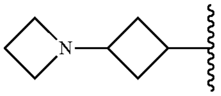

(2-1-1-a-2)

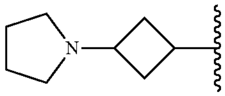

(2-1-1-a-3)

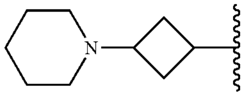

(2-1-1-a-4)

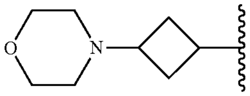

(2-1-1-a-5)

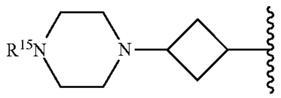

(2-1-1-a-6)

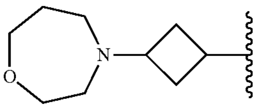

(2-1-1-a-7)

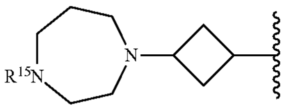

the saturated ring may be substituted with the same or different 1 to 3 substituents selected from the group $G^3$;

$R^{15}$ is —H, $C_{1-6}$ alkyl, halogeno-$C_{1-6}$ alkyl, hydroxy-$C_{1-6}$ alkyl, $C_{1-6}$ alkoxy-$C_{1-6}$ alkyl, —$C(O)R^{16}$, —$S(O_2)R^{16}$, —$C(O)NR^{16}R^{17}$, —$C(O)OR^{16}$, or a 3- to 7-membered saturated ring group, $R^5$ may be substituted with the same or different 1 to 3 substituents selected from the group $G^1$;

$R^{16}$ is $C_{1-6}$ alkyl, halogeno-$C_{1-6}$ alkyl, $C_{1-6}$ alkoxy-$C_{1-6}$ alkyl, halogeno-$C_{1-6}$ alkoxy-$C_{1-6}$ alkyl, phenyl, 5- or 6-membered heteroaryl, or a 3- to 7-membered saturated ring group, the phenyl and 5- or 6-membered heteroaryl as $R^{16}$ may be substituted with the same or different 1 to 3 substituents selected from the group $G^{Ar}$; and $R^{17}$ is —H, $C_{1-6}$ alkyl, halogeno-$C_{1-6}$ alkyl, $C_{1-6}$ alkoxy-$C_{1-6}$ alkyl, halogeno-$C_1$_6 alkoxy-$C_{1-6}$ alkyl, phenyl, 5- or 6-membered heteroaryl, or a 3- to 7-membered saturated ring group, and the phenyl and 5- or 6-membered heteroaryl as $R^7$ may be substituted with the same or different 1 to 3 substituents selected from the group $G^{Ar}$; or $R^{16}$ and $R^{17}$ combine to form a 4- to 7-membered saturated ring or a 7- to 11-membered spiro ring, and the 4- to 7-membered saturated ring and 7- to 11-membered spiro ring may contain the same or different 1 or 2 heteroatoms selected from the group consisting of O and N, or —$S(O_2)$—, in addition to N.

[6-8] The compound or a salt thereof according to any one of [2] to [5] mentioned above, wherein $R^{11}$ and $R^{12}$ combine to form a saturated ring represented by the following general formula (2-1-1-b-1):

[Formula 7]

(2-1-1-b-1)

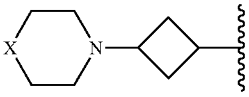
, the saturated ring may be substituted with the same or different 1 to 3 substituents selected from the group $G^3$; and X is 0 or $NR^{15}$ ($R^{15}$ has the same meaning as that defined above).

[6-9] The compound or a salt thereof according to any one of [2] to [5] mentioned above, wherein $R^{11}$ and $R^{12}$ combine to form a saturated ring represented by any one of the following general formulas (2-1-1-c-1) to (2-1-1-c-3):

[Formula 8]

(2-1-1-c-1)

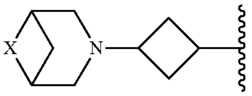

(2-1-1-c-2)

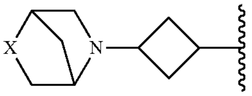

(2-1-1-c-3)

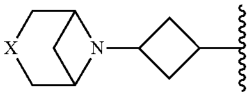
, the saturated ring may be substituted with the same or different 1 to 3 substituents selected from the group $G^3$; and X is O or $NR^{15}$ ($R^{15}$ has the same meaning as that defined above).

[6-10] The compound or a salt thereof according to any one of [2] to [5] mentioned above, wherein $R^1$ and $R^{12}$ combine to form a saturated ring having a crosslink represented by any one of the following general formula (2-1-1-d-1) to (2-1-1-d-15):

[Formula 9]

(2-1-1-d-1)

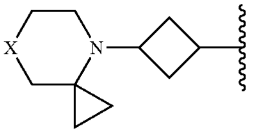

(2-1-1-d-2)

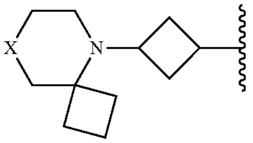

-continued (2-1-1-d-3)

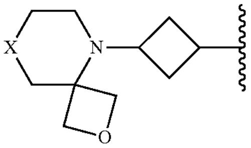

(2-1-1-d-4)

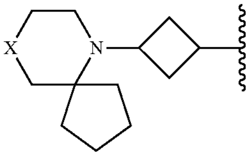

(2-1-1-d-5)

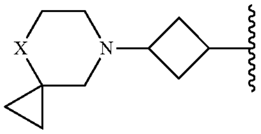

(2-1-1-d-6)

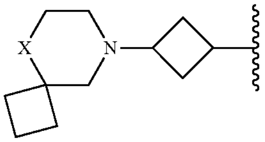

(2-1-1-d-7)

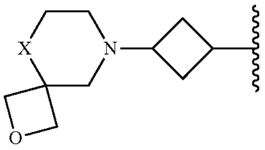

(2-1-1-d-8)

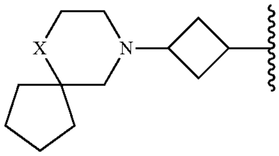

(2-1-1-d-9)

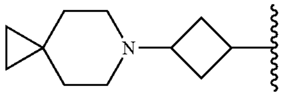

(2-1-1-d-10)

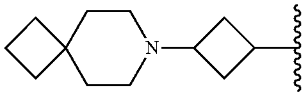

(2-1-1-d-11)

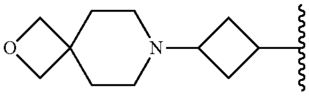

(2-1-1-d-12)

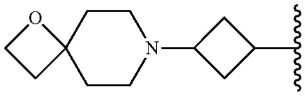

(2-1-1-d-13)

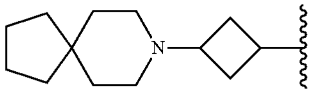

(2-1-1-d-14)

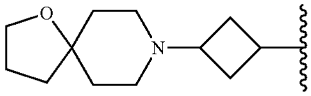

-continued (2-1-1-d-15)

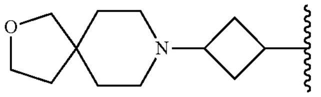

the saturated ring having a crosslink may be substituted with the same or different 1 to 3 substituents selected from the group $G^3$; and X is O or $NR^{15}$ ($R^{15}$ has the same meaning as that defined above).

[6-11] The compound or a salt thereof according to any one of [2] to [5] mentioned above, wherein $R^{11}$ and $R^{12}$ combine to form a saturated ring having a condensed ring represented by the following general formula (2-1-1-e-1):

[Formula 10]

(2-1-1-e-1)

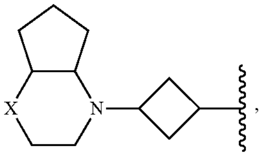

the saturated ring having a condensed ring may be substituted with the same or different 1 to 3 substituents selected from the group $G^3$; and X is O or $NR^{15}$ ($R^{15}$ has the same meaning as that defined above).

[7] The compound or a salt thereof according to any one of [2] to [6-11], wherein Cy is a group represented by the following general formula (2-1-2):

[Formula 11]

(2-1-2)

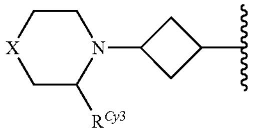

;

[in the formula (2-1-2), $R^{Cy3}$ is $C_{1-4}$ alkyl, or halogeno-$C_{1-4}$ alkyl;

X is O or $NR^{15}$;

$R^{15}$ is —H, $C_{1-6}$ alkyl, halogeno-$C_{1-6}$ alkyl, hydroxy-$C_{1-6}$ alkyl, $C_{1-6}$ alkoxy-$C_{1-6}$ alkyl, —C(O)$R^{16}$, —S($O_2$)$R^{16}$, —C(O)$NR^{16}R^{17}$, —C(O)$OR^{16}$, or a 3- to 7-membered saturated ring group, $R^{75}$ may be substituted with the same or different 1 to 3 substituents selected from the group $G^1$;

$R^{16}$ is $C_{1-6}$ alkyl, halogeno-$C_{1-6}$ alkyl, $C_{1-6}$ alkoxy-$C_{16}$ alkyl, halogeno-$C_{16}$ alkoxy-$C_{1-6}$ alkyl, phenyl, 5- or 6-membered heteroaryl, or a 3- to 7-membered saturated ring group, the phenyl and 5- or 6-membered heteroaryl as $R^{16}$ may be substituted with the same or different 1 to 3 substituents selected from the group $G^{Ar}$;

$R^{17}$ is —H, $C_{1-6}$ alkyl, halogeno-$C_{1-6}$ alkyl, $C_{1-3}$ alkoxy-$C_{1-6}$ alkyl, halogeno-$C_{1-6}$ alkoxy-$C_{1-6}$ alkyl, phenyl, 5- or 6-membered heteroaryl, or a 3- to 7-membered saturated ring group, and the phenyl and 5- or 6-membered heteroaryl as $R^{17}$ may be substituted with the same or different 1 to 3 substituents selected from the group $G^{Ar}$; or $R^{16}$ and $R^{17}$ combine to form a 4- to 7-membered saturated ring or a 7- to 11-membered spiro ring, and the 4- to 7-membered saturated ring and 7- to 11-membered spiro ring may contain the same or different 1 or 2 heteroatoms selected from the group consisting of O and N, or —S($O_2$)—, in addition to N].

When the cited item numbers are indicated with a range such as "[2] to [6-11] mentioned above", and an item having a subnumber such as [6-6] is included in such a range, it is meant that the item assigned with the subnumber such as [6-6] is also cited. The same shall apply to the following descriptions.

[8] The compound or a salt thereof according to any one of [2] to [7] mentioned above, wherein X is $NR^{15}$ ($R^{15}$ has the same meaning as that defined above).

[9] The compound or a salt thereof according to any one of [2] to [8] mentioned above, wherein Cy is a group represented by the following general formula (2-1-3):

[Formula 12]

(2-1-3)

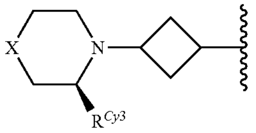

($R^{Cy3}$ and X have the same meanings as those defined above).

[10] The compound or a salt thereof according to any one of [2] to [9] mentioned above, wherein $R^2$ is a group represented by the following formula (3-1):

[Formula 13]

(3-1)

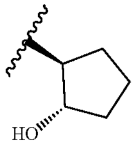

or normal propyl.

[11] The compound or a salt thereof according to any one of [2] to [9] mentioned above, wherein $R^2$ is a group represented by the following formula (3-1):

[Formula 14]

(3-1)

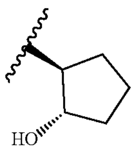

.

[12] A compound represented by the following formula:

[Formula 15]

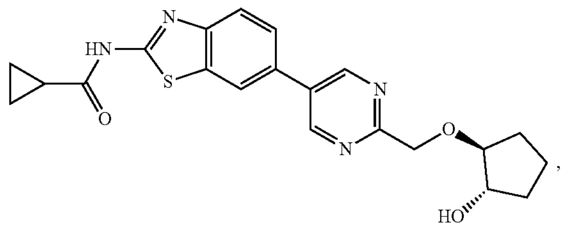

or a salt thereof.

[13] A compound represented by the following formula:

[Formula 16]

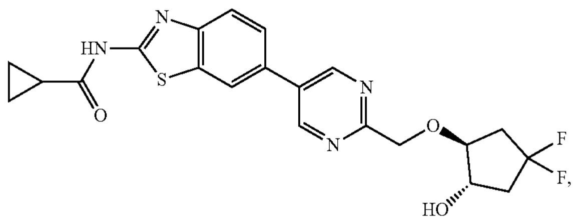

or a salt thereof.

[14] A compound represented by the following formula:

[Formula 17]

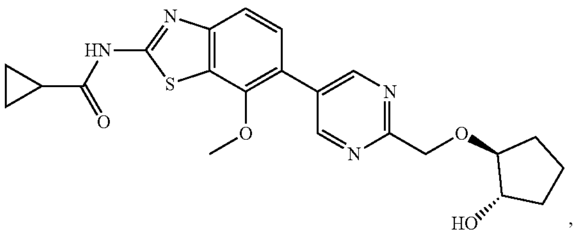

or a salt thereof.

[15] A compound represented by the following formula:

[Formula 18]

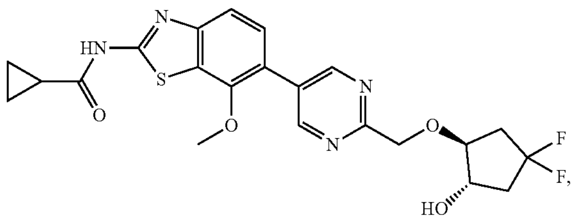

or a salt thereof.

[16] A compound represented by the following formula:

[Formula 19]

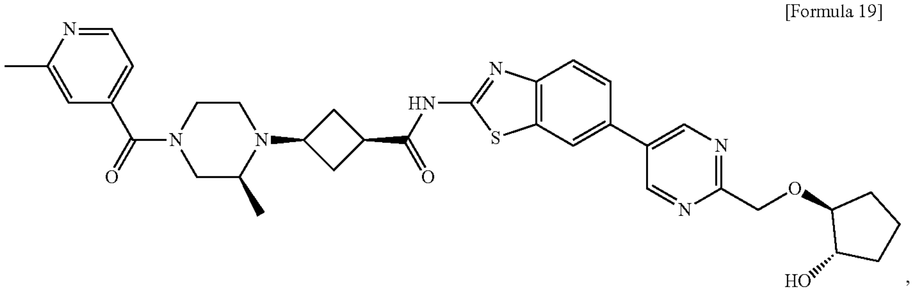 [SMILES: Cc1cc(C(=O)N2CCN([C@H]3C[C@@H](C(=O)Nc4nc5ccc(-c6cnc(CO[C@H]7CCC[C@@H]7O)nc6)cc5s4)C3)[C@@H](C)C2)ccn1]

or a salt thereof.

[17] A compound represented by the following formula:

[Formula 20]

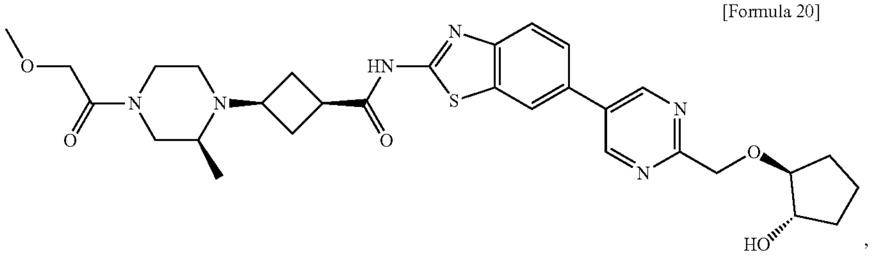 [SMILES: COCC(=O)N1CCN([C@H]2C[C@@H](C(=O)Nc3nc4ccc(-c5cnc(CO[C@H]6CCC[C@@H]6O)nc5)cc4s3)C2)[C@@H](C)C1]

or a salt thereof.

[18] A compound represented by the following formula:
[Formula 21]
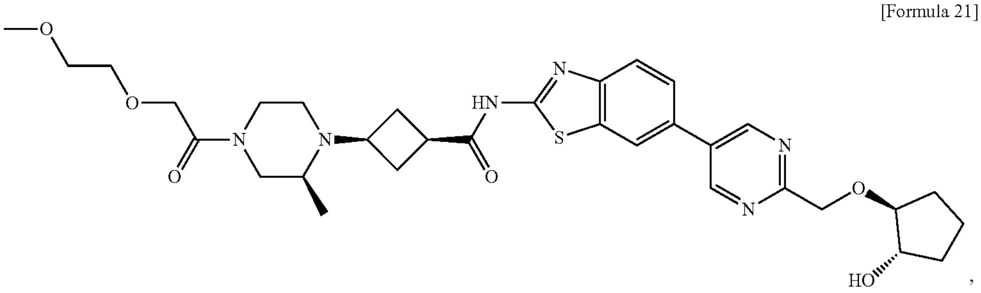 [SMILES: COCCOCC(=O)N1CCN([C@H]2C[C@@H](C(=O)Nc3nc4ccc(-c5cnc(CO[C@H]6CCC[C@@H]6O)nc5)cc4s3)C2)[C@@H](C)C1]
or a salt thereof.
[19] A compound represented by the following formula:
[Formula 22]
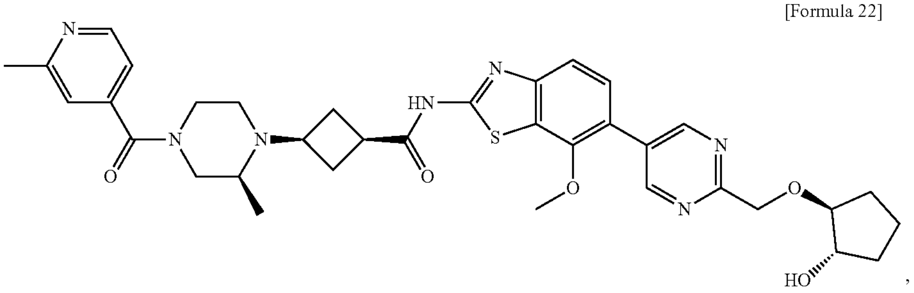 [SMILES: COc1c(-c2cnc(CO[C@H]3CCC[C@@H]3O)nc2)ccc2nc(NC(=O)[C@H]3C[C@@H](N4CCN(C(=O)c5ccnc(C)c5)C[C@@H]4C)C3)sc12]
or a salt thereof.
[20] A compound represented by the following formula:
[Formula 23]
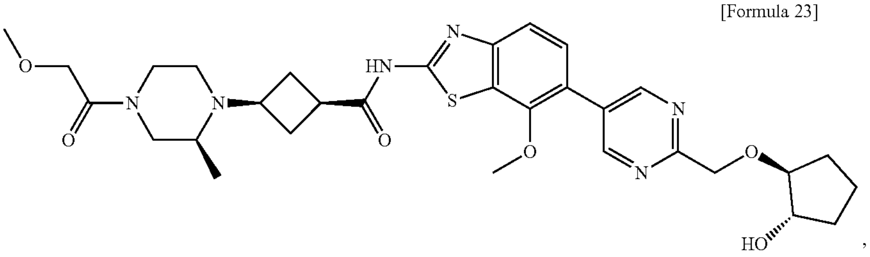 [SMILES: COCC(=O)N1CCN([C@H]2C[C@@H](C(=O)Nc3nc4ccc(-c5cnc(CO[C@H]6CCC[C@@H]6O)nc5)c(OC)c4s3)C2)[C@@H](C)C1]
or a salt thereof.
[21] A compound represented by the following formula:
[Formula 24]
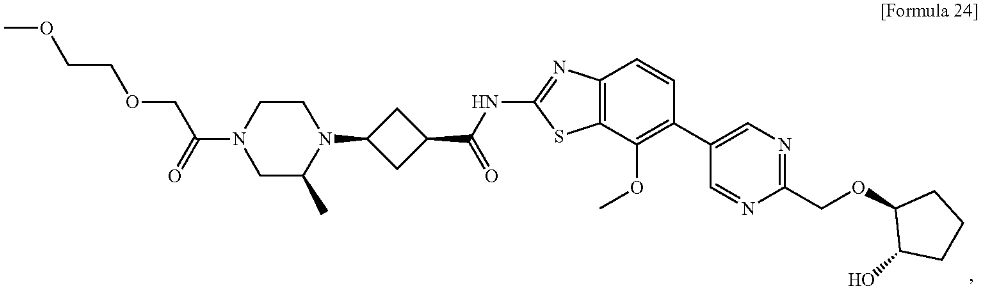 [SMILES: COCCOCC(=O)N1CCN([C@H]2C[C@@H](C(=O)Nc3nc4ccc(-c5cnc(CO[C@H]6CCC[C@@H]6O)nc5)c(OC)c4s3)C2)[C@@H](C)C1]
or a salt thereof.

[22] The compound or a salt thereof according to [1] mentioned above, wherein Rg is a group represented by the general formula (1-2).

[23] The compound or a salt thereof according to [22] mentioned above, wherein $R^1$ is —H or methoxy.

[24] The compound or a salt thereof according to [22] mentioned above, wherein $R^1$ is —H.

[25] The compound or a salt thereof according to any one of [22] to [24] mentioned above, wherein Cy is a group represented by the general formula (2-1);

[in the formula (2-1), k is an integer of 1;

$R^{Cy1}$ and $R^{Cy2}$ are independently —H, —F, hydroxy, cyano, $C_{1-6}$ alkyl, halogeno-$C_{1-6}$ alkyl, $C_{1-6}$ alkoxy, —$NR^{11}R^{12}$, phenyl, 5- or 6-membered heteroaryl, or a 3- to 7-membered saturated ring group, the phenyl and 5- or 6-membered heteroaryl as $R^{Cy1}$ or $R^{Cy2}$ may be substituted with the same or different 1 to 3 substituents selected from the group $G^A$, and $R^{Cy1}$ and $R^{Cy2}$ may be substituted with the same or different 1 to 3 substituents selected from the group $G^1$ ($R^{11}$ and $R^{12}$ have the same meanings as those defined above)].

[26] The compound or a salt thereof according to any one of [22] to [25] mentioned above, wherein Cy is a group represented by the following general formula (2-1-1):

[Formula 25]

(2-1-1)

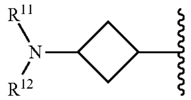

($R^{11}$ and $R^{12}$ have the same meanings as those defined above).

[26-2] The compound or a salt thereof according to any one of [22] to [25] mentioned above, wherein $R^{11}$ and $R^{22}$ are independently —H, $C_{1-6}$ alkyl, halogeno-$C_{1-6}$ alkyl, hydroxy-$C_{1-6}$ alkyl, $C_{1-6}$ alkoxy-$C_{1-6}$ alkyl, a 3- to 7-membered saturated ring group, phenyl, or 5- or 6-membered heteroaryl, and $R^{11}$ and $R^{12}$ may be substituted with the same or different 1 to 3 substituents selected from the group $G^1$.

[26-3] The compound or a salt thereof according to any one of [22] to [25] mentioned above, wherein $R^{11}$ and $R^{22}$ are independently —H, $C_{1-6}$ alkyl, halogeno-$C_{1-6}$ alkyl, a 3- to 7-membered saturated ring group, or 5- or 6-membered heteroaryl, and $R^1$ and $R^{12}$ may be substituted with the same or different 1 to 3 substituents selected from the group G.

[26-4] The compound or a salt thereof according to any one of [22] to [25] mentioned above, wherein $R^{11}$ and $R^{22}$ are independently —H, $C_{1-6}$ alkyl, halogeno-$C_{1-6}$ alkyl, or 3- to 5-membered saturated ring group, and $R^{11}$ and $R^{12}$ may be substituted with the same or different 1 to 3 substituents selected from the group $G^1$.

[26-5] The compound or a salt thereof according to any one of [22] to [25] mentioned above, wherein $R^{11}$ and $R^{12}$ combine to form a 4- to 10-membered saturated ring or a 7- to 11-membered spiro ring, the 4- to 10-membered saturated ring and 7- to 11-membered spiro ring may contain the same or different 1 or 2 heteroatoms selected from the group consisting of O and N, or —$S(O_2)$—, in addition to N, and the 4- to 10-membered saturated ring and 7- to 11-membered spiro ring may be substituted with the same or different 1 to 3 substituents selected from the group $G^3$.

[26-6] The compound or a salt thereof according to any one of [22] to [25] mentioned above, wherein $R^{11}$ and $R^{12}$ combine to form a 4- to 10-membered saturated ring or a 7- to 11-membered spiro ring, the 4- to 10-membered saturated ring and 7- to 11-membered spiro ring may contain the same or different 1 or 2 heteroatoms selected from the group consisting of O and N, or —$S(O_2)$—, in addition to N, and the 4- to 10-membered saturated ring and 7- to 11-membered spiro ring may be substituted with the same or different 1 to 3 substituents selected from the group $G^3$.

[26-7] The compound or a salt thereof according to any one of [22] to [25] mentioned above, wherein $R^{11}$ and $R^{12}$ combine to form a saturated ring group represented by any one of the following general formulas (2-1-1-a-1) to (2-1-1-a-7):

[Formula 26]

(2-1-1-a-1)

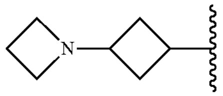

(2-1-1-a-2)

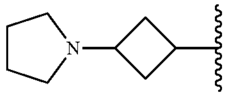

(2-1-1-a-3)

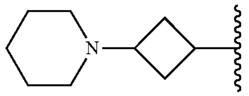

(2-1-1-a-4)

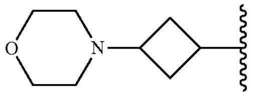

(2-1-1-a-5)

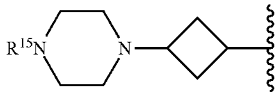

(2-1-1-a-6)

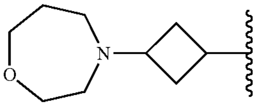

(2-1-1-a-7)

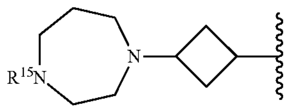

($R^{15}$ has the same meaning as that defined above), and the saturated ring may be substituted with the same or different 1 to 3 substituents selected from the group $G^3$.

[26-8] The compound or a salt thereof according to any one of [22] to [25] mentioned above, wherein $R^{11}$ and $R^{12}$ combine to form a saturated ring represented by the following general formula (2-1-1-b-1):

[Formula 27]

(2-1-1-b-1)

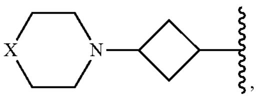

the saturated ring may be substituted with the same or different 1 to 3 substituents selected from the group $G^3$; and X is O or $NR^{15}$ ($R^{15}$ has the same meaning as that defined above).

[26-9] The compound or a salt thereof according to any one of [22] to [25] mentioned above, wherein $R^{11}$ and $R^{12}$ combine to form a saturated ring represented by any one of the following general formulas (2-1-1-c-1) to (2-1-1-c-3):

[Formula 28]

(2-1-1-c-1)

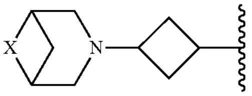

(2-1-1-c-2)

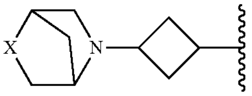

(2-1-1-c-3)

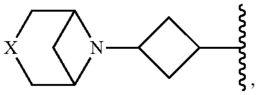

the saturated ring may be substituted with the same or different 1 to 3 substituents selected from the group $G^3$; and X is O or $NR^{15}$ ($R^{15}$ has the same meaning as that defined above).

[26-10] The compound or a salt thereof according to any one of [22] to [25] mentioned above, wherein $R^{11}$ and $R^{12}$ combine to form a spiro ring represented by any one of the following general formulas (2-1-1-d-1) to (2-1-1-d-15):

[Formula 29]

(2-1-1-d-1)

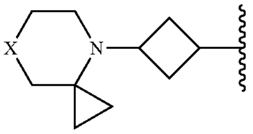

(2-1-1-d-2)

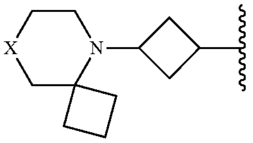

-continued (2-1-1-d-3)

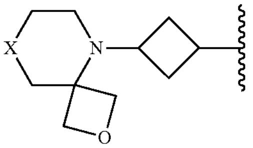

(2-1-1-d-4)

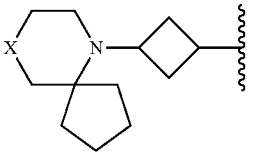

(2-1-1-d-5)

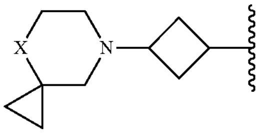

(2-1-1-d-6)

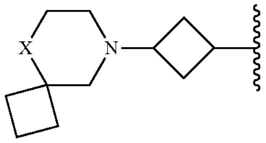

(2-1-1-d-7)

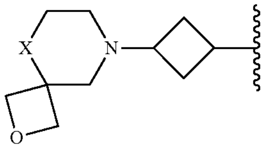

(2-1-1-d-8)

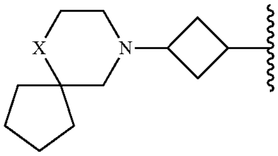

(2-1-1-d-9)

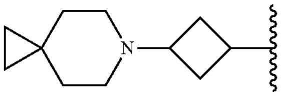

(2-1-1-d-10)

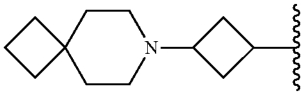

(2-1-1-d-11)

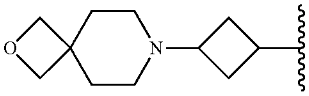

(2-1-1-d-12)

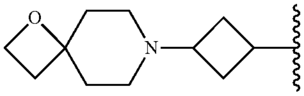

(2-1-1-d-13)

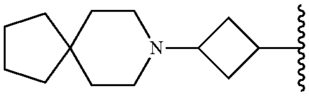

-continued (2-1-1-d-14)

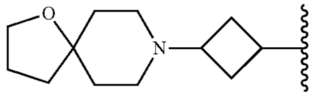

(2-1-1-d-15)

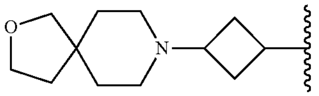

the spiro ring may be substituted with the same or different 1 to 3 substituents selected from the group $G^3$; and X is O or $NR^{15}$ ($R^{15}$ has the same meaning as that defined above).

[26-11] The compound or a salt thereof according to any one of [22] to [25] mentioned above, wherein $R^{11}$ and $R^{12}$ may combine to form a saturated ring having a condensed ring represented by the following general formula (2-1-1-e-1):

[Formula 30]

(2-1-1-e-1)

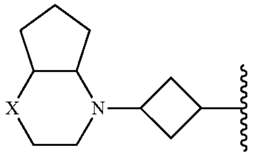

the saturated ring having a condensed ring may be substituted with the same or different 1 to 3 substituents selected from the group $G^3$; and X is O or $NR^{15}$ ($R^{15}$ has the same meaning as that defined above).

[27] The compound or a salt thereof according to any one of [22] to [26-11] mentioned above, wherein Cy is a group represented by the following general formula (2-1-2):

[Formula 31]

(2-1-2)

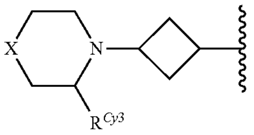

($R^{Cy3}$ has the same meaning as that defined above); and

X is O or $NR^{15}$ ($R^{15}$ has the same meaning as that defined above).

[28] The compound or a salt thereof according to any one of [22] to [27] mentioned above, wherein X is $NR^{15}$ ($R^{15}$ has the same meaning as that defined above).

[29] The compound or a salt thereof according to any one of [22] to [28] mentioned above, wherein Cy is a group represented by the following general formula (2-1-3):

[Formula 32]

(2-1-3)

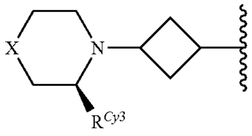

($R^{Cy3}$ and X have the same meanings as those defined above).

[30] The compound or a salt thereof according to any one of [22] to [29] mentioned above, wherein $R^2$ is a group represented by the following formula (3-1):

[Formula 33]

(3-1)

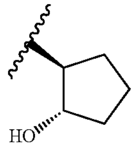

or normal propyl.

[31] The compound or a salt thereof according to any one of [22] to [29] mentioned above, wherein $R^2$ is a group represented by the following formula (3-1):

[Formula 34]

(3-1)

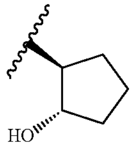
.

[32] A compound represented by the following formula:

[Formula 35]

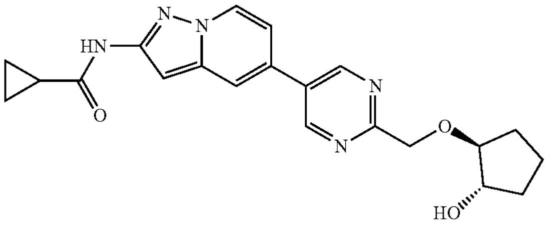
, or a salt thereof.

[33] A compound represented by the following formula:

[Formula 36]

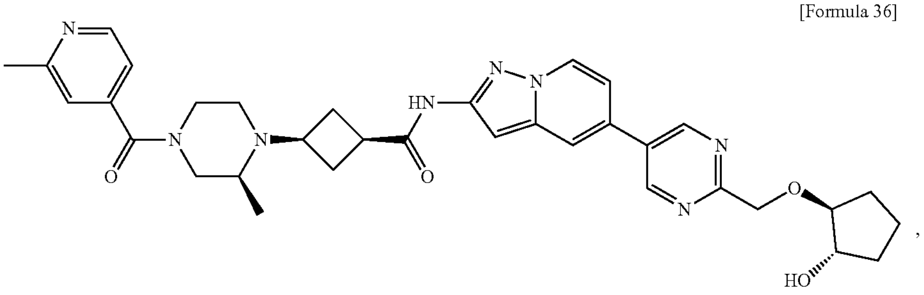 [SMILES: Cc1cc(C(=O)N2CCN([C@H]3C[C@@H](C(=O)Nc4cc5cc(-c6cnc(CO[C@H]7CCC[C@@H]7O)nc6)ccn5n4)C3)[C@@H](C)C2)ccn1]

or a salt thereof.

[34] A compound represented by the following formula:

[Formula 37]

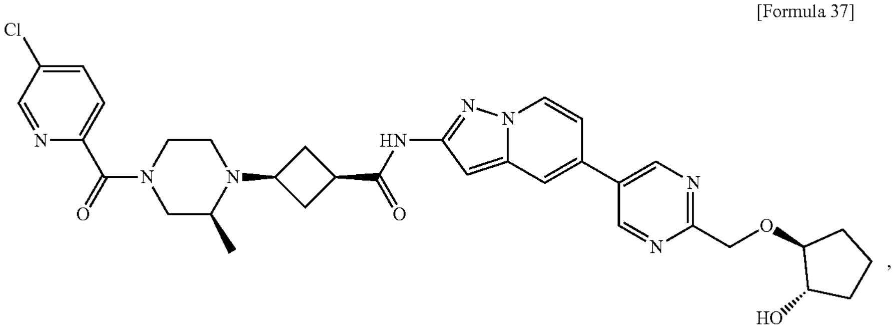 [SMILES: C[C@H]1CN(C(=O)c2ccc(Cl)cn2)CCN1[C@H]1C[C@@H](C(=O)Nc2cc3cc(-c4cnc(CO[C@H]5CCC[C@@H]5O)nc4)ccn3n2)C1]

or a salt thereof.

[35] A compound represented by the following formula:

[Formula 38]

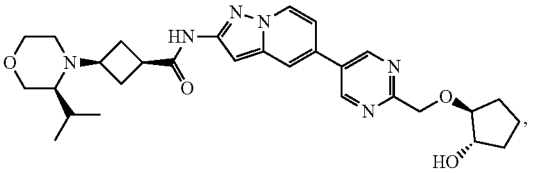

or a salt thereof.

[36] A medicament containing the compound according to any one of [1] to [35] mentioned above, or a pharmaceutically acceptable salt thereof as an active ingredient.

[37] The medicament according to [36] mentioned above, which is for prophylactic and/or therapeutic treatment of a disease relating to inhibition of IRAK4.

[38] The medicament according to [36] mentioned above, which is for prophylactic and/or therapeutic treatment of rheumatism.

[39] An IRAK4 inhibitor containing the compound according to any one of [1] to [35] mentioned above, or a pharmaceutically acceptable salt thereof as an active ingredient.

[40] A pharmaceutical composition for prophylactic and/or therapeutic treatment of rheumatism, which contains the compound according to any one of [1] to [35] mentioned above, or a pharmaceutically acceptable salt thereof, and a pharmaceutically acceptable carrier.

[41] The compound according to any one of [1] to [35] mentioned above, or a pharmaceutically acceptable salt thereof, which is used for prophylactic and/or therapeutic treatment of rheumatism.

[42] A method for prophylactic and/or therapeutic treatment of rheumatism in a mammal, which comprises the step of administrating an effective amount of the compound according to any one of [1] to [35] mentioned above, or a pharmaceutically acceptable salt thereof to the mammal.

Effect of the Invention

The "compounds represented by the formula (1) or a salt thereof" (henceforth also simply referred to as the "compounds of the present invention" have a superior IRAK-4 inhibitory activity. The compounds of the present invention according to a certain embodiment exhibit strong selectivity for other kinases, especially FLT3. Moreover, the compounds of the present invention according to a certain embodiment show low genetic toxicity. Furthermore, the compounds of the present invention according to a certain embodiment can be used as an active ingredient of a medicament for prophylactic and/or therapeutic treatment of a disease relating to IRAK-4 inhibition, for example, prophylactic and/or therapeutic treatment of an autoimmune disease. The compounds of the present invention according to a certain embodiment can also be used as a reagent having an IRAK-4 inhibitory activity.

BRIEF EXPLANATION OF THE DRAWING

FIG. 1 is a graph showing swelling-suppressing effect of a compound of the present invention according to a certain embodiment (Example c-01-01) in rat arthritis.

Hereafter, the present invention will be specifically explained.

In the present description, unless especially indicated, carbon atom may be simply represented as "C", hydrogen atom as H", oxygen atom as "O", sulfur atom as "S", and nitrogen atom as N". Further, carbonyl group may be simply represented as "—C(O)—", carboxyl group as "—COO—", sulfinyl group as "—S(O)—", sulfonyl group as "—$S(O)_2$—", ether bond as "—O—", and thioether bond as "—S—" (each "-" in these groups indicates a bond).

In this description, alkyl may be a linear, branched, or cyclic saturated hydrocarbon group, or a combination of such groups, unless it is particularly indicated. Examples include, for example, methyl, ethyl, propyl, butyl, an isomer thereof [normal (n), iso, secondary (sec), tertiary (t) and the like], and cycloalkyl such as cyclopropyl and cyclobutyl. Examples of alkyl include alkyl having 1 to 6 carbon atoms. According to another embodiment, examples include alkyl having 1 to 3 carbon atoms. Alkyl having 1 to 6 carbon atoms may be indicated as $C_{1-6}$ alkyl.

"Alkoxy" may be linear, branched, or cyclic saturated alkyloxy, or a combination of such groups, unless it is especially indicated. Examples include, for example, methoxy, ethoxy, propoxy, butoxy, an isomer thereof [normal (n), iso, secondary (see), tertiary (t) and the like], and cycloalkyloxy such as cyclopropoxy and cyclobutoxy. Examples of alkoxy include alkoxy having 1 to 6 carbon atoms. In another embodiment, examples include alkoxy having 1 to 3 carbon atoms. Alkoxy having 1 to 6 carbon atoms may be indicated as $C_{1-6}$ alkoxy.

"Alkylene" may be linear or branched alkylene. Examples include, for example, methylene, ethylene, propylene, butylene, methylmethylene, ethylmethylene, methylethylene, 1,2-dimethylethylene, 1,1,2,2-tetramethylethylene, and 1-methylbutylene. Examples of alkylene include alkylene having 1 to 6 carbon atoms. According to another embodiment, examples thereof include alkylene having 1 to 3 carbon atoms. Alkylene having 1 to 6 carbon atoms may be referred to as $C_{1-6}$ alkylene.

"Halogen" is fluoro (—F), chloro (—Cl), bromo (—Br), or iodo (—I). According to another embodiment, examples thereof include —F and —Cl. According to further another embodiment, examples thereof include —F. The term "halogeno-" means substitution with the same or different 1 to 7 halogens. According to another embodiment, it means substitution with the same or different 1 to 5 halogens. According to further another embodiment, it means substitution with 1 to 3 halogens. According to further another embodiment, it means substitution with 1 of halogen. Examples include substitution with —F.

The "aromatic ring" is not particularly limited so long as it is a ring having aromaticity, and examples include a monocyclic to tricyclic aromatic ring. Examples of the aromatic ring include an aromatic hydrocarbon ring and an aromatic heterocyclic ring. Specific examples thereof include benzene, naphthalene, phenanthrene, thiophene, furan, thiazole, isothiazole, oxazole, isoxazole, oxadiazole, pyrrole, pyrazole, imidazole, pyridine, pyrimidine, pyrazine, pyridazine, pyridone, pyrimidinone, indole, isoindole, indazole, quinoline, isoquinoline, benzimidazole, benzotriazole, benzothiophene, benzofuran, benzothiazole, phthalazine, quinoxaline, pyrrolopyridine, and carbazole.

Examples of the "aromatic ring group" include a monovalent group formed by eliminating one arbitrary hydrogen atom from an aromatic ring. The aromatic ring group may be a monocyclic to tricyclic aromatic ring group. Examples thereof include, for example, aryl and heteroaryl.

"Aryl" may be a monocyclic to tricyclic aromatic hydrocarbon ring group. The aryl may also be an aromatic hydrocarbon ring group condensed with a saturated hydrocarbon ring described later. Examples thereof include 6- to 14-membered aryl. According to another embodiment, examples thereof include 6- to 10-membered aryl. According to further another embodiment, examples thereof include 6-membered aryl. Specific examples thereof include phenyl, naphthyl, anthranyl, phenanthrenyl, fluorenyl, indanyl, and 1,2,3,4-tetrahydronaphthalenyl. According to another embodiment, examples thereof include phenyl, and according to still another embodiment, examples thereof include naphthyl. Indanyl and 1,2,3,4-tetrahydronaphthalenyl fall within the scope of 6- to 10-membered aryl.

"Heteroaryl" may be a monocyclic to tricyclic aromatic heterocyclic ring group containing 1 to 4 heteroatoms as ring-constituting atoms. Examples of heteroatom include O, S, and N. Examples thereof include 5- to 14-membered heteroaryl. According to another embodiment, examples thereof include 5- to 10-membered heteroaryl. According to further another embodiment, examples thereof include 5- or 6-membered heteroacyl. Specific examples thereof include thienyl, furanyl, thiazolyl, isothiazolyl, oxazolyl, isoxazolyl, oxadiazolyl, pyrrolyl, pyrazolyl, imidazolyl, pyridyl, pyrimidinyl, pyrazinyl, pyridazinyl, pyridon-yl, pyrimidinon-yl, indolyl, isoindolyl, indazolyl, quinolyl, isoquinolyl, benzimidazolyl, benzotriazolyl, benzothienyl, benzofuranyl, benzothiazolyl, phthalazinyl, quinoxalinyl, pyrrolopyridyl, and carbazolyl.

Examples of "saturated ring" include a saturated hydrocarbon ring and saturated heterocyclic ring. The saturated ring may have a crosslink, or condense with the aforementioned aromatic ring.

The "saturated hydrocarbon ring" may be a monocyclic to tricyclic saturated hydrocarbon ring. Examples thereof include a 3- to 10-membered saturated hydrocarbon ring. According to another embodiment, examples thereof include a 3- to 7-membered saturated hydrocarbon ring. According to further another embodiment, examples thereof include a 5 or 6-membered saturated hydrocarbon ring. The saturated hydrocarbon ring may contain a crosslink, and may condense with the aforementioned aromatic ring. Specific examples thereof include cyclopropane, cyclobutane, cyclopentane, cyclohexane, and adamantane.

The "saturated heterocyclic ring" may be a monocyclic to tricyclic saturated heterocyclic ring containing 1 to 4 heteroatoms as ring-constituting atoms. Examples of heteroatom include O, S, and N. Examples thereof include a 3- to 10-membered saturated heterocyclic ring. According to another embodiment, examples thereof include a 3- to 7-membered saturated heterocyclic ring. According to further another embodiment, examples thereof include a 5- or 6-membered saturated heterocyclic ring. This saturated heterocyclic ring may contain a crosslink, and may condense with the aforementioned aromatic ring. Specific examples thereof include tetrahydropyran, tetrahydrofuran, piperidine, pyrrolidine, azetidine, oxetane, aziridine, oxirane, tetrahydrothiopyran, tetrahydrothiophene, morpholine, oxazepane, and piperazine.

Examples of the "condensed ring" include a cyclic compound consisting of two or more rings bonding together so that the rings share two or more atoms, where the two or more rings are independently a 3- to 7-membered saturated ring. The condensed ring may contain 1 to 3 heteroatoms selected from O, S, and N. Examples of the condensed ring include a cyclic compound where two rings share two adjacent atoms.

Examples of the “spiro ring” include a cyclic compound consisting of two rings sharing one carbon atom, wherein the two rings are independently a 3- to 7-membered saturated ring. The spiro ring may contain 1 to 3 heteroatoms selected from O, S, and N. When the spiro ring is constituted by 7 to 11 atoms, this spiro ring may be referred to as 7- to 11-membered spiro ring. Examples of the spiro ring include a 7- to 13-membered spiro ring. According to another embodiment, examples thereof include a 7- to 11-membered spiro ring. According to further another embodiment, examples thereof include a 7- to 9-membered spiro ring.

Examples of the “saturated ring group” include a monovalent group formed by eliminating one arbitrary hydrogen atom from a saturated ring, and a divalent group formed by eliminating one each of hydrogen atom from two different ring-constituting atoms of a saturated ring. Examples thereof include a saturated hydrocarbon ring group and a saturated heterocyclic ring group. Examples thereof include a 3- to 10-membered saturated ring group. According to another embodiment, examples thereof include a 3- to 7-membered saturated ring group. According to further another embodiment, examples thereof include a 5- or 6-membered saturated ring group.

Examples of the “saturated hydrocarbon ring group” include a monovalent group formed by eliminating one arbitrary hydrogen atom from a saturated hydrocarbon ring, and a divalent group formed by eliminating one each of hydrogen atom from two different ring-constituting atoms of a saturated hydrocarbon ring. The saturated hydrocarbon ring group may be a monocyclic to tricyclic saturated hydrocarbon ring group. The saturated hydrocarbon ring group may contain a crosslink, and may condense with the aforementioned aromatic ring. Examples thereof include a 3- to 10-membered saturated hydrocarbon ring group. According to another embodiment, examples thereof include a 3- to 7-membered saturated hydrocarbon ring group. According to further another embodiment, examples thereof include a 5- or 6-membered saturated hydrocarbon ring group. Specific examples of the monovalent group include cyclopropyl, cyclobutyl, cyclopentyl, cyclohexyl, and adamantyl. Specific examples of the divalent group include a divalent group formed from any of the aforementioned specific examples of the monovalent group by further eliminating hydrogen atom from a ring-constituting atom other than the ring-constituting atom from which hydrogen atom has been eliminated when the monovalent group has been formed.

Examples of the “saturated heterocyclic ring group” include a monovalent group formed by eliminating one arbitrary hydrogen atom from a saturated heterocyclic ring, and a divalent group formed by eliminating one each of hydrogen atom from two different ring-constituting atoms of a saturated heterocyclic ring. The saturated heterocyclic ring group may be a monocyclic to tricyclic saturated heterocyclic ring group containing 1 to 4 heteroatoms as ring-constituting atoms. This saturated heterocyclic ring group may contain a crosslink, and may condense with the aforementioned aromatic ring. Examples of heteroatom include O, S, and N. Examples thereof include a 3- to 10-membered heterocyclic ring group. According to another embodiment, examples thereof include a 3- to 7-membered saturated heterocyclic ring group. According to further another embodiment, examples thereof include a 5- or 6-membered saturated heterocyclic ring group. Specific examples of the monovalent group include tetrahydropyranyl, tetrahydrofuranyl, piperidinyl, pyrrolidinyl, azetidinyl, oxetanyl, tetrahydrothiopyranyl, tetrahydrothienyl, morpholinyl, and piperazinyl.

The “partially unsaturated ring group” may be a saturated ring group a part of which is unsaturated, and examples include a partially unsaturated hydrocarbon ring group, and a partially unsaturated heterocyclic ring group. Examples include a 3- to 10-membered partially unsaturated ring group. According to another embodiment, examples thereof include a 3- to 7-membered partially unsaturated ring group. According to further another embodiment, examples thereof include a 5- or 6-membered partially unsaturated ring group.

The “partially unsaturated hydrocarbon ring group” may be a saturated hydrocarbon ring group a part of which is unsaturated. Specific examples thereof include cyclopentenyl, cyclopentadienyl, cyclohexenyl, cyclohexadienyl, and bicyclooctatrienyl.

The “partially unsaturated heterocyclic ring group” may be a saturated heterocyclic ring group a part of which is unsaturated. Specific examples thereof include dihydropyranyl, dihydrofuranyl, dihydrothiopyranyl, dihydrothienyl, 1,2-dihydroquinolyl, and 1,2,3,4-tetrahydroquinolyl.

In the present invention, all isomers are included, unless specifically indicated. For example, alkyl, alkenyl, alkynyl, alkoxy, alkylthio, alkylene, alkenylene, and alkynylene include linear and branched groups. Further, any of isomers based on a double bond, ring, or condensed ring (E- or Z-isomer, or cis- or trans-isomer), isomers based on the presence of an asymmetric carbon, or the like (R- or S-isomer, isomers based on α- or β-configuration, enantiomers, diastereomers, and the like), optically active substances having optical rotation (D- or L-isomer, or d- or l-isomer), isomers based on polarity observed in chromatographic separation (high polarity isomer or low polarity isomer), equilibrated compounds, rotational isomers, mixtures of these isomers at arbitrary ratios, and racemates fall within the scope of the present invention.

In the present description, as apparent for those skilled in the art, the symbol:

[Formula 39]

indicates that the bond is on the back of the plane (i.e., α-configuration), the symbol:

[Formula 40]

indicates that the bond is in front of the plane (i.e., β-configuration), and the symbol:

[Formula 41]

means α-configuration or β-configuration, or a mixture thereof, unless especially indicated.

Hereafter, the compounds represented by the formula (1) and a salt thereof will be explained in detail.

[Formula 42]

(1)

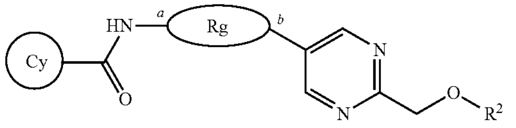

In this description, the expression “which may be substituted” means that the corresponding group has no substituent or the same or different 1 to 5 substituents, unless especially indicated. According to another embodiment, the expression means that the corresponding group has no substituent or the same or different 1 to 3 substituents. According to further another embodiment, the expression means that the corresponding group has no substituent or 1 substituent. According to further another embodiment, the expression means that the corresponding group has no substituent.

Examples of Rg include a group represented by the following general formula (1-1):

[Formula 43]

(1-1)

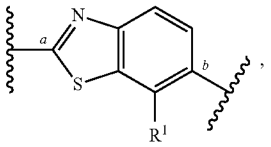

the following general formula (1-2):

[Formula 44]

(1-2)

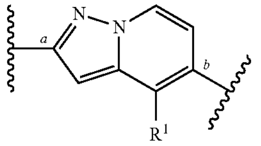

(a and b represent direction of bonding).

Examples of $R^1$ include —H, —F, —Cl, methyl, and $C_{1-3}$ alkoxy. According to another embodiment, examples thereof include —H and $C_{1-3}$ alkoxy. According to further another embodiment, examples thereof include —H and methoxy.

$R^1$ may be substituted with the same or different 1 to 3 substituents selected from the group $G^1$.

Examples of the group $G^1$ include a group consisting of —F, hydroxy, cyano, halogeno-$C_{1-6}$ alkyl, $C_{1-4}$ alkoxy, phenyl, 5- or 6-membered heteroaryl, and a 3- to 7-membered saturated ring group. According to another embodiment, examples thereof include the group $G^{11}$ consisting of —F, hydroxy, halogeno-$C_{1-6}$ alkyl, $C_{1-4}$ alkoxy, 5- or 6-membered heteroaryl, and a 3- to 7-membered saturated ring group. According to further another embodiment, examples thereof include the group $G^{12}$ consisting of —F, hydroxy, $C_{1-4}$ alkoxy, 5-membered heteroaryl, and a 4- or 5-membered saturated ring group.

The phenyl and 5- or 6-membered heteroaryl included in the group $G^1$ may be substituted with the same or different 1 to 3 substituents selected from the group $G^{Ar}$.

Examples of the group $G^1$ include a group consisting of —F, —Cl, hydroxy, cyano, $C_{1-6}$ alkyl, halogeno-$C_{1-6}$ alkyl, and —$NH_2$. According to another embodiment, examples thereof include the group $G^{Ar1}$ consisting of —F, —Cl, cyano, $C_{1-6}$ alkyl, and halogeno-$C_{1-6}$ alkyl.

Examples of $R^2$ include $C_{1-6}$ alkyl, halogeno-$C_{1-6}$ alkyl, and a 3- to 7-membered saturated ring group. According to another embodiment, examples thereof include a 3- to 7-membered saturated ring group.

$R^2$ may be substituted with the same or different 1 to 3 substituents selected from the group $G^2$.

Examples of the group $G^2$ include a group consisting of —F, hydroxy, halogeno-$C_{1-3}$ alkyl, and $C_{1-4}$ alkoxy. According to another embodiment, examples thereof include the group $G^{21}$ consisting of —F and hydroxy.

Specific examples of $R^2$ include the following groups.

[Formula 45]

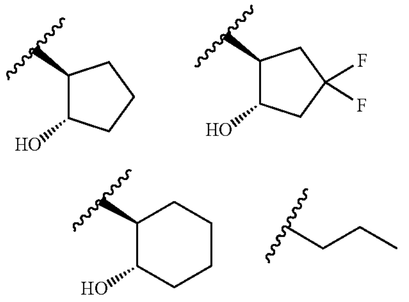

According to another embodiment, specific examples of $R^2$ include the following groups.

[Formula 46]

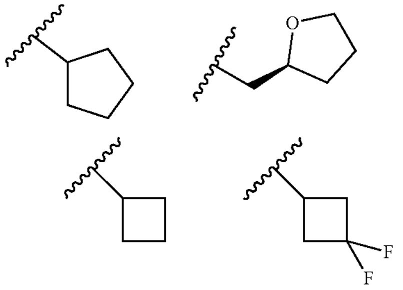

According to further another embodiment, specific examples of $R^2$ include the following groups.

[Formula 47]

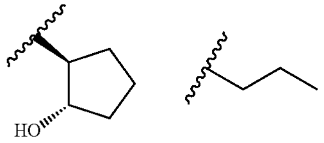

According to further another embodiment, specific examples of $R^2$ include the following group.

[Formula 48]

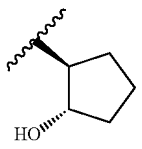

Examples of Cy include a group represented by the following general formula (2-1).

[Formula 49]

(2-1)

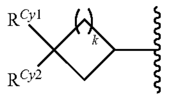

Examples of k include integers of 0 and 1. According to another embodiment, examples thereof include an integer of 1.

Examples of $R^{Cy1}$ and $R^{Cy2}$ independently include —H, —F, hydroxy, cyano, $C_{1-6}$ alkyl, halogeno-$C_{16}$ alkyl, $C_{1-6}$ alkoxy, —$NR^{11}R^{12}$, phenyl, 5- or 6-membered heteroaryl, and a 3- to 7-membered saturated ring group. According to another embodiment, examples thereof include —H, —F, $C_{1-6}$ alkyl, $C_{1-6}$ alkoxy, and —$NR^{11}R^{12}$. According to further another embodiment, examples thereof include —$NR^{11}R^{12}$.

The phenyl and 5- or 6-membered heteroaryl as $R^{Cy1}$ and $R^{Cy2}$ may be substituted with the same or different 1 to 3 substituents selected from the group $G^{Ar}$.

There is also exemplified another embodiment wherein the group $G^1$ is the group $G^{Ar}$, in addition to the embodiment using the group $G^{Ar}$ mentioned above.

$R^{Cy1}$ and $R^{Cy2}$ may be substituted with the same or different 1 to 3 substituents selected from the group $G^1$.

There is also exemplified another embodiment wherein the group $G^1$ is any one of the groups $G^{11}$ and $G^{12}$, in addition to the embodiment using the group $G^1$ mentioned above.

Examples of $R^{11}$ and $R^{12}$ independently include —H, $C_{1-6}$ alkyl, halogeno-$C_{1-6}$ alkyl, hydroxy-$C_{1-6}$ alkyl, $C_{1-6}$ alkoxy-$C_{1-6}$ alkyl, a 3- to 7-membered saturated ring group, phenyl, and 5- or 6-membered heteroaryl. According to another embodiment, examples thereof include —H, $C_{1-6}$ alkyl, halogeno-$C_{1-6}$ alkyl, and a 3- to 7-membered saturated ring group. Examples of the 3- to 7-membered saturated ring group include cyclopropane, cyclobutane, cyclopentane, oxetane, and bicyclo[1.1.1]pentane.

$R^{11}$ and $R^{12}$ may be substituted with the same or different 1 to 3 substituents selected from the group $G^1$.

There is also exemplified another embodiment wherein the group $G^1$ is any one of the groups $G^{11}$ and $G^{12}$, in addition to the embodiment using the group $G^1$ mentioned above.

$R^{11}$ and $R^{12}$ also can combine to form a 4- to 10-membered saturated ring or a 7- to 11-membered spiro ring. The 4- to 10-membered saturated ring and 7- to 11-membered spiro ring may contain the same or different 1 or 2 heteroatoms selected from the group consisting of O and N, or —$S(O_2)$—, in addition to N.

Examples of the 4- to 10-membered saturated ring include azetidine, pyrrolidine, piperidine, morpholine, oxazepane, piperazine, and homopiperazine. According to another embodiment, examples thereof include piperidine, morpholine, and piperazine. According to further another embodiment, examples thereof include morpholine, and piperazine.

Examples of the 4- to 10-membered saturated ring containing a crosslink formed by combined $R^{11}$ and $R^{12}$ include the following groups:

[Formula 50]

(2-1-1-c-1)

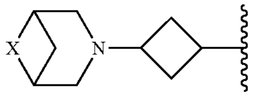

(2-1-1-c-2)

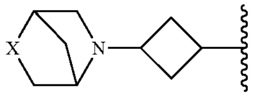

(2-1-1-c-3)

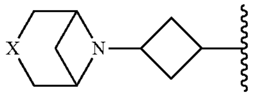

(X has the same meaning as that defined above).

Examples of the 7- to 11-membered spiro ring formed by combined $R^{11}$ and $R^{12}$ include the following groups:

[Formula 51]

(2-1-1-d-1)

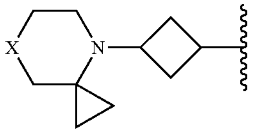

(2-1-1-d-2)

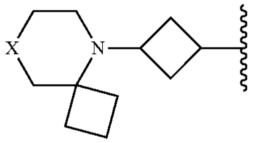

(2-1-1-d-3)

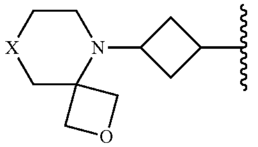

(2-1-1-d-4)

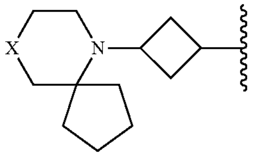

(2-1-1-d-5)

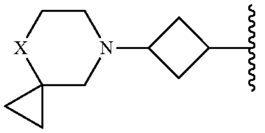

(2-1-1-d-6)

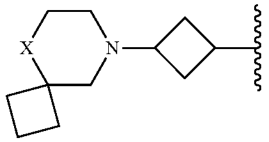

(2-1-1-d-7)

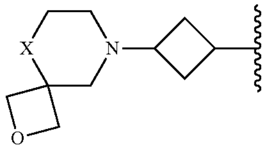

-continued (2-1-1-d-8)

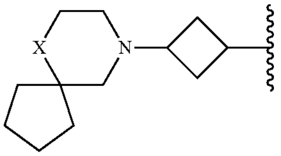

(2-1-1-d-9)

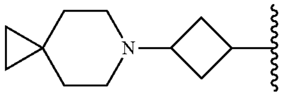

(2-1-1-d-10)

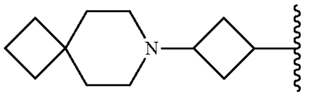

(2-1-1-d-11)

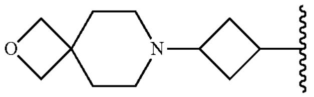

(2-1-1-d-12)

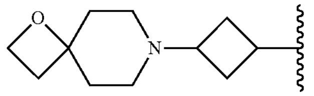

(2-1-1-d-13)

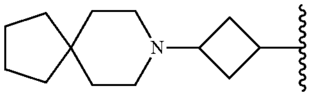

(2-1-1-d-14)

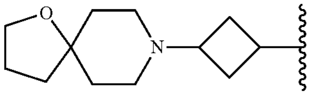

(2-1-1-d-15)

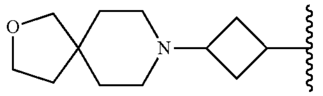

(X has the same meaning as that defined above).

Examples of the 4- to 10-membered saturated ring containing a crosslink formed by combined $R^{11}$ and $R^{12}$ include the following group:

[Formula 52]

(2-1-1-e-1)

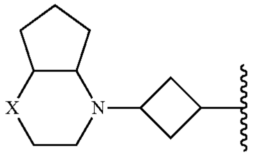

(X has the same meaning as that defined above).

The 4- to 10-membered saturated ring or 7- to 11-membered spiro ring formed by combined $R^{11}$ and $R^{12}$ may be substituted with the same or different 1 to 3 substituents selected from the group $G^3$.

Examples of the group $G^3$ include a group consisting of —F, hydroxy, $C_{1-6}$ alkyl, halogeno-$C_{1-6}$ alkyl, hydroxy-$C_{1-6}$ alkyl, $C_{1-6}$ alkoxy, $C_{1-6}$ alkoxy-$C_{1-6}$ alkyl, halogeno-$C_{1-6}$ alkoxy, —C(O)$R^{14}$, —$NR^{13}$C(O)$R^{14}$, —C(O)$NR^{13}R^{14}$, —C(O)$NH_2$, —$NR^{13}S(O_2)R^{14}$, —$S(O_2)NR^{13}R^{14}$, —$S(O_2)NH_2$, —$S(O_2)R^{14}$, phenyl, 5- or 6-membered heteroaryl, and a 3- to 7-membered saturated ring group. According to another embodiment, examples thereof include a group consisting of —F, $C_{1-6}$ alkyl, halogeno-$C_{1-6}$ alkyl, —C(O)$R^{14}$, and —C(O)$NR^{13}R^{14}$.

The phenyl and 5- or 6-membered heteroaryl included in the group $G^3$ may be substituted with the same or different 1 to 3 substituents selected from the group $G^{Ar}$.

There is also exemplified another embodiment wherein the group $G^{Ar}$ is the group $G^{Ar1}$, in addition to the embodiment using the group $G^{Ar}$ mentioned above.

Examples of $R^{13}$ include —H, $C_{1-6}$ alkyl, halogeno-$C_{1-6}$ alkyl, $C_{1-6}$ alkoxy-$C_{1-6}$ alkyl, halogeno-$C_{1-6}$ alkoxy-$C_{1-6}$ alkyl, phenyl, 5- or 6-membered heteroaryl, and a 3- to 7-membered saturated ring group. According to another embodiment, examples thereof include —H, $C_{1-6}$ alkyl, and halogeno-$C_{16}$ alkyl. According to further another embodiment, examples thereof include —H.

Examples of $R^{14}$ include $C_{1-6}$ alkyl, halogeno-$C_{1-6}$ alkyl, $C_{1-6}$ alkoxy-$C_{1-6}$ alkyl, halogeno-$C_{1-6}$ alkoxy-$C_{1-6}$ alkyl, phenyl, 5- or 6-membered heteroaryl, and a 3- to 7-membered saturated ring group. According to another embodiment, examples thereof include $C_{1-6}$ alkoxy-$C_{1-6}$ alkyl, 5- or 6-membered heteroaryl, and a 3- to 7-membered saturated ring group. According to further another embodiment, examples thereof include 5- or 6-membered heteroaryl.

Examples of the 5- or 6-membered heteroaryl include pyridine, oxazole, isoxazole, and thiazole. According to another embodiment, examples thereof include pyridine.

The phenyl and 5- or 6-membered heteroaryl as $R^{13}$ and $R^{14}$ may be substituted with the same or different 1 to 3 substituents selected from the group $G^{Ar}$.

There is also exemplified another embodiment wherein the group $G^{Ar}$ is the group $G^{Ar}$, in addition to the embodiment using the group $G^{Ar}$ mentioned above.

$R^{13}$ and $R^{14}$ also can combine to form a 4- to 7-membered saturated ring or a 7- to 11-membered spiro ring. The 4- to 7-membered saturated ring and 7- to 11-membered spiro ring may contain the same or different 1 or 2 heteroatoms selected from the group consisting of O and N, or —$S(O_2)$—, in addition to N.

Examples of the 4- to 7-membered saturated ring include azetidine, pyrrolidine, piperidine, morpholine, oxazepane, and piperazine. According to another embodiment, examples thereof include azetidine, and pyrrolidine. According to further another embodiment, examples thereof include azetidine.

According to another embodiment, examples of the 4- to 10-membered saturated ring formed by combined $R^{11}$ and $R^{12}$ include, when the 4- to 10-membered saturated ring is morpholine or piperazine, the following group.

[Formula 53]

(2-1-2)

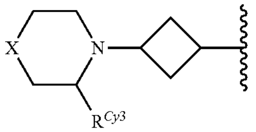

Examples of X include O and $NR^{15}$. According to another embodiment, examples thereof include $NR^{15}$.

Examples of $R^{Cy3}$ include $C_{1-4}$ alkyl, and halogeno-$C_{1-4}$ alkyl. According to another embodiment, examples thereof include methyl, ethyl, and isopropyl. According to further another embodiment, examples thereof include methyl.

Examples of $R^{15}$ include —H, $C_{1-6}$ alkyl, halogeno-$C_{1-6}$ alkyl, hydroxy-$C_{1-6}$ alkyl, $C_{1-6}$ alkoxy-$C_{1-6}$ alkyl, —C(O)$R^{16}$, —S($O_2$)$R^{16}$, —C(O)N$R^{16}R^{17}$, —C(O)O$R^{16}$, and a 3- to 7-membered saturated ring group. According to another embodiment, examples thereof include halogeno-$C_{1-6}$ alkyl, —C(O)$R^{16}$, —S($O_2$)$R^{16}$, and —C(O)N$R^{16}R^{17}$. According to further another embodiment, examples thereof include —C(O)$R^{16}$.

Examples of $R^{16}$ include $C_{1-6}$ alkyl, halogeno-$C_{1-6}$ alkyl, $C_{1-6}$ alkoxy-$C_{1-6}$ alkyl, halogeno-$C_{1-6}$ alkoxy-$C_{1-6}$ alkyl, phenyl, 5- or 6-membered heteroaryl, and a 3- to 7-membered saturated ring group. According to another embodiment, examples thereof include $C_{1-6}$ alkoxy-$C_{1-6}$ alkyl, 5- or 6-membered heteroaryl, and a 3- to 7-membered saturated ring group. According to further another embodiment, examples thereof include 5- or 6-membered heteroaryl.

Examples of the 5- or 6-membered heteroaryl include pyridine, oxazole, isoxazole, and thiazole. According to another embodiment, examples thereof include pyridine.

Examples of $R^{17}$ include —H, $C_{1-3}$ alkyl, halogeno-$C_{1-3}$ alkyl, $C_{1-6}$ alkoxy-$C_{1-6}$ alkyl, halogeno-$C_{1-6}$ alkoxy-$C_{1-3}$ alkyl, phenyl, 5- or 6-membered heteroaryl, and a 3- to 7-membered saturated ring group. According to another embodiment, examples thereof include —H, $C_{1-6}$ alkyl, and halogeno-$C_{1-6}$ alkyl. According to further another embodiment, examples thereof include —H.

The phenyl and 5- or 6-membered heteroacyl as $R^{16}$ or $R^{17}$ may be substituted with the same or different 1 to 3 substituents selected from the group $G^{Ar}$.

There is also exemplified another embodiment wherein the group $G^{Ar}$ is the group $G^{Ar1}$, in addition to the embodiment using the group $G^{Ar}$ mentioned above.

$R^{16}$ and $R^{17}$ also can combine to form a 4- to 7-membered saturated ring or a 7- to 11-membered spiro ring. The 4- to 7-membered saturated ring and 7- to 11-membered spiro ring may contain the same or different 1 or 2 heteroatoms selected from the group consisting of O and N, or —S($O_2$)—, in addition to N.

Examples of the 4- to 7-membered saturated ring include azetidine, pyrrolidine, piperidine, morpholine, oxazepane, and piperazine. According to another embodiment, examples thereof include azetidine and pyrrolidine. According to further another embodiment, examples thereof include azetidine.

$R^{15}$ may be substituted with the same or different 1 to 3 substituents selected from the group $G^1$.

There is also exemplified another embodiment wherein the group $G^1$ is any one of the groups $G^{11}$ and $G^{12}$, in addition to the embodiment using the group $G^1$ mentioned above.

Specific examples of $R^1$ include the following groups.

[Formula 54]

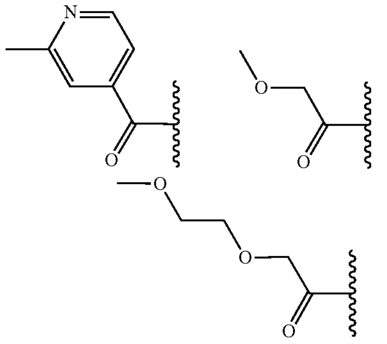

According to another embodiment, specific examples of $R^{15}$ include the following groups.

[Formula 55]

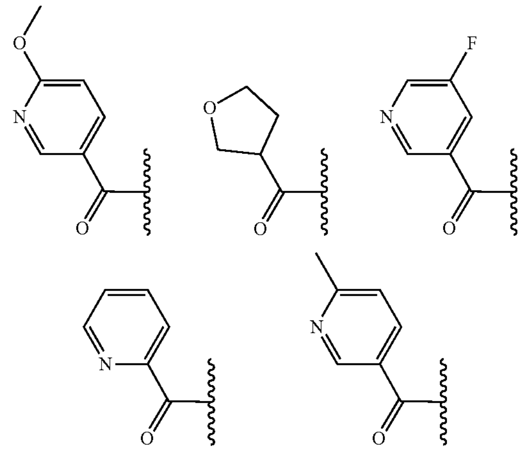

According to further another embodiment, examples of the 4- to 10-membered saturated ring formed by combined $R^{11}$ and $R^{12}$ include, when the 4- to 7-membered saturated ring is morpholine or piperazine, the following group:

[Formula 56]

(2-1-3)

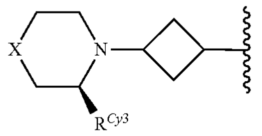

($R^{Cy3}$ and X have the same meanings as those defined above).

$R^{Cy1}$ and $R^{Cy2}$ also can combine to form a 4- to 7-membered saturated ring or a 7- to 11-membered spiro ring. The 4- to 7-membered saturated ring and 7- to 11-membered spiro ring may contain the same or different 1 or 2 heteroatoms selected from the group consisting of O and N, or —S($O_2$)—, in addition to N.

Examples of 4- to 7-membered saturated ring formed by combined $R^{Cy1}$ and $R^{Cy2}$ include azetidine, pyrrolidine, and piperidine. According to another embodiment, examples thereof include piperidine.

The 4- to 7-membered saturated ring and 7- to 11-membered spiro ring formed by combined $R^{Cy1}$ and $R^{Cy2}$ may be substituted with the same or different 1 to 3 substituents selected from the group $G^1$.

There is also exemplified another embodiment wherein the group $G^1$ is any one of the groups $G^{11}$ and $G^{12}$, in addition to the embodiment using the group $G^1$ mentioned above.

Specific examples of the compounds falling within the scope of the present invention include the following compounds. However, the scope of the present invention is not limited to these.

TABLE 1
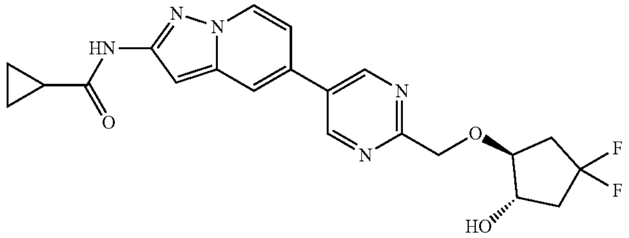 [SMILES: O=C(Nc1cc2cc(-c3cnc(CO[C@H]4CC(F)(F)C[C@@H]4O)nc3)ccn2n1)C1CC1]
Ref. 001
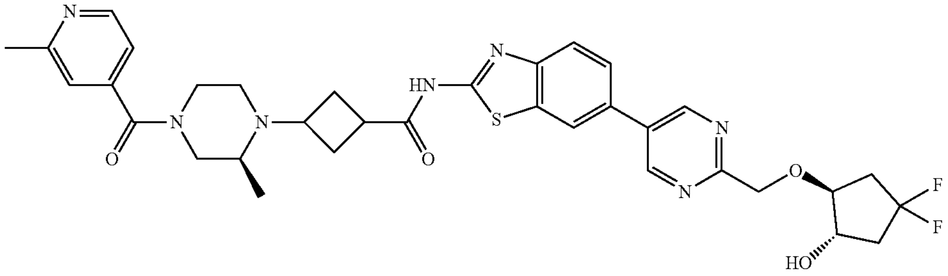 [SMILES: Cc1cc(C(=O)N2CCN(C3CC(C(=O)Nc4nc5ccc(-c6cnc(CO[C@H]7CC(F)(F)C[C@@H]7O)nc6)cc5s4)C3)[C@@H](C)C2)ccn1]
Ref. 002
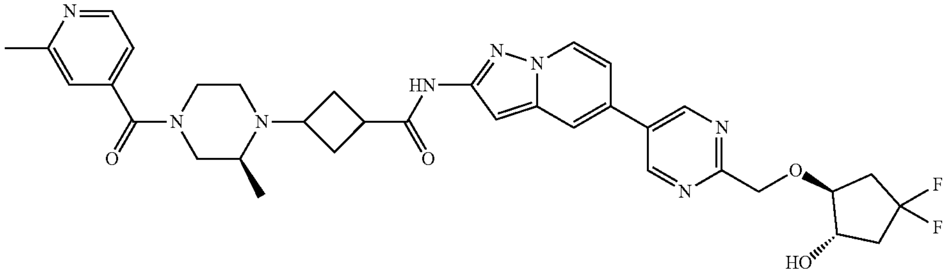 [SMILES: Cc1cc(C(=O)N2CCN(C3CC(C(=O)Nc4cc5cc(-c6cnc(CO[C@H]7CC(F)(F)C[C@@H]7O)nc6)ccn5n4)C3)[C@@H](C)C2)ccn1]
Ref. 003
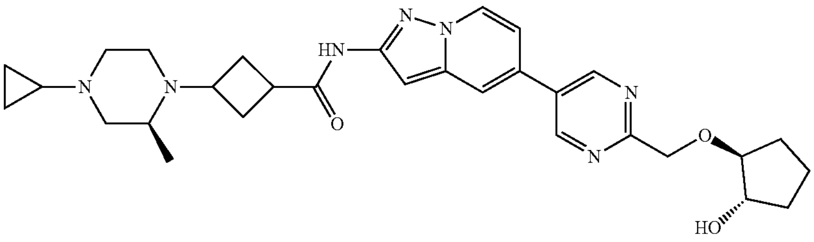 [SMILES: C[C@H]1CN(C2CC2)CCN1C1CC(C(=O)Nc2cc3cc(-c4cnc(CO[C@H]5CCC[C@@H]5O)nc4)ccn3n2)C1]
Ref. 004
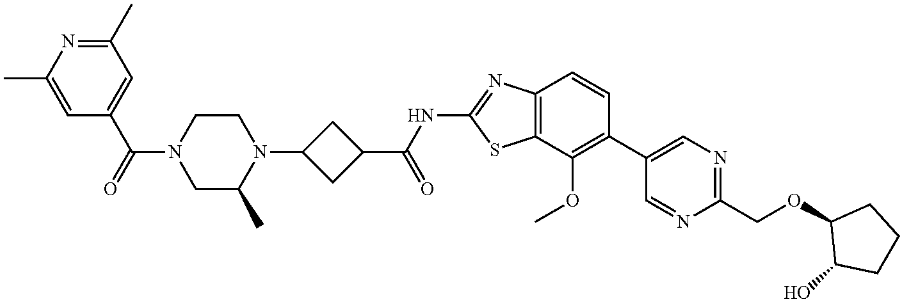 [SMILES: COc1c(-c2cnc(CO[C@H]3CCC[C@@H]3O)nc2)ccc2nc(NC(=O)C3CC(N4CCN(C(=O)c5cc(C)nc(C)c5)C[C@@H]4C)C3)sc12]
Ref. 005

TABLE 1-continued

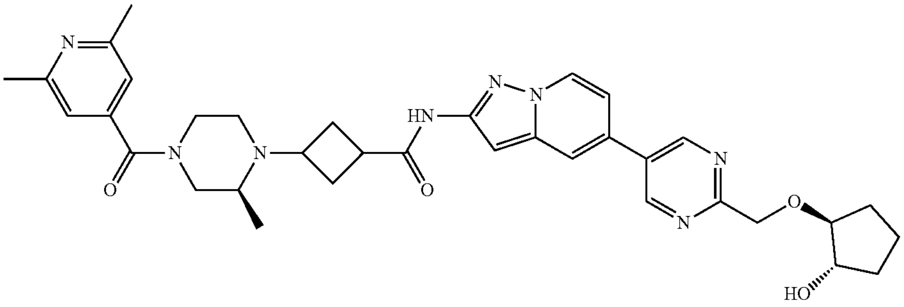 [SMILES: Cc1cc(C(=O)N2CCN(C3CC(C(=O)Nc4cc5cc(-c6cnc(CO[C@H]7CCC[C@@H]7O)nc6)ccn5n4)C3)[C@@H](C)C2)cc(C)n1]

Ref. 006

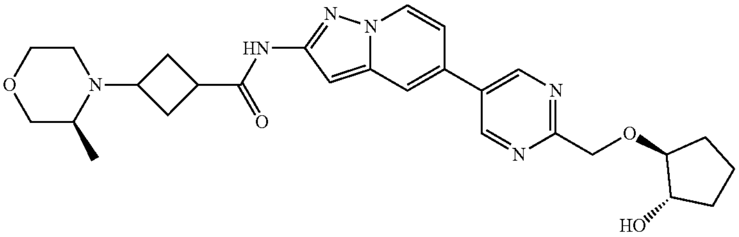 [SMILES: C[C@H]1COCCN1C1CC(C(=O)Nc2cc3cc(-c4cnc(CO[C@H]5CCC[C@@H]5O)nc4)ccn3n2)C1]

Ref. 007

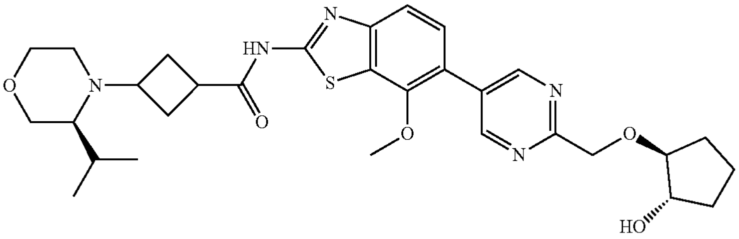 [SMILES: COc1c(-c2cnc(CO[C@H]3CCC[C@@H]3O)nc2)ccc2nc(NC(=O)C3CC(N4CCOC[C@@H]4C(C)C)C3)sc12]

Ref. 008

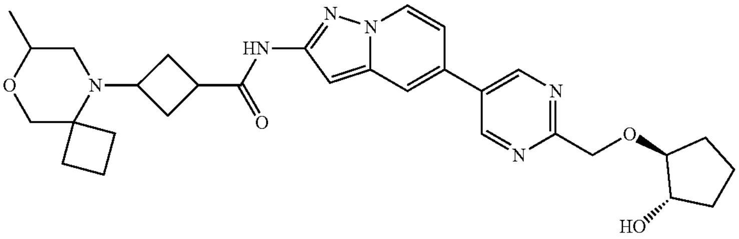 [SMILES: CC1CN(C2CC(C(=O)Nc3cc4cc(-c5cnc(CO[C@H]6CCC[C@@H]6O)nc5)ccn4n3)C2)C2(CCC2)CO1]

Ref. 009

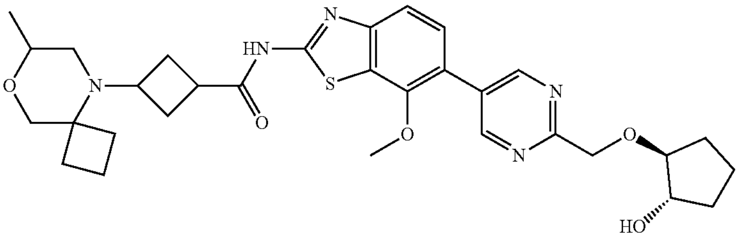 [SMILES: COc1c(-c2cnc(CO[C@H]3CCC[C@@H]3O)nc2)ccc2nc(NC(=O)C3CC(N4CC(C)OCC45CCC5)C3)sc12]

Ref. 010

In this description, the "compounds represented by the formula (1)" are generally understood as the compounds represented by the formula (1) in the free form. Examples of the salt thereof include the following salts.

The type of the salt of the compounds represented by the formula (1) is not particularly limited, and it may be an acid addition salt, or a base addition salt, and may be in the form of an intramolecular counter ion. In particular, when the salt is used as an active ingredient of a medicament, the salt is preferably a pharmaceutically acceptable salt. When disclosure is made for use as a medicament in this description, the salt of the compounds represented by the formula (1) is usually understood to be a pharmaceutically acceptable salt.

Acid addition salts include, for example, acid addition salts with an inorganic acid such as hydrochloric acid, hydrobromic acid, hydroiodic acid, sulfuric acid, nitric acid, and phosphoric acid, and acid addition salts with an organic acid such as formic acid, acetic acid, propionic acid, oxalic acid, malonic acid, succinic acid, methanesulfonic acid, ethanesulfonic acid, benzenesulfonic acid, citric acid, malic acid, tartaric acid, dibenzoyltartaric acid, mandelic acid, maleic acid, fumaric acid, aspartic acid, and glutamic acid. As base addition salts, for example, base addition salts with an inorganic base such as sodium, potassium, magnesium, calcium, and aluminum, base addition salts with an organic base such as methylamine, 2-aminoethanol, arginine, lysine, and ornithine, and the like can be exemplified. However, the type of the salt is not limited to these, and it can of course be appropriately selected by those skilled in the art.

The compounds of the present invention may be in the form of hydrate. The compounds of the present invention may also be in the form of anhydride.

The compounds of the present invention may be in the form of solvate. The compounds of the present invention may also be in the form of non-solvate.

The compounds of the present invention may be in the form of crystal. The compounds of the present invention may also be in an amorphous form.

The compounds of the present invention may be labeled with any of various radioactive or non-radioactive isotopes.

More specifically, the compounds of the present invention include anhydrides and non-solvates of the "compounds represented by the formula (1)", hydrates and/or solvates thereof, and crystals thereof.

The compounds of the present invention also include anhydrides and non-solvates of "salts of the compounds represented by the formula (1)", hydrates and/or solvates of the salts, and crystals thereof.

The compounds of the present invention may also be a pharmaceutically acceptable prodrug of the "compounds represented by the formula (1)". The pharmaceutically acceptable prodrug is a compound having a group that can be changed into amino group, hydroxyl group, carboxyl group, or the like by solvolysis or under physiological conditions. For example, as a group that forms a prodrug for hydroxy group, or amino group, for example, an acyl group and an alkoxycarbonyl group are exemplified. As a group that forms a prodrug for carboxyl group, for example, methyl group, ethyl group, n-propyl group, isopropyl group, n-butyl group, isobutyl group, s-butyl group, t-butyl group, amino group, methylamino group, ethylamino group, dimethylamino group, and diethylamino group are exemplified.

Such a prodrug can be prepared by, for example, appropriately introducing a group that forms a prodrug into any of the compounds of the present invention at one or more arbitrary groups selected from hydroxyl group and amino group using a prodrug-forming reagent such as a corresponding halide in a conventional manner, then, if desired, appropriately isolating and purifying the compound in a conventional manner. A group that forms a prodrug can also be appropriately introduced into the compounds of the present invention at carboxyl group by using such a prodrug-forming reagent as a corresponding alcohol or amine in a conventional manner.

General Preparation Methods

The compounds represented by the formula (1) can be prepared according to known methods such as the methods described below, methods similar to these, or the methods described in the examples. The compounds used in the following preparation methods as starting materials are commercially available, or can be prepared by using known methods described in, for example, "Compendium of Organic Synthesis Methods, Vols. I to XII, Wiley Inter-Science".

Some of the intermediates can be used after introduction of protective groups or deprotection according to known methods, for example, the methods described in Peter G. M., Wuts, Greene's Protective Groups in Organic Chemistry, John Wiley & Sons, 2014".

A mixture of stereoisomers can be resolved by a known method, for example, the methods described in "E. L. Eloel, S. H. Wilen, Stereochemistry of Organic Compounds, John Wiley & Sons, 1994", methods similar to these, and the method described in the examples. Conglomerates can also be resolved by such methods as mentioned above.

The reactions for synthesizing the compounds of the present invention are performed in appropriate solvents selected according to known methods. The appropriate solvents do not substantially react with starting materials, intermediates, or products at the temperatures at which the reactions are performed (for example, temperatures in the range of from the melting point to the boiling point of the solvent). The reactions can be performed in a single kind of solvent or a mixed solvent. A solvent suitable for each reaction is used.

The reactions can be monitored by an appropriate method according to a known method. For example, a product can be monitored by a spectroscopic method using, for example, nuclear magnetic resonance (NMR) apparatus using $^1H$, $^{13}C$, or the like, infrared spectrophotometer (IR), mass spectrometer (MS), high speed liquid chromatography (HPLC), thin layer chromatography (TLC), or the like.

The compounds represented by the formula (1), and intermediates thereof can be prepared by the synthesis methods described below. Unless especially noted, $R^1$, $R^2$, $R^{11}$, $R^{12}$, $R^{15}$, $R^{Cy3}$, and Cy mentioned in the following reaction formulas and descriptions have the same meanings as those defined above. The compounds of the present invention may be prepared by methods other than the methods described in this description by appropriately utilizing the methods described in this description and common general technical knowledge of this technical field. The reaction formulas and the examples are mentioned for the purpose of exemplification, and do not limit the scope of the present invention.

The abbreviations used in the schemes mentioned below are the abbreviations generally used in this technical field. The meanings of the abbreviations for chemical terms used in this description including examples are defines as follows: DMF, N,N-dimethylformamide; DMSO, dimethyl sulfoxide; THF, tetrahydrofuran; DME, 1,2-dimethoxyethane; TFA, trifluoroacetic acid; h, hour; rt, room temperature; RT, retention time; LG, leaving group.

The compounds of the present invention represented by the formula (1) can be prepared in accordance with, for example, the following reaction schemes. In the following schemes, "STEP" means a process step, for example, "STEP 1" means step 1.

SCHEME 1

[Formula 57]

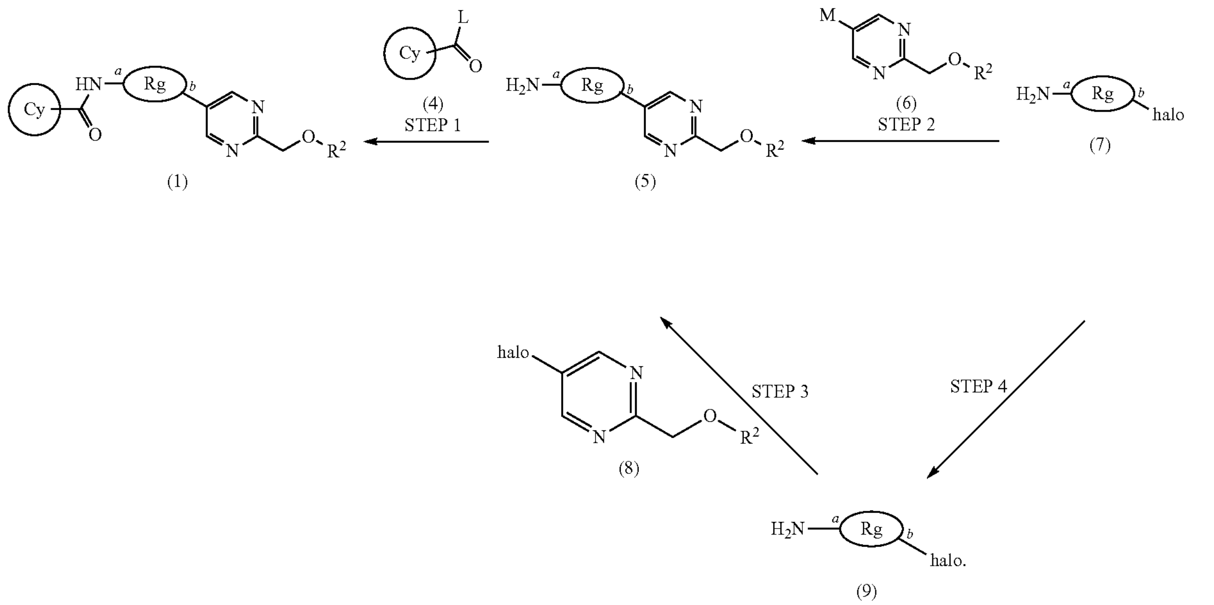

The compounds represented by the formula (1) can be prepared by, for example, the method described in the reaction scheme 1 (in the formulas of the compounds, L represents a leaving group such as —Cl, —Br, and pentafluorophenyl group, or a substituent capable of forming an amide bond such as hydroxyl group, halo represents —Cl, —Br, or —I, and M represents a substituent that can react through various types of coupling using ZnI, MgBr, boronic acid, boronic acid ester, or the like). The compounds represented by the formulas (4) to (9) are commercially available, or can be prepared according to known methods, for example, the methods shown below, or methods similar to these.

Step 1

The compounds represented by the formula (1) can be prepared by, for example, amidation or acylation reaction of a compound represented by the formula (4) and a compound represented by the formula (5). As the condensing agent for the amidation, 1-propanephosphonic acid anhydride, 1-(3-dimethylaminopropyl)-3-ethylcarbodiimide, HATU, or the like can be used. As the nucleophile for the amidation, HOBt, HOAt, or the like can be used. As the base, diisopropylethylamine or the like can be used. As the reaction solvent, for example, DMF, dichloromethane, THF, or the like can be used. The reaction temperature can usually be from 0 to 150° C. By further converting a substituent of the substituent Cy, Rt, or $R^2$ through, for example, deprotection, reduction, reductive amination, alkylation, and fluorination, the compounds represented by the formula (1) can be converted.

Step 2

The compound represented by the formula (5) can be prepared by a coupling reaction with a compound represented by the formula (7) using a metal catalyst. More specifically, the compound can be prepared by, for example, the Suzuki-Miyaura coupling of a compound represented by the formula (7) and a reagent represented by the formula (6). As the reaction catalyst, for example, $Pd(dppf)Cl_2$, PdAmphos, $Pd(PPh_3)_4$, or the like can be used. As the base, cesium carbonate, cesium fluoride, sodium carbonate, or the like can be used. As the reaction solvent, THF, 1,4-dioxane, DMF, acetonitrile, or the like can be used. The reaction temperature can usually be room temperature to 180° C.

Step 3

The compound represented by the formula (5) can be prepared by a coupling reaction with a compound represented by the formula (9) using a metal catalyst. More specifically, the compound can be prepared by, for example, the Suzuki-Miyaura coupling of a compound represented by the formula (9) and a reagent represented by the formula (8). As the reaction catalyst, for example, $Pd(dppf)Cl_2$, PdAmphos, $Pd(PPh_3)_4$, or the like can be used. As the base, cesium carbonate, cesium fluoride, sodium carbonate, or the like can be used. As the reaction solvent, THF, 1,4-dioxane, DMF, acetonitrile, or the like can be used. The reaction temperature can usually be room temperature to 180° C.

The compound represented by the formula (9) can be prepared by, for example, a metal-catalyzed coupling reaction or halogen-metal exchange reaction with a compound represented by the formula (7). More specifically, the compound can be prepared by, for example, the Suzuki-Miyaura coupling of a compound represented by the formula (5) with bis(pinacolato)diboron, or the like As the reaction catalyst, for example, $Pd(dppf)Cl_2$, or the like can be used. As the base, potassium acetate or the like can be used. As the reaction solvent, 1,4-dioxane or the like can be used. The reaction temperature can usually be 40 to 150° C.

SCHEME 2

[Formula 58]

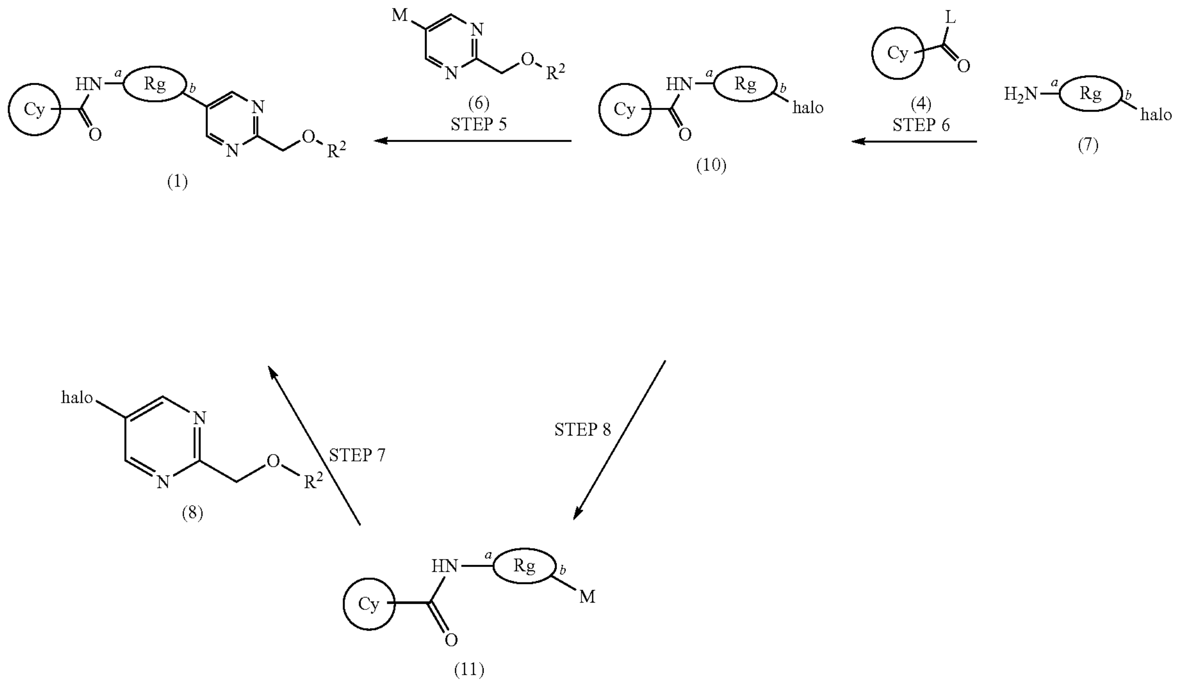

The compounds represented by the formula (1) can be prepared by, for example, the method described in the reaction scheme 2 (in the formulas of the compounds, L represents a leaving group such as —Cl, —Br, and pentafluorophenyl group, or a substituent capable of forming an amide bond such as hydroxyl group, halo represents —Cl, —Br, or —I, and M represents a substituent that can react through various types of coupling using ZnI, MgBr, boronic acid, boronic acid ester, or the like). The compounds represented by the formulas (4), (6) to (8), (10), and (11) are commercially available, or can be prepared according to known methods, for example, the methods shown below, or methods similar to these.

Step 5

The compounds represented by the formula (1) can be prepared by a coupling reaction with a compound represented by the formula (10) using a metal catalyst. More specifically, the compounds can be prepared by, for example, the Suzuki-Miyaura coupling of a compound represented by the formula (10) and a reagent represented by the formula (6). As the reaction catalyst, for example, $Pd(dppf)Cl_2$, PdAmphos, $Pd(PPh_3)_4$, or the like can be used. As the base, cesium carbonate, cesium fluoride, sodium carbonate, or the like can be used. As the reaction solvent, THF, 1,4-dioxane, DMF, acetonitrile, or the like can be used. The reaction temperature can usually be room temperature to 180° C. By further converting a substituent of the substituent Cy, $R^1$, or $R^2$ through, for example, deprotection, reduction, reductive amination, alkylation, and fluorination, the compounds represented by the formula (1) can be converted.

Step 6

The compound represented by the formula (10) can be prepared by, for example, amidation or acylation reaction of a compound represented by the formula (4) and a compound represented by the formula (7). As the condensing agent for the amidation, 1-propanephosphonic acid anhydride, 1-(3-dimethylaminopropyl)-3-ethylcarbodiimide, HATU, or the like can be used. As the nucleophile for the amidation, HOBt, HOAt, or the like can be used. As the base, diisopropylethylamine or the like can be used. As the reaction solvent, for example, DMF, dichloromethane, THF, or the like can be used. The reaction temperature can usually be 0 to 150° C.

Step 7

The compounds represented by the formula (1) can be prepared by a coupling reaction with a compound represented by the formula (11) using a metal catalyst. More specifically, the compounds can be prepared by, for example, the Suzuki-Miyaura coupling of a compound represented by the formula (11) and a reagent represented by the formula (8). As the reaction catalyst, for example, $Pd(dppf)Cl_2$, PdAmphos, $Pd(PPh_3)_4$, or the like can be used. As the base, cesium carbonate, cesium fluoride, sodium carbonate, or the like can be used. As the reaction solvent, THF, 1,4-dioxane, DMF, acetonitrile, or the like can be used. The reaction temperature can usually be room temperature to 180° C.

Step 8

The compound represented by the formula (9) can be prepared by, for example, a metal-catalyzed coupling reaction or halogen-metal exchange reaction with a compound represented by the formula (10). More specifically, the compound can be prepared by, for example, the Suzuki-Miyaura coupling of a compound represented by the formula (10) with bis(pinacolato)diboron, or the like As the reaction catalyst, for example, $Pd(dppf)Cl_2$, or the like can be used. As the base, potassium acetate or the like can be used. As the reaction solvent, 1,4-dioxane or the like can be used. The reaction temperature can usually be 40 to 150° C.

SCHEME 3

[Formula 59]

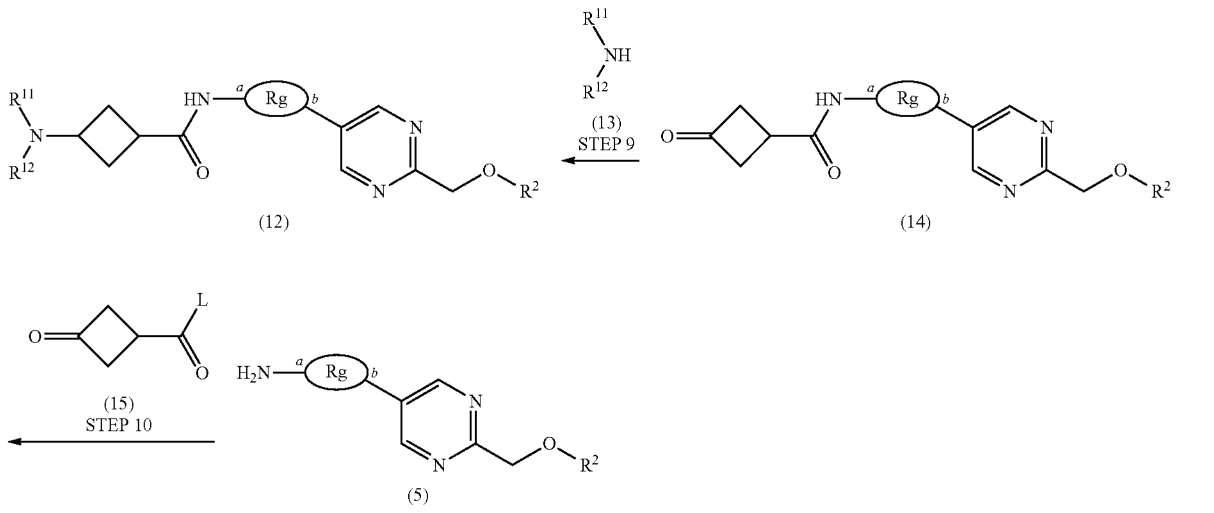

A compound represented by the formula (12), which is a compound represented by the formula (1) wherein Cy is a group represented by the formula (2-1-1), can be prepared by, for example, the method described in the reaction scheme 3 (in the formulas of the compounds, L represents a leaving group such as —Cl, —Br, and pentafluorophenyl group, or a substituent capable of forming an amide bond such as hydroxyl group). The compounds represented by the formulas (5), (13), and (14) are commercially available, or can be prepared according to known methods, for example, the methods shown below, or methods similar to these.

Step 9

The compound represented by the formula (10) can be prepared by a reductive amination reaction of a compound represented by the formula (14). For example, the compound can be prepared by formation of an imine in the presence of a substituent of the substituent $R^{11}$, $R^{12}$, $R^1$, or $R^2$ through, for example, deprotection, reduction, alkylation, and fluorination, the compound represented by the formula (12) can be converted.

Step 10

The compound represented by the formula (14) can be prepared by amidation or acylation reaction of a compound represented by the formula (5) and a compound represented by the formula (16). As the condensing agent for the amidation, 1-propanephosphonic acid anhydride, 1-(3-dimethylaminopropyl)-3-ethylcarbodiimide, HATU, or the like can be used. As the nucleophile for the amidation, HOBt, HOAt, or the like can be used. As the base, diisopropylethylamine or the like can be used. As the reaction solvent, for example, DMF, dichloromethane, THF, or the like can be used. The reaction temperature can usually be 0 to 150° C.

SCHEME 4

[Formula 60]

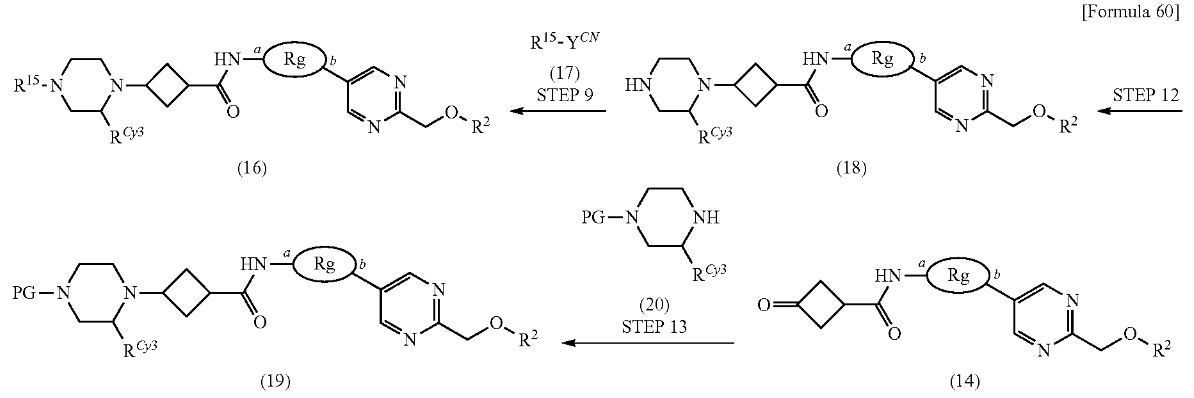

$R^{11}R^{12}NH$, followed by a reduction reaction of the imine using sodium triacetoxyborohydride. As the reaction solvent, THF, dichloromethane can be used. The reaction temperature can usually be 0 to 80° C. By further converting A compound represented by the formula (16), which is a compound represented by the formula (1) wherein Cy is a group represented by the formula (1-1-2), can be prepared by, for example, the method described in the reaction scheme 4 (in the formulas of the compounds, $Y^{CN}$ represents a substituent capable of forming a C—N bond, such as carboxyl group, acid chloride group, haloalkyl group, and isocyanate group). The compounds represented by the formulas (14), and (17) to (20) are commercially available, or can be prepared according to known methods, for example, the methods shown below, or methods similar to these.

Step 11

The compound represented by the formula (16) can be prepared by a C—N bond-forming reaction such as amidation, acylation, alkylation, and ureation with a compound represented by the formula (18). More specifically, the compound can be prepared by amidation reaction or the like of a compound represented by the formula (18) and a reagent represented by the formula (17). As the condensing agent for the amidation, 1-propanephosphonic acid anhydride, 1-(3-dimethylaminopropyl)-3-ethylcarbodiimide, HATU, or the like can be used. As the nucleophile for the amidation, HOBt, HOAt, or the like can be used. As the base, diisopropylethylamine or the like can be used. As the reaction solvent, for example, DMF, dichloromethane, THF, or the like can be used. The reaction temperature can usually be 0 to 150° C. By further converting a substituent of the substituent $R^{15}$, $R^1$, or $R^2$ through, for example, deprotection, reduction, reductive amination, alkylation, and fluorination, the compound represented by the formula (16) can be converted.

Step 12

The compound represented by the formula (18) can be prepared by deprotection of a compound represented by the formula (19). The deprotection reaction can be performed according to a known method, for example, the methods described in Greene's Protective Groups in Organic Synthesis, published by John Wiley and Sons (2014 edition), and the like.

Step 13

The compound represented by the formula (19) can be prepared by a reductive amination reaction of a compound represented by the formula (14). For example, the compound can be prepared by formation of an imine in the presence a compound represented by the formula (20), followed by a reduction reaction of the imine using sodium triacetoxyborohydride. As the reaction solvent, THF, dichloromethane can be used. The reaction temperature can usually be 0 to 80° C.

bromine, and $R^1$ is —$OR^{a1}$ ($R^{a1}$ is substituted or unsubstituted $C_{1-3}$ alkyl), can be prepared by, for example, the method described in the reaction scheme 5 (in the formulas of the compounds, $Y^{CO}$ represents a leaving group such as —Cl, —Br, —I, OTf, OMs, and Ots, or a substituent capable of forming a C—O bond, such as hydroxyl group, $R^{ac}$ represents an acyl group such as acetyl group and cyclopropyl group, L represents a leaving group such as —Cl, —Br, and pentafluorophenyl group, or a substituent capable of forming an amide bond such as hydroxyl group, and PG represents a protective group listed in Greene's Protective Groups in Organic Synthesis, published by John Wiley and Sons (2014 edition)). The compounds represented by the formulas (22) to (30) are commercially available, or can be prepared according to known methods, for example, the methods shown below, or methods similar to these.

Step 14

The compound represented by the formula (21) can be prepared by deprotection of a compound represented by the formula (19). The deprotection reaction can be performed according to a known method, for example, the methods described in Greene's Protective Groups in Organic Synthesis, published by John Wiley and Sons (2014 edition), and the like. By further converting a substituent of the substituent $R^{a1}$ through, for example, deprotection, reduction, reductive amination, alkylation, and fluorination, the compound represented by the formula (21) can be converted.

Step 15

The compound represented by the formula (22) can be prepared by a C—O bond formation reaction such as alkylation and Mitsunobu reaction of a compound represented by the formula (24) and a compound represented by the formula (23). More specifically, the compound can be prepared by an alkylation reaction, or the like of a compound represented by the formula (24) and a reagent represented by the formula (23). As the alkylation agent, iodomethane or the like can be used. As the base, diisopropylethylamine, potassium carbonate, or the like can be used. As the reaction solvent, DMF, dichloromethane, THF, or the like can be used. The reaction temperature can usually be −78 to 150° C.

Step 16

The compound represented by the formula (24) can be prepared by protecting a compound represented by the formula (25). The protection reaction can be performed according to a known method, for example, the methods

SCHEME 5

[Formula 61]

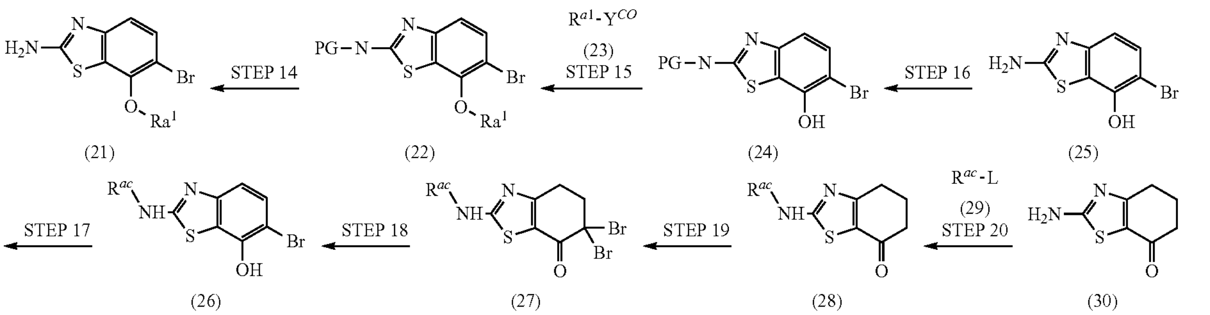

(21) (22) (24) (25)
(26) (27) (28) (30)

A compound represented by the formula (21), which is a compound represented by the formula (7) wherein Rg is a group represented by the general formula (1-1), halo is described in Greene's Protective Groups in Organic Synthesis, published by John Wiley and Sons (2014 edition), and the like.

Step 17

The compound represented by the formula (25) can be prepared by deacylating a compound represented by the formula (26). More specifically, the compound can be prepared by hydrolyzing a compound represented by the formula (26) in the presence of an acid. As the acid, hydrochloric acid or the like can be used. As the reaction solvent, methanol, water, THF, or the like can be used. The reaction temperature can usually be room temperature to 100° C.

Step 18

The compound represented by the formula (26) can be prepared by aromatization of a compound represented by the formula (27) in the presence of a base. As the base, DBU or the like can be used. As the reaction solvent, THF or the like can be used. The reaction temperature can usually be −20 to 80° C.

Step 19

The compound represented by the formula (27) can be prepared by bromination of a compound represented by the formula (28) in the presence of an acid. As the bromination agent, bromine, NBS, or the like can be used. As the acid, hydrobromic acid or the like can be used. As the reaction solvent, acetic acid or the like can be used. The reaction temperature can usually be room temperature to 60° C.

A compound represented by the formula (31), which is a compound represented by the formula (10) wherein Rg is a group represented by the general formula (1-1), and $R^1$ is —O—$R^{a1}$ ($R^{a1}$ is substituted or unsubstituted $C_{1-3}$ alkyl), can be prepared by, for example, the method described in the reaction scheme 6 (in the formula of the compound, $Y^{CO}$ represents a leaving group such as —Cl, —Br, —I, OTf, OMs, and OTs, or a substituent capable of forming a C—O bond, such as hydroxyl group). The compound represented by the formula (32) is commercially available, or can be prepared according to known methods, for example, the methods shown below, or methods similar to these.

Step 21

The compound represented by the formula (31) can be prepared by a C—O bond formation reaction such as alkylation and Mitsunobu reaction of a compound represented by the formula (32) and a compound represented by the formula (23). More specifically, the compound can be prepared by Mitsunobu reaction or the like of a compound represented by the formula (32) and a reagent represented by the formula (23) wherein $Y^{CO}$ represents hydroxyl group. As the reagent for the Mitsunobu reaction, diethyl azodicarboxylate, triphenylphosphine, or the like can be used. As the reaction solvent, THF, toluene, or the like can be used. The reaction temperature can usually be 0 to 110° C.

SCHEME 7

[Formula 63]

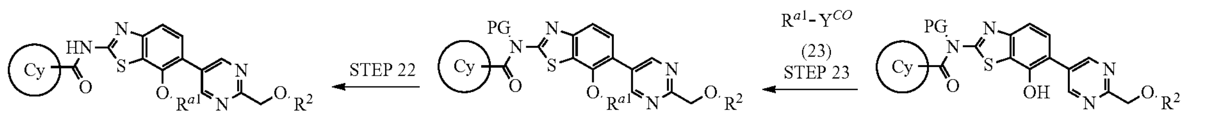

(33) (34) (35)

Step 20

The compound represented by the formula (28) can be prepared by an amidation reaction, acylation reaction, or the like of a compound represented by the formula (30) and a compound represented by the formula (29). As the acylation agent, acid anhydride such as acetic anhydride, or the like can be used. As the condensing agent for the amidation, 1-propanephosphonic acid anhydride, 1-(3-dimethylaminopropyl)-3-ethylcarbodiimide, HATU, or the like can be used. As the nucleophile for the amidation, HOBt, HOAt, or the like can be used. As the base, diisopropylethylamine or the like can be used. As the reaction solvent, for example, DMF, dichloromethane, THF, or the like can be used. The reaction temperature can usually be 0 to 150° C.

A compound represented by the formula (33), which is a compound represented by the formula (1) wherein Rg is a group represented by the general formula (1-1), and $R^1$ is —O—$R^{a1}$ ($R^{a1}$ is substituted or unsubstituted $C_{1-3}$ alkyl), can be prepared by, for example, the method described in the reaction scheme 7 (in the formulas of the compounds, $Y^{CO}$ represents a leaving group such as —Cl, —Br, —I, OTf, OMs, and OTs, or a substituent capable of forming a C—O bond, such as hydroxyl group, and PG represents a protective group listed in Greene's Protective Groups in Organic Synthesis, published by John Wiley and Sons (2014 edition)). The compounds represented by the formulas (23), (34), and (35) are commercially available, or can be prepared according to known methods, for example, the methods shown below, or methods similar to these.

SCHEME 6

[Formula 62]

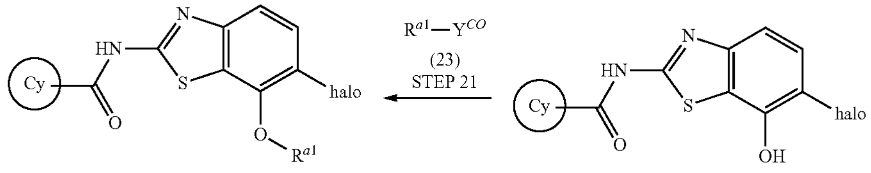

(31) (32)

Step 22

The compound represented by the formula (33) can be prepared by deprotection of a compound represented by the formula (34). The deprotection reaction can be performed according to a known method, for example, the methods described in Greene's Protective Groups in Organic Synthesis, published by John Wiley and Sons (2014 edition), and the like. By further converting a substituent of the substituent $R^{a1}$ through, for example, deprotection, reduction, reductive amination, alkylation, and fluorination, the compound represented by the formula (33) can be converted.

Step 23

The compound represented by the formula (34) can be prepared by a C—O bond formation reaction such as alkylation and Mitsunobu reaction of a compound represented by the formula (35) and a compound represented by the formula (23). More specifically, the compound can be prepared by an alkylation reaction, or the like of a compound represented by the formula (35) and a reagent represented by the formula (23) wherein $Y^{CO}$ represents a halogen group such as —Br and —I. As the base, diisopropylethylamine, cesium carbonate, or the like can be used. As the reaction solvent, DMF, dichloromethane, THF, or the like can be used. The reaction temperature can usually be 0 to 150° C.

SCHEME 8

[Formula 64]

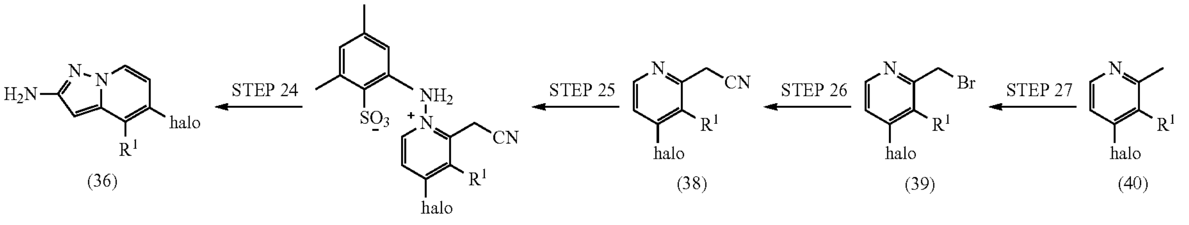

(36) (37) (38) (39) (40)

A compound represented by the formula (36), which is a compound represented by the formula (7) wherein Rg is a group represented by the general formula (1-2), can be prepared by, for example, the method described in the reaction scheme 8. The compounds represented by the formulas (37) to (40) are commercially available, or can be prepared according to known methods, for example, the methods shown below, or methods similar to these.

Step 24

The compound represented by the formula (36) can be prepared by a cyclization reaction of a compound represented by the formula (37). As the base, potassium carbonate, DBU, or the like can be used. As the reaction solvent, DMF or the like can be used. The reaction temperature can usually be 0 to 180° C. By further converting a substituent of the substituent $R^1$ through, for example, deprotection, reduction, reductive amination, alkylation, and fluorination, the compound represented by the formula (36) can be converted.

Step 25

The compound represented by the formula (37) can be prepared by reacting a compound represented by the formula (38) with O-(mesitylenesulfonyl)hydroxylamine. As the reaction solvent, chloroform, dichloromethane can be used. The reaction temperature can usually be 0 to 50° C.

Step 26

The compound represented by the formula (38) can be prepared by cyanation of a compound represented by the formula (39). As the cyanating agent, sodium cyanide, potassium cyanide, or the like can be used. As the reaction solvent, ethanol, water, DMF, or the like can be used. The reaction temperature can usually be 0 to 120° C.

Step 27

The compound represented by the formula (39) can be prepared by bromination of a compound represented by the formula (40). As the brominating agent, N-bromosuccinimide, bromine, or the like can be used. As the reaction solvent, ethanol, water, DMF, or the like can be used. The reaction temperature can usually be 0 to 120° C.

SCHEME 9

[Formula 65]

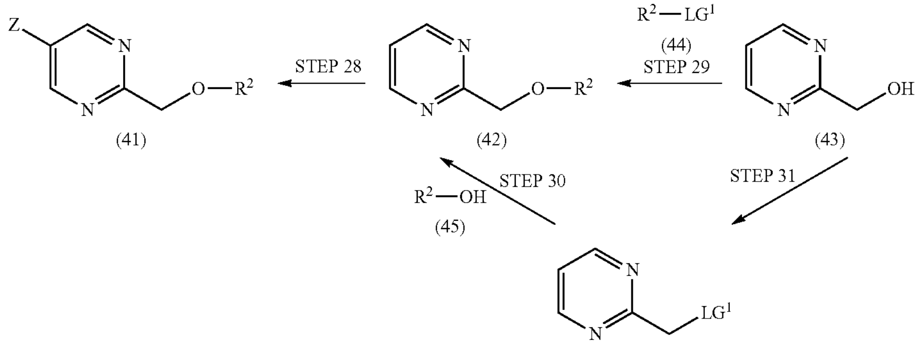

(41) (42) (43) (46)

A compound represented by the formula (41), which is a compound represented by the formula (6) wherein M is Z (Z represents a borane derivative such as boronic acid $B(OH)_2$ or a boronic acid ester) can be prepared by, for example, the method described in the reaction scheme 8 (in the formulas of the compounds, $LG^1$ represents a leaving group such as —Cl, —Br, —I, OTf, OMs, and OTs). The compounds represented by the formulas (42) to (46) are commercially available, or can be prepared according to known methods, for example, the methods shown below, or methods similar to these.

Step 28

The compound represented by the formula (41) can be prepared by C—H borylation of a compound represented by the formula (42) using an iridium catalyst. As the borane source, for example, bis(pinacolato)diboron can be used. As the reaction solvent, THE can be used. The reaction temperature can usually be 20 to 80° C.

dichloromethane can be used. The reaction temperature can usually be 0 to 150° C.

Step 30

The compound represented by the formula (42) can be prepared by etherification of a compound represented by the formula (46) and a compound represented by the formula (45) under a basic condition. As the base, for example, sodium hydride, or sodium hydroxide can be used. As the catalyst, for example, tetrabutylammonium chloride, or the like can be used. As the reaction solvent, THF, DMF, dichloromethane can be used. The reaction temperature can usually be 0 to 150° C.

Step 31

The compound represented by the formula (46) can be prepared by halogenation such as chlorination of a compound represented by the formula (44). As the chlorinating agent, for example, thionyl chloride can be used. As the reaction solvent, dichloromethane can be used. The reaction temperature can usually be 0 to

SCHEME 10

[Formula 66]

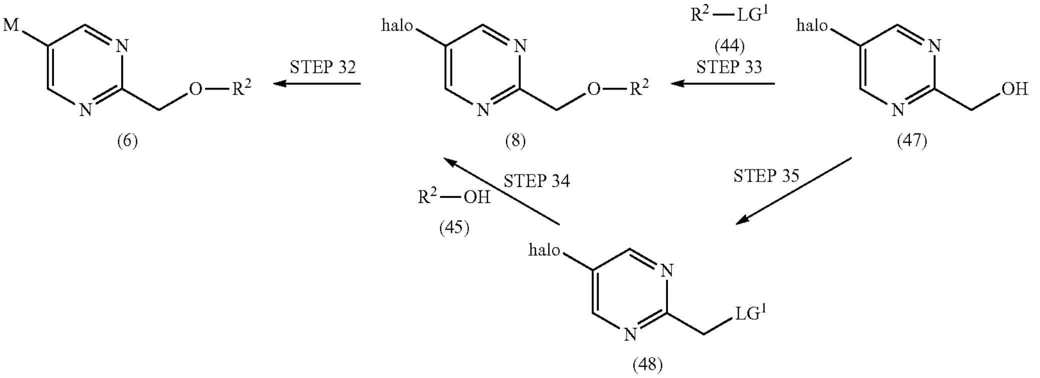

(6) (8) (47) (48)

Step 29

The compound represented by the formula (42) can be prepared by etherification of a compound represented by the formula (44) and a compound represented by the formula (43) under a basic condition. As the base, for example, sodium hydride, or sodium hydroxide can be used. As the catalyst, for example, tetrabutylammonium chloride, or the like can be used. As the reaction solvent, THF, DMF, The compound represented by the formula (6) can be prepared by, for example, the method described in the reaction scheme 10 (in the formulas of the compounds, $LG^1$ represents a leaving group such as —Cl, —Br, —I, OTf, OMs, and OTs, halo represents —Cl, —Br, or —I, and M represents a substituent that can be react through various types of coupling using ZnI, MgBr, boronic acid, boronic acid ester, or the like). The compounds represented by the formulas (8), (44), (45), (47), and (48) are commercially available, or can be prepared according to known methods, for example, the methods shown below, or methods similar to these.

Step 32

The compound represented by the formula (6) can be prepared by, for example, a metal-catalyzed coupling reaction or halogen-metal exchange reaction with a compound represented by the formula (8). More specifically, the compound can be prepared by, for example, the Suzuki-Miyaura coupling of a compound represented by the formula (6) with bis(pinacolato)diboron, or the like As the reaction catalyst, for example, $Pd(dppf)Cl_2$, or the like can be used. As the base, potassium acetate or the like can be used. As the reaction solvent, 1,4-dioxane or the like can be used. The reaction temperature can usually be 40 to 150° C.

Step 33

The compound represented by the formula (8) can be prepared by etherification of a compound represented by the formula (47) and a compound represented by the formula (44) under a basic condition. As the base, for example, sodium hydride, or sodium hydroxide can be used. As the catalyst, for example, tetrabutylammonium chloride, or the like can be used. As the reaction solvent, THF, DMF, dichloromethane can be used. The reaction temperature can usually be 0 to 150° C.

Step 34

The compound represented by the formula (8) can be prepared by etherification of a compound represented by the formula (48) and a compound represented by the formula (45) under a basic condition. As the base, for example, sodium hydride, or sodium hydroxide can be used. As the catalyst, for example, tetrabutylammonium chloride can be used. As the reaction solvent, THF, DMF, dichloromethane, or the like can be used. The reaction temperature can usually be 0 to 150° C.

Step 35

The compound represented by the formula (48) can be prepared by halogenation such as chlorination of a compound represented by the formula (47). As the chlorinating agent, for example, thionyl chloride can be used. As the reaction solvent, dichloromethane or the like can be used. The reaction temperature can usually be 0 to 40° C.

The preparation methods of the compounds of the present invention are not limited to the methods described herein. For example, the compounds of the present invention can be prepared by modifying or converting substituents of compounds as precursors of the compounds of the present invention using one or a combination of two or more of reactions described in ordinary chemical articles, and the like.

Examples of the preparation method for the compounds of the present invention which contain an asymmetric carbon include a preparation method based on asymmetric reduction, a method of using a commercially available starting material (or starting material that can be prepared by a known method or a method similar to a known method) of which moiety corresponding to the asymmetric carbon is originally optically active, a method of performing optical resolution, or preparing an optically active compound using an enzyme, and the like. A method is also available in which a compound of the present invention or a precursor thereof is separated as an optically active isomer by a conventional method. Examples of such a method include, for example, a method utilizing high performance liquid chromatography (HPLC) using a chiral column, or supercritical fluid chromatography (SFC), the classical fractional crystallization for separation of optically active substances comprising formation of a salt with an optically active regent, separation by fractional crystallization or the like, and conversion of the salt into a compound of free form, a method comprising condensation with an optically active regent to form a diastereomer, followed by separation, purification, and decomposition of the produced diastereomer, and the like. When a precursor is separated to obtain an optically active substance, an optically active compound of the present invention can then be prepared by performing the aforementioned preparation methods with the optically active substance.

When a compound of the present invention contains an acidic functional group such as carboxyl group, phenolic hydroxyl group, or tetrazole ring, the compound can be converted into a pharmaceutically acceptable salt (e.g., inorganic salts with sodium, and the like, or organic salts with triethylamine and the like) by a known means. For example, when an inorganic salt is to be obtained, it is preferable to dissolve the compound of the present invention in water containing hydroxide, carbonate, bicarbonate or the like corresponding to the desired inorganic salt. For the reaction, a water-miscible inactive organic solvent such as methanol, ethanol, acetone, and dioxane may be mixed. For example, by using sodium hydroxide, sodium carbonate, or sodium hydrogencarbonate, a solution of sodium salt can be obtained.

When a compound of the present invention contains amino group, another basic functional group, or an aromatic ring which itself has a basicity (e.g., pyridine ring and the like), the compound can also be converted into a pharmaceutically acceptable salt (e.g., salt with an inorganic acid such as hydrochloric acid, or salt with an organic acid such as acetic acid) by a known means. For example, when a salt with an inorganic acid is to be obtained, it is preferable to dissolve the compound of the present invention in an aqueous solution containing a desired inorganic acid. For the reaction, a water-miscible inactive organic solvent such as methanol, ethanol, acetone, and dioxane may be mixed. For example, by using hydrochloric acid, a solution of hydrochloride can be obtained.

If a solid salt is desired, the solution may be evaporated, or a water-miscible organic solvent having polarity to some extent, such as n-butanol or ethyl methyl ketone, can be added to the solution to obtain a solid salt.

The various compounds disclosed by the present invention can be purified by known methods such as variety of chromatography techniques (column chromatography, flash column chromatography, thin layer chromatography, high performance liquid chromatography, supercritical fluid chromatography, and the like).

The compounds of the present invention according to a certain embodiment have an IRAK-4 inhibitory activity, and can be used as an IRAK-4 inhibitor. That is, the compounds of the present invention according to a certain embodiment can be used as a medicament for prophylactic and/or therapeutic treatment of a disease relating to IRAK-4 inhibition. More precisely, the disease relating to IRAK-4 inhibition is a disease for which IRAK-4 inhibition is effective, and more specifically, the disease relating to IRAK-4 inhibition is not particularly limited so long as it is a disease that can be prevented and/or treated by suppressing production of inflammatory mediators such as TNFα, and IL-6 through inhibition of TLRs or IL-1 family signal transduction system.

The IRAK-4 inhibitory activity can be measured by, for example, the method described in Test Example 1 or 2 mentioned later.

The disease relating to IRAK-4 inhibition is not particularly limited so long as it is a disease for which IRAK-4 inhibition is effective, and specific examples include, for example, acute or chronic inflammation, autoimmune diseases (rheumatoid arthritis, systemic erythematodes, lupus nephritis, and the like), autoinflammatory diseases (TNF receptor-associated periodic syndrome (TRAPS), familial mediterranean fever, cryopyrin-associated periodic syndrome, high IgD syndrome, and the like), metabolic disorders (gout and the like), and the like.

According to a certain embodiment, the compounds of the present invention have a TLR/IL-1β signaling-suppressing action, and are useful as an active ingredient of a medicament as shown in the test examples mentioned later. In particular, it is preferred that the compounds of the present invention according to a certain embodiment are used for prophylactic and/or therapeutic treatment of a disease in which IRAK-4 signaling is involved.

The compounds of the present invention according to a certain embodiment show strong selectivity for other kinases. Examples of the other kinases include FLT3, ITK, CK2, IKKb, JAK1, Syk, PKCθ, and p38. According to another embodiment, examples include, especially, FLT3.

Usefulness of the medicament of present invention according to a certain embodiment for prophylactic and/or therapeutic treatment of a disease in which IRAK-4 signaling is involved can be confirmed by, for example, a cytokine production inhibition test using immunocytes, or by using a collagen-induced arthritis model. Specifically, the method described in Test Example 3 mentioned later can be exemplified.

The medicament of the present invention according to a certain embodiment can be prepared as a medicament containing a compound represented by the formula (1) or a pharmaceutically acceptable salt thereof as an active ingredient, and for example, a medicament containing a compound or pharmaceutically acceptable salt thereof that is metabolized in a living body to produce a compound represented by the formula (1) or a pharmaceutically acceptable salt thereof when it is administered as a prodrug also falls within the scope of the medicament of the present invention.

Although administration route of the medicament of the present invention according to a certain embodiment is not particularly limited, the administration scheme can be appropriately selected from, for example, oral administration, subcutaneous administration, intracutaneous administration, intramuscular injection, intravenous administration, pernasal administration, intravaginal administration, intrarectal administration, local administration to an affected part, and the like.

As the medicament of the present invention, a compound represented by the formula (1) or a pharmaceutically acceptable salt thereof, per se, may be used. However, it is preferable to add one or more kinds of pharmaceutically acceptable carriers to a compound represented by the formula (1) or a pharmaceutically acceptable salt thereof to prepare a pharmaceutical composition and administer the composition. Further, as the active ingredient of the medicament of the present invention, a hydrate or solvate of a compound represented by the general formula (1) or a pharmaceutically acceptable salt thereof may be used.

Examples of dosage form used for preparing the aforementioned pharmaceutical composition include tablet, powder, granule, syrup, suspension, capsule, inhalant, injection, and the like. For the manufacture of them, various carriers suitable for these preparations are used. For example, examples of the carrier for oral preparations include excipients, binders, lubricants, fluid accelerators, and colorants. Examples of the method for using the composition as an inhalant include a method of inhaling powder of the pharmaceutical composition or a liquid dosage form prepared by dissolving or suspending the pharmaceutical composition in a solvent as it is, a method of inhaling mist thereof by using a sprayer called atomizer or nebulizer, and the like. When the composition is formulated as an injection, distilled water for injection, physiological saline, aqueous glucose solution, vegetable oil for injection, propylene glycol, polyethylene glycol, and the like can generally be used as a diluent. Disinfectants, antiseptics, stabilizers, isotonic agents, soothing agents, and the like may be further added, as required. A clathrate compound in which a compound of the present invention is clathrated in cyclodextrin may also be prepared, and used as the medicament of the present invention.

When the medicament of the present invention according to a certain embodiment is administered, an appropriate dosage form can be suitably chosen and administered via an appropriate route. For example, it can be orally administered in the form of tablet, powder, granule, syrup, suspension, capsule, or the like. The medicament can also be administered via the respiratory tract in the form of an inhalant. In addition, the medicament can be subcutaneously, intracutaneously, intravascularly, intramuscularly, or intraperitoneally administered in the form of an injection including drip infusion. Furthermore, the medicament can be transmucosally administered in the form of sublingual tablet, suppository, or the like, and can be percutaneously administered in the form of gel, lotion, ointment, cream, spray, or the like. In addition, the medicament can also be administered as a prolonged action drug, for example, a sustained-release injection, or an embedding preparation (e.g., film preparation, and the like).

The administration period of the medicament of the present invention according to a certain embodiment is not particularly limited. In principle, the medicament is administered during a period where it is judged that clinical symptoms of a disease are expressed, and it is common to continue the administration for several weeks to one year. However, it is also possible to extend the administration period depending on pathological conditions, or continue the administration even after recovery from the clinical symptoms. The medicament may also be prophylactically administered by a decision of a clinician even if any clinical symptom is not expressed. The dose of the medicament of the present invention according to a certain embodiment is not particularly limited. For example, when the medicament of the present invention is orally administered, 0.01 to 1000 mg of the active ingredient can be administered to an adult per each time of administration. As for administration frequency in the above case, the administration can be performed at a frequency of every 6 months to every day, preferably once a day.

The daily dose and/or dose per one time, administration period, and administration frequency may be suitably increased or decreased depending on various conditions such as age, weight, degree of physical healthiness of a patient, type and severity of a disease to be treated, administration route, and dosage form (sustained release property of carrier for active ingredient, and the like).

When the medicament of the present invention according to a certain embodiment is used for prophylactic treatment and/or therapeutic treatment of the aforementioned diseases, the medicament of the present invention according to a certain embodiment can be used together with one or more kinds of medicaments selected from the drugs mentioned below at the same time or different times. Further, the medicament of the present invention according to a certain embodiment can also be prepared as a so-called combined drug together with the drugs exemplified above, and then administered. Such a combined drug may be in a dosage form of a complete mixture of the active ingredients similar to typical compositions of such type, as well as a dosage form, kit, or package including a non-mixed combination of ingredients separately administered from two or more containers each of which contains each active ingredient.

Examples of the drugs that can be used together with the medicament of the present invention according to a certain embodiment include, for example, immunosuppressants (tacrolimus, cyclosporin, rapamycin, mofetil mycophenolate, interferon preparations, cyclophosphamide, azathioprine, methotrexate, and the like), antiphlogistics (steroids (prednisolone, dexamethasone, betamethasone, cortisone, and the like) and non-steroidal anti-inflammatory drugs (NSAIDs, ibuprofen, celecoxib, and the like), disease-modifying antirheumatic drugs (gold preparations, methotrexate, leflunomide, sulfasalazine, penicillamine, iguratimod, chloroquine, tofacitinib, etc.), antimalarials (hydroxychloroquine, and the like), therapeutic agents for multiple sclerosis (interferon, anti-α4 integrin preparations, fingolimod, mitoxantrone, and the like), and anti-cytokine drugs (anti-TNFα preparations, anti-IL-6 preparations, anti-IL-12/23 preparations, and the like). Examples further include biological preparations used as therapeutic agents for autoimmune diseases (anti-CD20 preparations, CTLA-4-Ig, and the like), drugs for disturbances in uric acid metabolism (colchicine, probenecid, bucolome, benzbromarone, allopurinol, and the like), hypoglycemic agents (alogliptin, nateglinide, acarbose, metformin, pioglitazone, insulin preparations, and the like), hypotensive drugs (imidapril, valsartan, candesartan, and the like), choleretics (ursodeoxycholic acid, and the like), bronchodilators (salmeterol and salbutamol, which are adrenalin β2 agonists, ipratropium and tiotropium, which are anticholinergic drugs, and the like), therapeutic drugs for allergic diseases (theophylline and the like), antiallergic drugs (fexoquinadine, epinastine, olopatadine, loratadine, cetirizine, bepotastine, ketotifen, sodium cromoglycate, pemirolast, chlorpheniramine, and the like) leukotriene antagonists (zafirlukast, montelukast, pranlukast, and the like), antihyperlipidemic drugs (atorvastatin, simvastatin, clinofibrate, bezafibrate, probucol, elastase, ethyl icosapentate, and the like), neurotransmitter controlling agents (donepezil, galanthamine, memantine, and the like), antioxidants (vitamin E, acetyleysteine, carnitine, betaine, pentoxifylline, and the like), and antibiotics (various antibiotics of P lactam type, macrolide type, tetracycline type, aminoglycoside type, quinolone type, and the like, chloramphenicol and the like). The medicament of the present invention can also be used together with various kinds of drugs to be created in the future. These combined drugs are no way limited so long as the combinations are clinically meaningful.

The compounds of the present invention according to a certain embodiment include compounds showing superior safety (concerning various toxicities and safety pharmacology), pharmacokinetic performance, and the like, and usefulness thereof as an active ingredient of a medicament can be confirmed by, for example, the methods shown below.

Examples of tests concerning safety include, for example, those listed below. However, they are not limited to these examples. Examples include cytotoxic tests (tests using HL60 cells, hepatocytes, and the like), genotoxicity tests (Ames test, mouse lymphoma TK test, chromosomal aberration test, micronucleus test, and the like), skin sensitization tests (Buehler method, GPMT method, APT method, LLNA test, and the like), skin photosensitization tests (adjuvant and strip method, and the like), eye irritation tests (single instillation, short-term continuous instillation, repetitive instillation, and the like), safety pharmacology tests for the cardiovascular system (telemetry method, APD method, hERG inhibition assay, and the like), safety pharmacology tests for the central nervous system (FOB method, modified Irwin method, and the like), safety pharmacology tests for the respiratory system (measurement method utilizing a respiratory function measuring apparatus, measurement method utilizing a blood gas analyzer, and the like), general toxicity tests, reproductive and developmental toxicity tests, and the like.

Examples of tests concerning pharmacokinetic performance include, for example, those listed below. However, they are not limited to these examples. Examples include cytochrome P450 enzyme inhibition or induction tests, cell permeability tests (tests using CaCO-2 cells, MDCK cells, and the like), drug transporter ATPase assay, oral absorption tests, blood concentration transition measurement tests, metabolism tests (stability test, metabolite molecular species test, reactivity test, and the like), solubility tests (solubility test based on turbidity method, and the like), and the like.

Usefulness of the compounds of the present invention according to a certain embodiment as an active ingredient of a medicament can be confirmed by performing, for example, a cytotoxic test. Examples of the cytotoxic test include methods utilizing various cultured cells, for example, HL-60 cells, which are human preleukemia cells, primary isolated cultured cells of hepatocytes, a neutrophil fraction prepared from human peripheral blood, and the like. Although the test can be carried out by the method described below, the method is not limited only to the following description. Cells are prepared as a suspension of $10^5$ to $10^7$ cells/ml, and the suspension is added to microtubes or microplate in a volume of 0.01 to 1 mL. To the suspension, a solution dissolving a compound is added in a volume of 1/100 to 1 fold volume of the cell suspension, and the cells were cultured in a cell culture medium having a final concentration of the compound of 0.001 to 1000 μM for 30 minutes to several days at 37° C. under 5% $CO_2$. After terminating the culture, survival rate of the cells is evaluated by using the MTT method, WST-1 method (Ishiyama, M., et al., In Vitro Toxicology, 8, p. 187, 1995), or the like. By measuring cytotoxicity of a compound to cells, usefulness of the compound as an active ingredient of a medicament can be confirmed.

Usefulness of the compounds of the present invention according to a certain embodiment as an active ingredient of a medicament can be confirmed by performing, for example, a genotoxicity test. Examples of the genotoxicity test include, the Ames test, mouse lymphoma TK test, chromosomal aberration test, micronucleus test, and the like. The Ames test is a method of determining reverse mutation by culturing *Salmonella* or *Escherichia* bacteria of designated species on a culture dish or the like to which a compound is added (refer to IYAKUSHIN (Notification by the chief of Evaluation and Licensing Division, Pharmaceutical and Medical Safety Bureau, Ministry of Health, Labor and Welfare, Japan), No. 1604, 1999, "Guideline for Genotoxicity Test", II-1. Genotoxicity Test, and the like). The mouse lymphoma TK test is a genetic mutation ability detection test targeting the thymidine kinase gene of the mouse lymphoma L5178Y cell (refer to IYAKUSHIN No. 1604, 1999, "Guideline for Genotoxicity Test", II-3. Mouse Lymphoma TK Test; Clive, D. et al., Mutat. Res., 31, pp. 17-29, 1975; Cole, J., et al., Mutat. Res., 111, pp. 371-386, 1983, and the like). The chromosomal aberration test is a method for determining activity of causing chromosomal aberration by culturing mammalian cultured cells in the presence of a compound, then after fixation of the cells, staining and observing chromosomes of the cells (refer to IYAKUSHIN No. 1604, 1999, "Guideline for Genotoxicity Test", II-2. Chromosomal Aberration Test Utilizing Mammalian Cultured Cells, and the like). The micronucleus test is a method of evaluating micronucleus-forming ability caused by chromosomal aberration, and a method of using a rodent (in vivo test) (IYAKUSHIN No. 1604, 1999, "Guideline for Genotoxicity Test", II-4. Micronucleus Test Using Rodent; Hayashi M. et al., Mutat. Res., 312, pp. 293-304, 1994; Hayashi, M. et al., Environ. Mol. Mutagen., 35, pp. 234-252, 2000), a method of using cultured cells (in vitro test) (Fenech M., et al., Mutat. Res., 147, pp. 29-36, 1985; Miller, B., et al., Mutat. Res., 392, pp. 45-59, 1997), and the like are available. By elucidating genotoxicity of a compound using one or more of these methods, usefulness of the compound as an active ingredient of a medicament can be confirmed.

Usefulness of the compounds of the present invention according to a certain embodiment as an active ingredient of a medicament can be confirmed by performing, for example, a skin sensitization test. Skin sensitization tests include, as the skin sensitization tests using guinea pig, the Buehler method (Buehler, E. V., Arch. Dermatol., 91, pp. 171-177, 1965), GPMT method (maximization method, Magnusson B., et al., J. Invest. Dermatol., 52, pp. 268-276, 1969), APT method (adjuvant and patching test method (Sato, Y. et al., Contact Dermatitis, 7, pp. 225-237, 1981)), and the like. Further, as the skin sensitization test using mouse, the LLNA (local lymph node assay) method (OECD Guideline for the testing of chemicals 429, Skin sensitization 2002; Takeyoshi, M. et al., Toxicol. Lett., 119 (3), pp. 203-8, 2001; Takeyoshi, M. et al., J. Appl. Toxicol., 25 (2), pp. 129-34, 2005), and the like are available. By elucidating skin sensitization property of a compound using one or more of these methods, usefulness of the compound as an active ingredient of a medicament can be confirmed.

Usefulness of the compounds of the present invention according to a certain embodiment as an active ingredient of a medicament can be confirmed by performing, for example, a skin photosensitization test. Examples of the skin photosensitization test include a skin photosensitization test using guinea pig (refer to "Drug Nonclinical Test Guideline Commentary 2002", Yakuji Nippo, published on 2002, 1-9: Skin Photosensitization Test, and the like), and the like, and examples of the method include the adjuvant and strip method (Ichikawa, H. et al., J. Invest. Dermatol., 76, pp. 498-501, 1981), Harber method (Harber, L. C., Arch. Dermatol., 96, pp. 646-653, 1967), Horio method (Ilorio, T., J. Invest. Dermatol., 67, pp. 591-593, 1976), Jordan method (Jordan, W. P., Contact Dermatitis, 8, pp. 109-116, 1982), Kochever method (Kochever, I. E. et al., J. Invest. Dermatol., 73, pp. 144-146, 1979), Maurer method (Maurer, T. et al., Br. J. Dermatol., 63, pp. 593-605, 1980), Morikawa method (Morikawa, F. et al., "Sunlight and Man", Tokyo Univ. Press, Tokyo, pp. 529-557, 1974), Vinson method (Vinson, L. J., J. Soc. Cosm. Chem., 17, pp. 123-130, 1966), and the like. By elucidating skin photosensitization property of a compound using one or more of these methods, usefulness of the compound as an active ingredient of a medicament can be confirmed.

Usefulness of the compounds of the present invention according to a certain embodiment as an active ingredient of a medicament can be confirmed by performing, for example, an eye irritation test. Examples of the eye irritation test include the single instillation test method (instillation of one time), short term continuous instillation test method (instillation of multiple times in a short period of time with equal intervals), repetitive instillation test method (repetitive intermittent instillation over several days to several 10 days) using rabbit eyes, monkey eyes, and the like, and the like, and a method of evaluating eye irritation symptoms at a certain time point after the instillation according to the improved Draize scores (Fukui, N. et al., Gendai no Rinsho, 4 (7), pp. 277-289, 1970), and the like is available. By elucidating eye irritation of a compound using one or more of these methods, usefulness of the compound as an active ingredient of a medicament can be confirmed.

Usefulness of the compounds of the present invention according to a certain embodiment as an active ingredient of a medicament can be confirmed by performing, for example, a safety pharmacology test for the cardiovascular system. Examples of the safety pharmacology test for the cardiovascular system include the telemetry method (method for measuring influence of administration of a compound under no anesthetization on electrocardiogram, heart rate, blood pressure, blood stream, and the like (Electrocardiogram, Echocardiography, Blood Pressure and Pathological Tests of Animals for Fundamental and Clinical Medicine, edited by Sugano S., Tsubone H., Nakada Y, published on 2003, Maruzen), APD method (method for measuring cardiac muscle cell action potential retention time (Muraki, K. et al., A M. J. Physiol., 269, H524-532, 1995; Ducic, I. et al., J. Cardiovasc. Pharmacol., 30 (1), pp. 42-54, 1997)), hERG inhibition evaluation method (patch clamping method (Chachin, M. et al., Nippon Yakurigaku Zasshi, 119, pp. 345-351, 2002), binding assay method (Gilbert, J. D. et al., J. Pharm. Tox. Methods, 50, pp. 187-199, 2004), $Rb^+$ efflex assay method (Cheng, C. S. et al., Drug Develop. Indust. Pharm., 28, pp. 177-191, 2002), membrane potential assay method (Dorn, A. et al., J. Biomol. Screen., 10, pp. 339-347, 2005), and the like. By elucidating influence on the cardiovascular system of a compound using on one or more of these methods, usefulness of the compound as an active ingredient of a medicament can be confirmed.

Usefulness of the compounds of the present invention according to a certain embodiment as an active ingredient of a medicament can be confirmed by performing, for example, a safety pharmacology test for the central nervous system. Examples of the safety pharmacology test for the central nervous system include the FOB method (Functional Observational Battery, Mattson, J. L. et al., J. American College of Technology, 15 (3), pp. 239-254, 1996)), modified Irwin method (method for evaluating observation of general symptoms and behavior (Irwin, S., Comprehensive Observational Assessment (Berl.) 13, pp. 222-257, 1968)), and the like. By elucidating action on the central nervous system of a compound using one or more of these methods, usefulness of the compound as an active ingredient of a medicament can be confirmed.

Usefulness of the compounds of the present invention according to a certain embodiment as an active ingredient of a medicament can be confirmed by performing, for example, a safety pharmacology test for the respiratory system. Examples of the safety pharmacology test for the respiratory system include the measurement method using a respiratory function measuring apparatus (method of measuring respiration rate, single ventilation volume, minute ventilation, and the like, Drorbaugh, J. E. et al., Pediatrics, 16, pp. 81-87, 1955; Epstein, M. A. et al., Respir. Physiol., 32, pp. 105-120, 1978), measurement method of using a blood gas analyzer (method of measuring blood gas, hemoglobin oxygen saturation, and the like, Matsuo, S., Medicina, 40, pp. 188-, 2003), and the like. By elucidating action on the respiratory system of a compound using one or more of these methods, usefulness of the compound as an active ingredient of a medicament can be confirmed.

Usefulness of the compounds of the present invention according to a certain embodiment as an active ingredient of a medicament can be confirmed by performing, for example, a general toxicity test. The general toxicity test is a method of orally or intravenously administering a compound dissolved or suspended in an appropriate solvent once or repetitively (over several days) to a rodent such as rat and mouse or non-rodent such as monkey and dog, and evaluating observation of general conditions, clinic chemical changes, pathohistological changes, and the like of the administered animal. By elucidating general toxicity of a compound using these methods, usefulness of the compound as an active ingredient of a medicament can be confirmed.

Usefulness of the compounds of the present invention according to a certain embodiment as an active ingredient of a medicament can be confirmed by performing, for example, a reproductive and developmental toxicity test. The reproductive and developmental toxicity test is a test for examining induction of harmful effect caused by a compound on the reproductive and developmental processes by using a rodent such as rat and mouse, or non-rodent such as monkey and dog (refer to “Drug Nonclinical Test Guideline Commentary 2002”, Yakuji Nippo, published on 2002, $_{1-6}$: Reproductive and Developmental Toxicity Test, and the like). Examples of the reproductive and developmental toxicity test include tests concerning fertility and early embryogenesis up to nidation, tests concerning development and maternal functions before and after birth, tests concerning embryogenesis and fetal development (refer to IYAKUSHIN No. 1834, 2000, Appendix, “Guideline for Drug Toxicity Test”, [3] Reproductive and Developmental Toxicity Test, and the like), and the like. By elucidating reproductive and developmental toxicity of a compound using these methods, usefulness of the compound as an active ingredient of medicament can be confirmed.

Usefulness of the compounds of the present invention according to a certain embodiment as an active ingredient of a medicament can be confirmed by performing, for example, a cytochrome P450 enzyme inhibition or induction test (Gomez-Lechon, M. J. et al., Curr. Drug Metab., 5 (5), pp. 443-462, 2004). Examples of the cytochrome P450 enzyme inhibition or induction test include, for example, the method of determining in vitro whether a compound inhibits activity of a cytochrome P450 enzyme by using a cytochrome P450 enzyme of each molecular species purified from cells or prepared by using a genetic recombinant, or a human P450 expression system microsome (Miller, V. P. et al., Ann. N.Y. Acad. Sci., 919, pp. 26-32, 2000), method of measuring changes of expression of cytochrome P450 enzyme of each molecular species or enzyme activity thereof by using human liver microsomes or disrupted cell suspension (Hengstler, J. G. et al., Drug Metab. Rev., 32, pp. 81-118, 2000), method of extracting RNA from human hepatocytes exposed to a compound, and comparing mRNA expression amount with that of a control to investigate enzyme induction ability of the compound (Kato, M. et al., Drug Metab. Pharmacokinet., 20 (4), pp. 236-243, 2005), and the like. By elucidating action of a compound on inhibition or induction of cytochrome P450 enzyme using one or more of these methods, usefulness of the compound as an active ingredient of a medicament can be confirmed.

Usefulness of the compounds of the present invention according to a certain embodiment as an active ingredient of a medicament can be confirmed by performing, for example, a reactive metabolite production-confirming test. Examples of the reactive metabolite production-confirming test include, for example, the method of incubating human liver microsomes in the presence of NADPH and glutathione labeled with fluorescence using dansyl group (dGSH), trapping the reactive metabolites as dGSH-adducts, and comprehensively detecting peaks of the reactive metabolites from the production amounts of the dGSH-adducts on the basis of fluorescence intensity used as an index (Junping Gan, et al., Chem. Res. Toxicol., 2005, 18, 896-903), method of incubating a $^{14}C$-labeled compound with human liver microsomes in the presence of NADPH, and measuring radioactivity of the carbon atom covalently bonded to proteins (Baillie T. A., Drug Metabolizing Enzymes. Cytochrome P450 and Other Enzymes in Drug Discovery and Development, pp. 147-154, 2003), and the like. By elucidating risk of a compound for generation of idiosyncratic drug toxicity, which is generated through production of reactive metabolite of a compound, using one or two or more of these methods, usefulness of the compound as an active ingredient of a medicament can be confirmed.

Usefulness of the compounds of the present invention according to a certain embodiment as an active ingredient of a medicament can be confirmed by performing, for example, a cell permeability test. Examples of the cell permeability test include, for example, the method of measuring cell membrane permeability of a compound in an in vitro cell culture system using CaCO-2 cells (Delie, F. et al., Crit. Rev. Ther. Drug Carrier Syst., 14, pp. 221-286, 1997; Yamashita, S. et al., Eur. J. Pham. Sci., 10, pp. 195-204, 2000; Ingels, F. M. et al., J. Pham. Sci., 92, pp. 1545-1558, 2003), method of measuring cell membrane permeability of a compound in an in vitro cell culture system using MDCK cells (Irvine, J. D. et al., J. Pham. Sci., 88, pp. 28-33, 1999), and the like. By elucidating cell permeability of a compound using one or more of these methods, usefulness of the compound as an active ingredient of a medicament can be confirmed.

Usefulness of the compounds of the present invention according to a certain embodiment as an active ingredient of a medicament can be confirmed by performing, for example, a drug transporter ATPase assay for ATP-binding cassette (ABC) transporter. Examples of the drug transporter ATPase assay include the method of examining whether a compound is a substrate of P-glycoprotein (P-gp) by using a P-gp baculovirus expression system (German, U. A., Methods Enzymol., 292, pp. 427-41, 1998), and the like Furthermore, the usefulness can also be confirmed by performing, for example, a transport test using oocytes collected from African clawed frog (*Xenopus laevis*) for a solute carrier (SLC) transporter. Transport tests include a method of examining whether a test compound is a substrate of OATP2 using OATP2-expressing oocytes (Tamai I. et al., Pharm. Res., 2001 September; 18 (9), 1262-1269), and the like. By elucidating action of a compound on the ABC transporter or SLC transporter using these methods, usefulness of the compound as an active ingredient of a medicament can be confirmed.

Usefulness of the compounds of the present invention according to a certain embodiment as an active ingredient of a medicament can be confirmed by performing, for example, an oral absorption test. Examples of the oral absorption test include a method of orally administering a compound of a certain amount dissolved or suspended in an appropriate solvent to a rodent, monkey, dog or the like, and measuring blood level of the compound after the oral administration over time using the LC-MS/MS method ("Newest Mass Spectrometry for Life Science", Kodansha Scientific, 2002, edited by Harada K. et al, and the like) to evaluate blood transition of the compound by oral administration, and the like. By elucidating oral absorption of a compound using these methods, usefulness of the compound as an active ingredient of a medicament can be confirmed.

Usefulness of the compounds of the present invention according to a certain embodiment as an active ingredient of a medicament can be confirmed by performing, for example, a blood concentration transition measurement test. Examples of the blood concentration transition measurement test include a method of administering a compound orally or parenterally (e.g., intravenously, intramuscularly, intraperitoneally, subcutaneously, transdermally, by instillation, transnasally, and the like) to a rodent, monkey, dog or the like, and measuring change of the blood level of the compound over time after the administration using the LC-MS/MS method ("Newest Mass Spectrometry for Life Science", Kodansha Scientific, 2002, edited by Harada K. et al, and the like), and the like. By elucidating blood concentration transition of a compound using these methods, usefulness of the compound as an active ingredient of a medicament can be confirmed.

Usefulness of the compounds of the present invention according to a certain embodiment as an active ingredient of a medicament can be confirmed by performing, for example, a metabolic test. Examples of the metabolic test include the blood stability test method (method of predicting metabolic clearance in vivo on the basis of metabolic rate of a compound in hepatic microsomes of human or other animal species (refer to Shou, W. Z. et al., J. Mass Spectrom., 40 (10) pp. 1347-1356, 2005; Li, C. et al., Drug Metab. Dispos., 34 (6), 901-905, 2006, and the like), metabolite molecular species test method, reactive metabolite test method, and the like. By elucidating metabolic profile of a compound by using one or more of these methods, usefulness of the compound as an active ingredient of a medicament can be confirmed.

Usefulness of the compounds of the present invention according to a certain embodiment as an active ingredient of a medicament can be confirmed by performing, for example, a solubility test. As the method for evaluating solubility in water, the methods of confirming the solubility under acidic conditions, neutral conditions, or basic conditions are exemplified, and confirming change of solubility depending on the presence or absence of bile acid is also included. Examples of the solubility test include the solubility test based on the turbidity method (Lipinski, C. A. et al., Adv. Drug Deliv. Rev., 23, pp. 3-26, 1997; Bevan, C. D. et al., Anal. Chem., 72, pp. 1781-1787, 2000), and the like. By elucidating solubility of a compound using these methods, usefulness of the compound as an active ingredient of a medicament can be confirmed.

Usefulness of the compounds of the present invention according to a certain embodiment as an active ingredient of a medicament can be confirmed by examining, for example, upper gastrointestinal injury, renal dysfunction, and the like. As a pharmacological test for the upper gastrointestinal tract, actions on gastric mucosa can be investigated by using a starved rat gastric mucosa injury model. Examples of pharmacological test for kidney functions include renal blood flow and glomerular filtration rate measuring method [Physiology, 18th edition, Bunkodo, 1986, Chapter 17], and the like. By elucidating actions of a compound on the upper gastrointestinal tract and renal functions using one or more of these methods, usefulness of the compound as an active ingredient of a medicament can be confirmed.

EXAMPLES

Hereafter, the present invention will be further specifically explained with reference to examples, and test examples (these may be henceforth collectively referred to as "examples and the like"). However, the scope of the present invention is not limited to the following examples and the like.

All the purchased reagents were used without further purification. The purchased anhydrous solvents were used without further drying. For the column chromatography, the medium pressure preparative purification system produced by YAMAZEN, SmartFlash, or the medium pressure preparative purification system produced by BIOTAGE, Isolera ONE, to which BIOTAGE Dalton was connected as an MS detector, was used. As the column, SNAP Ultra produced by BIOTAGE, or DispoPackAT produced by YMC was used. In some cases, purification was performed by using BondElute SCX produced by Agilent as an ion exchange resin. BondElute SCX may be henceforth referred to simply as SCX. An exemplary method for using SCX is a method of washing the cartridge with methanol and dichloromethane, then allowing adsorption of a crude product dissolved in a minimum volume of solvent (for example, a mixed solvent of dichloromethane and methanol, or the like), then flushing impurities with methanol with pressurization, and eluting the product with 2.0 M ammonia in methanol. For the thin layer chromatography (TLC), Precoated Silica Gel 60 F254 (produced by Merck, product number 5715-1M)) was used. After development with chloroform:methanol (1:0 to 1:1), or ethyl acetate:hexane (1:0 to 0:1), confirmation was performed by UV irradiation (254 nm or 365 nm), or coloration with iodine solution, aqueous potassium permanganate, phosphomolybdic acid (ethanol solution), or the like. Preparative thin layer chromatography (henceforth also referred to as "PTLC") was performed by using one or several plates of PLC Plate Silica Gel 60 F254 (20×20 cm, layer thickness 2 mm, including concentration zone (4 cm), produced by Merck, product number 13793-1M) were used depending on the amount of sample. For drying organic solvents, anhydrous magnesium sulfate or anhydrous sodium sulfate was used.

NMR

For 1H (400 MHx) nuclear magnetic resonance (henceforth also abbreviated as NMR) analysis, AVANCE III HD-400 MHz produced by Bruker, or AVANCE III HD-600 MHz produced by Bruker was used.

As the internal standard, known values of used solvents or additives were used. As the 1H NMR data, chemical shifts, parts per million (henceforth abbreviated as ppm), integral values (described as, for example, 1H), and multiplets (s means singlet, d means doublet, t means triplet, q means quartet, qui means quintet, m means multiplet, br means broad, dd means double doublet, and the like) are mentioned.

For LCMS, mass spectrum was measured by liquid chromatography-mass spectrometry (LC-MS). Unless especially indicated, a single quadrupole mass spectrometer, SQD System (produced by Waters) was used as the mass spectrometer, and the measurement was performed by the electrospray ionization (ESI) method. As the liquid chromatography apparatus, Acquity Ultra Performance LC System produced by Waters was used. As the separation column, ACQUITY UPLC BEH C18 (2.1×50 mm, 1.7 μm, produced by Waters) was used.

When the LC conditions are especially mentioned in the examples and reference examples, it means that the measurement was performed with the following solvent conditions. m/z means mass spectrum data ($MH^+$, or MH− is also indicated).

(LC-1) The measurement was performed under the conditions that the elution was performed at a flow rate of 0.6 ml/minute using a linear gradient of 5 to 90% (v/v) of Solution B (acetonitrile) in Solution A (10 mM aqueous ammonium acetate) from 0 minute to 2.0 minutes, and then a linear gradient of 90 to 98% (v/v) of Solution B in Solution A from 2.0 to 2.5 minutes.

(LC-6) The measurement was performed under the conditions that the elution was performed at a flow rate of 0.6 ml/minute using a linear gradient of 70 to 90% (v/v) of Solution B (acetonitrile) in Solution A (10 mM aqueous ammonium acetate) from 0 minute to 2.0 minutes, and then a linear gradient of 90 to 98% (v/v) of Solution B in Solution A from 2.0 to 2.5 minutes.

For the HPLC purification, the preparative purification system produced by Waters Japan, and Triart C18 ExRS (produced by YMC), or the like as the column were used, and 10 mM aqueous ammonium acetate/acetonitrile solution was used as the eluent.

The abbreviation, quant., mentioned in the descriptions of the following examples and synthesis methods of intermediates means that the objective substance was quantitatively obtained.

Intermediate A-1-1: 2-(Chloromethyl)pyrimidine

[Formula 67]

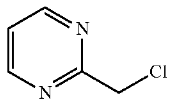

A solution of pyrimidin-2-ylmethanol (150 g, 1.36 mol) in dichloromethane (1350 mL) was cooled to 0° C., thionyl chloride (148.4 mL, 2.04 mol) was added to the solution over 20 minutes, and the resulting mixture was stirred at room temperature for 17 hours. The reaction mixture was cooled to 0° C., and water (150 mL) was added dropwise to the mixture. Then, 5 N aqueous sodium hydroxide (780 mL) was added dropwise to the mixture, 1 N aqueous hydrochloric acid (30 mL) and 5 N aqueous sodium hydroxide (280 mL) were added to the mixture with stirring at 0° C. so that pH was maintained to be 7.2 to 7.5, and the resulting mixture was stirred at 0° C. for 2 hours. The organic layer was separated, and the aqueous layer was extracted with chloroform. The organic layer was dried over anhydrous magnesium sulfate, filtered, and then concentrated under reduced pressure. The resulting crude product was purified by using silica gel column chromatography (eluent, hexane:ethyl acetate=1:0 to 1:2) to obtain 2-(chloromethyl)pyrimidine (118.0 g, yield 67%).

1H-NMR ($CDCl_3$): δ (ppm) 8.78 (2H, d, J=4.9 Hz), 7.26 (1H, t, J=4.9 Hz), 4.76 (2H, s)

Intermediate A-1-2-a: 2-(((1S,2S)-2-(((tert-Butyldimethylsilyl)oxy)cyclopentyl)oxy)methyl)pyrimidine

[Formula 68]

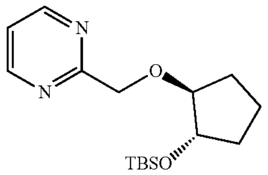

Intermediate A-1-2-b: 2-(((1R,2R)-2-(((tert-Butyldimethylsilyl)oxy)cyclopentyl)oxy)methyl)pyrimidine

[Formula 69]

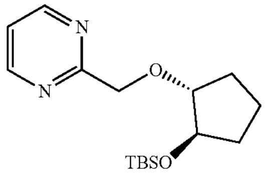

2-(Chloromethyl)pyrimidine (Intermediate A-1-1, 117.9 g, 917 mmol) and trans-cyclopentane-1,2-diol (93.7 g, 917 mmol) were dissolved in DMF (920 mL). The solution was cooled to 0° C., sodium hydride (60 weight %, dispersed in liquid paraffin, TCI, 44.0 g, 917 mmol) was added 6 times as divided portions with 5 minutes intervals, and the resulting mixture was stirred at 0° C. for 20 minutes and then at room temperature for 1 hour. Then, the reaction mixture was cooled to 0° C., imidazole (156 g, 2.29 mol), and TBS chloride (207 g, 1.38 mol) were successively added, and the resulting mixture was stirred at room temperature for 1 hour and 30 minutes. The resulting crude reaction mixture was cooled to 0° C., water (530 mL) was added, the resulting mixture was filtered through a Celite layer, and extracted with ethyl acetate, and then the organic layer was washed with water and saturated brine. The organic layer was dried over anhydrous magnesium sulfate, filtered, and then concentrated under reduced pressure. The resulting crude product was purified by using silica gel column chromatography (eluent, hexane:ethyl acetate=1:0 to 1:1) to obtain 2-((trans-2-(((tert-butyldimethylsilyl)oxy)cyclopentyl)oxy)methyl) pyrimidine (97.9 g, yield 35%). LCMS (LC-1): RT=2.10, m/z 309 $[M+H]^+$ 1H-NMR ($CDCl_3$): δ (ppm) 8.75 (2H, d, J=4.9 Hz), 7.20 (1H, t, J=4.9 Hz), 4.78 (2H, d, 7.3 Hz), 4.26-4.23 (1H, m), 3.86-3.83 (1H, m), 2.03-1.87 (2H, m), 1.75-1.67 (3H, m), 1.56-1.49 (1H, m), 0.86 (9H, s), 0.05 (6H, s)

The optical isomers were separated and analysed with the chiral HPLC conditions mentioned below to obtain the optically active substances at optical purities of 99.7% ee or higher.

Separation conditions: column, CHIRALART CelluLose-SC (10 μm), 245×150 mm I.D.; eluent, heptane/2-propanol (80/20, v/v); flow rate, 518 mL/min; temperature, 24° C.; detection, UV (245 nm); load, 180 mL (9 g)

Analysis conditions: column, CHIRALART CelluLose-SC (5 μm) 250×4.6 mm I.D.; eluent, heptane/2-propanol (80/20, v/v); flow rate, 0.5 mL/min; temperature, 25° C.; detection, UV (245 nm); injection, 10 μL (0.5 mg/mL), RT=11.6 (1S,2S-isomer, Intermediate A-1-2-a), RT=16.5 (1R,2R-isomer, Intermediate A-1-2-b)

Intermediate A-1-3: 2-((((1S,2S)-2-((tert-Butyldimethylsilyl)oxy)cyclopentyl)oxy)methyl)-5-(4,4,5,5-tetramethyl-1,3,2-dioxaboran-2-yl)pyrimidine

[Formula 70]

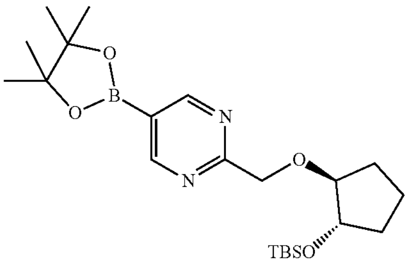

2-((((1S,2S)-2-((tert-Butyldimethylsilyl)oxy)cyclopentyl)oxy)methyl)pyrimidine (Intermediate A-1-2-a, 76.7 g, 249 mmol) was dissolved in THF (500 mL), bis(pinacolato) diboron (63.1 g, 249 mmol), (1,5-cyclooctadiene)(methoxy) iridium(I) (dimmer, 1.64 g, 2.49 mmol), and 3,4,7,8-tetramethyl-1,10-phenanthroline (1.17 g, 4.97 mmol) were added to the solution, and the resulting mixture was stirred at 80° C. for 15 hours to obtain 2-((((1S,2S)-2-((tert-butyldimethylsilyl)oxy)cyclopentyl)oxy)methyl)-5-(4,4,5,5-tetramethyl-1,3,2-dioxaboran-2-yl)pyrimidine as a crude product.

LCMS (LC-1): RT=1.80, m/z 353 $[M+H]^+$ (detected as boronic acid) 1H-NMR ($CDCl_3$): δ (ppm) 9.00 (2H, s), 4.78 (2H, d, 6.2 Hz), 4.25-4.22 (1H, m), 3.84-3.81 (1H, m), 1.97-1.87 (2H, m), 1.72-1.65 (3H, m), 1.55-1.48 (1H, m), 1.35 (121H, s), 0.85 (9H, s), 0.05 (6H, s)

Intermediate A-1-4: 6-(2-((((1S,2S)-2-((tert-Butyldimethylsilyl)oxy)cyclopentyl)oxy)methyl)pyrimidin-5-yl)benzo[d]thiazol-2-amine

[Formula 71]

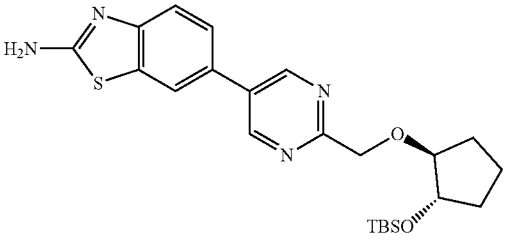

6-Bromo-1,3-benzothiazol-2-amine (1.50 g, 6.5 mmol) was dissolved in THF (15 mL), the aforementioned crude product, 2-((((1S,2S)-2-((tert-butyldimethylsilyl)oxy)cyclopentyl)oxy)methyl)-5-(4,4,5,5-tetramethyl-1,3,2-dioxaboran-2-yl)pyrimidine (Intermediate A-1-3, 4.4 mmol), [1,1'-bis(diphenylphosphino)ferrocene]dichloropalladium(II) (0.32 g, 0.44 mmol), cesium carbonate (4.3 g, 13.1 mmol), and water (2.9 mL) were added to the solution, and the resulting mixture was irradiated with microwaves at 100° C. for 1.5 hours. The crude reaction mixture was diluted with ethyl acetate (29 mL), and the resulting mixture was washed with 10% brine (15 mL). The aqueous layer was extracted again with ethyl acetate, and the combined organic layer was dried over anhydrous sodium sulfate, then filtered through a Celite layer, and concentrated under reduced pressure. The resulting crude product was purified by using automatic silica gel column chromatography (eluent, hexane:ethyl acetate=98:12 to 12:100) to obtain 6-(2-((((1S,2S)-2-((tert-butyldimethylsilyl)oxy)cyclopentyl)oxy)methyl)pyrimidin-5-yl)benzo[d]thiazol-2-amine (1.13 g, yield 57%).

LCMS (LC-1): RT=2.07, m/z 457 $[M+H]^+$

1H-NMR ($CDCl_3$): δ (ppm) 8.95 (2H, s), 7.79 (1H, J=2.0), 7.76 (1H, J=8.4), 7.51 (1H, J=8.4, 2.0), 7.26 (2H, s), 5.33 (2H, s), 4.83-4.79 (2H, m), 4.29-4.26 (1H, m), 3.90-3.87 (1H, m), 2.05-1.89 (2H, m), 1.78-1.68 (3H, m), 1.58-1.50 (1H, m), 0.88 (9H, s), 0.07 (6H, s)

Intermediate A-1-5: N-(6-(2-((((1 S,2S)-2-((tert-Butyldimethylsilyl)oxy)cyclopentyl)oxy)methyl) pyrimidin-5-yl)benzo[d]thiazol-2-yl)cyclopropanecarboxamide

[Formula 72]

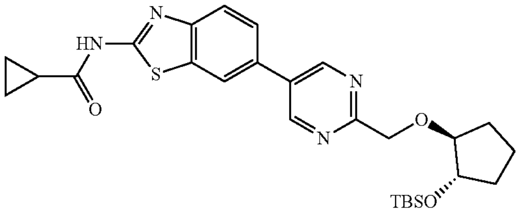

6-(2-((((1S,2S)-2-((tert-Butyldimethylsilyl)oxy)cyclopentyl)oxy)methyl)pyrimidin-5-yl)benzo[d]thiazol-2-amine (Intermediate A-1-4, 30 mg, 66 μmol) was dissolved in dichloromethane (660 μL), cyclopropanecarboxylic acid (19 mg, 0.22 mmol), N,N-diisopropylethylamine (100 μL, 0.59 mmol), and 1-propanephosphonic acid anhydride (50 weight % solution in ethyl acetate, 0.13 mL, 0.22 mmol) were added to the solution, and the resulting mixture was stirred at room temperature for 16 hours. Saturated aqueous sodium hydrogencarbonate was added to the resulting crude reaction mixture, and the resulting mixture was extracted with dichloromethane to obtain a crude reaction mixture containing N-(6-(2-((((1S,2S)-2-((tert-butyldimethylsilyl)oxy)cyclopentyl)oxy)methyl)pyrimidin-5-yl)benzo[d]thiazol-2-yl) cyclopropanecarboxamide.

LCMS (LC-1): RT=2.27, m/z 525 $[M+H]^+$

Example a-01-01: N-(6-(2-((((1S,2S)-2-Hydroxycyclopentyl)oxy)methyl)pyrimidin-5-yl)benzo[d]thiazol-2-yl)cyclopropanecarboxamide

[Formula 73]

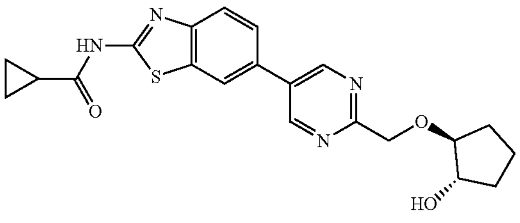

To the crude reaction mixture containing N-(6-(2-((((1S, 2S)-2-((tert-butyldimethylsilyl)oxy)cyclopentyl)oxy) methyl)pyrimidin-5-yl)benzo[d]thiazol-2-yl)cyclopropanecarboxamide (Intermediate A-1-5, 2 mL), a solution of hydrochloric acid in methanol (2 mol/L, 2 mL) was added dropwise under ice cooling, and the resulting mixture was stirred at room temperature for 30 minutes. The resulting crude reaction mixture was concentrated under reduced pressure, and the residue was purified by using SCX and HPLC to obtain N-(6-(2-((((1S,2S)-2-hydroxycyclopentyl) oxy)methyl)pyrimidin-5-yl)benzo[d]thiazol-2-yl)cyclopropanecarboxamide (12 mg, yield 44%).

LCMS (LC-1): RT=1.13, m/z 411 $[M+H]^+$

1H-NMR ($DMSOd_6$): δ (ppm) 9.17 (2H, s), 8.45 (11H, m), 7.86 (2H, m), 4.71-4.69 (3H, m), 4.04-4.00 (1H, m), 3.83-3.80 (1H, m), 2.03-1.40 (7H, m), 0.98-0.96 (4H, m)

The following compounds mentioned in the following tables were synthesized by similar methods. In the following table, the examples of which preparation methods should be referred to are mentioned in the column of "Reference Methods".

TABLE 2-1

| Example | Structure | Reference Methods | LCMS Data |
| --- | --- | --- | --- |
| a-01-02 | 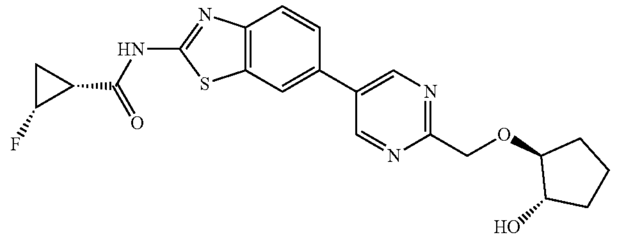 [SMILES: O=C(Nc1nc2ccc(-c3cnc(CO[C@H]4CCC[C@@H]4O)nc3)cc2s1)[C@H]1C[C@H]1F] | Example a-01-01 Intermediate A-1-5 | (LC-1): RT = 0.97, m/z 429 $[M + H]^+$ |
| a-01-03 | 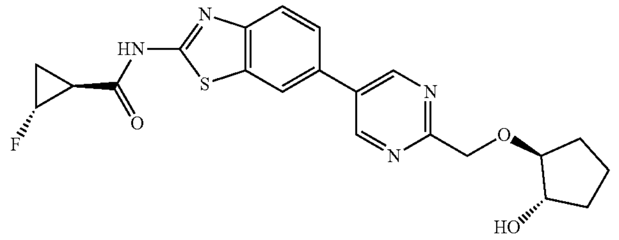 [SMILES: O=C(Nc1nc2ccc(-c3cnc(CO[C@H]4CCC[C@@H]4O)nc3)cc2s1)[C@@H]1C[C@H]1F] | Example a-01-01 Intermediate A-1-5 | (LC-1): RT = 01.16, m/z 429 $[M + H]^+$ |
| a-01-04 | 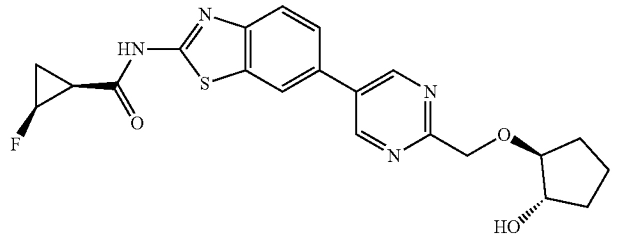 [SMILES: O=C(Nc1nc2ccc(-c3cnc(CO[C@H]4CCC[C@@H]4O)nc3)cc2s1)[C@@H]1C[C@@H]1F] | Example a-01-01 Intermediate A-1-5 | (LC-1): RT = 1.09, m/z 429 $[M + H]^+$ |
| a-01-05 | 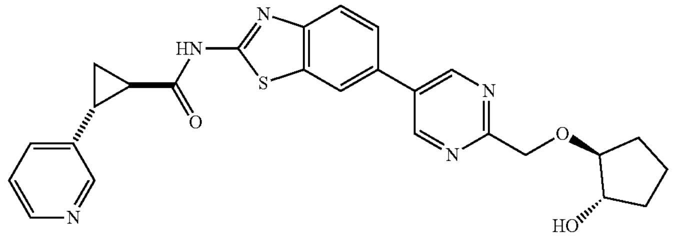 | Example a-01-01 Intermediate A-1-5 | (LC-1): RT = 1.15, m/z 488 $[M + H]^+$ |
| a-01-06 | 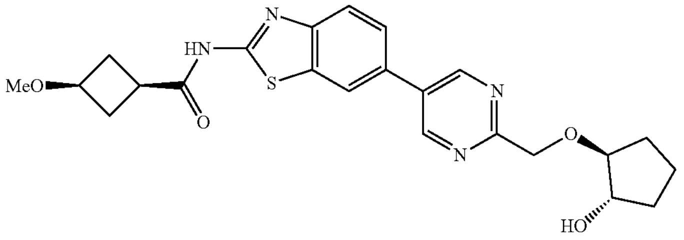 [SMILES: CO[C@H]1C[C@@H](C(=O)Nc2nc3ccc(-c4cnc(CO[C@H]5CCC[C@@H]5O)nc4)cc3s2)C1] | Example a-01-01 Intermediate A-1-5 | (LC-1): RT = 1.17, m/z 454 $[M + H]^+$ |

TABLE 2-1-continued
| Example | Structure | Reference Methods | LCMS Data |
| --- | --- | --- | --- |
| a-01-07 | 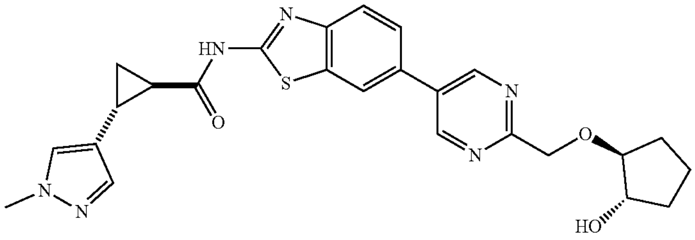 | Example a-01-01 Intermediate A-1-5 | (LC-1): RT = 1.13, m/z 491 [M + H]+ |
| a-01-08 | 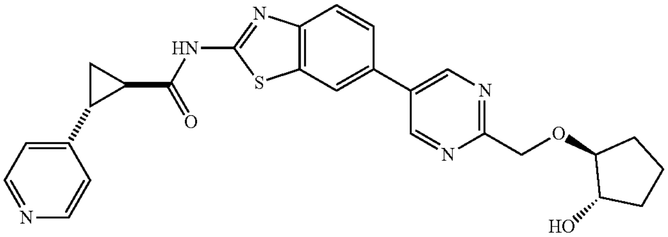 | Example a-01-01 Intermediate A-1-5 | (LC-1): RT = 1.14, m/z 488 [M + H]+ |
| a-01-09 | 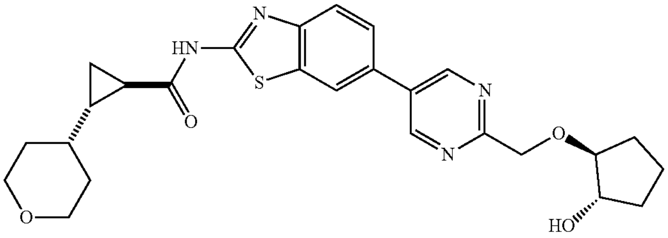 | Example a-01-01 Intermediate A-1-5 | (LC-1): RT = 1.22, m/z 495 [M + H]+ |
| a-01-10 | 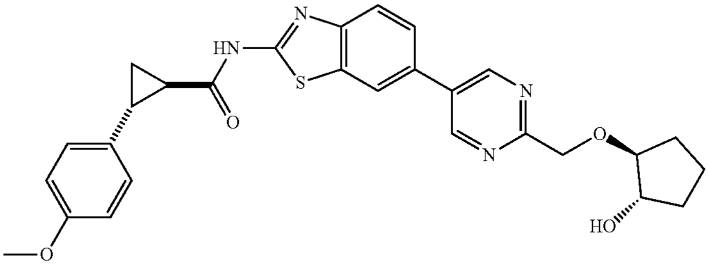 | Example a-01-01 Intermediate A-1-5 | (LC-1): RT = 1.48, m/z 517 [M + H]+ |
TABLE 2-2
| | | | |
| --- | --- | --- | --- |
| a-01-11 | 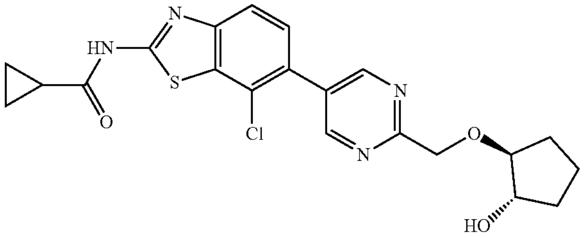 [SMILES: O=C(Nc1nc2ccc(-c3cnc(CO[C@H]4CCC[C@@H]4O)nc3)c(Cl)c2s1)C1CC1] | Example a-01-01 Intermediate A-1-4,5 | (LC-1): RT = 1.30, m/z 445 [M + H]+ |

TABLE 2-2-continued

| | | | |
|---|---|---|---|
| a-01-12 | 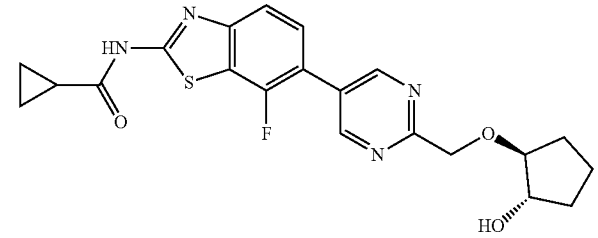 [SMILES: O=C(Nc1nc2ccc(-c3cnc(CO[C@H]4CCC[C@@H]4O)nc3)c(F)c2s1)C1CC1] | Example a-01-01 Intermediates A-1-4, and 5 | (LC-1): RT = 1.24, m/z 429 [M + H]$^+$ |

Intermediate A-2-1: 2-(Propoxymethyl)pyrimidine

[Formula 74]

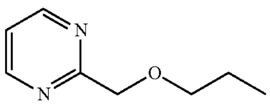

Pyrimidin-2-ylmethanol (10 g, 91 mmol) was dissolved in DMF (300 mL), sodium hydride (4.8 g, 55 weight %, 109 mmol) was added to the solution under ice cooling, and the resulting mixture was stirred for 10 minutes. To the reaction mixture, 1-iodopropane (13.2 mL, 136 mmol) was added dropwise, the resulting mixture was stirred at room temperature for 2 hours, then sodium hydride (4 g, 55 weight %, 91 mmol), and 1-iodopropane (10 mL, 103 mmol) were added, and the resulting mixture was stirred at room temperature for further 1 hour. To the resulting crude reaction mixture, water (300 mL) was added to terminate the reaction, and the reaction mixture was extracted three times with ethyl acetate (300 mL). The resulting organic layer was dried over anhydrous sodium sulfate, filtered, and then concentrated under reduced pressure. The resulting crude product was purified by using automatic silica gel column chromatography (eluent, hexane:ethyl acetate=88:12 to 0:100) to obtain 2-(propoxymethyl)pyrimidine (10.1 g, yield 73%).

1H-NMR ($CDCl_3$): δ (ppm) 8.76 (2H, d, J=4.9 Hz), 7.21 (11H, dd, J=4.9 Hz), 4.75 (2H, s), 3.60 (2H, t, J=6.9 Hz), 1.73 (2H, tt, J=6.9, 7.4 Hz), 0.96 (3H, t, J=7.4 Hz)

Intermediate A-2-2: 2-(Propoxymethyl)-5-(4,4,5,5-tetramethyl-1,3,2-dioxaboran-2-yl)pyrimidine

[Formula 75]

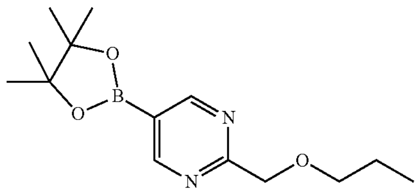

According to the synthesis method of Intermediate A-1-3, synthesis was performed by using 2-(propoxymethyl)pyrimidine (Intermediate A-2-1, 10.1 g) instead of 2-(((tert-butyldimethylsilyl)oxy)methyl)pyrimidine (Intermediate A-1-2-a) to obtain 2-propoxymethyl-5-(4,4,5,5-tetramethyl-1,3,2-dioxaboran-2-yl)pyrimidine as a crude product.

LCMS (LC-1): RT=0.62, m/z 197 [M+H]$^+$ (detected as boronic acid)

Intermediate A-2-3: N-(6-Bromo-1,3-benzothiazol-2-yl)cyclopropanecarbamide

[Formula 76]

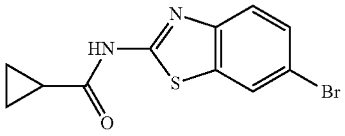

2-Amino-6-bromobenzothiazole (1 g, 4.36 mmol) was dissolved in DCM (44 mL), cyclopropanecarbonyl chloride (0.91 g, 8.73 mmol) and triethylamine (0.88 g, 8.37 mmol) were added to the solution, and the resulting mixture was stirred at room temperature for 2 hours. Water was added to the obtained reaction mixture, the resulting mixture was extracted with chloroform, and the organic layer was separated and concentrated under reduced pressure to obtain a crude reaction mixture containing N-(6-bromo-1,3-benzothiazol-2-yl)cyclopropanecarbamide (739 mg, yield 57%).

LCMS (LC-1): RT=1.58, m/z 297 [M+H]

1H-NMR ($CDCl_3$): δ (ppm) 7.95 (1H, m), 7.68 (1H, m), 7.62 (2H, d, J=8.5 Hz), 7.53 (2H, dd, J=8.5, 2.0 Hz), 1.98-1.91 (1H, m), 1.27-1.23 (4H, m)

Example a-02-01: N-(6-(2-(Propoxymethyl)pyrimidin-5-yl)benzo[d]thiazol-2-yl)cyclopropanecarboxamide

[Formula 77]

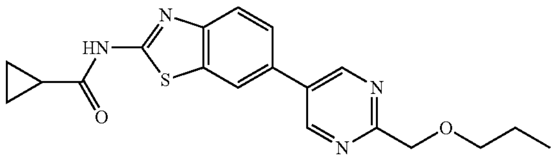

According to the synthesis method of Intermediate A-1-4, synthesis was performed by using N-(6-bromo-1,3-benzothiazol-2-yl)cyclopropanecarbamide (Intermediate A-2-3, 20 mg) instead of 6-bromo-1,3-benzothiazol-2-amine, and 2-(propoxymethyl)-5-(4,4,5,5-tetramethyl-1,3,2-dioxaboran-2-yl)pyrimidine (Intermediate A-2-2) instead of 2-((((1S,2S)-2-((tert-butyldimethylsilyl)oxy)cyclopentyl)oxy)methyl)-5-(4,4,5,5-tetramethyl-1,3,2-dioxaboran-2-yl)pyrimidine (Intermediate A-1-3) to obtain N-(6-(2-

(propoxymethyl)pyrimidin-5-yl)benzo[d]thiazol-2-yl) cyclopropanecarboxamide (10 mg, yield 20%).

LCMS (LC-1): RT=1.37, m/z 369 $[M+H]^+$

1H-NMR ($DMSOd_6$): δ (ppm) 9.17 (2H, s), 8.38 (1H, m), 7.83-7.77 (2H, m), 4.65 (2H, s), 3.52 (2H, J=6.7 Hz), 1.97-1.91 (1H, m), 1.62-1.53 (2H, m), 0.93-0.88 (7H, m)

Intermediate A-3-1: 5-Bromo-2-(((trans-2-((tert-butyldimethylsilyl)oxy)-4,4-difluorocyclopentyl)oxy)methyl)pyrimidine

[Formula 78]

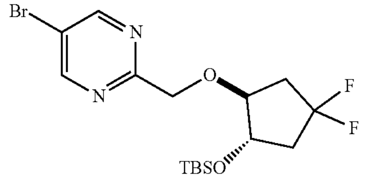

5-Bromo-2-(chloromethyl)pyrimidine (500 mg, 2.41 mmol), and trans-4,4-difluorocyclopentane-1,2-diol (500 mg, 3.62 mmol) were dissolved in dichloromethane (4 mL), tetrabutylammonium chloride (70 mg, 241 μmol), and 25 weight % aqueous sodium hydroxide (4 mL) were added to the solution, and the resulting mixture was stirred under reflux by heating for 14 hours. The organic layer of the resulting reaction mixture was separated, dried over anhydrous magnesium sulfate, and then filtered. Imidazole (330 mg, 4.82 mmol), and TBS chloride (545 mg, 3.62 mmol) were added to the filtrate, and the resulting mixture was stirred at room temperature for 6 hours. Then, imidazole (330 mg, 4.82 mmol), and TBS chloride (545 mg, 3.62 mmol) were further added, and the resulting mixture was stirred at room temperature for 52 hours. Imidazole (330 mg, 4.82 mmol), and TBS chloride (545 mg, 3.62 mmol) were further added, and the resulting mixture was stirred at room temperature for 24 hours. Water was added to the obtained reaction mixture, the resulting mixture was extracted with chloroform, the organic layer was separated and concentrated under reduced pressure, and the residue was purified by using automatic silica gel column chromatography (eluent, hexane:ethyl acetate) to obtain 5-bromo-2-(((trans-2-((tert-butyldimethylsilyl)oxy)-4,4-difluorocyclopentyl)oxy)methyl)pyrimidine (131 mg, yield 13%).

LCMS (LC-1): RT=2.25, m/z 424 $[M+H]^+$

1H-NMR ($CDCl_3$): δ (ppm) 8.79 (2H, s), 4.77 (2H, d, J=2.1 Hz), 4.36-4.31 (1H, m), 4.00-3.96 (1H, m), 2.62-2.44 (2H, m), 2.32-2.19 (1H, m), 2.13-2.00 (1H, m), 0.87 (9H, s), 0.07 (6H, s)

Intermediate A-3-2: N-(6-(4,4,5,5-Tetramethyl-1,3,2-dioxaborolan-2-yl)benzo[d]thiazol-2-yl)cyclopropanecarboxamide

[Formula 79]

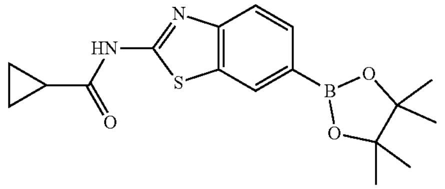

N-(6-Bromo-1,3-benzothiazol-2-yl)cyclopropanecarbamide (Intermediate A-2-3, 400 mg, 1.35 mmol) was dissolved in 1,4-dioxane (13 mL), bis(pinacolato)diboron (513 mg, 2.03 mmol), [1,1'-bis(diphenylphosphino)ferrocene]dichloropalladium(II) (98 mg, 0.13 mmol), and potassium acetate (400 mg, 2.69 mmol) were added to the solution, the resulting mixture was stirred at 80° C. for 3 hours, and cooled to room temperature, and then the solvent was concentrated under reduced pressure to obtain a crude reaction mixture containing N-[6-(4,4,5,5-tetramethyl-1,3,2-dioxaborolan-2-yl)-1,3-benzothiazol-2-yl]cyclopropanecarboxamide.

LCMS (LC-1): RT=1.73, m/z 346 $[M+2H]^+$

1H-NMR ($CDCl_3$): δ (ppm) 8.28 (2H, s), 7.86 (1H, d, J=8.0 Hz), 7.71 (1H, d, J=8.0 Hz), 1.80-1.74 (1H, m), 1.37 (12H, s), 1.26 (4H, s)

Intermediate A-3-3: N-(6-(2-(((trans-2-((tert-Butyldimethylsilyl)oxy)-4,4-difluorocyclopentyl)oxy)methyl)pyrimidin-5-yl)benzo[d]thiazol-2-yl)cyclopropanecarboxamide

[Formula 80]

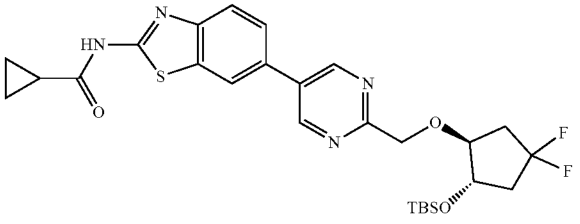

5-Bromo-2-(((trans-2-((tert-butyldimethylsilyl)oxy)-4,4-difluorocyclopentyl)oxy)methyl)pyrimidine (Intermediate A-3-1, 30 mg, 71 μmol), and N-(6-(4,4,5,5-tetramethyl-1,3,2-dioxaborolan-2-yl)benzo[d]thiazol-2-yl)cyclopropanecarboxamide (Intermediate A-3-2, 36 mg, 0.11 mmol) were dissolved in 1,4-dioxane (1 mL), water (200 μL), cesium carbonate (69 mg, 0.22 mmol), and [1,1'-bis(diphenylphosphino)ferrocene]dichloropalladium(II) (5.8 mg, 7 μmol) were added to the solution, and the resulting mixture was stirred overnight at 80° C. The resulting crude reaction mixture was filtered through a Celite layer, and concentrated under reduced pressure. The resulting crude product was purified by using automatic silica gel column chromatography (eluent, chloroform:methanol) and HPLC to obtain N-(6-(2-(((trans-2-((tert-butyldimethylsilyl)oxy)-4,4-difluorocyclopentyl)oxy)methyl)pyrimidin-5-yl)benzo[d]thiazol-2-yl)cyclopropanecarboxamide (13.7 mg, yield 34%).

LCMS (LC-1): RT=2.11, m/z 561 $[M+H]^+$

1H-NMR ($CDCl_3$): δ (ppm) 9.95 (1H, brs), 9.00 (2H, s), 8.02 (1H, d, J=2.0 Hz), 7.89 (1H, d, J=8.4 Hz), 7.63 (1H, dd, J=8.4, 2.0 Hz), 4.92-4.84 (2H, m), 4.40-4.36 (1H, m), 4.06-4.02 (1H, m), 2.65-2.47 (2H, m), 2.37-2.25 (1H, m), 2.15-2.03 (1H, m), 1.73-1.66 (1H, m), 1.30-1.26 (2H, m), 1.08-1.04 (2H, m), 0.88 (9H, s), 0.09 (6H, d, J=1.6 Hz)

Example a-03-01: N-(6-(2-((((1 S,2S)-4,4-Difluoro-2-hydroxycyclopentyl)oxy)methyl)pyrimidin-5-yl) benzo[d]thiazol-2-yl)cyclopropanecarboxamide

[Formula 81]

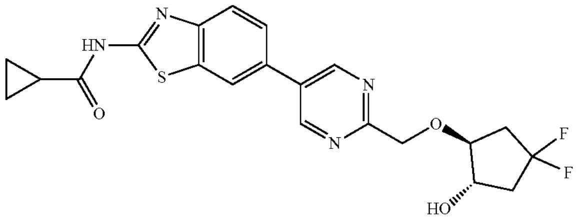

According to the synthesis method of Example a-01-01, synthesis was performed by using N-(6-(2-((((1S,2S)-2-((tert-butyldimethylsilyl)oxy)-4,4-difluorocyclopentyl)oxy) methyl)pyrimidin-5-yl)benzo[d]thiazol-2-yl)cyclopropanecarboxamide (Intermediate A-3-5, 13.7 mg) instead of N-(6-(2-(((trans-2-((tert-butyldimethylsilyl)oxy)cyclopentyl)oxy)methyl)pyrimidin-5-yl)benzo[d]thiazol-2-yl)cyclopropanecarboxamide (Intermediate A-1-5), and the resulting stereoisomer mixture was resolved by using HPLC purification and chiral HPLC purification (column, CHIRALPAK IB (DAICEL); mobile phase, normal hexane:ethanol=30:70) to obtain the desired N-(6-(2-((((1S,2S)-4,4-difluoro-2-hydroxycyclopentyl)oxy)methyl)pyrimidin-5-yl)benzo[d]thiazol-2-yl)cyclopropanecarboxamide (2.3 mg, yield 21%).

LCMS (LC-1): RT=1.23, m/z 447 $[M+H]^+$

1H-NMR ($DMSOd_6$): δ (ppm) 12.76 (1H, brs), 9.19 (2H, s), 8.46 (1H, m), 7.89-7.85 (2H, m), 5.36-5.35 (1H, m), 4.76 (2H, s), 4.19 (1H, m), 4.03 (1H, m), 2.62-2.40 (2H, m), 2.26-2.14 (1H, m), 2.08-1.97 (2H, m), 0.99-0.97 (4H, m)

Intermediate A-4-1: 5-Bromo-2-(cyclopentoxymethyl)pyrimidine

[Formula 82]

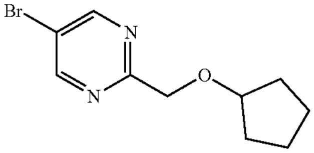

5-Bromo-2-(chloromethyl)pyrimidine (100 mg, 0.4 mmol), and cyclopentanol (41 mg, 0.48 mmol) were dissolved in dichloromethane (4 mL), tetrabutylammonium chloride (11 mg, 40 μmol), and 25 weight % aqueous sodium hydroxide (2 mL) were added to the solution, and the resulting mixture was stirred at 60° C. for 14 hours. Water was added to the obtained reaction mixture, the resulting mixture was extracted with chloroform, the organic layer was separated and concentrated under reduced pressure, and the residue was purified by using automatic silica gel column chromatography (eluent, chloroform:methanol) to obtain 5-bromo-2-(cyclopentoxymethyl)pyrimidine (87 mg, yield 85%).

LCMS (LC-1): RT=1.41, m/z 258 $[M+H]^+$

1H-NMR ($CDCl_3$): δ (ppm) 8.79 (2H, s), 4.67 (2H, s), 4.15-4.09 (1H, m), 1.88-1.68 (6H, m), 1.58-1.50 (2H, m)

The following compound mentioned in the following table was synthesized by similar methods. In the following table, the preparation methods should be referred to is mentioned in the column of "Reference Methods".

TABLE 3

| Intermediate | Structure | Reference Methods | LCMS Data |
|---|---|---|---|
| A-4-2 | 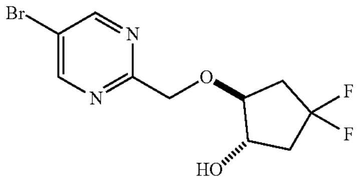 | Intermediate A-4-1 | (LC-1): RT = 1.05, m/z 308 $[M + H]^+$ |

Example a-04-01: N-(6-(2-(Cyclopentoxymethyl) pyrimidin-5-yl)-1,3-benzo[d]thiazol-2-yl)cyclopropanecarboxamide

[Formula 83]

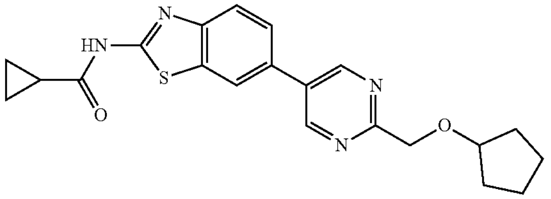

5-Bromo-2-(cyclopentoxymethyl)pyrimidine (Intermediate A-4-1, 40 mg, 0.16 mmol) was dissolved in 1,4-dioxane (778 μL), N-[6-(4,4,5,5-tetramethyl-1,3,2-dioxaborolan-2-yl)-1,3-benzothiazol-2-yl]cyclopropanecarboxamide (Intermediate A-3-2, 53.6 mg, 0.16 mmol), cesium carbonate (101 mg, 0.31 mmol), and [1,1'-bis(diphenylphosphino)ferrocene]dichloropalladium(II) (11 mg, 0.02 mmol) were added to the solution, the resulting mixture was refluxed by heating for 15 hours, and cooled to room temperature, then the solvent was concentrated under reduced pressure, and the residue was purified by using automatic silica gel column chromatography (eluent, chloroform:methanol) to obtain N-[6-[2-(cyclopentoxymethyl)pyrimidin-5-yl]-1,3-benzothiazol-2-yl]cyclopropanecarboxamide (4.8 mg, yield 8%).

LCMS (LC-1): RT=1.52, m/z 395 $[M+H]^+$

1H-NMR ($CDCl_3$): δ (ppm) 9.00 (2H, s), 8.00 (2H, s), 7.89 (2H, d, J=8.0 Hz), 7.63 (2H, d, J=8.0 Hz), 4.79 (2H, s), 4.25-4.22 (1H, m), 4.21-4.13 (1H, m), 1.84-1.74 (4H, m), 1.72-1.70 (1H, m), 1.29-1.25 (2H, m), 1.09-1.05 (2H, m)

The following compounds mentioned in the following table were synthesized by similar methods. In the following table, the examples of which preparation methods should be referred to are mentioned in the columns of "Reference Methods".

TABLE 4

| Example | Structure | Reference Methods | LCMS Data |
|---|---|---|---|
| a-04-02 | 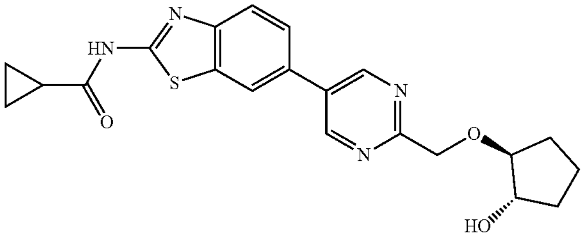 [SMILES: O=C(Nc1nc2ccc(-c3cnc(CO[C@H]4CCC[C@@H]4O)nc3)cc2s1)C1CC1] | Example a-02-01 Intermediate A-2-1 | (LC-1): RT 1.32, m/z 425 $[M + H]^+$ |
| a-04-03 | 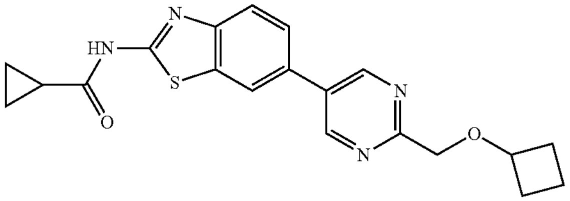 [SMILES: O=C(Nc1nc2ccc(-c3cnc(COC4CCC4)nc3)cc2s1)C1CC1] | Example a-02-01 Intermediate A-2-1 | (LC-1): RT = 1.41, m/z 381 $[M + H]^+$ |
| a-04-04 | 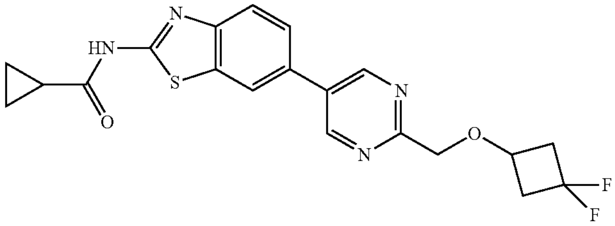 [SMILES: O=C(Nc1nc2ccc(-c3cnc(COC4CC(F)(F)C4)nc3)cc2s1)C1CC1] | Example a-02-01 Intermediate A-2-1 | (LC-1): RT = 1.41, m/z 417 $[M + H]^+$ |

Intermediate A-5-1: (S)-5-Bromo-2-(((tetrahydrofuran-2-yl)methoxy)methyl)pyrimidine

[Formula 84]

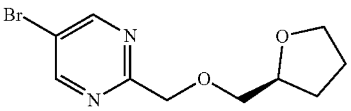

5-Bromo-2-(bromomethyl)pyrimidine (6.7 g, 27 mmol), and (S)-(tetrahydrofuran-2-yl)methanol (2.5 g, 24 mmol) were dissolved in tetrahydrofuran (80 mL), 33% aqueous sodium hydroxide (30 mL), and tetrabutylammonium chloride (667 mg, 2.4 mmol) were added to the solution, and the resulting mixture was stirred overnight at 40° C. Water (100 mL) was added to the obtained crude reaction mixture, and the resulting mixture was extracted 3 times with dichloromethane (150 mL). The obtained organic layers were washed with water, and saturated brine, dried over anhydrous sodium sulfate, filtered, and concentrated to dryness. The resulting crude product was purified by using silica gel column chromatography (eluent, petroleum ether:ethyl acetate=5:1) to obtain (S)-5-bromo-2-(((tetrahydrofuran-2-yl)methoxy)methyl)pyrimidine (2.55 g, yield 39%).

LCMS (LC-1): RT=1.03, m/z 273 $[M+H]^+$

1H-NMR ($CDCl_3$): δ (ppm) 8.79 (2H, s), 4.84-4.75 (2H, m), 4.19-4.13 (1H, m), 3.92-3.86 (1H, m), 3.80-3.75 (1H, m), 3.70-3.61 (2H, m), 2.03-1.95 (1H, m), 1.93-1.84 (2H, m), 1.70-1.61 (1H, m)

Example a-05-01: (S)—N-(6-(2-((Tetrahydrofuran-2-yl)methoxy)methyl)pyrimidin-5-yl)benzo[d]thiazol-2-yl)cyclopropanecarboxamide

[Formula 85]

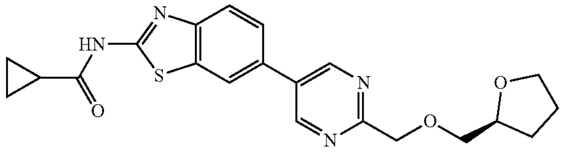

(S)-5-Bromo-2-(((tetrahydrofuran-2-yl)methoxy)methyl)pyrimidine (Intermediate A-5-1, 150 mg, 0.55 mmol), and N-(6-(4,4,5,5-tetramethyl-1,3,2-dioxaborolan-2-yl)benzo[d]thiazol-2-yl)cyclopropanecarboxamide (Intermediate A-3-2, 246 mg, 0.71 mmol) were dissolved in N,N-dimethylformamide (9 mL), water (1 mL), potassium carbonate (152 mg, 1.1 mmol), and tetrakis(triphenylphosphine)palladium(0) (64 mg, 55 μmol) were added to the solution, and the resulting mixture was stirred overnight at 130° C. The resulting crude reaction mixture was concentrated under reduced pressure, and the residue was purified by using automatic silica gel column chromatography (eluent, petroleum ether:ethyl acetate=1:2) and HPLC to obtain (S)—N-(6-(2-((tetrahydrofuran-2-yl)methoxy)methyl)pyrimidin-5-yl)benzo[d]thiazol-2-yl)cyclopropanecarboxamide (45 mg, yield 20%).

LCMS (LC-1): RT=1.20, m/z 411 $[M+H]^+$

1H-NMR ($DMSOd_6$): δ (ppm) 12.76 (1H, s), 9.18 (2H, s), 8.47 (1H, s), 7.90-7.85 (2H, m), 4.71 (2H, s), 4.03-3.97 (1H, m), 3.77-3.71 (1H, m), 3.65-3.60 (1H, m), 3.56 (2H, d, J=5.3 Hz), 2.06-1.99 (1H, m), 1.95-1.74 (3H, m), 1.65-1.55 (1H, m), 0.99-0.97 (4H, m)

Intermediate B-1-1: N-(6-(2-((((1S,2S)-2-((tert-Butyldimethylsilyl)oxy)cyclopentyl)oxy)methyl)pyrimidin-5-yl)benzo[d]thiazol-2-yl)-3-oxocyclobutane-1-carboxamide

[Formula 86]

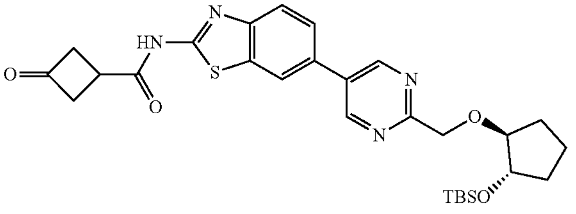

6-(2-((((1S,2S)-2-((tert-Butyldimethylsilyl)oxy)cyclopentyl)oxy)methyl)pyrimidin-5-yl)benzo[d]thiazol-2-amine (Intermediate A-1-4, 400 mg, 0.88 mmol) was suspended in dichloromethane (8.6 mL), N-ethyldiisopropylamine (1.37 mL, 7.88 mmol), 3-oxocyclobutanecarboxylic acid (0.23 mL, 2.89 mmol), and 1-propylphosphonic acid anhydride (0.78 mL, 2.63 mmol) were added to the suspension, and the resulting mixture was stirred at room temperature for 1.5 hours. To the obtained reaction mixture, saturated aqueous sodium hydrogencarbonate was added, the resulting mixture was extracted with chloroform, the organic layer was dried over sodium sulfate, filtered, and concentrated, and the residue was purified by using automatic silica gel column chromatography (eluent, chloroform containing 2% methanol) to obtain N-(6-(2-((((1S,2S)-2-((tert-butyldimethylsilyl)oxy)cyclopentyl)oxy)methyl)pyrimidin-5-yl)benzo[d]thiazol-2-yl)-3-oxocyclobutane-1-carboxamide (296.9 mg, yield: 61%).

LCMS (LC-1): RT=2.18, m/z 553 $[M+H]^+$

1H-NMR ($CDCl_3$): δ (ppm) 10.4 (1H, brs), 9.02 (2H, s), 8.06 (1H, d, J=1.5 Hz), 7.88 (1H, d, J=8.0 Hz), 7.69-7.65 (1H, m), 7.59-7.55 (1H, m), 7.64-7.55 (1H, m), 4.98-4.74 (2H, m), 4.35-4.18 (1H, m), 3.98-3.80 (1H, m), 3.71-3.59 (2H, m), 3.42-3.28 (3H, m), 2.11-1.84 (2H, m), 1.80-1.71 (3H, m), 1.61-1.37 (1H, m), 0.88 (9H, s), 0.08 (3H, s), 0.07 (3H, s)

Intermediate B-1-2: N-(6-2-((((1S,2S)-2-((tert-Butyldimethylsilyl)oxy)cyclopentyl)oxy)methyl)pyrimidin-5-yl)benzo[d]thiazol-2-yl)-3-morpholinocyclobutane-1-carboxamide

[Formula 87]

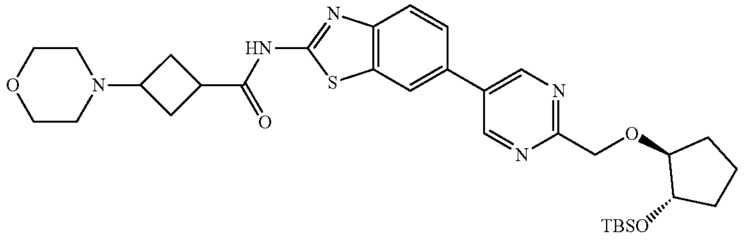

N-(6-(2-((((1S,2S)-2-((tert-Butyldimethylsilyl)oxy)cyclopentyl)oxy)methyl)pyrimidin-5-yl)benzo[d]thiazol-2-yl)-3-oxocyclobutane-1-carboxamide (Intermediate B-1-1, 100 mg, 0.18 mmol) was dissolved in tetrahydrofuran (0.9 mL), acetic acid (0.1 mL), sodium triacetoxyborohydride (77 mg, 0.36 mmol), and morpholine (23.74 μL, 0.27 mmol) were added to the solution, and the resulting mixture was stirred at room temperature for 1.5 hours. To the obtained reaction mixture, water and saturated aqueous sodium hydrogencarbonate were added, the resulting mixture was extracted with chloroform, the organic layer was dried over sodium sulfate, filtered, and concentrated, and the residue was purified by using automatic silica gel column chromatography (eluent, chloroform containing 2% methanol) and HPLC to obtain the objective compound, N-(6-2-((((1S,2S)-2-((tert-butyldimethylsilyl)oxy)cyclopentyl)oxy)methyl)pyrimidin-5-yl)benzo[d]thiazol-2-yl)-3-morpholinocyclobutane-1-carboxamide (73.9 mg, yield 65.8%).

LCMS (LC-1): RT=2.15, m/z 624 $[M+H]^+$

Example b-01-01: N-(6-(2-((((1S,2S)-2-Hydroxycyclopentyl)oxy)methyl)pyrimidin-5-yl)benzo[d]thiazol-2-yl)-3-moipholinocyclobutane-1-carboxamide

[Formula 88]

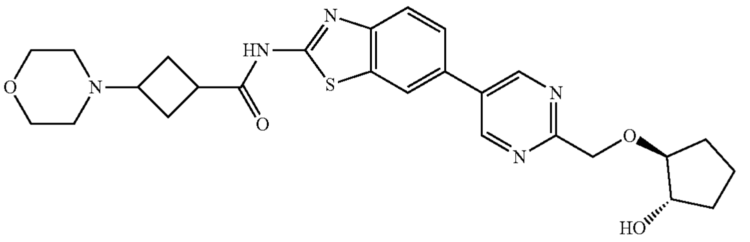

To N-(6-2-((((1S,2S)-2-((tert-butyldimethylsilyl)oxy)cyclopentyl)oxy)methyl)pyrimidin-5-yl)benzo[d]thiazol-2-yl)-3-morpholinocyclobutane-1-carboxamide (Intermediate B-1-2, 45.5 mg, 0.07 mmol), a 2 N solution of hydrochloric acid in methanol (500 μL) was added, and the resulting mixture was stirred at room temperature. After 10 minutes, the reaction was terminated, and the solvent was evaporated by nitrogen blow. A part of the residue was purified by using SCX and automatic silica gel column chromatography (eluent, chloroform containing 2% methanol) to obtain N-(6-(2-((((1S,2S)-2-hydroxycyclopentyl)oxy)methyl)pyrimidin-5-yl)benzo[d]thiazol-2-yl)-3-morpholinocyclobutane-1-carboxamide (2 mg). The remained reaction mixture was purified by using HPLC to obtain N-(6-(2-((((1S,2S)-2-hydroxycyclopentyl)oxy)methyl)pyrimidin-5-yl)benzo[d]thiazol-2-yl)-3-morpholinocyclobutane-1-carboxamide (13.6 mg, yield: 37%).

LCMS (LC-1): RT=1.01, m/z 510 $[M+H]^+$

1H-NMR ($CDCl_3$): δ (ppm) 9.00 (2H, s), 8.00 (1H, d, J=1.5 Hz), 7.93-7.87 (1H, m), 7.65-7.58 (1H, m), 5.09-4.77 (3H, m), 4.30-4.19 (1H, m), 4.07-3.98 (3H, m), 3.97-3.91 (1H, m), 3.91-3.84 (1H, m), 3.30-3.15 (2H, m), 3.00-2.89 (11H, m), 2.76-2.63 (2H, m), 2.35-2.22 (21H, m), 2.14-1.99 (2H, m), 1.77-1.69 (2H, m), 1.29-1.23 (2H, m)

The following compound mentioned in the following table was synthesized by similar methods. In the following table, the example of which preparation methods should be referred to is mentioned in the column of "Reference Methods".

Intermediate B-2-1: (1S,2S)-2-((5-(2-Aminobenzo[d]thiazol-6-yl)pyrimidin-2-yl)methoxy)cyclopentan-1-ol

[Formula 89]

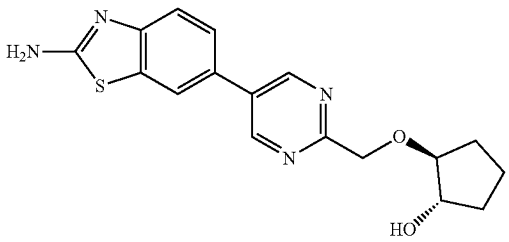

To 6-(2-((((1S,2S)-2-((tert-butyldimethylsilyl)oxy)cyclopentyl)oxy)methyl)pyrimidin-5-yl)benzo[d]thiazol-2-amine (Intermediate A-1-4, 1.5 g, 3.28 mmol), a 2 N hydrochloric acid solution in methanol (6 mL) was added, and the resulting mixture was stirred at room temperature for 15 minutes. Saturated aqueous sodium hydrogencarbonate was added to the reaction mixture, the resulting mixture was extracted with chloroform, the organic layer was dried over sodium sulfate, filtered, and concentrated, and the residue was purified by using automatic silica gel column chromatography (eluent, ethyl acetate:methanol) to obtain (1S,2S)-

TABLE 5

| Example | Structure | Reference Methods | LCMS Data |
|---|---|---|---|
| b-01-02 | 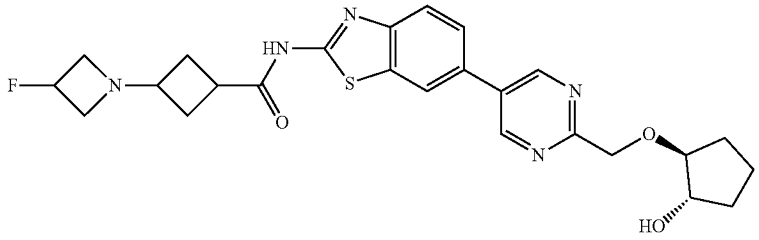 [SMILES: O=C(Nc1nc2ccc(-c3cnc(CO[C@H]4CCC[C@@H]4O)nc3)cc2s1)C1CC(N2CC(F)C2)C1] | Example b-01-01 Intermediate B-1-2 | (LC-1): RT = 1.06, m/z 498 [M + H]+ |

2-((5-(2-aminobenzo[d]thiazol-6-yl)pyrimidin-2-yl)methoxy)cyclopentan-1-ol (1.41 g) as a crude product.

LCMS (LC-1): RT=0.89, m/z 343 $[M+H]^+$

1H-NMR ($CDCl_3$): δ (ppm) 9.91-9.65 (2H, brs), 9.12 (2H, s), 8.34 (1H, d, J=2.0 Hz), 8.12 (1H, d, J=2.0 Hz), 7.86 (1H, dd, J=8.5, 2.0 Hz), 7.65 (1H, d, J=8.5 Hz), 7.60-7.50 (1H, m), 7.50-7.32 (1H, m), 4.70-4.69 (2H, m), 4.02 (2H, m), 3.99-3.72 (3H, m), 1.97-1.71 (31H, m), 1.68-1.52 (5H, m), 1.52-1.34 (2H, m)

Intermediate B-2-2: N-(6-(2-((((1S,2S)-2-Hydroxycyclopentyl)oxy)methyl)pyrimidin-5-yl)benzo[d]thiazol-2-yl)-3-oxocyclobutane-1-carboxamide

[Formula 90]

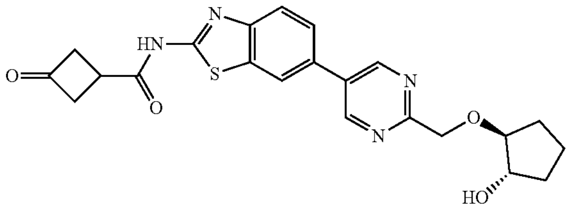

(1S,2S)-2-((5-(2-Aminobenzo[d]thiazol-6-yl)pyrimidin-2-yl)methoxy)cyclopentan-1-ol (Intermediate B-2-1, 1.41 g, 4.11 mmol) was dissolved in dimethylfornamide (20.5 mL), 3-oxocyclobutanecarboxylic acid (703 mg, 6.16 mmol), 1-hydroxybenzotriazole monohydrochloride (1.26 g, 8.21 mmol), and 1-(3-dimethylaminopropyl)-3-ethylcarbodiimide hydrochloride (1.57 g, 8, 21 mmol) were added to the solution, and the resulting mixture was stirred overnight at 60° C. with heating. Saturated aqueous sodium hydrogencarbonate was added to the reaction mixture, and the resulting mixture was extracted with chloroform. The organic layer was dried over sodium sulfate, filtered, and concentrated, and the residue was purified by using automatic silica gel column chromatography (eluent, chloroform:methanol) to obtain N-(6-(2-((((1S,2S)-2-hydroxycyclopentyl)oxy)methyl)pyrimidin-5-yl)benzo[d]thiazol-2-yl)-3-oxocyclobutane-1-carboxamide (264 mg, yield 15%).

LCMS (LC-1): RT=1.03, m/z 439 $[M+H]^+$

1H-NMR ($CDCl_3$): δ (ppm) 9.00 (2H, s), 8.06-8.00 (1H, m), 7.89-7.77 (1H, m), 7.66-7.56 (1H, m), 4.97 (1H, d, J=14.4 Hz), 4.80 (1H, d, J=14.4 Hz), 4.31-4.11 (1H, m), 3.92-3.83 (1H, m), 3.70-3.56 (21H, m), 3.52-3.30 (3H, m), 2.17-1.99 (2H, m), 1.81-1.50 (4H, m)

Example b-02-01: 3-((R)-3-Fluoropyrrolidin-1-yl)-N-6-((((1S,2S)-2-hydroxycyclopentyl)oxy)methyl)pyrimidin-5-yl)benzo[d]thiazol-2-yl)cyclobutane-1-carboxamide

[Formula 91]

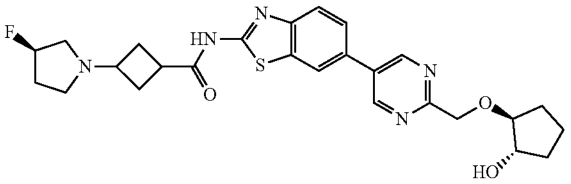

N-(6-(2-((((1S,2S)-2-Hydroxycyclopentyl)oxy)methyl)pyrimidin-5-yl)benzo[d]thiazol-2-yl)-3-oxocyclobutane-1-carboxamide (Intermediate B-2-2, 53.6 mg, 0.12 mmol) was dissolved in THF (2 mL), (R)-(−)-3-fluoropyrrolidine hydrochloride (23 mg, 0.18 mmol), and sodium triacetoxyborohydride (51.81 mg, 0.24 mmol) were added to the solution, and the resulting mixture was stirred at room temperature. After 1 hour, acetic acid (50 μL) was added to the reaction mixture, and the stirring was continued for 1 hour. After completion of the reaction, water, chloroform, and saturated aqueous sodium hydrogencarbonate were added to the reaction mixture, the resulting mixture was stirred, the organic layer was separated, and concentrated by nitrogen blow, and the residue was purified by using HPLC to obtain 3-[(3R)-3-fluoropyridin-1-yl]-N-[6-[2-[[(1S,2S)-2-hydroxycyclopentoxy]methyl]pyrimidin-5-yl]-1,3-benzothiazol-2-yl]cyclobutanecarboxamide (10.3 mg, yield 16%).

LCMS (LC-1): RT=1.06, m/z 512 $[M+H]^+$

1H-NMR ($CDCl_3$): δ (ppm) 9.00 (2H, s), 8.04-7.92 (1H, m), 7.83 (1H, brd, J=7.1 Hz), 7.63-7.53 (1H, m), 5.53-5.18 (2H, m), 5.10-4.79 (2H, m), 4.30-4.20 (1H, m), 3.93-3.82 (11H, m), 3.28-3.14 (3H, m), 2.78 (51H, brs), 2.35-2.23 (3H, m), 2.16-1.99 (3H, m), 1.62-1.48 (2H, m)

The following compounds mentioned in the following tables were synthesized by similar methods. In the following tables, the examples of which preparation methods should be referred to are mentioned in the column of "Reference Methods".

TABLE 6-1

| Example | Structure | Reference Methods | LCMS Data |
|---|---|---|---|
| b-02-02 | 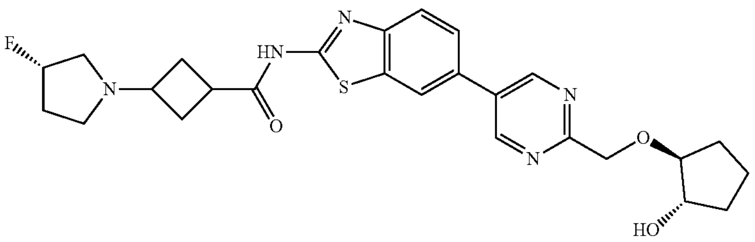 [SMILES: O=C(Nc1nc2ccc(-c3cnc(CO[C@H]4CCC[C@@H]4O)nc3)cc2s1)C1CC(N2CC[C@H](F)C2)C1] | Example b-02-01 | (LC-1): RT = 1.06, m/z 512 $[M + H]^+$ |

TABLE 6-1-continued
| Example | Structure | Reference Methods | LCMS Data |
| --- | --- | --- | --- |
| b-02-03 | 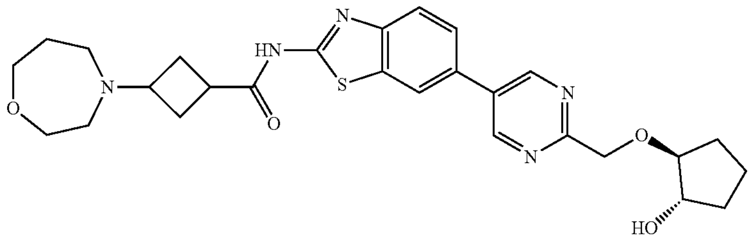 [SMILES: O=C(Nc1nc2ccc(-c3cnc(CO[C@H]4CCC[C@@H]4O)nc3)cc2s1)C1CC(N2CCCOCC2)C1] | Example b-02-01 | (LC-1): RT = 0.98, m/z 524 $[M + H]^+$ |
| b-02-04 | 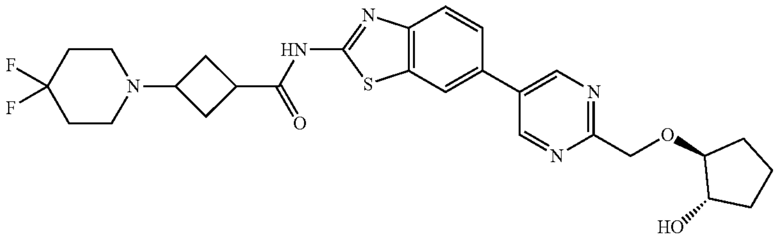 [SMILES: O=C(Nc1nc2ccc(-c3cnc(CO[C@H]4CCC[C@@H]4O)nc3)cc2s1)C1CC(N2CCC(F)(F)CC2)C1] | Example b-02-01 | (LC-1): RT = 1.29, m/z 544 $[M + H]^+$ |
| b-02-05 | 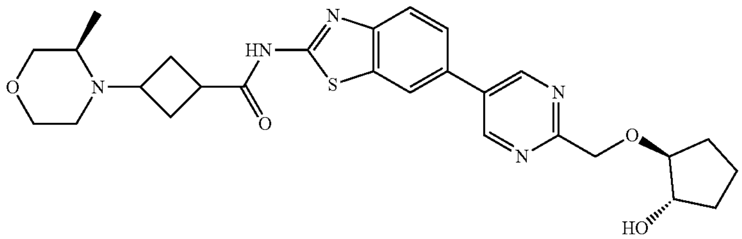 [SMILES: C[C@@H]1COCCN1C1CC(C(=O)Nc2nc3ccc(-c4cnc(CO[C@H]5CCC[C@@H]5O)nc4)cc3s2)C1] | Example b-02-01 | (LC-1): RT = 1.05, m/z 524 $[M + H]^+$ |
| b-02-06 | 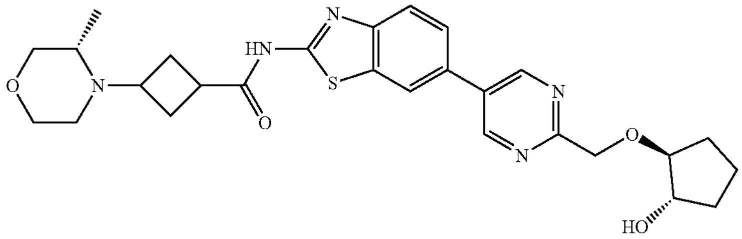 [SMILES: C[C@H]1COCCN1C1CC(C(=O)Nc2nc3ccc(-c4cnc(CO[C@H]5CCC[C@@H]5O)nc4)cc3s2)C1] | Example b-02-01 | (LC-1): RT = 1.05, m/z 524 $[M + H]^+$ |
| b-02-07 | 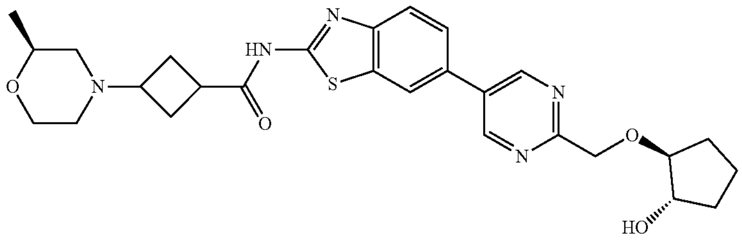 [SMILES: C[C@H]1CN(C2CC(C(=O)Nc3nc4ccc(-c5cnc(CO[C@H]6CCC[C@@H]6O)nc5)cc4s3)C2)CCO1] | Example b-02-01 | (LC-1): RT = 1.08, m/z 524 $[M + H]^+$ |
| b-02-08 | 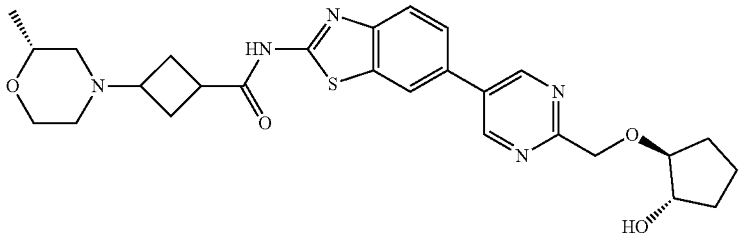 [SMILES: C[C@@H]1CN(C2CC(C(=O)Nc3nc4ccc(-c5cnc(CO[C@H]6CCC[C@@H]6O)nc5)cc4s3)C2)CCO1] | Example b-02-01 | (LC-1): RT = 1.08, m/z 524 $[M + H]^+$ |

TABLE 6-1-continued
| Example | Structure | Reference Methods | LCMS Data |
|---|---|---|---|
| b-02-09 | 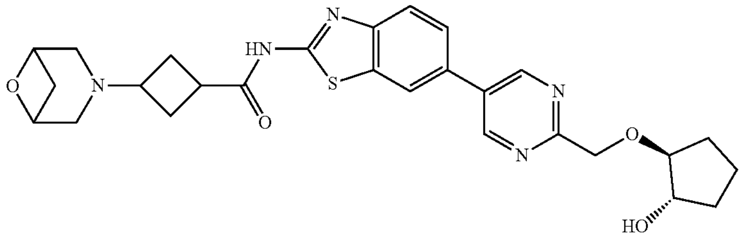 [SMILES: O=C(Nc1nc2ccc(-c3cnc(CO[C@H]4CCC[C@@H]4O)nc3)cc2s1)C1CC(N2CC3CC(C2)O3)C1] | Example b-02-01 | (LC-1): RT = 1.02, m/z 522 $[M + H]^+$ |
TABLE 6-2
| | | | |
|---|---|---|---|
| b-02-10 | 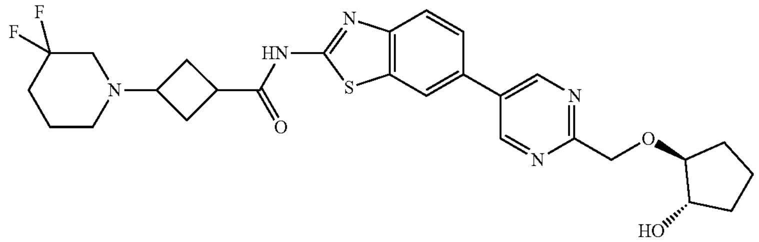 [SMILES: O=C(Nc1nc2ccc(-c3cnc(CO[C@H]4CCC[C@@H]4O)nc3)cc2s1)C1CC(N2CCCC(F)(F)C2)C1] | Example b-02-01 | (LC-1): RT = 1.29, m/z 544 $[M + H]^+$ |
| b-02-11 | 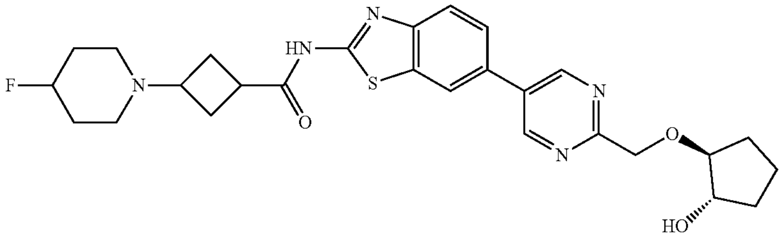 [SMILES: O=C(Nc1nc2ccc(-c3cnc(CO[C@H]4CCC[C@@H]4O)nc3)cc2s1)C1CC(N2CCC(F)CC2)C1] | Example b-02-01 | (LC-1): RT = 1.11, m/z 526 $[M + H]^+$ |
| b-02-12 | 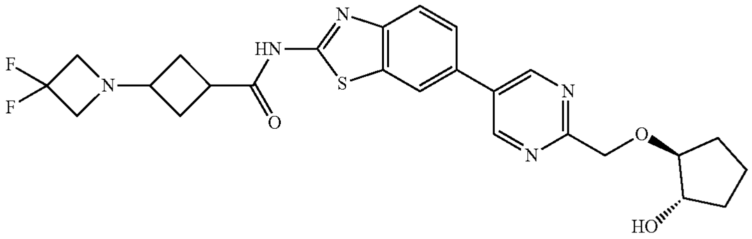 [SMILES: O=C(Nc1nc2ccc(-c3cnc(CO[C@H]4CCC[C@@H]4O)nc3)cc2s1)C1CC(N2CC(F)(F)C2)C1] | Example b-02-01 | (LC-1): RT = 1.17, m/z 516 $[M + H]^+$ |
| b-02-13 | 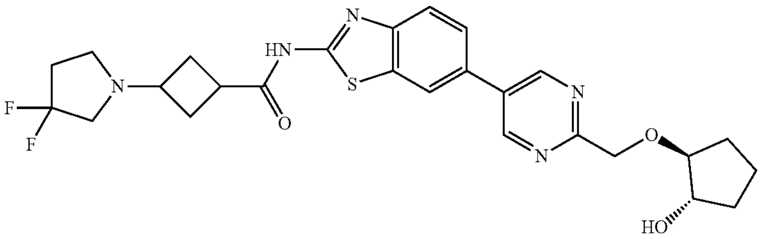 [SMILES: O=C(Nc1nc2ccc(-c3cnc(CO[C@H]4CCC[C@@H]4O)nc3)cc2s1)C1CC(N2CCC(F)(F)C2)C1] | Example b-02-01 | (LC-1): RT = 1.24, m/z 530 $[M + H]^+$ |
| b-02-14 | 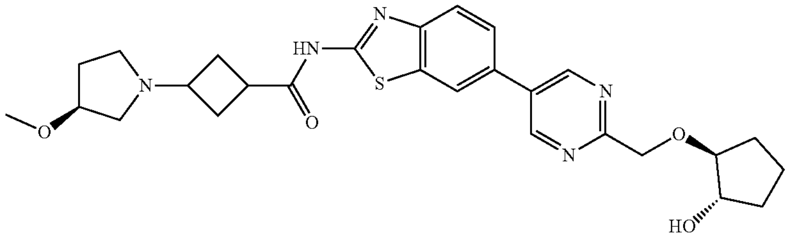 [SMILES: CO[C@H]1CCN(C2CC(C(=O)Nc3nc4ccc(-c5cnc(CO[C@H]6CCC[C@@H]6O)nc5)cc4s3)C2)C1] | Example b-02-01 | (LC-1): RT = 0.97, m/z 524 $[M + H]^+$ |

TABLE 6-2-continued
| | | | |
|---|---|---|---|
| b-02-15 | 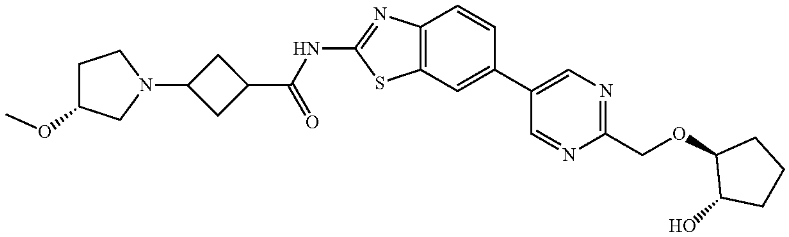 [SMILES: CO[C@@H]1CCN(C2CC(C(=O)Nc3nc4ccc(-c5cnc(CO[C@H]6CCC[C@@H]6O)nc5)cc4s3)C2)C1] | Example b-02-01 | (LC-1): RT = 0.97, m/z 524 $[M + H]^+$ |
| b-02-16 | 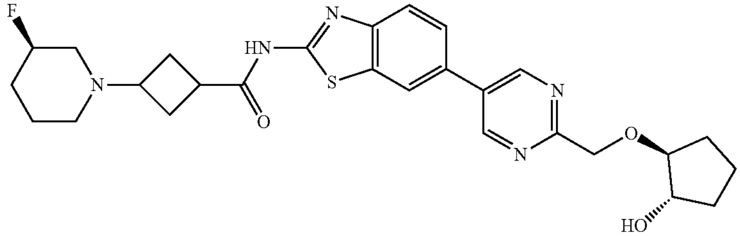 [SMILES: O=C(Nc1nc2ccc(-c3cnc(CO[C@H]4CCC[C@@H]4O)nc3)cc2s1)C1CC(N2CCC[C@@H](F)C2)C1] | Example b-02-01 | (LC-1): RT = 1.18, m/z 526 $[M + H]^+$ |
| b-02-17 | 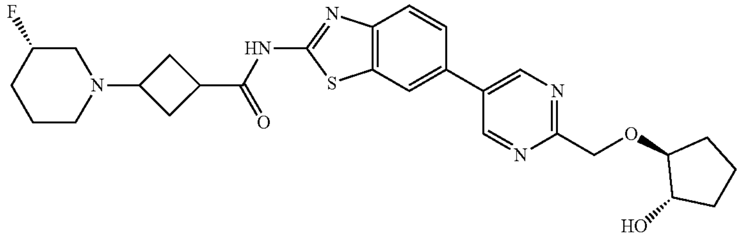 [SMILES: O=C(Nc1nc2ccc(-c3cnc(CO[C@H]4CCC[C@@H]4O)nc3)cc2s1)C1CC(N2CCC[C@H](F)C2)C1] | Example b-02-01 | (LC-1): RT = 1.17, m/z 526 $[M + H]^+$ |
| b-02-18 | 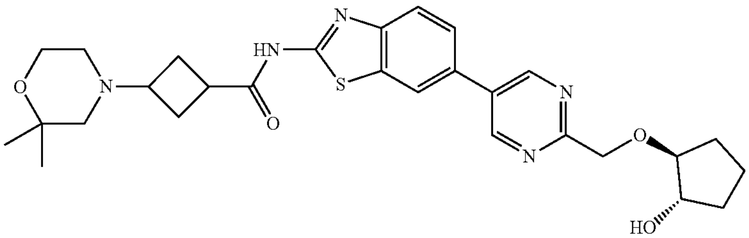 [SMILES: CC1(C)CN(C2CC(C(=O)Nc3nc4ccc(-c5cnc(CO[C@H]6CCC[C@@H]6O)nc5)cc4s3)C2)CCO1] | Example b-02-01 | (LC-1): RT = 1.23, m/z 538 $[M + H]^+$ |
TABLE 6-3
| | | | |
|---|---|---|---|
| b-02-19 | 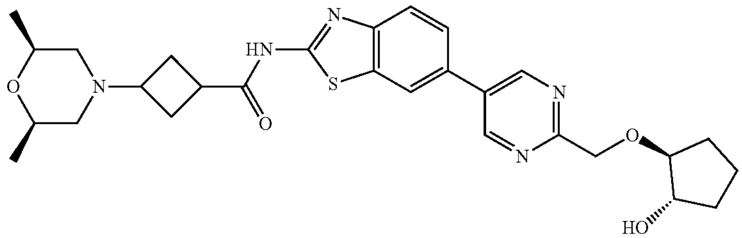 [SMILES: C[C@@H]1CN(C2CC(C(=O)Nc3nc4ccc(-c5cnc(CO[C@H]6CCC[C@@H]6O)nc5)cc4s3)C2)C[C@H](C)O1] | Example b-02-01 | (LC-1): RT = 1.15, m/z 538 $[M + H]^+$ |
| b-02-20 | 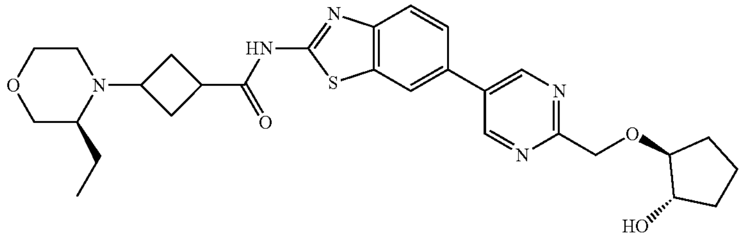 [SMILES: CC[C@H]1COCCN1C1CC(C(=O)Nc2nc3ccc(-c4cnc(CO[C@H]5CCC[C@@H]5O)nc4)cc3s2)C1] | Example b-02-01 | (LC-1): RT = 1.15, m/z 538 $[M + H]^+$ |

TABLE 6-3-continued
| | | | |
|---|---|---|---|
| b-02-21 | 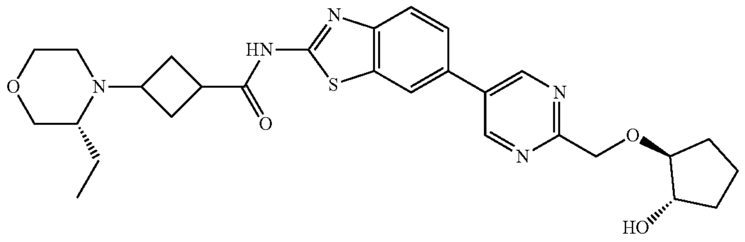 [SMILES: CC[C@@H]1COCCN1C1CC(C(=O)Nc2nc3ccc(-c4cnc(CO[C@H]5CCC[C@@H]5O)nc4)cc3s2)C1] | Example b-02-01 | (LC-1): RT = 1.15, m/z 538 [M + H]$^+$ |
| b-02-22 | 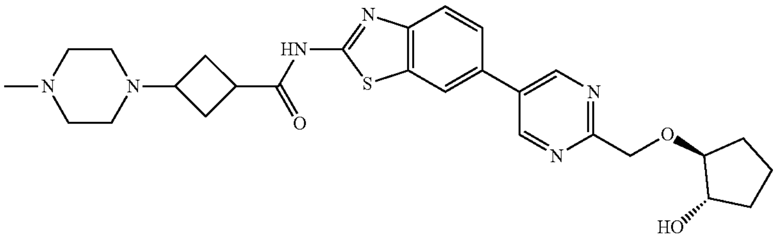 [SMILES: CN1CCN(C2CC(C(=O)Nc3nc4ccc(-c5cnc(CO[C@H]6CCC[C@@H]6O)nc5)cc4s3)C2)CC1] | Example b-02-01 | (LC-1): RT = 0.90, m/z 523 [M + H]$^+$ |
| b-02-23 | 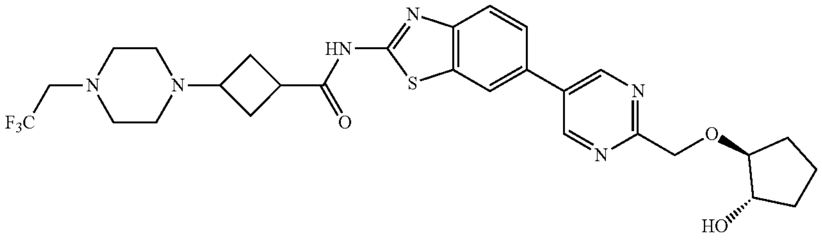 [SMILES: O=C(Nc1nc2ccc(-c3cnc(CO[C@H]4CCC[C@@H]4O)nc3)cc2s1)C1CC(N2CCN(CC(F)(F)F)CC2)C1] | Example b-02-01 | (LC-1): RT = 1.31, m/z 591 [M + H]$^+$ |
| b-02-24 | 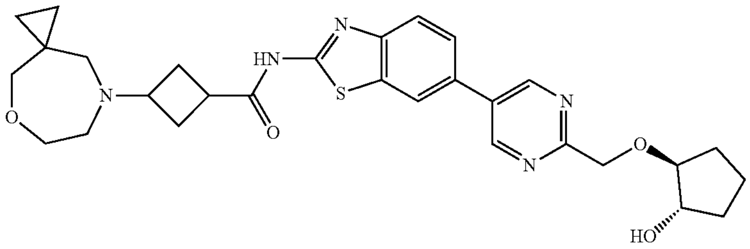 [SMILES: O=C(Nc1nc2ccc(-c3cnc(CO[C@H]4CCC[C@@H]4O)nc3)cc2s1)C1CC(N2CCOCC3(CC3)C2)C1] | Example b-02-01 | (LC-1): RT = 1.09 m/z 550 [M + H]$^+$ |
| b-02-25 | 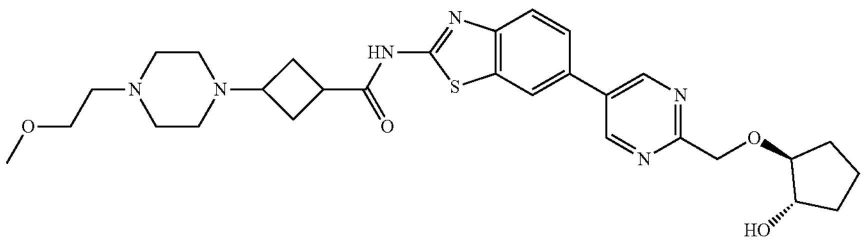 [SMILES: COCCN1CCN(C2CC(C(=O)Nc3nc4ccc(-c5cnc(CO[C@H]6CCC[C@@H]6O)nc5)cc4s3)C2)CC1] | Example b-02-01 | (LC-1): RT = 0.96, m/z 567 [M + H]$^+$ |
| b-02-26 | 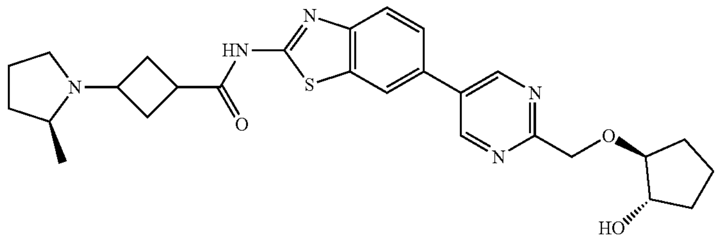 [SMILES: C[C@H]1CCCN1C1CC(C(=O)Nc2nc3ccc(-c4cnc(CO[C@H]5CCC[C@@H]5O)nc4)cc3s2)C1] | Example b-02-01 | (LC-1): RT = 0.93, m/z 508 [M + H]$^+$ |

TABLE 6-3-continued
| | | | |
|---|---|---|---|
| b-02-27 | 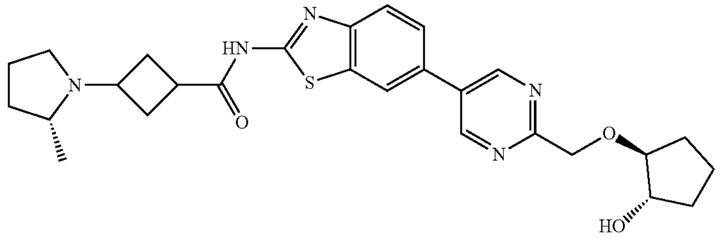 [SMILES: C[C@@H]1CCCN1C1CC(C(=O)Nc2nc3ccc(-c4cnc(CO[C@H]5CCC[C@@H]5O)nc4)cc3s2)C1] | Example b-02-01 | (LC-1): RT = 0.93, m/z 508 [M + H]+ |
TABLE 6-4
| | | | |
|---|---|---|---|
| b-02-28 | 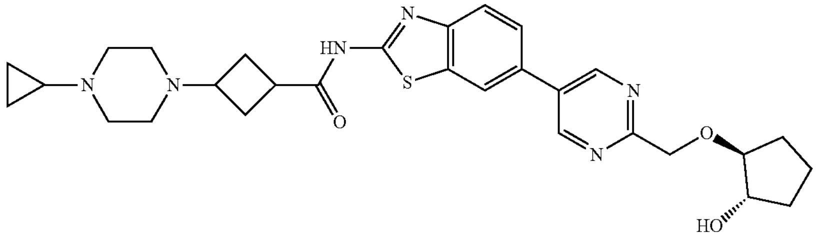 [SMILES: O=C(Nc1nc2ccc(-c3cnc(CO[C@H]4CCC[C@@H]4O)nc3)cc2s1)C1CC(N2CCN(C3CC3)CC2)C1] | Example b-02-01 | (LC-1): RT = 1.09, m/z 549 [M + H]+ |
| b-02-29 | 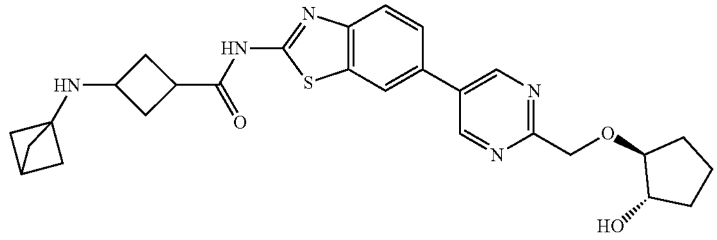 [SMILES: O=C(Nc1nc2ccc(-c3cnc(CO[C@H]4CCC[C@@H]4O)nc3)cc2s1)C1CC(NC23CC(C2)C3)C1] | Example b-02-01 | (LC-1): RT = 1.21, m/z 506 [M + H]+ |
| b-02-30 | 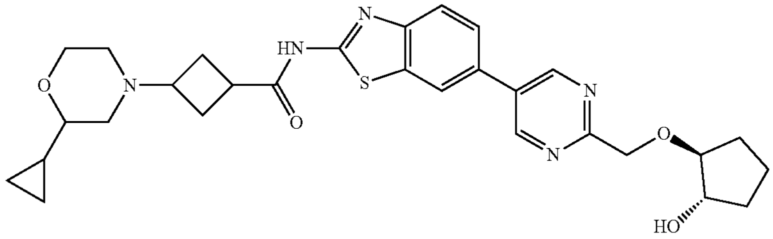 [SMILES: O=C(Nc1nc2ccc(-c3cnc(CO[C@H]4CCC[C@@H]4O)nc3)cc2s1)C1CC(N2CCOC(C3CC3)C2)C1] | Example b-02-01 | (LC-1): RT = 1.18, m/z 550 [M + H]+ |
| b-02-31 | 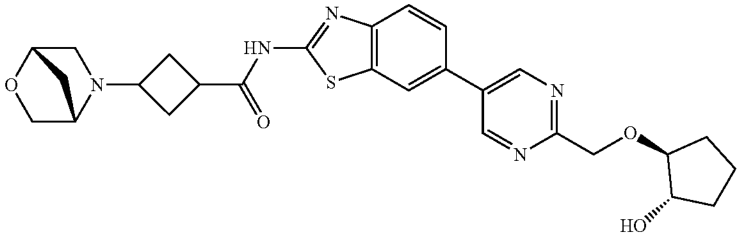 [SMILES: O=C(Nc1nc2ccc(-c3cnc(CO[C@H]4CCC[C@@H]4O)nc3)cc2s1)C1CC(N2C[C@@H]3C[C@H]2CO3)C1] | Example b-02-01 | (LC-1): RT = 0.95, m/z 522 [M + H]+ |
| b-02-32 - | 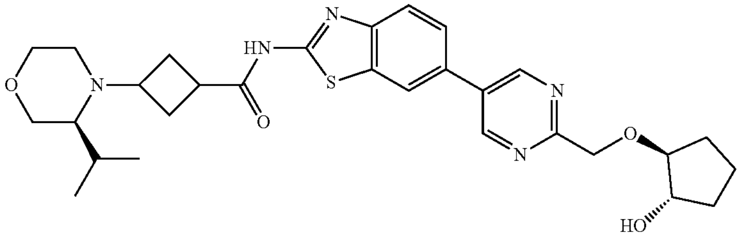 [SMILES: CC(C)[C@H]1COCCN1C1CC(C(=O)Nc2nc3ccc(-c4cnc(CO[C@H]5CCC[C@@H]5O)nc4)cc3s2)C1] | Example b-02-01 | (LC-1): RT = 1.26, m/z 552 [M + H]+ |

TABLE 6-4-continued
| | | | |
|---|---|---|---|
| b-02-33 | 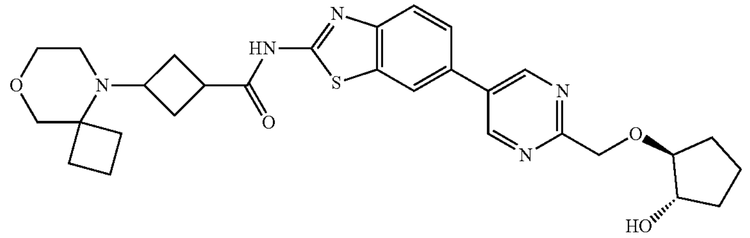 [SMILES: O=C(Nc1nc2ccc(-c3cnc(CO[C@H]4CCC[C@@H]4O)nc3)cc2s1)C1CC(N2CCOCC23CCC3)C1] | Example b-02-01 | (LC-1): RT = 1.15, m/z 550 $[M + H]^+$ |
| b-02-34 | 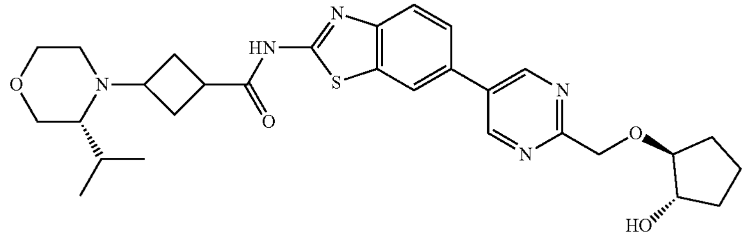 [SMILES: CC(C)[C@@H]1COCCN1C1CC(C(=O)Nc2nc3ccc(-c4cnc(CO[C@H]5CCC[C@@H]5O)nc4)cc3s2)C1] | Example b-02-01 | (LC-1): RT = 1.26, m/z 552 $[M + H]^+$ |
| b-02-35 | 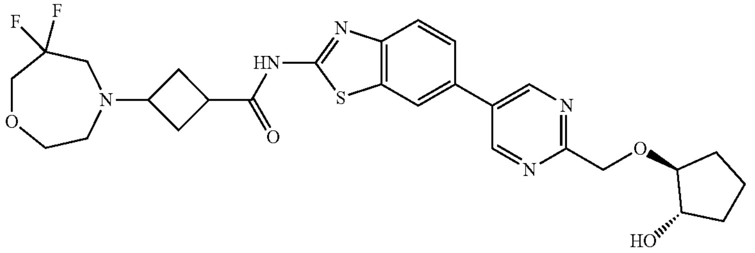 [SMILES: O=C(Nc1nc2ccc(-c3cnc(CO[C@H]4CCC[C@@H]4O)nc3)cc2s1)C1CC(N2CCOCC(F)(F)C2)C1] | Example b-02-01 | (LC-1): RT = 1.31, m/z 560 $[M + H]^+$ |
| b-02-36 | 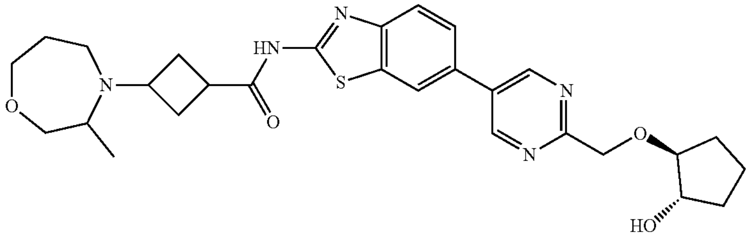 [SMILES: CC1COCCCN1C1CC(C(=O)Nc2nc3ccc(-c4cnc(CO[C@H]5CCC[C@@H]5O)nc4)cc3s2)C1] | Example b-02-01 | (LC-1): RT = 0.98, m/z 538 $[M + H]^+$ |
TABLE 6-5
| | | | |
|---|---|---|---|
| b-02-37 | 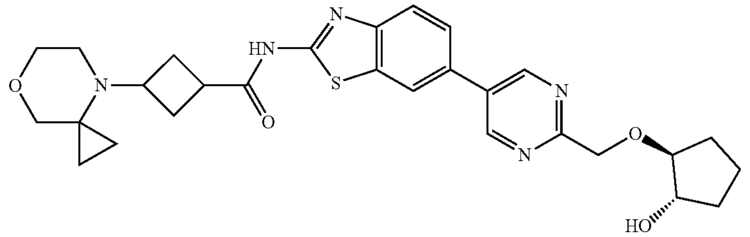 [SMILES: O=C(Nc1nc2ccc(-c3cnc(CO[C@H]4CCC[C@@H]4O)nc3)cc2s1)C1CC(N2CCOCC23CC3)C1] | Example b-02-01 | (LC-1): RT = 1.08, m/z 536 $[M + H]^+$ |
| b-02-38 | 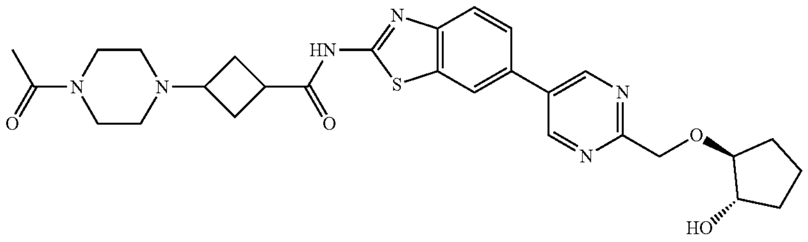 [SMILES: CC(=O)N1CCN(C2CC(C(=O)Nc3nc4ccc(-c5cnc(CO[C@H]6CCC[C@@H]6O)nc5)cc4s3)C2)CC1] | Example b-02-01 | (LC-1): RT = 0.96, m/z 551 $[M + H]^+$ |

TABLE 6-5-continued
| | | | |
|---|---|---|---|
| b-02-39 | 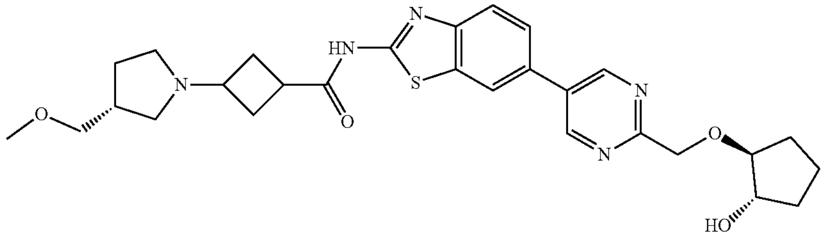 [SMILES: COC[C@@H]1CCN(C2CC(C(=O)Nc3nc4ccc(-c5cnc(CO[C@H]6CCC[C@@H]6O)nc5)cc4s3)C2)C1] | Example b-02-01 | (LC-1): RT = 0.97, m/z 538 [M + H]+ |
| b-02-40 | 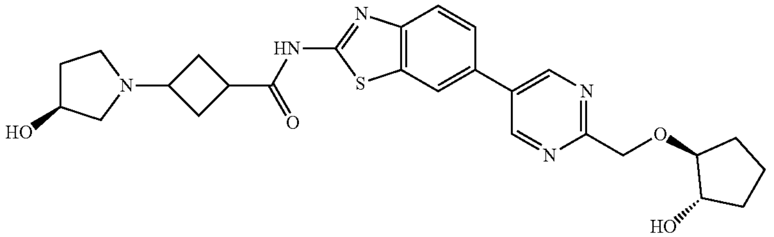 [SMILES: O=C(Nc1nc2ccc(-c3cnc(CO[C@H]4CCC[C@@H]4O)nc3)cc2s1)C1CC(N2CC[C@H](O)C2)C1] | Example b-02-01 | (LC-1): RT = 0.87, m/z 510 [M + H]+ |
| b-02-41 - | 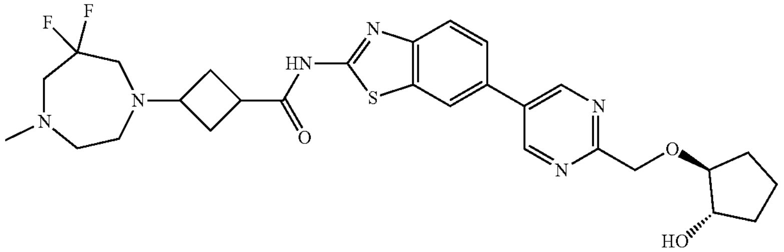 [SMILES: CN1CCN(C2CC(C(=O)Nc3nc4ccc(-c5cnc(CO[C@H]6CCC[C@@H]6O)nc5)cc4s3)C2)CC(F)(F)C1] | Example b-02-01 | (LC-1): RT = 1.27, m/z 573 [M + H]+ |
| b-02-42 | 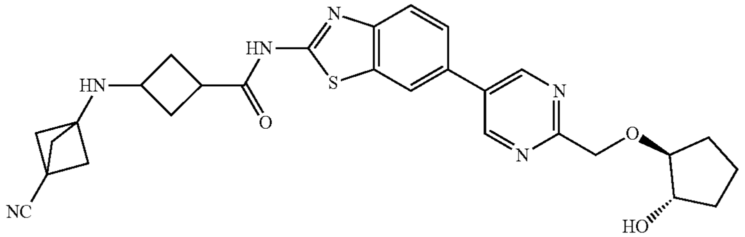 [SMILES: N#CC12CC(NC3CC(C(=O)Nc4nc5ccc(-c6cnc(CO[C@H]7CCC[C@@H]7O)nc6)cc5s4)C3)(C1)C2] | Example b-02-01 | (LC-1): RT = 1.13, m/z 531 [M + H]+ |
| b-02-43 | 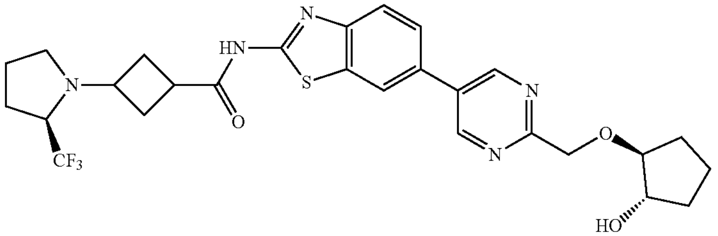 [SMILES: O=C(Nc1nc2ccc(-c3cnc(CO[C@H]4CCC[C@@H]4O)nc3)cc2s1)C1CC(N2CCC[C@@H]2C(F)(F)F)C1] | Example b-02-01 | (LC-1): RT = 1.46, m/z 562 [M + H]+ |
| b-02-44 | 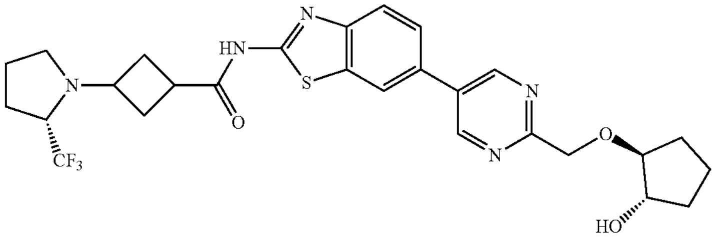 | Example b-02-01 | (LC-1): RT = 1.46, m/z 562 [M + H]+ |

TABLE 6-5-continued
| | | | |
|---|---|---|---|
| b-02-45 | 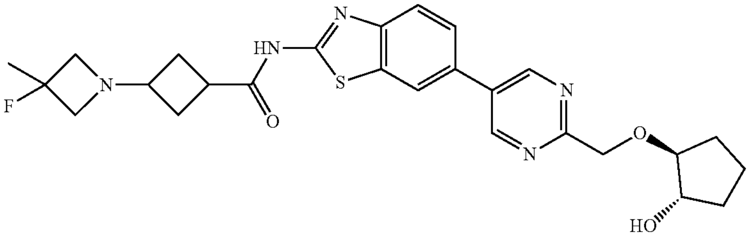 [SMILES: CC1(F)CN(C2CC(C(=O)Nc3nc4ccc(-c5cnc(CO[C@H]6CCC[C@@H]6O)nc5)cc4s3)C2)C1] | Example b-02-01 | (LC-1): RT = 1.16, m/z 512 [M + H]+ |
TABLE 6-6
| | | | |
|---|---|---|---|
| b-02-46 | 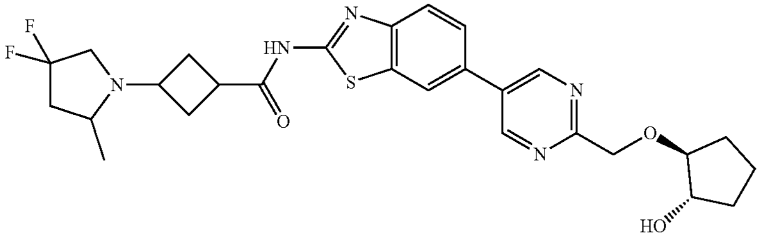 [SMILES: CC1CC(F)(F)CN1C1CC(C(=O)Nc2nc3ccc(-c4cnc(CO[C@H]5CCC[C@@H]5O)nc4)cc3s2)C1] | Example b-02-01 | (LC-1): RT = 1.32, m/z 544 [M + H]+ |
| b-02-47 | 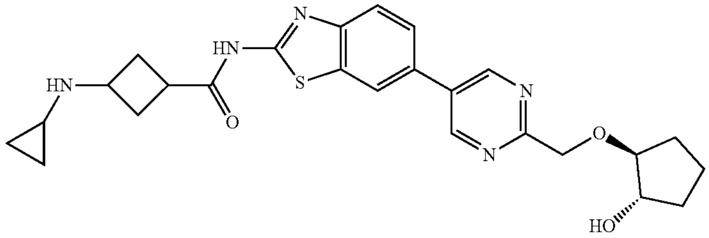 [SMILES: O=C(Nc1nc2ccc(-c3cnc(CO[C@H]4CCC[C@@H]4O)nc3)cc2s1)C1CC(NC2CC2)C1] | Example b-02-01 | (LC-1): RT = 1.03, m/z 480 [M + H]+ |
| b-02-48 | 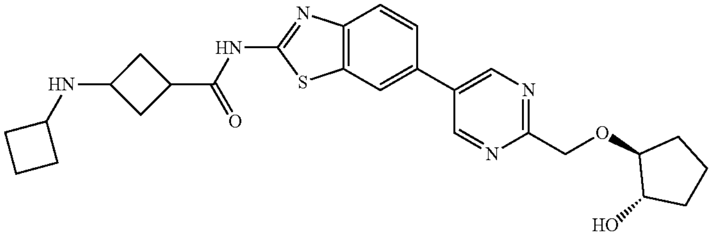 [SMILES: O=C(Nc1nc2ccc(-c3cnc(CO[C@H]4CCC[C@@H]4O)nc3)cc2s1)C1CC(NC2CCC2)C1] | Example b-02-01 | (LC-1): RT = 0.96, m/z 494 [M + H]+ |
| b-02-49 - | 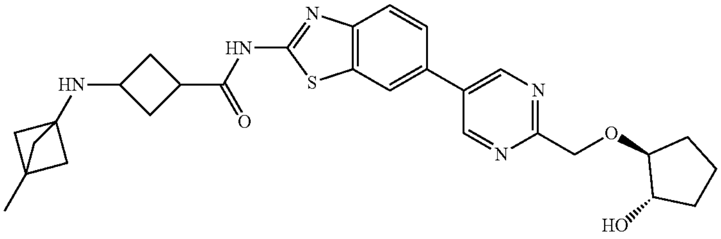 [SMILES: CC12CC(NC3CC(C(=O)Nc4nc5ccc(-c6cnc(CO[C@H]7CCC[C@@H]7O)nc6)cc5s4)C3)(C1)C2] | Example b-02-01 | (LC-1): RT = 1.31, m/z 520 [M + H]+ |
| b-02-50 | 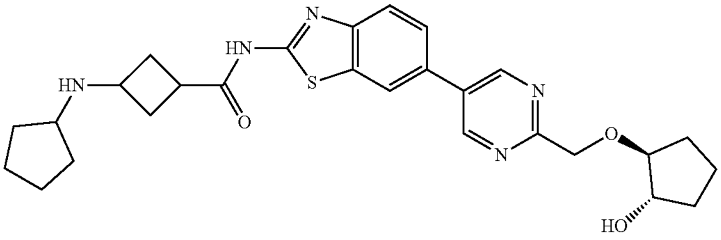 [SMILES: O=C(Nc1nc2ccc(-c3cnc(CO[C@H]4CCC[C@@H]4O)nc3)cc2s1)C1CC(NC2CCCC2)C1] | Example b-02-01 | (LC-1): RT = 0.97, m/z 508 [M + H]+ |

TABLE 6-6-continued
| | | | |
|---|---|---|---|
| b-02-51 | 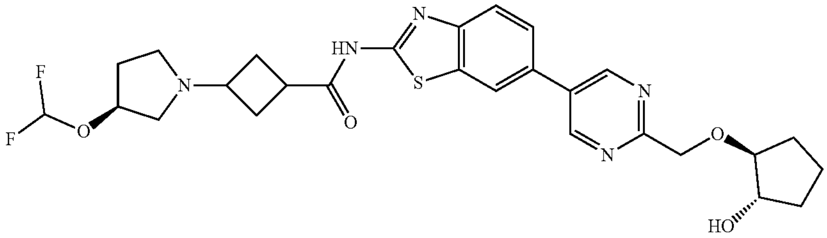 [SMILES: O=C(Nc1nc2ccc(-c3cnc(CO[C@H]4CCC[C@@H]4O)nc3)cc2s1)C1CC(N2CC[C@H](OC(F)F)C2)C1] | Example b-02-01 | (LC-1): RT = 1.21, m/z 560 $[M + H]^+$ |
| b-02-52 | 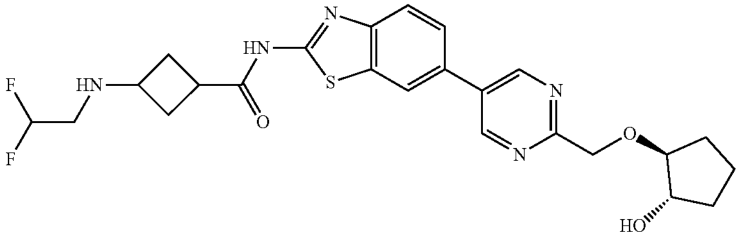 [SMILES: O=C(Nc1nc2ccc(-c3cnc(CO[C@H]4CCC[C@@H]4O)nc3)cc2s1)C1CC(NCC(F)F)C1] | Example b-02-01 | (LC-1): RT = 1.10, m/z 504 $[M + H]^+$ |
| b-02-53 | 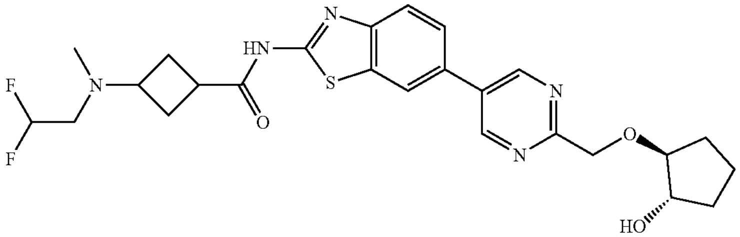 [SMILES: CN(CC(F)F)C1CC(C(=O)Nc2nc3ccc(-c4cnc(CO[C@H]5CCC[C@@H]5O)nc4)cc3s2)C1] | Example b-02-01 | (LC-1): RT = 1.23, m/z 518 $[M + H]^+$ |
| b-02-54 | 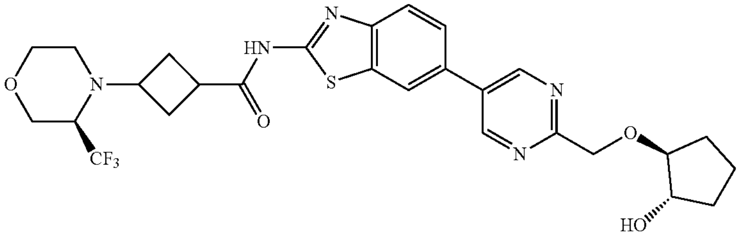 [SMILES: O=C(Nc1nc2ccc(-c3cnc(CO[C@H]4CCC[C@@H]4O)nc3)cc2s1)C1CC(N2CCOC[C@@H]2C(F)(F)F)C1] | Example b-02-01 | (LC-1): RT = 1.35, m/z 578 $[M + H]^+$ |
TABLE 6-7
| | | | |
|---|---|---|---|
| b-02-55 | 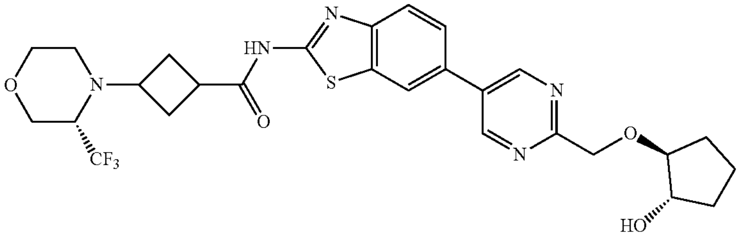 [SMILES: O=C(Nc1nc2ccc(-c3cnc(CO[C@H]4CCC[C@@H]4O)nc3)cc2s1)C1CC(N2CCOC[C@H]2C(F)(F)F)C1] | Example b-02-01 | (LC-1): RT = 1.36, m/z 578 $[M + H]^+$ |
| b-02-56 | 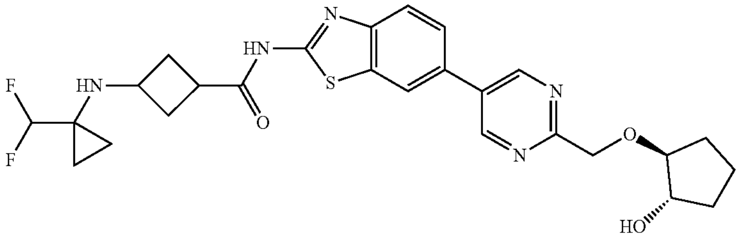 [SMILES: O=C(Nc1nc2ccc(-c3cnc(CO[C@H]4CCC[C@@H]4O)nc3)cc2s1)C1CC(NC2(C(F)F)CC2)C1] | Example b-02-01 | (LC-1): RT = 1.26, m/z 530 $[M + H]^+$ |

TABLE 6-7-continued
| | | | |
|---|---|---|---|
| b-02-57 | 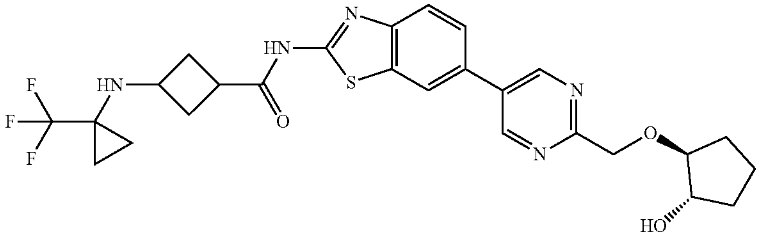 [SMILES: O=C(Nc1nc2ccc(-c3cnc(CO[C@H]4CCC[C@@H]4O)nc3)cc2s1)C1CC(NC2(C(F)(F)F)CC2)C1] | Example b-02-01 | (LC-1): RT = 1.43, m/z 548 [M + H]+ |
| b-02-58 | 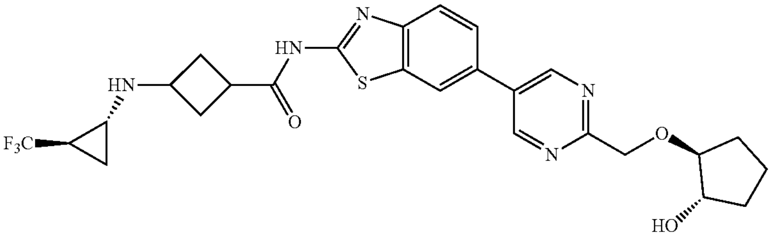 [SMILES: O=C(Nc1nc2ccc(-c3cnc(CO[C@H]4CCC[C@@H]4O)nc3)cc2s1)C1CC(N[C@@H]2C[C@H]2C(F)(F)F)C1] | Example b-02-01 | (LC-1): RT = 1.31, m/z 548 [M + H]+ |
| b-02-59 | 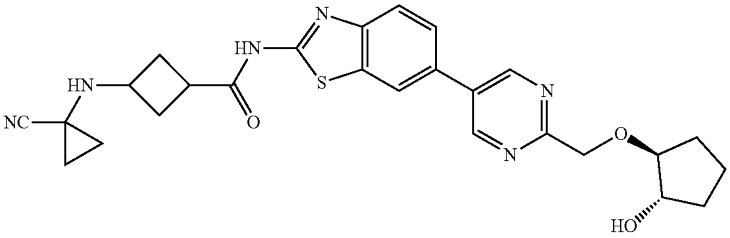 [SMILES: N#CC1(NC2CC(C(=O)Nc3nc4ccc(-c5cnc(CO[C@H]6CCC[C@@H]6O)nc5)cc4s3)C2)CC1] | Example b-02-01 | (LC-1): RT = 1.12, m/z 505 [M + H]+ |
| b-02-60 | 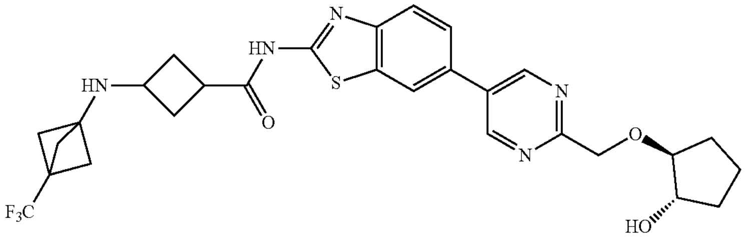 [SMILES: O=C(Nc1nc2ccc(-c3cnc(CO[C@H]4CCC[C@@H]4O)nc3)cc2s1)C1CC(NC23CC(C(F)(F)F)(C2)C3)C1] | Example b-02-01 | (LC-1): RT = 1.40, m/z 574 [M + H]+ |
| b-02-61 | 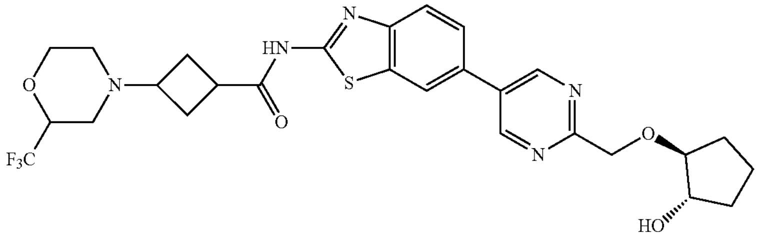 [SMILES: O=C(Nc1nc2ccc(-c3cnc(CO[C@H]4CCC[C@@H]4O)nc3)cc2s1)C1CC(N2CCOC(C(F)(F)F)C2)C1] | Example b-02-01 | (LC-1): RT = 1.35, m/z 578 [M + H]+ |
| b-02-62 | 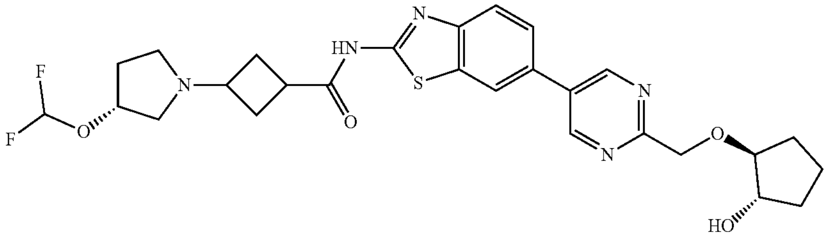 [SMILES: O=C(Nc1nc2ccc(-c3cnc(CO[C@H]4CCC[C@@H]4O)nc3)cc2s1)C1CC(N2CC[C@@H](OC(F)F)C2)C1] | Example b-02-01 | (LC-1): RT = 1.20, m/z 560 [M + H]+ |

TABLE 6-7-continued
| | | | |
|---|---|---|---|
| b-02-63 | 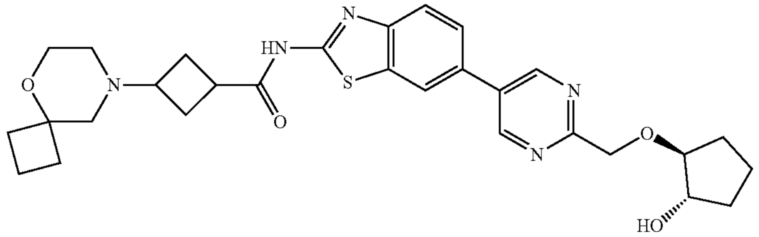 [SMILES: O=C(Nc1nc2ccc(-c3cnc(CO[C@H]4CCC[C@@H]4O)nc3)cc2s1)C1CC(N2CCOC3(CCC3)C2)C1] | Example b-02-01 | (LC-1): RT = 1.25, m/z 550 [M + H]+ |
TABLE 6-8
| | | | |
|---|---|---|---|
| b-02-64 | 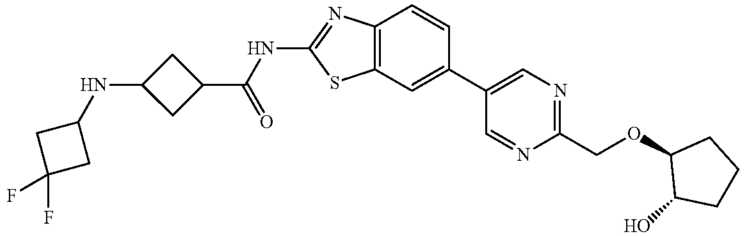 [SMILES: O=C(Nc1nc2ccc(-c3cnc(CO[C@H]4CCC[C@@H]4O)nc3)cc2s1)C1CC(NC2CC(F)(F)C2)C1] | Example b-02-01 | (LC-1): RT = 1.18, m/z 530 [M + H]+ |
| b-02-65 | 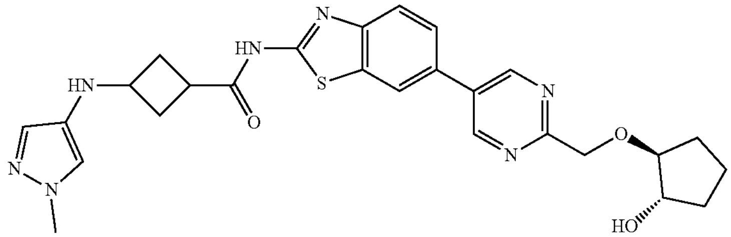 [SMILES: Cn1cc(NC2CC(C(=O)Nc3nc4ccc(-c5cnc(CO[C@H]6CCC[C@@H]6O)nc5)cc4s3)C2)cn1] | Example b-02-01 | (LC-1): RT = 0.99, m/z 520 [M + H]+ |
| b-02-66 | 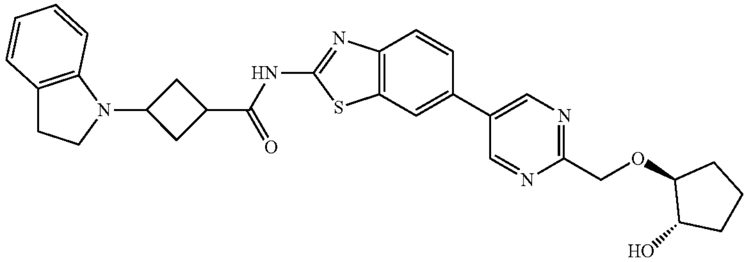 [SMILES: O=C(Nc1nc2ccc(-c3cnc(CO[C@H]4CCC[C@@H]4O)nc3)cc2s1)C1CC(N2CCc3ccccc32)C1] | Example b-02-01 | (LC-1): RT = 1.56, m/z 542 [M + H]+ |
| b-02-67 | 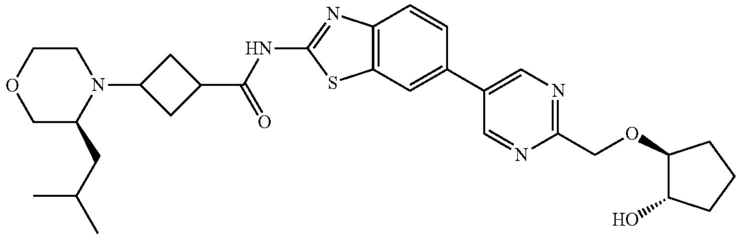 [SMILES: CC(C)C[C@H]1COCCN1C1CC(C(=O)Nc2nc3ccc(-c4cnc(CO[C@H]5CCC[C@@H]5O)nc4)cc3s2)C1] | Example b-02-01 | (LC-1): RT = 1.36, m/z 566 [M + H]+ |
| b-02-68 | 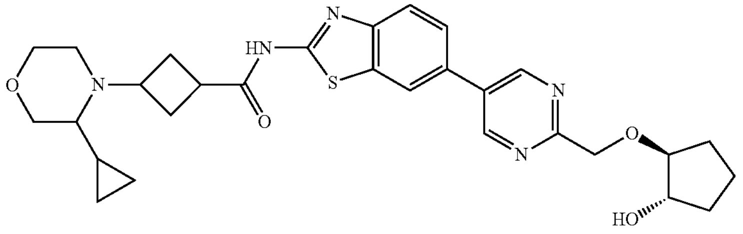 [SMILES: O=C(Nc1nc2ccc(-c3cnc(CO[C@H]4CCC[C@@H]4O)nc3)cc2s1)C1CC(N2CCOCC2C2CC2)C1] | Example b-02-01 | (LC-1): RT = 1.16, m/z 550 [M + H]+ |

TABLE 6-8-continued
| | | | |
|---|---|---|---|
| b-02-69 | 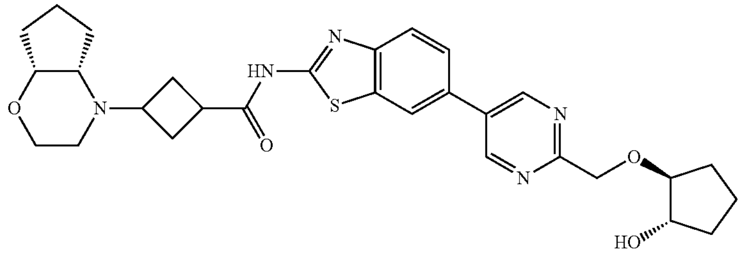 [SMILES: O=C(Nc1nc2ccc(-c3cnc(CO[C@H]4CCC[C@@H]4O)nc3)cc2s1)C1CC(N2CCO[C@@H]3CCC[C@@H]32)C1] | Example b-02-01 | (LC-1): RT = 1.17, m/z 550 [M + H]+ |
| b-02-70 | 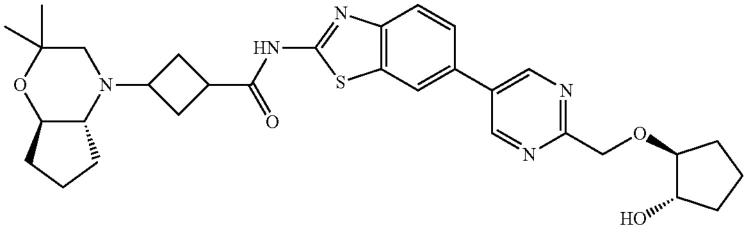 [SMILES: CC1(C)CN(C2CC(C(=O)Nc3nc4ccc(-c5cnc(CO[C@H]6CCC[C@@H]6O)nc5)cc4s3)C2)[C@@H]2CCC[C@H]2O1] | Example b-02-01 | (LC-1): RT = 1.37, m/z 578 [M + H]+ |
| b-02-71 | 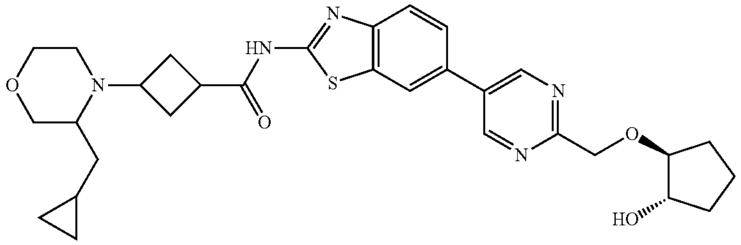 [SMILES: O=C(Nc1nc2ccc(-c3cnc(CO[C@H]4CCC[C@@H]4O)nc3)cc2s1)C1CC(N2CCOCC2CC2CC2)C1] | Example b-02-01 | (LC-1): RT = 1.29, m/z 564 [M + H]+ |
| b-02-72 | 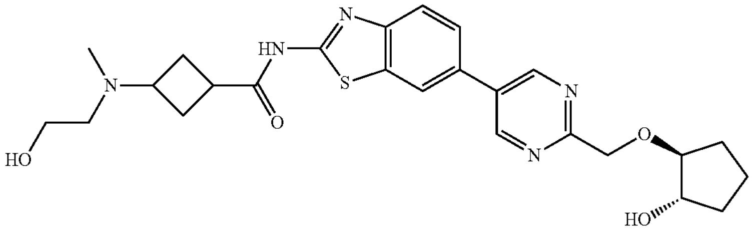 [SMILES: CN(CCO)C1CC(C(=O)Nc2nc3ccc(-c4cnc(CO[C@H]5CCC[C@@H]5O)nc4)cc3s2)C1] | Example b-02-01 | (LC-1): RT = 0.87, m/z 498 [M + H]+ |
TABLE 6-9
| | | | |
|---|---|---|---|
| b-02-73 | 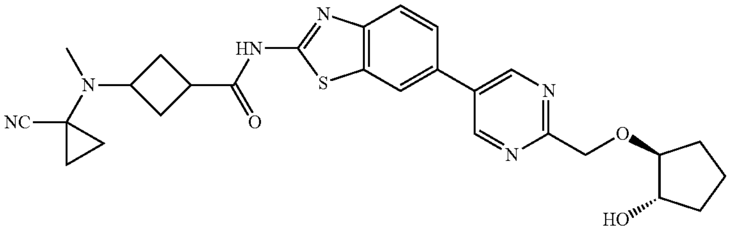 [SMILES: CN(C1CC(C(=O)Nc2nc3ccc(-c4cnc(CO[C@H]5CCC[C@@H]5O)nc4)cc3s2)C1)C1(C#N)CC1] | Example b-02-01 | (LC-1): RT = 1.26, m/z 519 [M + H]+ |
| b-02-74 | 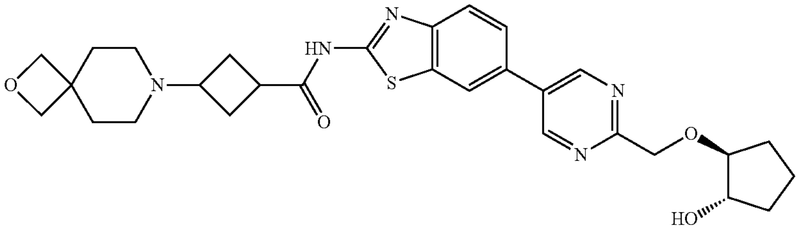 [SMILES: O=C(Nc1nc2ccc(-c3cnc(CO[C@H]4CCC[C@@H]4O)nc3)cc2s1)C1CC(N2CCC3(CC2)COC3)C1] | Example b-02-01 | (LC-1): RT = 0.97, m/z 550 [M + H]+ |

TABLE 6-9-continued
| | | | |
|---|---|---|---|
| b-02-75 | 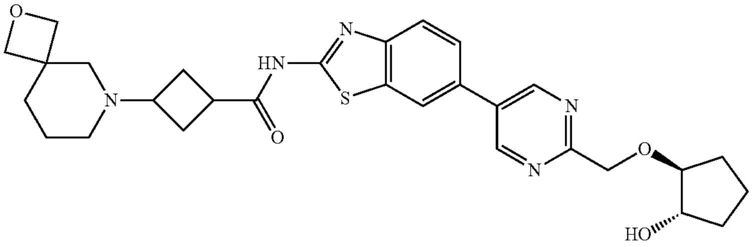 [SMILES: O=C(Nc1nc2ccc(-c3cnc(CO[C@H]4CCC[C@@H]4O)nc3)cc2s1)C1CC(N2CCCC3(COC3)C2)C1] | Example b-02-01 | (LC-1): RT = 1.09, m/z 550 $[M + H]^+$ |
| b-02-76 | 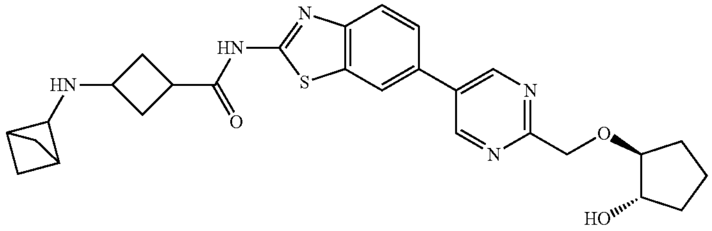 [SMILES: O=C(Nc1nc2ccc(-c3cnc(CO[C@H]4CCC[C@@H]4O)nc3)cc2s1)C1CC(NC2C3CC2C3)C1] | Example b-02-01 | (LC-1): RT = 1.23, m/z 506 $[M + H]^+$ |
| b-02-77 | 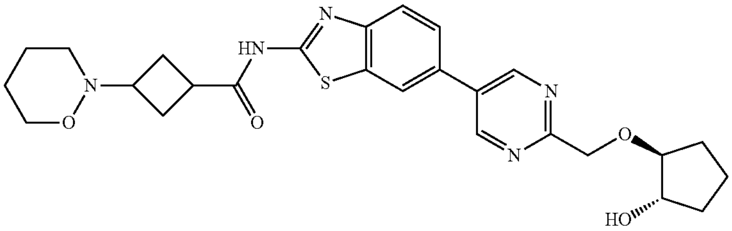 [SMILES: O=C(Nc1nc2ccc(-c3cnc(CO[C@H]4CCC[C@@H]4O)nc3)cc2s1)C1CC(N2CCCCO2)C1] | Example b-02-01 | (LC-1): RT = 1.36, m/z 510 $[M + H]^+$ |
| b-02-78 | 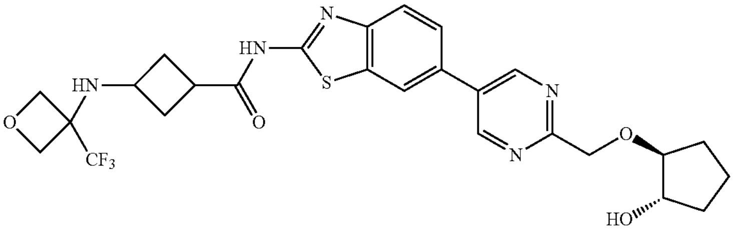 [SMILES: O=C(Nc1nc2ccc(-c3cnc(CO[C@H]4CCC[C@@H]4O)nc3)cc2s1)C1CC(NC2(C(F)(F)F)COC2)C1] | Example b-02-01 | (LC-1): RT = 1.21, m/z 564 $[M + H]^+$ |
| b-02-79 | 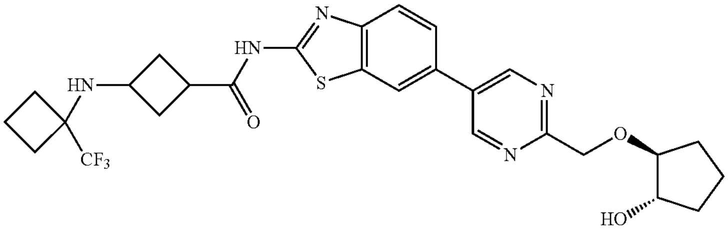 [SMILES: O=C(Nc1nc2ccc(-c3cnc(CO[C@H]4CCC[C@@H]4O)nc3)cc2s1)C1CC(NC2(C(F)(F)F)CCC2)C1] | Example b-02-01 | (LC-1): RT = 1.47, m/z 562 $[M + H]^+$ |
| b-02-80 | 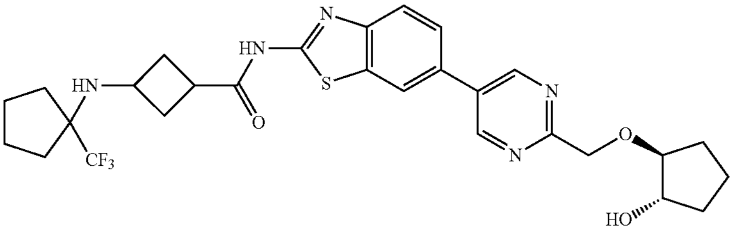 [SMILES: O=C(Nc1nc2ccc(-c3cnc(CO[C@H]4CCC[C@@H]4O)nc3)cc2s1)C1CC(NC2(C(F)(F)F)CCCC2)C1] | Example b-02-01 | (LC-1): RT = 1.59, m/z 576 $[M + H]^+$ |

TABLE 6-9-continued
| | | | |
|---|---|---|---|
| b-02-81 | 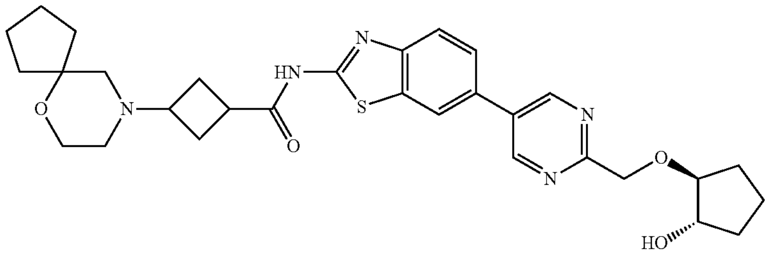 [SMILES: O=C(Nc1nc2ccc(-c3cnc(CO[C@H]4CCC[C@@H]4O)nc3)cc2s1)C1CC(N2CCOC3(CCCC3)C2)C1] | Example b-02-01 | (LC-1): RT = 1.35, m/z 564 $[M + H]^+$ |
TABLE 6-10
| | | | |
|---|---|---|---|
| b-02-82 | 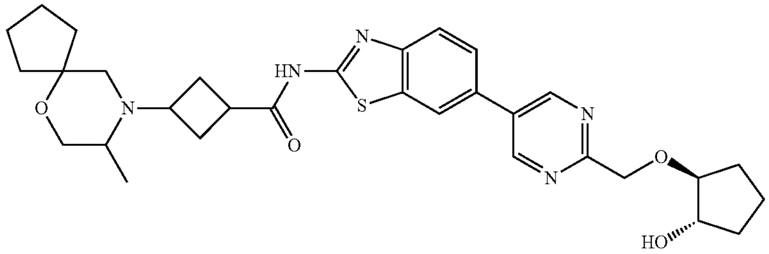 [SMILES: CC1COC2(CCCC2)CN1C1CC(C(=O)Nc2nc3ccc(-c4cnc(CO[C@H]5CCC[C@@H]5O)nc4)cc3s2)C1] | Example b-02-01 | (LC-1): RT = 1.41, m/z 578 $[M + H]^+$ |
| b-02-83 | 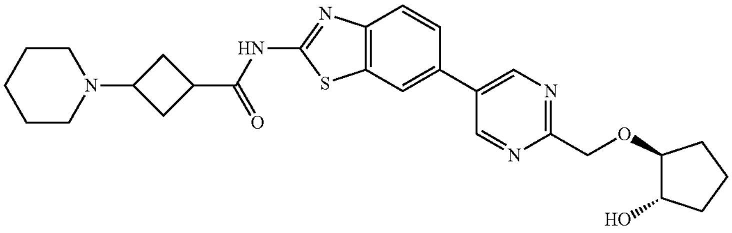 | Example b-02-01 | (LC-1): RT = 0.96, m/z 508 $[M + H]^+$ |
| b-02-84 | 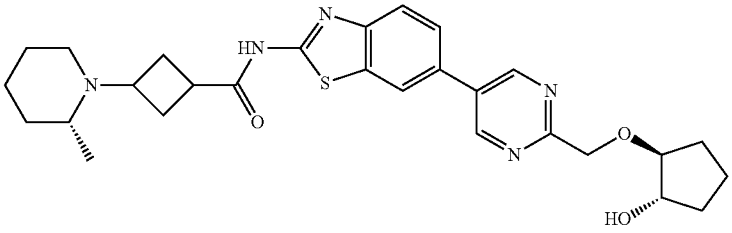 | Example b-02-01 | (LC-1): RT = 0.97, m/z 522 $[M + H]^+$ |
| b-02-85 | 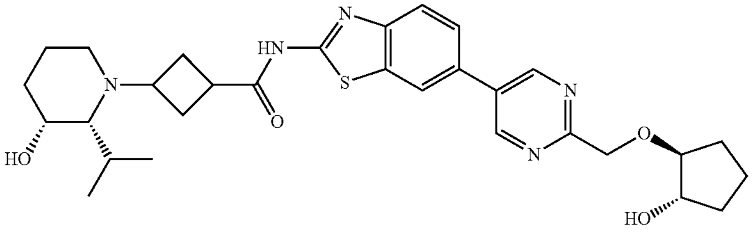 [SMILES: CC(C)[C@@H]1[C@H](O)CCCN1C1CC(C(=O)Nc2nc3ccc(-c4cnc(CO[C@H]5CCC[C@@H]5O)nc4)cc3s2)C1] | Example b-02-01 | (LC-1): RT = 1.01, m/z 566 $[M + H]^+$ |
| b-02-86 | 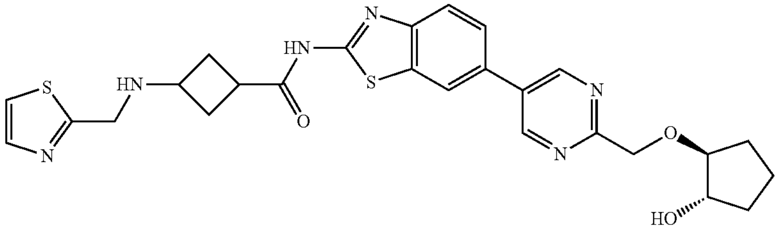 [SMILES: O=C(Nc1nc2ccc(-c3cnc(CO[C@H]4CCC[C@@H]4O)nc3)cc2s1)C1CC(NCc2nccs2)C1] | Example b-02-01 | (LC-1): RT = 1.06, m/z 537 $[M + H]^+$ |

TABLE 6-10-continued

| | | | |
|---|---|---|---|
| b-02-87 | 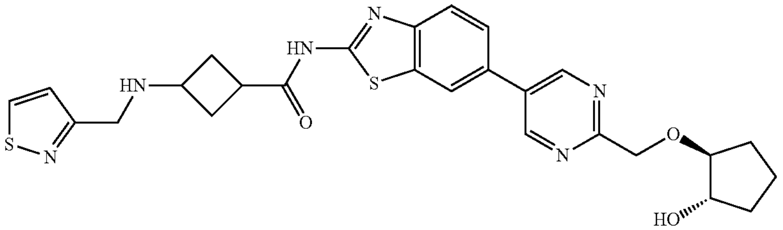 [SMILES: O=C(Nc1nc2ccc(-c3cnc(CO[C@H]4CCC[C@@H]4O)nc3)cc2s1)C1CC(NCc2ccsn2)C1] | Example b-02-01 | (LC-1): RT = 1.05, m/z 537 [M + H]$^+$ |

Example b-03-01: 3-(Bicyclo[1,1,1]pentan-1-yl (methyl)amino)-N-(6-(2-((((1S,2S)-2-hydroxycyclopentyl)oxy)methyl)pyrimidin-5-yl)benzo[d]thiazol-2-yl)cyclobutane-1-carboxamide

[Formula 92]

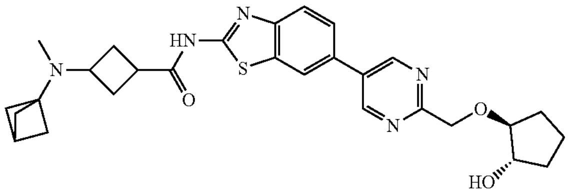

3-(3-Bicyclo[1,1,1]pentanylamino)-N-[6-[2-[[(1S,2S)]-2-hydroxycyclopentoxy]methyl]pyrimidin-5-yl]-1,3-benzothiazol-2-yl]cyclobutanecarboxamide (Example b-02-29, 29 mg, 0.06 mmol) was dissolved in dichloromethane (1.3 mL) and THF (1 mL), and formaldehyde (10 μL), and sodium triacetoxyborohydride (18.25 mg, 0.09 mmol) were added to the solution, and the resulting mixture was stirred overnight at room temperature. After completion of the reaction, water, chloroform, and saturated aqueous sodium hydrogencarbonate were added to the reaction mixture for extraction, the organic layer was concentrated by nitrogen blow, and the residue was purified by using HPLC to obtain 3-(bicyclo[1,1,1]pentan-1-yl(methyl)amino)-N-(6-(2-((((1S,2S)-2-hydroxycyclopentyl)oxy)methyl)pyrimidin-5-yl)benzo[d]thiazol-2-yl)cyclobutane-1-carboxamide (12.9 mg, yield 43%).

LCMS (LC-1): RT=1.31, m/z 520 [M+H]$^+$

1H-NMR ($CDCl_3$): δ (ppm) 9.00 (2H, s), 8.06-7.99 (11H, m), 7.91-7.84 (1H, m), 7.67-7.58 (1H, m), 5.01-4.90 (1H, m), 4.84-4.75 (1H, m), 4.26-4.15 (1H, m), 3.90-3.79 (1H, m), 3.18-3.08 (1H, m), 3.08-2.97 (11H, m), 2.52-2.34 (5H, m), 2.17 (3H, s), 2.14-2.00 (4H, m), 1.78-1.50 (5H, m)

The following compounds mentioned in the following table were synthesized by similar methods. In the following table, the examples of which preparation methods should be referred to are mentioned in the column of "Reference Methods".

TABLE 7

| Example | Structure | Reference Methods | LCMS Data |
|---|---|---|---|
| b-03-02 | 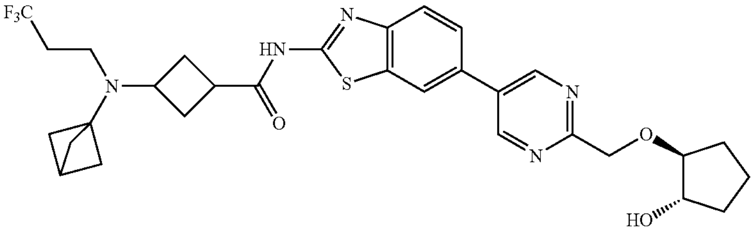 [SMILES: O=C(Nc1nc2ccc(-c3cnc(CO[C@H]4CCC[C@@H]4O)nc3)cc2s1)C1CC(N(CCC(F)(F)F)C23CC(C2)C3)C1] | Example b-03-01, Example b-02-29 | (LC-1): RT = 1.68, m/z 602 [M + H]$^+$ |
| b-03-03 | 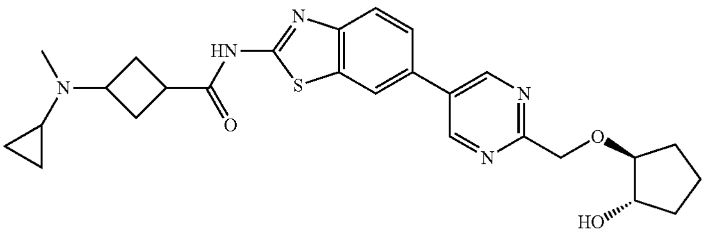 [SMILES: CN(C1CC1)C1CC(C(=O)Nc2nc3ccc(-c4cnc(CO[C@H]5CCC[C@@H]5O)nc4)cc3s2)C1] | Example b-03-01, Example b-02-47 | (LC-1): RT = 1.16, m/z 494 [M + H]$^+$ |

TABLE 7-continued
| Example | Structure | Reference Methods | LCMS Data |
|---|---|---|---|
| b-03-04 | 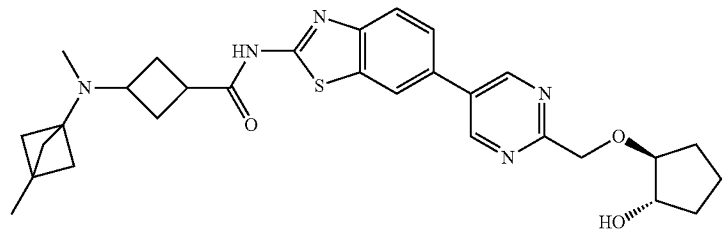 [SMILES: CN(C1CC(C(=O)Nc2nc3ccc(-c4cnc(CO[C@H]5CCC[C@@H]5O)nc4)cc3s2)C1)C12CC(C)(C1)C2] | Example b-03-01, Example b-02-49 | (LC-1): RT = 1.42, m/z 534 $[M + H]^+$ |
| b-03-05 | 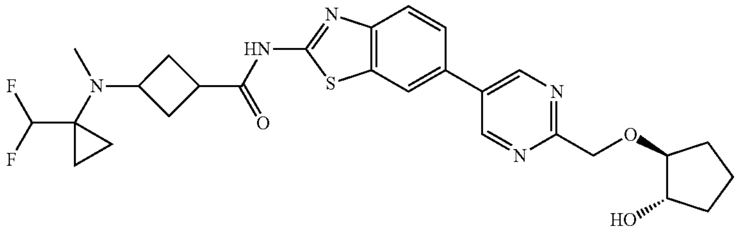 [SMILES: CN(C1CC(C(=O)Nc2nc3ccc(-c4cnc(CO[C@H]5CCC[C@@H]5O)nc4)cc3s2)C1)C1(C(F)F)CC1] | Example b-03-01, Example b-02-56 | (LC-1): RT = 1.42, m/z 544 $[M + H]^+$ |
| b-03-06 | 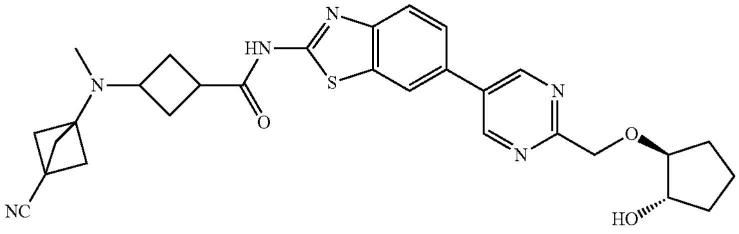 [SMILES: CN(C1CC(C(=O)Nc2nc3ccc(-c4cnc(CO[C@H]5CCC[C@@H]5O)nc4)cc3s2)C1)C12CC(C#N)(C1)C2] | Example b-03-01, Example b-02-42 | (LC-1): RT = 1.21, m/z 545 $[M + H]^+$ |
| b-03-07 | 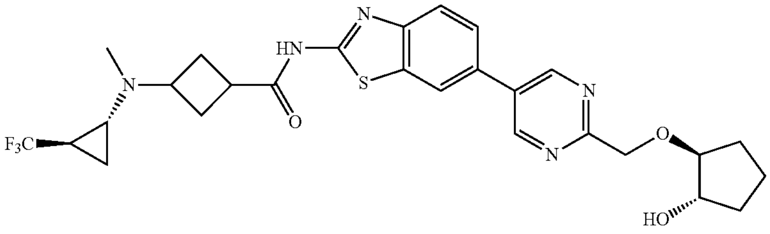 [SMILES: CN(C1CC(C(=O)Nc2nc3ccc(-c4cnc(CO[C@H]5CCC[C@@H]5O)nc4)cc3s2)C1)[C@@H]1C[C@H]1C(F)(F)F] | Example b-03-01, Example b-02-58 | (LC-1): RT = 1.43, m/z 562 $[M + H]^+$ |
| b-03-08 | 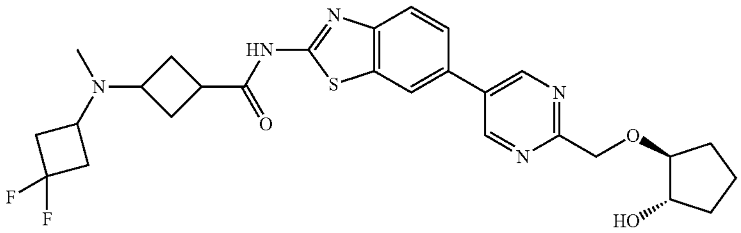 [SMILES: CN(C1CC(C(=O)Nc2nc3ccc(-c4cnc(CO[C@H]5CCC[C@@H]5O)nc4)cc3s2)C1)C1CC(F)(F)C1] | Example b-03-01, Example b-02-64 | (LC-1): RT = 1.27, m/z 544 $[M + H]^+$ |
| b-03-09 | 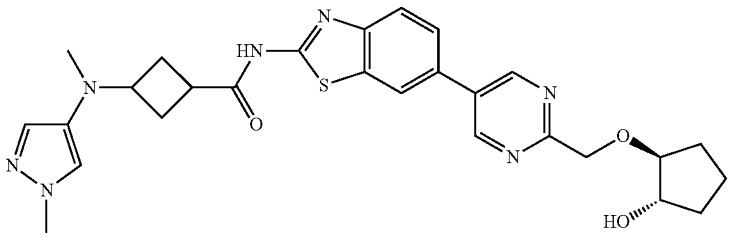 [SMILES: CN(c1cnn(C)c1)C1CC(C(=O)Nc2nc3ccc(-c4cnc(CO[C@H]5CCC[C@@H]5O)nc4)cc3s2)C1] | Example b-03-01, Example b-02-65 | (LC-1): RT = 1.07, m/z 534 $[M + H]^+$ |

Intermediate B-4-1: (1S,2S)-2-(Pyrimidin-2-ylmethoxy)cyclopentyl acetate

[Formula 93]

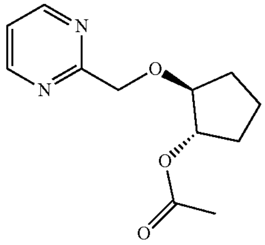

(1S,2S)-2-(Pyrimidin-2-ylmethoxy)cyclopentanol (39.03 g, 200.95 mmol) was dissolved in dichloromethane (402 mL), and the solution was stirred at 0° C. with cooling. Triethylamine (56.02 mL, 402 mmol), 4-dimethylaminopyridine (1.96 g, 16.08 mmol), and acetic anhydride (36.09 mL, 381.8 mmol) were added to the solution, and the resulting mixture was stirred. After 10 minutes, the reaction mixture was stirred at room temperature for 1 hour. The reaction mixture was cooled at 0° C., water and saturated aqueous sodium hydrogencarbonate were added, the resulting mixture was stirred, and dichloromethane was further added for extraction. The aqueous layer was extracted again with dichloromethane, the organic layers were combined, dried over sodium sulfate, filtered, and concentrated, and the residue was purified by using automatic silica gel column chromatography (eluent, chloroform containing 2% methanol) to obtain the objective compound, [(1S,2S)-2-(pyrimidin-2-ylmethoxy)cyclopentyl] acetate (22.73 g, yield 48%).

LCMS (LC-1): RT=0.92, m/z 238 $[M+H]^+$

1H-NMR ($CDCl_3$): δ (ppm) 8.73 (2H, d, J=5.0 Hz), 7.19 (1H, dd, J=5.0, 5.0 Hz), 4.85-4.82 (2H, m), 4.36-4.24 (1H, m), 4.24-4.16 (1H, n), 4.19 (1H, dd, J=4.0, 4.0 Hz), 2.12-1.95 (2H, m), 1.85-1.69 (4H, m), 1.75 (3H, s)

Intermediate B-4-2: (1S,2S)-2-((5-(4,4,5,5-Tetramethyl-1,3,2-dioxaboran-2-yl)pyrimidin-2-yl)methoxy)cyclopentyl acetate

[Formula 94]

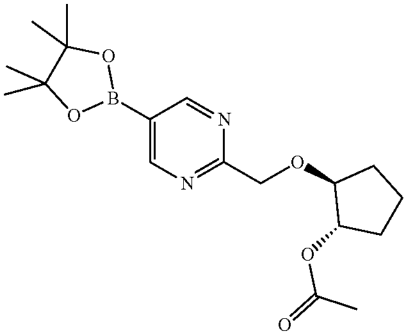

To (1S,2S)-2-(pyrimidin-2-ylmethoxy)cyclopentyl acetate (Intermediate B-4-1, 40.1 g, 169.7 mmol), THF (339.5 mL) was added, bis(pinacolato)diboron (47.41 g, 186.7 mmol), and 3,4,7,8-tetramethyl-1,10-phenantholine (0.8 g, 3.39 mmol) were added, the atmosphere was substituted to argon, (1,5-cyclooctadiene)methoxy)iridium(I) dimmer (1.13 g, 1.7 mmol) was further added, and the resulting mixture was stirred overnight at 80° C. with heating. (1,5-Cyclooctadiene)methoxy)iridium(I) dimmer (1.13 g, 1.7 mmol), 3,4,7,8-tetramethyl-1,10-phenantholine (0.8 g, 3.39 mmol), and bis(pinacolato)diboron (2.1 g, 8.5 mmol) were added to the reaction mixture, and the resulting mixture was stirred at 80° C. for 6.5 hours with heating. After completion of the reaction, the reaction mixture was concentrated, and vacuum dried to obtain (1S,2S)-2-((5-(4,4,5,5-tetramethyl-1,3,2-dioxaboran-2-yl)pyrimidin-2-yl)methoxy)cyclopentyl acetate (99.24 g) as a crude product.

LCMS (LC-1): RT=0.78, m/z 281 $[M+H]^+$ (detected as boronic acid)

1H-NMR ($CDCl_3$): δ (ppm) 9.01 (2H, s), 4.89-4.77 (2H, m), 4.06-4.02 (1H, m), 2.02-2.01 (3H, s), 1.88-1.83 (6H, m), 1.36-1.35 (12H, s)

Intermediate B-4-3: (1S,2S)-2-((5-(2-Aminobenzo[d]thiazol-6-yl)pyrimidin-2-yl)methoxy)cyclopentyl acetate

[Formula 95]

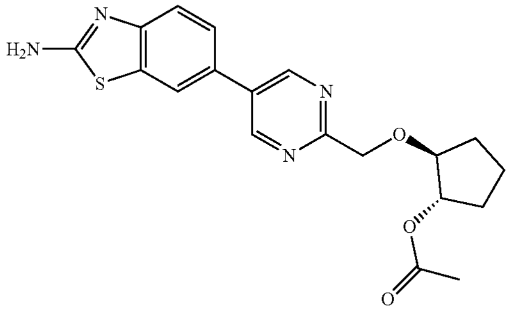

To 2-amino-6-bromobenzothiazole (20.3 mg, 88.61 mmol), 1,4-dioxane (243.6 mL) was added to dissolve the compound, cesium carbonate (88.61 g, 265.82 mmol), [1,1'-bis(diphenylphosphino)ferrocene]dichloropalladium(II) (6.48 g, 8.86 mmol), [(1S,2S)-2-[[5-(4,4,5,5-tetramethyl-1,3,2-dioxaborolan-2-yl)pyrimidin-2-yl]methoxy]cyclopentyl] acetate (88.15 g, 15, 63 mmol), and water (60.9 mL) were added to the solution, and the resulting mixture was stirred overnight at 80° C. with heating. [(1S,2S)-2-[[5-(4,4,5,5-Tetramethyl-1,3,2-dioxaborolan-2-yl)pyrimidin-2-yl]methoxy]cyclopentyl] acetate (21 g, 58 mmol), cesium carbonate (28.4 g, 88.61 mmol), and [1,1'-bis(diphenylphosphino)ferrocene]dichloropalladium(II) (2.1 g, 26.6 mmol) were added to the reaction mixture, and the resulting mixture was stirred overnight at 90° C. with heating. After completion of the reaction, the reaction mixture was filtered through a Celite layer, and the filtrate was extracted with ethyl acetate. The aqueous layer was extracted again with ethyl acetate, and the organic layers were combined, dried over sodium sulfate, filtered, and concentrated. The resulting crude product was purified by using automatic silica gel column chromatography (eluent, chloroform containing 1 to 2% methanol) to obtain (1S,2S)-2-((5-(2-aminobenzo[d]thiazol-6-yl)methoxy)cyclopentyl acetate (30.06 g, yield 88%).

LCMS (LC-1): RT=1.16, m/z 385 $[M+H]^+$

1H-NMR ($CDCl_3$): δ (ppm) 8.96 (2H, s), 7.84-7.75 (1H, m), 7.70-7.62 (1H, m), 7.57-7.45 (1H, m), 5.34-5.24 (2H, m), 5.24-5.12 (1H, m), 4.94-4.80 (2H, m), 4.13-4.06 (1H, m), 2.23-2.11 (1H, m), 2.09-2.00 (1H, m), 2.04 (3H, s), 1.89-1.63 (4H, m)

Intermediate B-4-4: (1S,2S)-2-((5-(2-(3-Oxocyclobutane-1-carboxamido)benzo[d]thiazol-6-yl)pyrimidin-2-yl)methoxy)cyclopentyl acetate

[Formula 96]

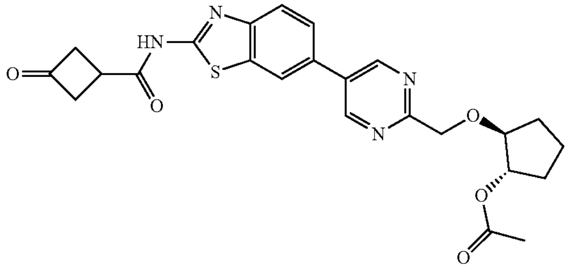

(1S,2S)-2-(((5-(2-Aminobenzo[d]thiazol-6-yl)pyrimidin-2-yl)methoxy)cyclopentyl acetate (Intermediate B-4-3, 17 g, 44.22 mmol) was dissolved in dichloromethane (250 mL) and THF (130 mL), N-diisopropylamine (23.11 mL, 132.66 mmol), 3-oxocyclobutane-1-carboxylic acid (6.05 g, 53.06 mmol), and 1-propanephosphonic acid anhydride (19.74 mL, 66.33 mmol) were added to the solution, and the resulting mixture was stirred overnight at room temperature. After completion of the reaction, aqueous sodium hydrogencarbonate was added to the reaction mixture, and the resulting mixture was extracted with chloroform. The aqueous layer was extracted again with chloroform, the organic layers were combined, dried over sodium sulfate, filtered, and concentrated, and the resulting crude product was purified by using silica gel column chromatography (eluent, chloroform containing 2 to 5% methanol) to obtain (1S,2S)-2-((5-(2-(3-oxocyclobutane-1-carboxamido)benzo[d]thiazol-6-yl)pyrimidin-2-yl)methoxy)cyclopentyl acetate (13.13 g, yield 62%).

LCMS (LC-1): RT=1.36, m/z 481 $[M+H]^+$

1H-NMR ($CDCl_3$): δ (ppm) 9.01 (2H, s), 8.04 (1H, m), 7.86 (1H, m), 7.68-7.61 (1H, m), 5.23-5.15 (1H, m), 4.89 (2H, m), 4.13-4.06 (1H, m), 3.69-3.58 (1H, m), 3.54-3.43 (1H, m), 3.43-3.31 (2H, m), 2.24-2.13 (1H, m), 2.06-2.02 (3H, m), 1.90-1.60 (5H, m)

Intermediate B-4-5: tert-Butyl (S)-4-((1s,3R)-3-((6-(2-((((1S,2S)-2-acetoxycyclopentyl)oxy)methyl)pyrimidin-5-yl)benzo[d]thiazol-2-yl)carbamoyl)cyclobutyl)-3-methylpiperazine-1-carboxylate

[Formula 97]

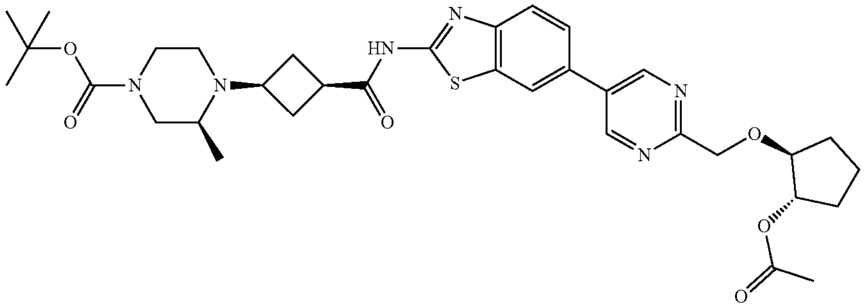

(1S,2S)-2-((5-(2-(3-Oxocyclobutane-1-carboxamido)benzo[d]thiazol-6-yl)pyrimidin-2-yl)methoxy)cyclopentyl acetate (Intermediate B-4-4, 13.14 g, 27.34 mmol) was dissolved in dichloromethane (250 mL) and THE (100 mL), (3S)-1-Boc-3-methylpiperazine (10.95 g, 54.68 mmol) was added to the solution, and the resulting mixture was stirred at room temperature. After 15 minutes, sodium triacetoxyborohydride (8.69 g, 41.01 mmol) was added to the reaction mixture, and the resulting mixture was stirred at room temperature for 2 hours. (3S)-1-Boc-3-Methylpiperazine (2.73 g, 13.7 mmol), and sodium triacetoxyborohydride (1.7 g, 8.2 mmol) were added to the reaction mixture, and the resulting mixture was stirred for further 2 hours. After completion of the reaction, aqueous sodium hydrogencarbonate was added to the reaction mixture, and the resulting mixture was extracted with chloroform. The aqueous layer was extracted again with chloroform, the organic layers were filtered, and concentrated, and the resulting crude product was purified by using silica gel column chromatography to obtain tert-butyl (S)-4-((1S,3R)-3-((6-(2-((((1S,2S)-2-acetoxycyclopentyl)oxy)methyl)pyrimidin-5-yl)benzo[d]thiazol-2-yl)carbamoyl)cyclobutyl)-3-methylpiperazine-1-carboxylate (9.2548 g, yield 51%).

LCMS (LC-1): RT=1.69, m/z 666 $[M+H]^+$

Example b-04-01: tert-Butyl (S)-4-((1S,3R)-3-((6-(2-((((1S,2S)-2-hydroxycyclopentyl)oxy)methyl)pyrimidin-5-yl)benzo[d]thiazol-2-yl)carbamoyl)cyclobutyl)-3-methylpiperazine-1-carboxylate

[Formula 98]

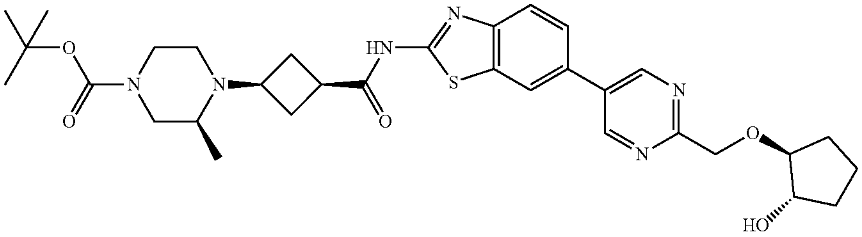

To tert-butyl (S)-4-((1s,3R)-3-((6-(2-((((1S,2S)-2-acetoxycyclopentyl)oxy)methyl)pyrimidin-5-yl)benzo[d]thiazol-2-yl)carbamoyl)cyclobutyl)-3-methylpiperazine-1-carboxylate (Intermediate B-4-5, 6.01 g, 9.04 mmol), methanol (30 mL) and THF (70 mL) were added to dissolve the compound, potassium carbonate (3.75 g, 27.12 mmol) was added to the solution, and the resulting mixture was stirred at room temperature for 1.5 hours. After completion of the reaction, water was added to the reaction mixture, and the resulting mixture was extracted with chloroform. The aqueous layer was extracted again with chloroform, and the organic layers were dried over sodium sulfate, filtered, and concentrated. The resulting crude product was purified by using silica gel column chromatography (eluent, chloroform:methanol=98:2) to obtain tert-butyl (S)-4-((1S,3R)-3-((6-(2-((((1S,2S)-2-hydroxycyclopentyl)oxy)methyl)pyrimidin-5-yl)benzo[d]thiazol-2-yl)carbamoyl)cyclobutyl)-3-methylpiperazine-1-carboxylate (4.88 g, yield 87%).

LCMS (LC-1): RT=1.44, m/z 623 $[M+H]^+$

Intermediate B-4-6: (1R,3s)-N-(6-(2-((((1S,2S)-2-Hydroxycyclopentyl)oxy)methyl)pyrimidin-5-yl)benzo[d]thiazol-2-yl)-3-((S)-2-methylpiperazin-1-yl)cyclobutane-1-carboxamide

[Formula 99]

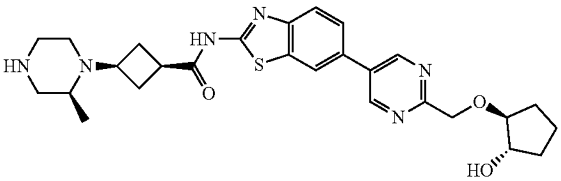

To tert-butyl (S)-4-((1S,3R)-3-((6-(2-((((1S,2S)-2-hydroxycyclopentyl)oxy)methyl)pyrimidin-5-yl)benzo[d]thiazol-2-yl)carbamoyl)cyclobutyl)-3-methylpiperazine-1-carboxylate (Example b-04-01, 4.88 g, 7.84 mmol), dichloromethane (280 mL) and THF (120 mL) were added to dissolve the compound, hydrochloric acid (13 mL, 428.67 mmol) was added to the solution, and the resulting mixture was stirred at room temperature for 15 minutes. The reaction mixture was purified with SCX to obtain (1R,3s)-N-(6-(2-((((1S,2S)-2-hydroxycyclopentyl)oxy)methyl)pyrimidin-5-yl)benzo[d]thiazol-2-yl)-3-((S)-2-methylpiperazin-1-yl)cyclobutane-1-carboxamide (3.05 g, yield 74%).

LCMS (LC-1): RT=0.88, m/z 524 $[M+H]^+$

1H-NMR ($CDCl_3$): δ (ppm) 9.18 (2H, s), 8.52-8.45 (1H, m), 7.68-7.63 (1H, m), 7.48-7.34 (11H, m), 4.72-4.67 (2H, m), 4.06-3.98 (1H, m), 3.89-3.77 (1H, m), 3.13-3.01 (4H, m), 2.97-2.87 (1H, m), 2.87-2.78 (1H, m), 2.72-2.61 (1H, m), 2.43-2.22 (3H, m), 2.23-2.05 (2H, m), 1.94-1.75 (2H, m), 1.68-1.53 (3H, m), 1.52-1.38 (1H, m), 1.07 (3H, d, J=5.5 Hz)

Example b-04-02: (1R,3s)-N-(6-(2-((((1S,2S)-2-Hydroxycyclopentyl)oxy)methyl)pyrimidin-5-yl)benzo[d]thiazol-2-yl)-3-((S)-2-methyl-4-(2-methylisonicotinoyl)piperazin-1-yl)cyclobutane-1-carboxamide

[Formula 100]

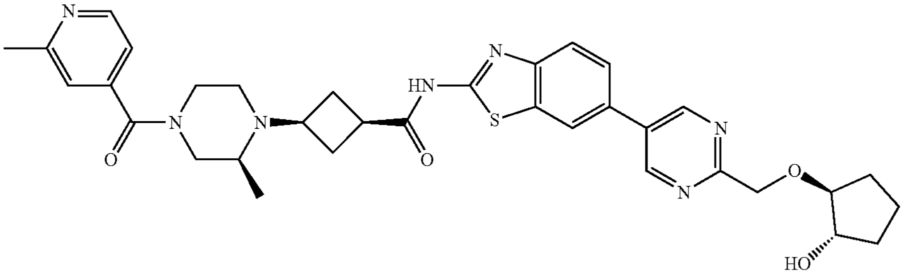

To (1R,3s)-N-(6-(2-((((1S,2S)-2-hydroxycyclopentyl)oxy)methyl)pyrimidin-5-yl)benzo[d]thiazol-2-yl)-3-((S)-2-methylpiperazin-1-yl)cyclobutane-1-carboxamide (3.05 g, 5.84 mmol), dichloromethane (320 mL) and THF (160 mL) were added to dissolve the compound, N-ethyldiisopropylamine (3.05 mL, 17.51 mmol), 2-methoxyisonicotinic acid (960.3 mg, 7 mmol), and 1-propanephosphonic acid anhydride (5.14 mL) were added to the solution, and the resulting mixture was stirred at room temperature for 2 hours. After completion of the reaction, aqueous sodium hydrogencarbonate was added to the reaction mixture, and the resulting mixture was extracted with chloroform. The aqueous layer was extracted again with chloroform, and the organic layers were combined, dried over sodium sulfate, filtered, and concentrated. The resulting crude product was purified by using silica gel column chromatography (eluent, ethyl acetate:methanol=80:20) to obtain (1R,3s)-N-(6-(2-((((1S,2S)-2-hydroxycyclopentyl)oxy)methyl)pyrimidin-5-yl)benzo[d]thiazol-2-yl)-3-((S)-2-methyl-4-(2-methylisonicotinoyl)piperazin-1-yl)cyclobutane-1-carboxamide (272.9 mg, yield 7%).

LCMS (LC-1): RT=1.08, m/z 642 $[M+1]^+$

1H-NMR ($CD_3OD$): δ (ppm) 9.01 (s, 2H), 8.62-8.46 (1H, m), 8.10-8.00 (1H, m), 7.95-7.81 (1H, m), 7.71-7.57 (1H, m), 7.22-7.14 (1H, m), 7.14-7.05 (1H, m), 5.02-4.90 (1H, m), 4.90-4.71 (11H, m), 4.28-4.07 (1H, m), 3.99-3.81 (2H, m), 3.81-3.67 (11H, m), 3.57-3.30 (2H, m), 3.29-3.09 (2H, m), 3.09-2.94 (1H, m), 2.84-2.73 (1H, m), 2.73-2.63 (211, m), 2.63-2.58 (3H, m), 2.49-2.32 (3H, m), 2.33-2.21 (1H, m), 2.18-1.96 (2H, m), 1.81-1.51 (4H, m), 1.18-1.09 (1H, m), 0.99-0.91 (1H, m)

The following compounds mentioned in the following tables were synthesized by similar methods. In the following tables, the examples of which preparation methods should be referred to are mentioned in the column of "Reference Methods".

TABLE 8-1

| Example | Structure | Reference Methods | LCMS Data |
|---|---|---|---|
| b-04-03 | 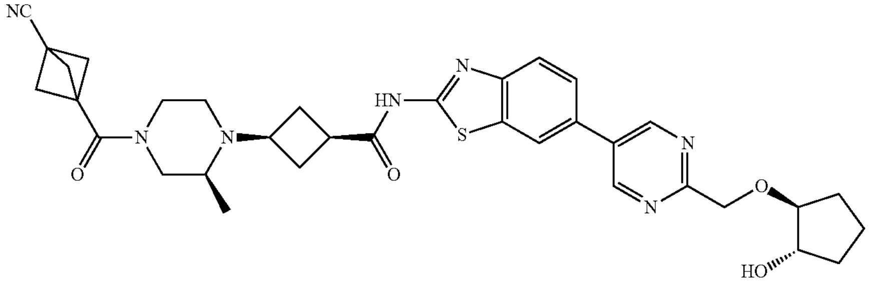 [SMILES: C[C@H]1CN(C(=O)C23CC(C#N)(C2)C3)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 1.14, m/z 642 $[M + H]^+$ |
| b-04-04 | 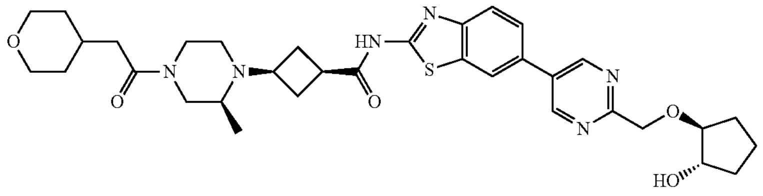 [SMILES: C[C@H]1CN(C(=O)CC2CCOCC2)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 1.07, m/z 649 $[M + H]^+$ |
| b-04-05 | 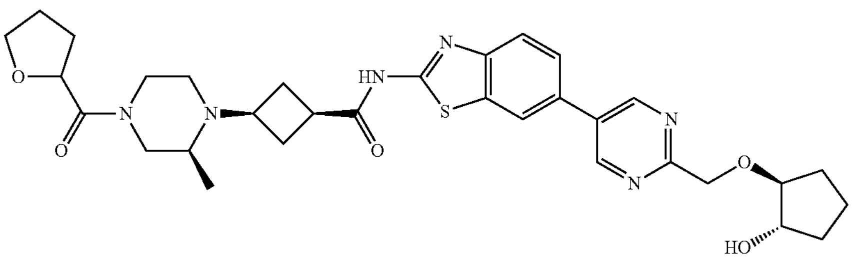 [SMILES: C[C@H]1CN(C(=O)C2CCCO2)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 1.05, m/z 621 $[M + H]^+$ |
| b-04-06 | 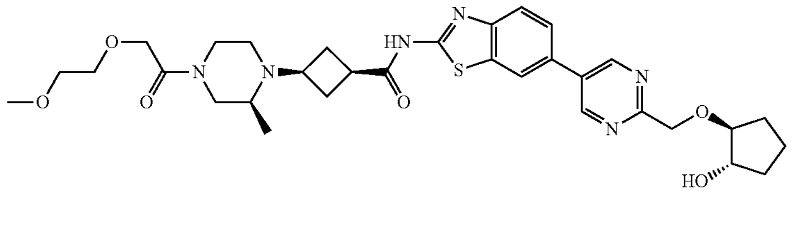 [SMILES: COCCOCC(=O)N1CCN([C@H]2C[C@@H](C(=O)Nc3nc4ccc(-c5cnc(CO[C@H]6CCC[C@@H]6O)nc5)cc4s3)C2)[C@@H](C)C1] | Example b-04-02 | (LC-1): RT = 1.03, m/z 639 $[M + H]^+$ |

TABLE 8-1-continued
| Example | Structure | Reference Methods | LCMS Data |
|---|---|---|---|
| b-04-07 | 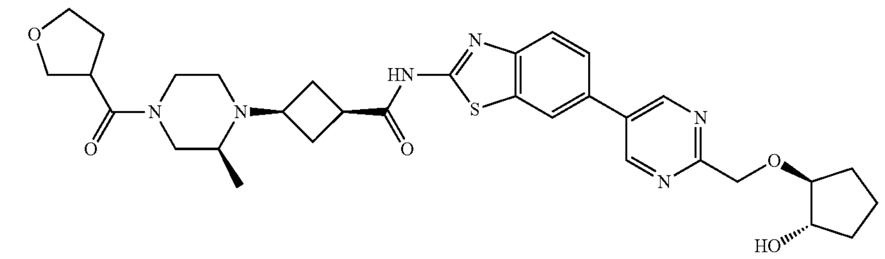 [SMILES: C[C@H]1CN(C(=O)C2CCOC2)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 1.03, m/z 621 [M + H]+ |
| b-04-08 | 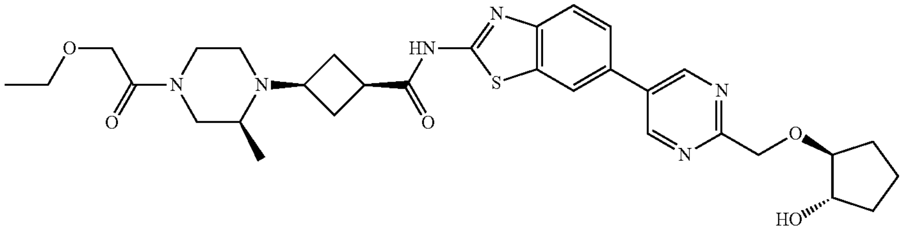 [SMILES: CCOCC(=O)N1CCN([C@H]2C[C@@H](C(=O)Nc3nc4ccc(-c5cnc(CO[C@H]6CCC[C@@H]6O)nc5)cc4s3)C2)[C@@H](C)C1] | Example b-04-02 | (LC-1): RT = 1.07, m/z 609 [M + H]+ |
| b-04-09 | 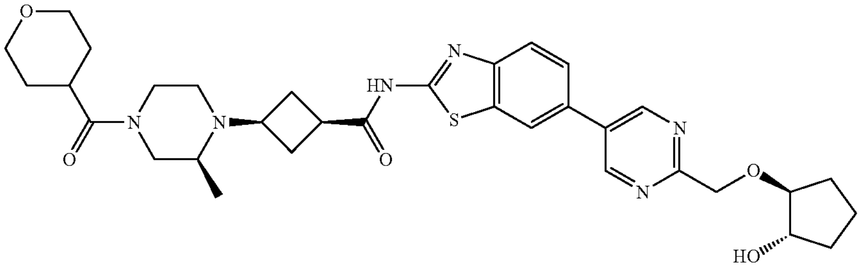 [SMILES: C[C@H]1CN(C(=O)C2CCOCC2)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 1.04, m/z 635 [M + H]+ |
| b-04-10 | 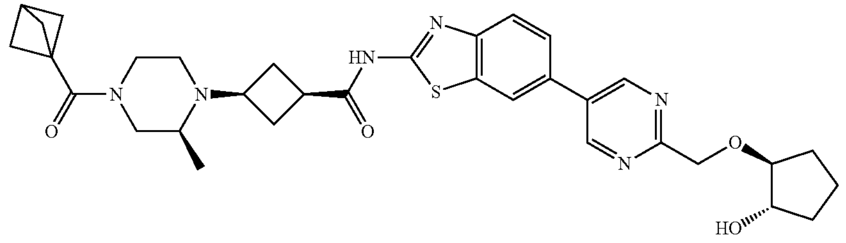 [SMILES: C[C@H]1CN(C(=O)C23CC(C2)C3)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 1.21, m/z 617 [M + H]+ |
TABLE 8-2
| | | | |
|---|---|---|---|
| b-04-11 | 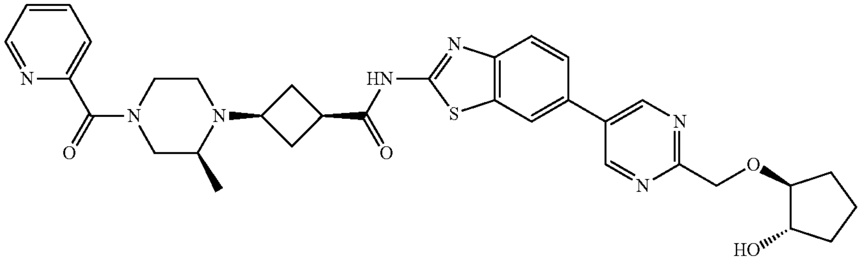 [SMILES: C[C@H]1CN(C(=O)c2ccccn2)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 1.06, m/z 628 [M + H]+ |

TABLE 8-2-continued
| | | | |
|---|---|---|---|
| b-04-12 | 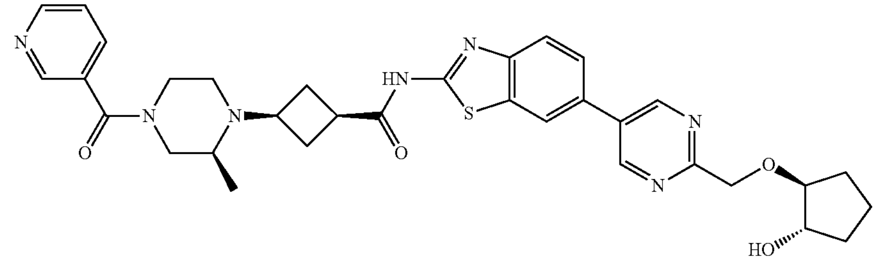 [SMILES: C[C@H]1CN(C(=O)c2cccnc2)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 1.03, m/z 628 [M + H]+ |
| b-04-13 | 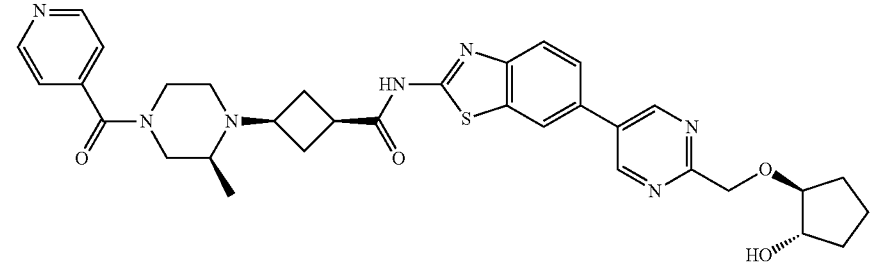 [SMILES: C[C@H]1CN(C(=O)c2ccncc2)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 1.02, m/z 628 [M + H]+ |
| b-04-14 | 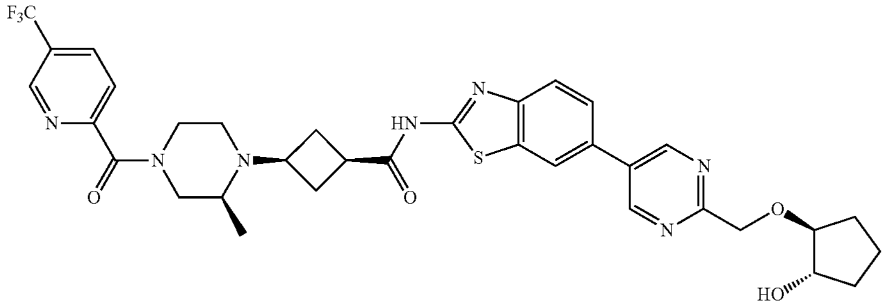 [SMILES: C[C@H]1CN(C(=O)c2ccc(C(F)(F)F)cn2)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 1.29, m/z 696 [M + H]+ |
| b-04-15 | 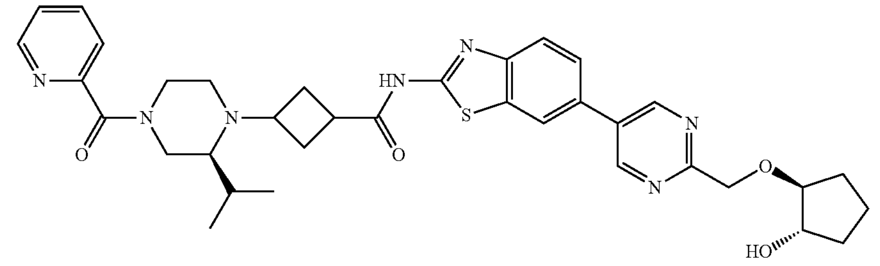 [SMILES: CC(C)[C@H]1CN(C(=O)c2ccccn2)CCN1C1CC(C(=O)Nc2nc3ccc(-c4cnc(CO[C@H]5CCC[C@@H]5O)nc4)cc3s2)C1] | Examples b-04-01, 02 Intermediates B-4-5, 6 | (LC-1): RT = 1.23, m/z 656 [M + H]+ |
| b-04-16 | 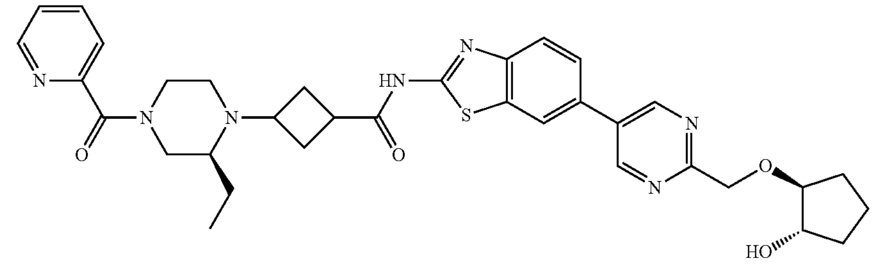 [SMILES: CC[C@H]1CN(C(=O)c2ccccn2)CCN1C1CC(C(=O)Nc2nc3ccc(-c4cnc(CO[C@H]5CCC[C@@H]5O)nc4)cc3s2)C1] | Examples b-04-01, 02 Intermediates B-4-5, 6 | (LC-1): RT = 1.13, m/z 642 [M + H]+ |
| b-04-17 | 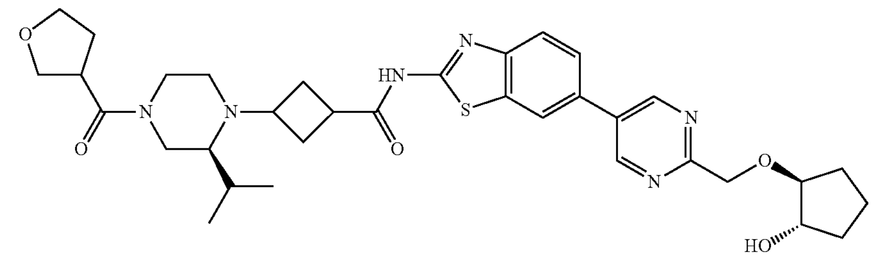 [SMILES: CC(C)[C@H]1CN(C(=O)C2CCOC2)CCN1C1CC(C(=O)Nc2nc3ccc(-c4cnc(CO[C@H]5CCC[C@@H]5O)nc4)cc3s2)C1] | Examples b-04-01, 02 Intermediates B-4-5, 6 | (LC-1): RT = 1.20, m/z 649 [M + H]+ |

TABLE 8-2-continued
| | | | |
|---|---|---|---|
| b-04-18 | 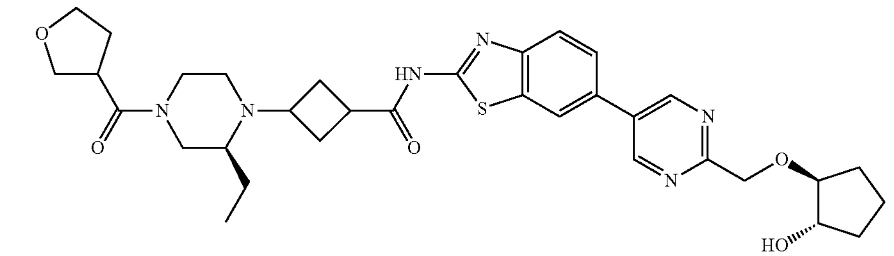 [SMILES: CC[C@H]1CN(C(=O)C2CCOC2)CCN1C1CC(C(=O)Nc2nc3ccc(-c4cnc(CO[C@H]5CCC[C@@H]5O)nc4)cc3s2)C1] | Examples b-04-01, 02 Intermediates B-4-5, 6 | (LC-1): RT = 1.10, m/z 635 [M + H]+ |
| b-04-19 | 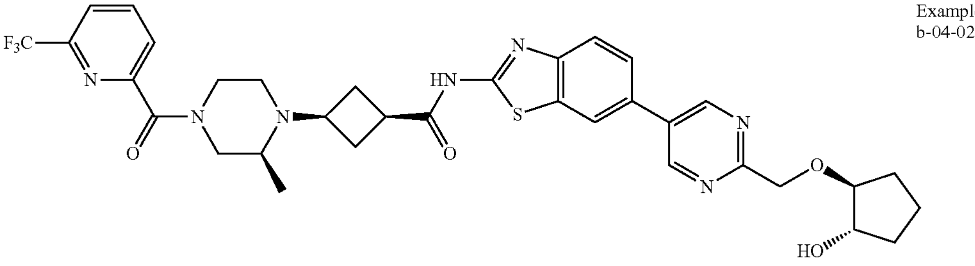 | Example b-04-02 | (LC-1): RT = 1.30, m/z 696 [M + H]+ |
TABLE 8-3
| | | | |
|---|---|---|---|
| b-04-20 | 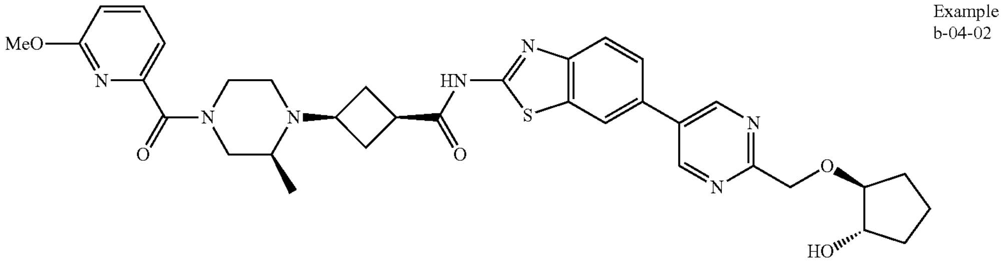 | Example b-04-02 | (LC-1): RT = 1.21, m/z 658 [M + H]+ |
| b-04-21 | 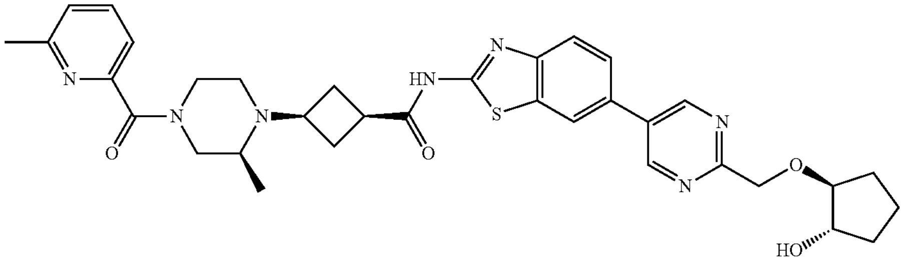 [SMILES: Cc1cccc(C(=O)N2CCN([C@H]3C[C@@H](C(=O)Nc4nc5ccc(-c6cnc(CO[C@H]7CCC[C@@H]7O)nc6)cc5s4)C3)[C@@H](C)C2)n1] | Example b-04-02 | (LC-1): RT = 1.11, m/z 642 [M + H]+ |
| b-04-22 | 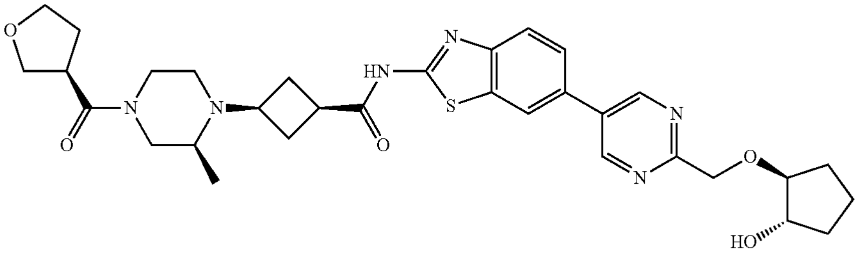 [SMILES: C[C@H]1CN(C(=O)[C@@H]2CCOC2)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 1.03, m/z 621 [M + H]+ |

TABLE 8-3-continued
| | | | |
|---|---|---|---|
| b-04-23 | 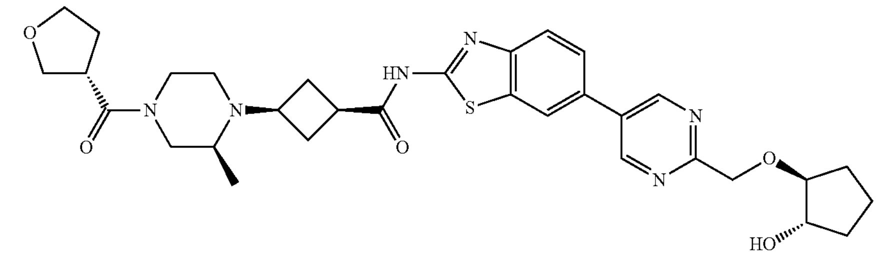 [SMILES: C[C@H]1CN(C(=O)[C@H]2CCOC2)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 1.03, m/z 621 [M + H]+ |
| b-04-24 | 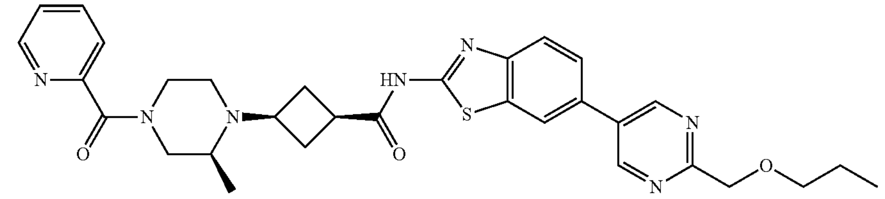 [SMILES: CCCOCc1ncc(-c2ccc3nc(NC(=O)[C@H]4C[C@@H](N5CCN(C(=O)c6ccccn6)C[C@@H]5C)C4)sc3c2)cn1] | Examples b-04-01, 02 Intermediates A-2-2, B-4-3,4,5,6 | (LC-1): RT = 1.24, m/z 586 [M + H]+ |
| b-04-25 | 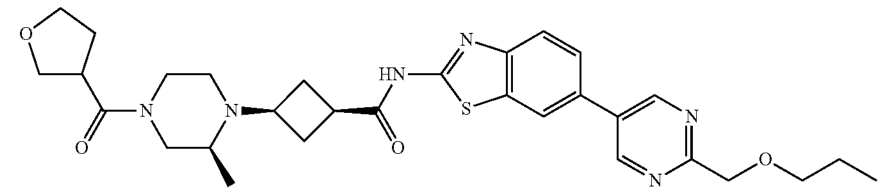 [SMILES: CCCOCc1ncc(-c2ccc3nc(NC(=O)[C@H]4C[C@@H](N5CCN(C(=O)C6CCOC6)C[C@@H]5C)C4)sc3c2)cn1] | Examples b-04-01, 02 Intermediates A-2-2, B-4-3, 4, 5, 6 | (LC-1): RT = 1.21, m/z 579 [M + H]+ |
| b-04-26 | 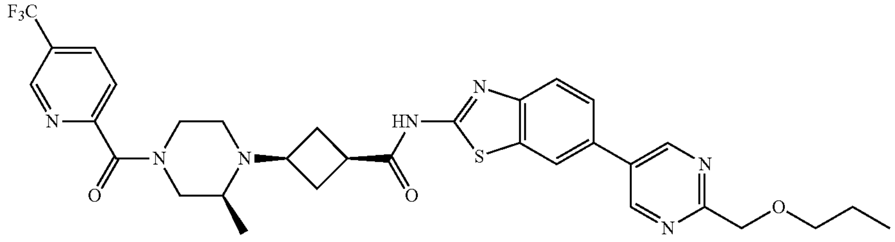 [SMILES: CCCOCc1ncc(-c2ccc3nc(NC(=O)[C@H]4C[C@@H](N5CCN(C(=O)c6ccc(C(F)(F)F)cn6)C[C@@H]5C)C4)sc3c2)cn1] | Examples b-04-01, 02 Intermediates A-2-2, B-4-3, 4, 5, 6 | (LC-1): RT = 1.50, m/z 654 [M + H]+ |
| b-04-27 | 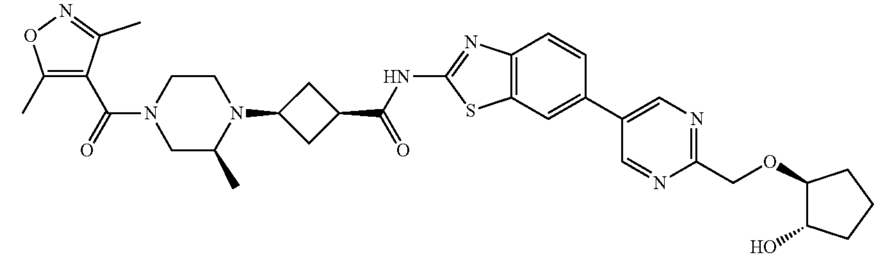 [SMILES: Cc1noc(C)c1C(=O)N1CCN([C@H]2C[C@@H](C(=O)Nc3nc4ccc(-c5cnc(CO[C@H]6CCC[C@@H]6O)nc5)cc4s3)C2)[C@@H](C)C1] | Example b-04-02 | (LC-1): RT = 1.12, m/z 646 [M + H]+ |
| b-04-28 | 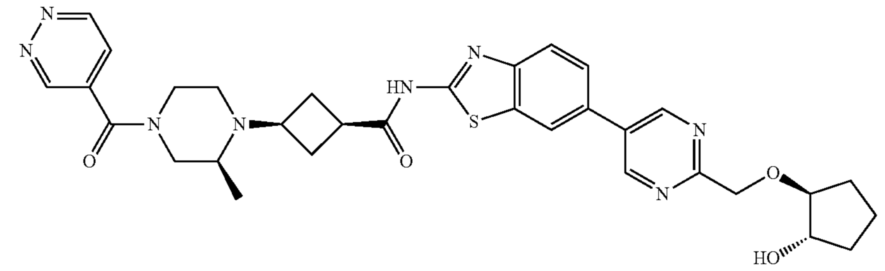 [SMILES: C[C@H]1CN(C(=O)c2ccnnc2)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 0.98, m/z 629 [M + H]+ |

TABLE 8-4
| | | | |
|---|---|---|---|
| b-04-29 | 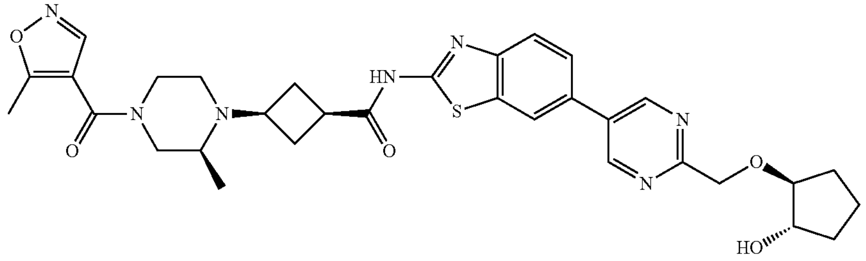 [SMILES: Cc1oncc1C(=O)N1CCN([C@H]2C[C@@H](C(=O)Nc3nc4ccc(-c5cnc(CO[C@H]6CCC[C@@H]6O)nc5)cc4s3)C2)[C@@H](C)C1] | Example b-04-02 | (LC-1): RT = 1.11, m/z 632 [M + H]+ |
| b-04-30 | 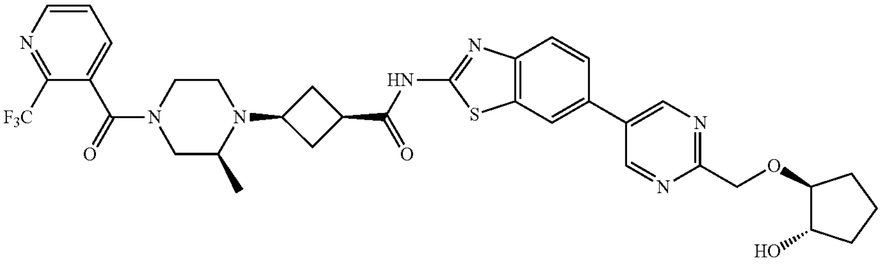 [SMILES: C[C@H]1CN(C(=O)c2cccnc2C(F)(F)F)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 1.21, m/z 696 [M + H]+ |
| b-04-31 | 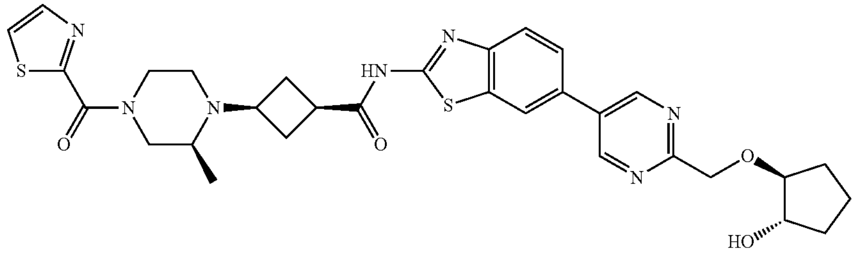 [SMILES: C[C@H]1CN(C(=O)c2nccs2)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 1.19, m/z 634 [M + H]+ |
| b-04-32 | 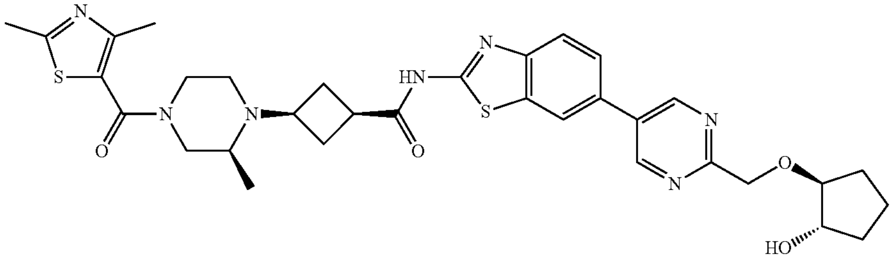 [SMILES: Cc1nc(C)c(C(=O)N2CCN([C@H]3C[C@@H](C(=O)Nc4nc5ccc(-c6cnc(CO[C@H]7CCC[C@@H]7O)nc6)cc5s4)C3)[C@@H](C)C2)s1] | Example b-04-02 | (LC-1): RT = 1.11, m/z 662 [M + H]+ |
| b-04-33 | 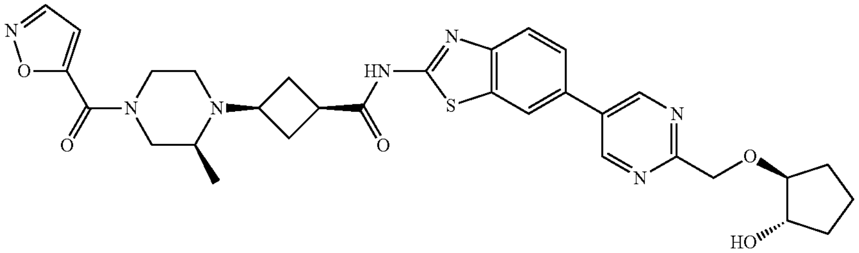 [SMILES: C[C@H]1CN(C(=O)c2ccno2)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 1.11, m/z 618 [M + H]+ |
| b-04-34 | 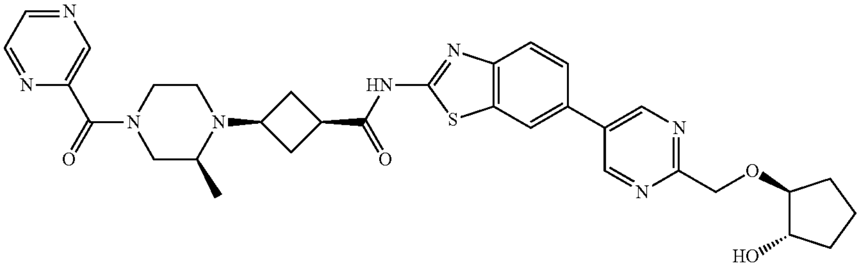 [SMILES: C[C@H]1CN(C(=O)c2cnccn2)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 1.03, m/z 629 [M + H]+ |

TABLE 8-4-continued
| | | | |
|---|---|---|---|
| b-04-35 | 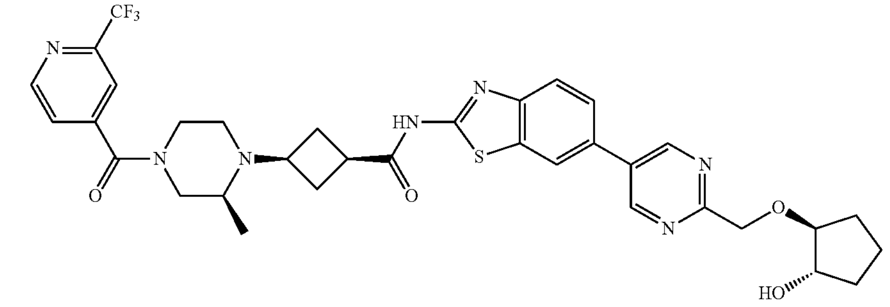 [SMILES: C[C@H]1CN(C(=O)c2ccnc(C(F)(F)F)c2)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 1.27, m/z 696 [M + H]+ |
| b-04-36 | 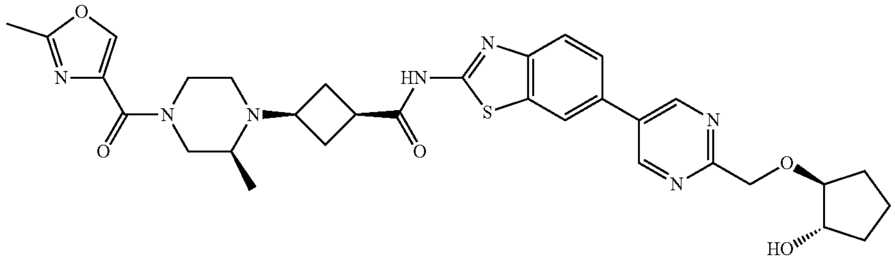 [SMILES: Cc1nc(C(=O)N2CCN([C@H]3C[C@@H](C(=O)Nc4nc5ccc(-c6cnc(CO[C@H]7CCC[C@@H]7O)nc6)cc5s4)C3)[C@@H](C)C2)co1] | Example b-04-02 | (LC-1): RT = 1.08, m/z 632 [M + H]+ |
| b-04-37 | 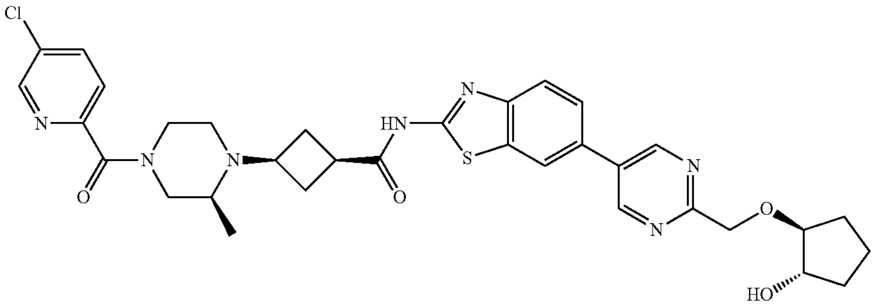 [SMILES: C[C@H]1CN(C(=O)c2ccc(Cl)cn2)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 1.21, m/z 662 [M + H]+ |
TABLE 8-5
| | | | |
|---|---|---|---|
| b-04-38 | 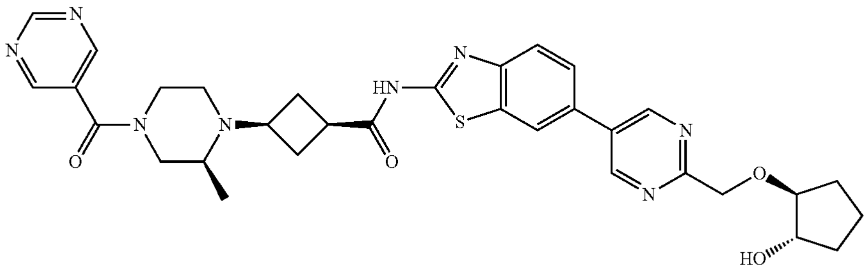 [SMILES: C[C@H]1CN(C(=O)c2cncnc2)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 1.00, m/z 629 [M + H]+ |
| b-04-39 | 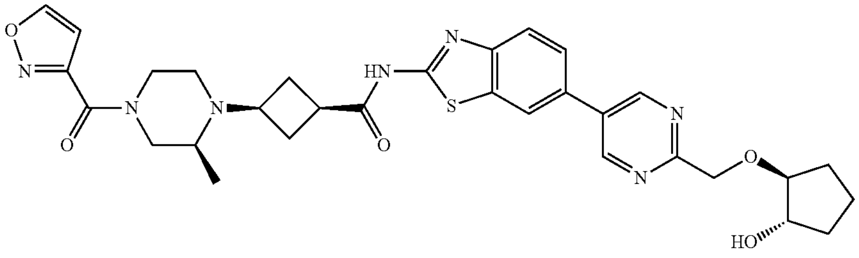 [SMILES: C[C@H]1CN(C(=O)c2ccon2)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 1.12, m/z 618 [M + H]+ |

TABLE 8-5-continued
| | | | |
|---|---|---|---|
| b-04-40 | 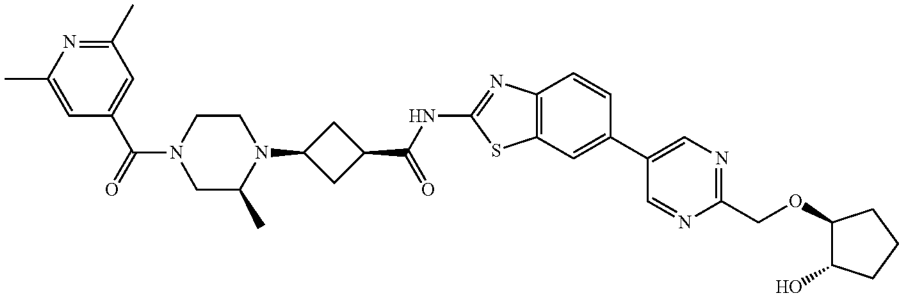 [SMILES: Cc1cc(C(=O)N2CCN([C@H]3C[C@@H](C(=O)Nc4nc5ccc(-c6cnc(CO[C@H]7CCC[C@@H]7O)nc6)cc5s4)C3)[C@@H](C)C2)cc(C)n1] | Example b-04-02 | (LC-1): RT = 1.09, m/z 656 $[M + H]^+$ |
| b-04-41 | 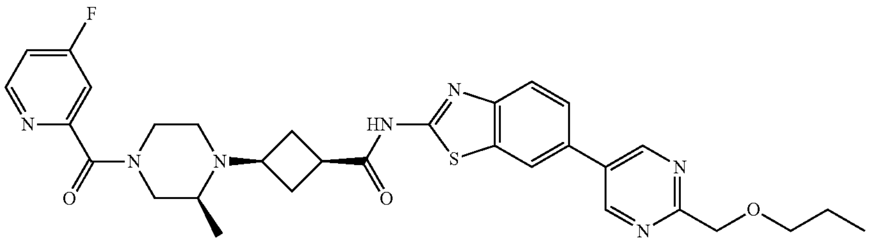 [SMILES: CCCOCc1ncc(-c2ccc3nc(NC(=O)[C@H]4C[C@@H](N5CCN(C(=O)c6cc(F)ccn6)C[C@@H]5C)C4)sc3c2)cn1] | Examples b-04-01, 02 Intermediates A-2-2, B-4-3, 4, 5, 6 | (LC-1): RT = 1.33, m/z 604 $[M + H]^+$ |
| b-04-42 | 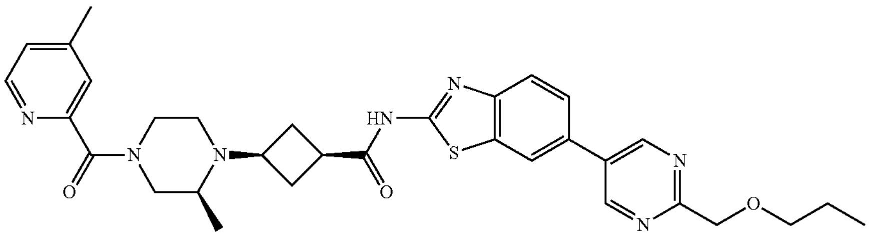 [SMILES: CCCOCc1ncc(-c2ccc3nc(NC(=O)[C@H]4C[C@@H](N5CCN(C(=O)c6cc(C)ccn6)C[C@@H]5C)C4)sc3c2)cn1] | Examples b-04-01, 02 Intermediates A-2-2, B-4-3, 4, 5, 6 | (LC-1): RT = 1.32, m/z 600 $[M + H]^+$ |
| b-04-43 | 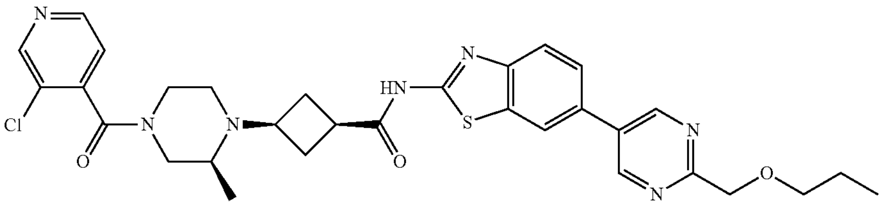 [SMILES: CCCOCc1ncc(-c2ccc3nc(NC(=O)[C@H]4C[C@@H](N5CCN(C(=O)c6ccncc6Cl)C[C@@H]5C)C4)sc3c2)cn1] | Examples b-04-01, 02 Intermediates A-2-2, B-4-3, 4, 5, 6 | (LC-1): RT = 1.34, m/z 620 $[M + H]^+$ |
| b-04-44 | 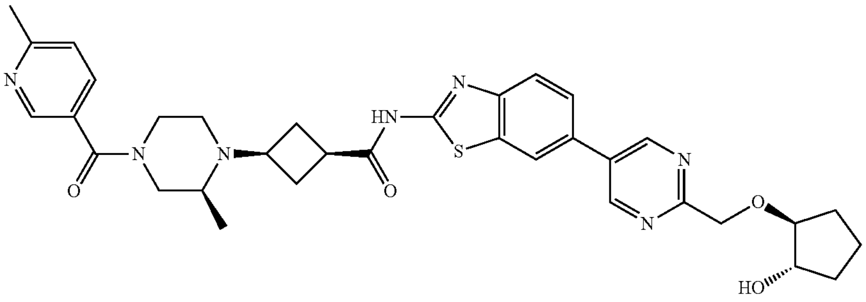 [SMILES: Cc1ccc(C(=O)N2CCN([C@H]3C[C@@H](C(=O)Nc4nc5ccc(-c6cnc(CO[C@H]7CCC[C@@H]7O)nc6)cc5s4)C3)[C@@H](C)C2)cn1] | Example b-04-02 | (LC-1): RT = 1.09, m/z 642 $[M + H]^+$ |
| b-04-45 | 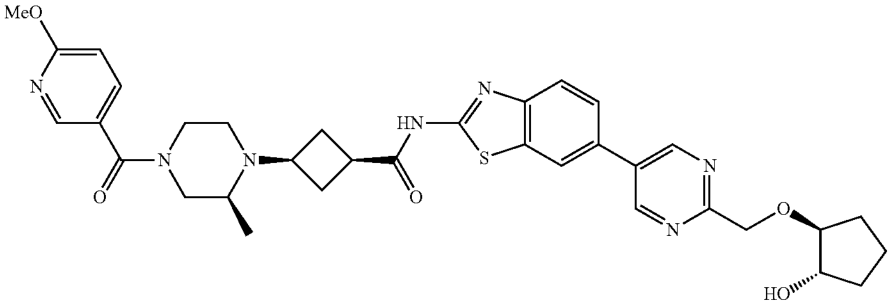 [SMILES: COc1ccc(C(=O)N2CCN([C@H]3C[C@@H](C(=O)Nc4nc5ccc(-c6cnc(CO[C@H]7CCC[C@@H]7O)nc6)cc5s4)C3)[C@@H](C)C2)cn1] | Example b-04-02 | (LC-1): RT = 1.17, m/z 658 $[M + H]^+$ |

TABLE 8-5-continued

| | | | |
|---|---|---|---|
| b-04-46 | 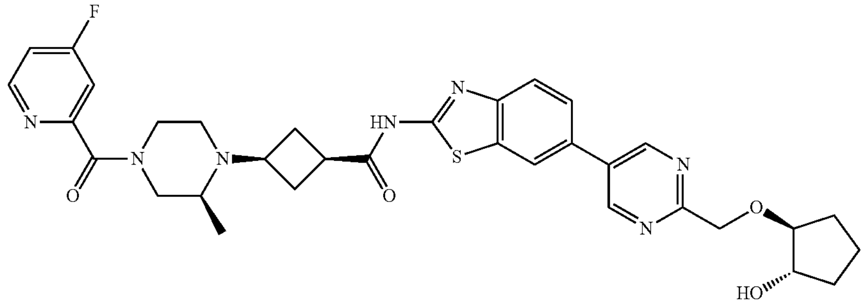 [SMILES: C[C@H]1CN(C(=O)c2cc(F)ccn2)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 1.14, m/z 646 [M + H]+ |

TABLE 8-6

| | | | |
|---|---|---|---|
| b-04-47 | 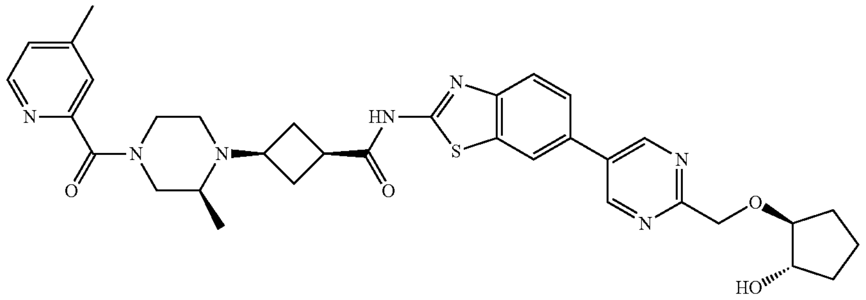 [SMILES: Cc1ccnc(C(=O)N2CCN([C@H]3C[C@@H](C(=O)Nc4nc5ccc(-c6cnc(CO[C@H]7CCC[C@@H]7O)nc6)cc5s4)C3)[C@@H](C)C2)c1] | Example b-04-02 | (LC-1): RT = 1.14, m/z 642 [M + H]+ |
| b-04-48 | 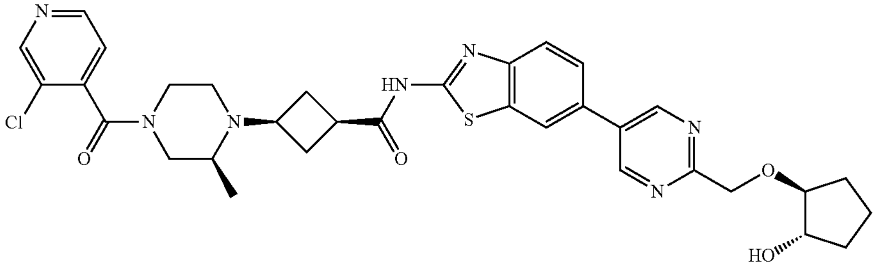 [SMILES: C[C@H]1CN(C(=O)c2ccncc2Cl)CCN1[C@H]1C[C@@H](C(=O)Nc2nc3ccc(-c4cnc(CO[C@H]5CCC[C@@H]5O)nc4)cc3s2)C1] | Example b-04-02 | (LC-1): RT = 1.14, m/z 662 [M + H]+ |

Example b-05-01: (1R,3s)-3-((S)-4-Acetyl-2-methylpiperazin-1-yl)-N-(6-(2-((((1S,2S)-2-hydroxycyclopentyl)oxy)methyl)pyrimidin-5-yl)benzo[d]thiazol-2-yl)cyclobutane-1-carboxamide

[Formula 101]

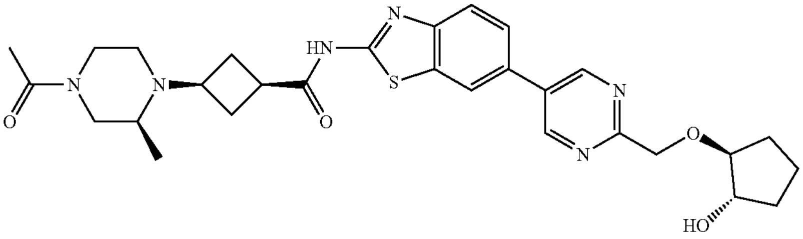

(1R,3s)-N-(6-(2-((((1S,2S)-2-Hydroxycyclopentyl)oxy)methyl)pyrimidin-5-yl)benzo[d]thiazol-2-yl)-3-((S)-2-methylpiperazin-1-yl)cyclobutane-1-carboxamide (Intermediate B-4-6, 27.7 mg, 0.05 mmol) was dissolved in dichloromethane (1.3 mL), acetyl chloride (4.52 μL, 0.06 mmol), and triethylamine (14.77 μL, 0.11 mmol) were added to the solution, and the resulting mixture was stirred at room temperature for 1 hour. Aqueous sodium hydrogencarbonate was added to the reaction mixture, the resulting mixture was extracted with chloroform, the organic layer was concentrated by nitrogen blow, and the resulting crude product was purified by using HPLC to obtain (1R,3s)-3-((S)-4-acetyl-2-methylpiperazin-1-yl)-N-(6-(2-((((1S,2S)-2-hydroxycyclopentyl)oxy)methyl)pyrimidin-5-yl)benzo[d]thiazol-2-yl)cyclobutane-1-carboxamide (14.2 mg, yield 47%).

LCMS (LC-1): RT=0.99, m/z 565 $[M+H]^+$

1H-NMR ($CDCl_3$): δ (ppm) 9.00-8.95 (2H, m), 8.02-7.98 (1H, m), 7.86-7.80 (1H, m), 7.63-7.57 (1H, m), 4.95-4.88 (1H, m), 4.81-4.71 (1H, m), 4.21-4.11 (1H, m), 3.85-3.78 (1H, m), 3.77-3.70 (1H, m), 3.59-3.52 (1H, m), 3.40-3.36 (1H, m), 3.35-3.25 (11H, m), 3.24-3.07 (2H, m), 3.06-2.96 (1H, m), 2.82-2.71 (1H, m), 2.69-2.57 (2H, m), 2.08 (4H, m), 2.03-1.96 (1H, m), 1.77-1.49 (5H, m), 1.06-0.99 (3H, m)

The following compounds mentioned in the following table were synthesized by similar methods. In the following table, the examples of which preparation methods should be referred to are mentioned in the column of "Reference Methods".

TABLE 9

| Example | Structure | Reference Methods | LCMS Data |
| --- | --- | --- | --- |
| b-05-02 | 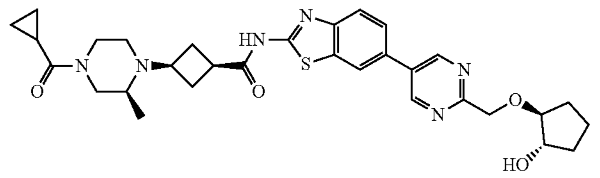 [SMILES: C[C@H]1CN(C(=O)C2CC2)CCN1[C@H]1C[C@@H](C(=O)Nc2nc3ccc(-c4cnc(CO[C@H]5CCC[C@@H]5O)nc4)cc3s2)C1] | Example b-05-01 | (LC-1): RT = 1.09, m/z 591 $[M + H]^+$ |
| b-05-03 | 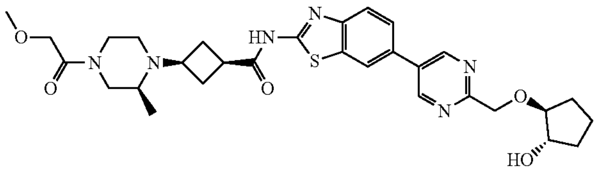 [SMILES: COCC(=O)N1CCN([C@H]2C[C@@H](C(=O)Nc3nc4ccc(-c5cnc(CO[C@H]6CCC[C@@H]6O)nc5)cc4s3)C2)[C@@H](C)C1] | Example b-05-01 | (LC-1): RT = 1.00, m/z 595 $[M + H]^+$ |
| b-05-04 | 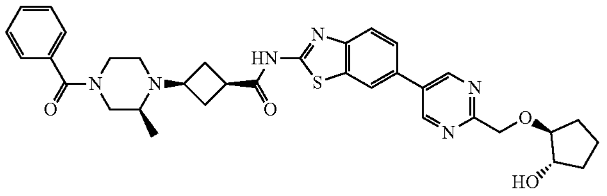 [SMILES: C[C@H]1CN(C(=O)c2ccccc2)CCN1[C@H]1C[C@@H](C(=O)Nc2nc3ccc(-c4cnc(CO[C@H]5CCC[C@@H]5O)nc4)cc3s2)C1] | Example b-05-01 | (LC-1): RT = 1.21, m/z 627 $[M + H]^+$ |
| b-05-05 | 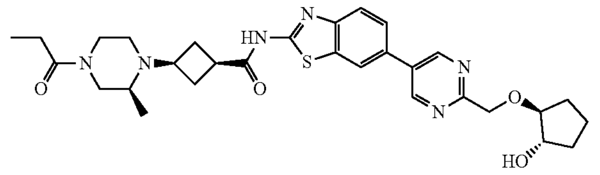 [SMILES: CCC(=O)N1CCN([C@H]2C[C@@H](C(=O)Nc3nc4ccc(-c5cnc(CO[C@H]6CCC[C@@H]6O)nc5)cc4s3)C2)[C@@H](C)C1] | Example b-05-01 | (LC-1): RT = 1.06, m/z 579 $[M + H]^+$ |
| b-05-06 | 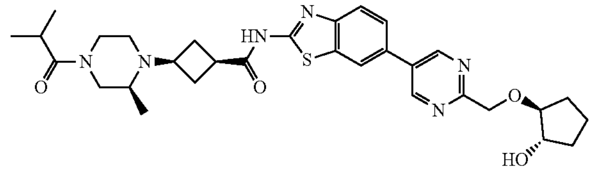 [SMILES: CC(C)C(=O)N1CCN([C@H]2C[C@@H](C(=O)Nc3nc4ccc(-c5cnc(CO[C@H]6CCC[C@@H]6O)nc5)cc4s3)C2)[C@@H](C)C1] | Example b-05-01 | (LC-1): RT = 1.13, m/z 593 $[M + H]^+$ |
| b-05-07 | 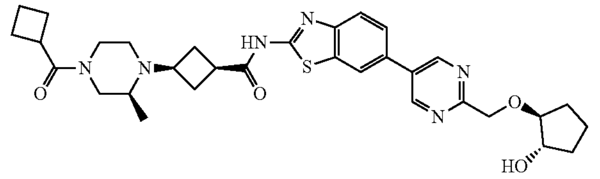 [SMILES: C[C@H]1CN(C(=O)C2CCC2)CCN1[C@H]1C[C@@H](C(=O)Nc2nc3ccc(-c4cnc(CO[C@H]5CCC[C@@H]5O)nc4)cc3s2)C1] | Example b-05-01 | (LC-1): RT = 1.18, m/z 605 $[M + H]^+$ |
| b-05-08 | 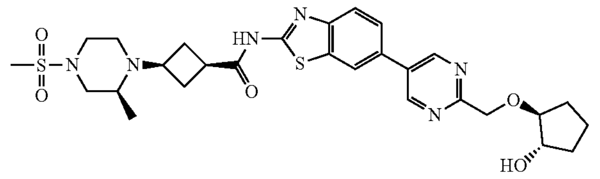 [SMILES: C[C@H]1CN(S(C)(=O)=O)CCN1[C@H]1C[C@@H](C(=O)Nc2nc3ccc(-c4cnc(CO[C@H]5CCC[C@@H]5O)nc4)cc3s2)C1] | Example b-05-01 | (LC-1): RT = 1.11, m/z 601 $[M + H]^+$ |

TABLE 9-continued

| Example | Structure | Reference Methods | LCMS Data |
|---|---|---|---|
| b-05-09 | 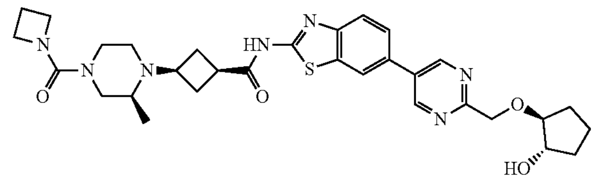 [SMILES: C[C@H]1CN(C(=O)N2CCC2)CCN1[C@H]1C[C@@H](C(=O)Nc2nc3ccc(-c4cnc(CO[C@H]5CCC[C@@H]5O)nc4)cc3s2)C1] | Example b-05-01 | (LC-1): RT = 1.07, m/z 606 [M + H]$^+$ |

Intermediate B-6-1: tert-Butyl (S)-4-((3R)-3-((6-(2-((((1S,2S)-2-acetoxycyclopentyl)oxy)methyl)pyrimidin-5-yl)benzo[d]thiazol-2-yl)carbamoyl)cyclobutyl)-3-methylpiperazine-1l-carboxylate

[Formula 102]

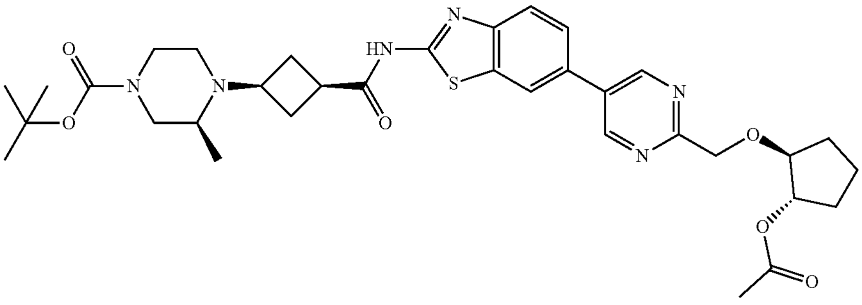

(1S,2S)-2-((5-(2-(3-Oxocyclobutane-1-carboxamido) benzo[d]thiazol-6-yl)pyrimidin-2-yl)methoxy)cyclopentyl acetate (Intermediate B-4-4, 15 g, 31.2 mmol) was dissolved in dichloromethane (156 mL), (3S)-1-Boc-3-methylpiperazine hydrochloride (1.5 g, 46.8 mmol), and sodium triacetoxyborohydride (13.2 g, 62.4 mmol) were added to the solution, and the resulting mixture was stirred at room temperature for 3 hours. 25% Aqueous ammonia was added to the resulting crude reaction mixture, and the resulting mixture was extracted with chloroform. The obtained organic layer was dried over magnesium sulfate, and the solvent was evaporated under reduced pressure to obtain tert-butyl (S)-4-((3R)-3-((6-(2-((((1S,2S)-2-acetoxycyclopentyl)oxy)methyl)pyrimidin-5-yl)benzo[d]thiazol-2-yl) carbamoyl)cyclobutyl)-3-methylpiperazine-1-carboxylate (10 g, yield 48%).

LCMS (LC-1): RT=1.68, m/z 665 [M+H1]$^+$

1H-NMR ($CDCl_3$): δ (ppm) 9.00 (s, 2H), 7.99 (brs, 1H), 7.87 (m, 1H), 7.61 (brd, J=7.5 Hz, 2H), 7.55-7.27 (m, 2H), 7.00 (s, 2H), 5.36-5.16 (m, 2H), 4.98-4.77 (m, 2H), 4.10 (m, 2H), 3.82-3.31 (m, 7H), 3.30-2.93 (m, 4H), 2.67-2.48 (m, 3H), 2.39-2.25 (m, 2H), 2.13 (s, 2H), 2.04 (s, 3H), 1.82 (m, 3H), 1.54-1.45 (m, 9H), 1.00-0.90 (m, 3H)

Intermediate B-6-2: (1S,2S)-2-((5-(2-((1R,3s)-3-((S)-2-Methylpiperazin-1-yl)cyclobutane-1-carboxamido)benzo[d]thiazol-6-yl)pyrimidin-2-yl) methoxy)cyclopentyl acetate

[Formula 103]

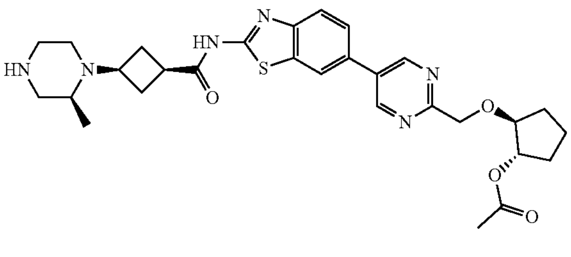

To tert-butyl (S)-4-((3R)-3-((6-(2-((((1S,2S)-2-acetoxycyclopentyl)oxy)methyl)pyrimidin-5-yl)benzo[d]thiazol-2-yl)carbamoyl)cyclobutyl)-3-methylpiperazine-1-carboxylate (Intermediate B-6-1, 5.3 g, 7.97 mol), dichloromethane (80 mL) was added to dissolve the compound, trifluoroacetic acid (6.1 mL, 79.7 mmol) was added to the solution, and the resulting mixture was stirred at room temperature. The resulting crude reaction mixture was neutralized with saturated aqueous sodium hydrogencarbonate, and extracted with chloroform. The resulting organic layer was dried over magnesium sulfate, and the solvent was evaporated under reduced pressure to obtain (1S,2S)-2-((5-(2-((1R,3s)-3-((S)-2-methylpiperazin-1-yl)cyclobutane-1-carboxamido)benzo [d]thiazol-6-yl)pyrimidin-2-yl)methoxy)cyclopentyl acetate (3.7 g, yield 82%).

LCMS (LC-1): RT=1.12, m/z 565 [M+H]$^+$

1H-NMR ($CDCl_3$): δ (ppm) 9.00 (s, 2H), 8.01 (d, J=2.0 Hz, 1H), 7.89 (d, J=8.5 Hz, 1H), 7.62 (dd, J=8.5, 2.0 Hz, 1H), 5.20 (d, J=6.5 Hz, 1H), 4.98-4.77 (m, 2H), 4.10 (d, J=6.5 Hz, 1H), 3.43-3.16 (m, 3H), 3.15-3.00 (m, 2H), 2.97 (brs, 1H), 2.92-2.70 (m, 2H), 2.68-2.44 (m, 31H), 2.44-2.30 (m, 2H), 2.22-1.98 (m, 5H), 1.88-1.60 (m, 4H), 1.43-1.19 (m, 1H), 1.12 (d, J=6.51 Hz, 3H)

Example b-06-01: (S)—N-Ethyl-4-((1s,3R)-3-((6-(2-((((1S,2S)-2-hydroxycyclopentyl)oxy)methyl)pyrimidin-5-yl)benzo[d]thiazol-2-yl)carbamoyl)-3-methylpiperazine-1-carboxamide

[Formula 104]

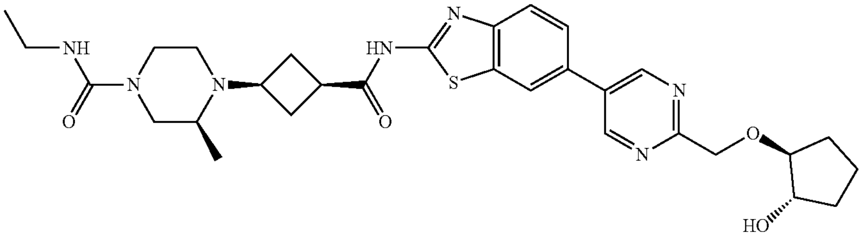

To (1S,2S)-2-((5-(2-((1R,3s)-3-((S)-2-methylpiperazin-1-yl)cyclobutane-1-carboxamido)benzo[d]thiazol-6-yl)pyrimidin-2-yl)methoxy)cyclopentyl acetate (Intermediate B-6-2, 31.9 mg, 0.06 mol), dichloromethane (1 mL) and THF (0.75 mL) were added to dissolve the compound, isocyanic acid ethyl ester (5.37 μL, 0.07 mmol), and triethylamine (15.75 uL, 0.11 mmol) were added to the solution, and the resulting mixture was stirred at room temperature. Methanol (1 mL) and triethylamine (12 uL) were added to the obtained reaction mixture, the resulting mixture was stirred, potassium carbonate (20 mg), and a 2 N-sodium hydroxide solution (50 uL) were further added, and the resulting mixture was stirred overnight at room temperature. After completion of the reaction, the solvent was evaporated by nitrogen blow, and the residue was purified by using HPLC to obtain (S)—N-ethyl-4-((1s,3R)-3-((6-(2-((((1S,2S)-2-hydroxycyclopentyl)oxy)methyl)pyrimidin-5-yl)benzo[d]thiazol-2-yl)carbamoyl)-3-methylpiperazine-1-carboxamide (8.4 mg, yield 25.0%).

LCMS (LC-1): RT=1.02, m/z 594 $[M+H]^+$

1H-NMR ($CDCl_3$): δ (ppm) 8.98-8.95 (2H, m), 8.02-7.94 (1H, m), 7.86-7.78 (1H, m), 7.62-7.56 (1H, m), 4.94-4.86 (1H, m), 4.78-4.69 (1H, m), 4.20-4.09 (1H, m), 3.86-3.76 (1H, m), 3.50-3.40 (2H, m), 3.39-3.32 (2H, m), 3.25-3.17 (2H, m), 3.17-3.08 (1H, m), 3.07-2.95 (2H, m), 2.74-2.65 (11H, m), 2.53-2.45 (1H, m), 2.45-2.29 (3H, m), 2.29-2.19 (1H, m), 2.11-1.95 (2H, m), 1.75-1.49 (4H, m), 1.01 (3H, d, J=6.6 Hz)

The following compound mentioned in the following table was synthesized by similar methods. In the following table, the example of which preparation methods should be referred to is mentioned in the column of "Reference Methods".

TABLE 10

| Example | Structure | Reference Methods | LCMS Data |
|---|---|---|---|
| b-06-02 | 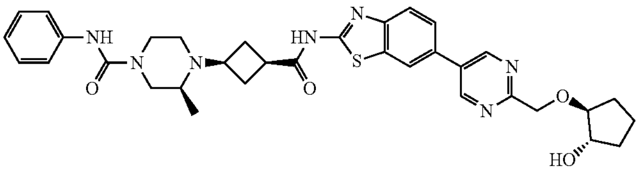 [SMILES: C[C@H]1CN(C(=O)Nc2ccccc2)CCN1[C@H]1C[C@@H](C(=O)Nc2nc3ccc(-c4cnc(CO[C@H]5CCC[C@@H]5O)nc4)cc3s2)C1] | Example b-06-01 | (LC-1): RT = 1.22, m/z 642 $[M + H]^+$ |

Example b-07-01: N-(6-(2-((((1S,2S)-2-Hydroxycyclopentyl)oxy)methyl)pyrimidin-5-yl)benzo[d]thiazol-2-yl)-3-((S)-2-methyl-4-(2,2,2-trifluoroethyl)piperazin-1-yl)cyclobutane-1-carboxamide

[Formula 105]

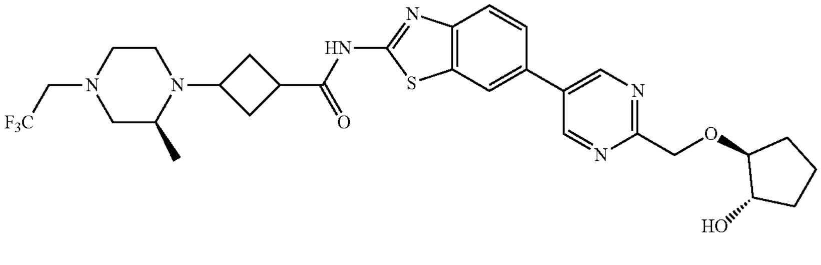

(1R,3s)-N-(6-(2-((((1S,2S)-2-Hydroxycyclopentyl)oxy)methyl)pyrimidin-5-yl)benzo[d]thiazol-2-yl)-3-((S)-2-methylpiperazin-1-yl)cyclobutane-1-carboxamide (Example B-4-6, 0.10 g, 0.19 mmol), and 2,2,2-trifluoroethyl trifluoromethanesulfonate (42 µL, 0.29 mmol) were suspended in THF (634 µL), N-ethyldiisopropylamine (83 µL, 0.48 mmol) was added to the suspension, and the resulting mixture was stirred at 50° C. for 15 hours. Methanol (4 mL) and 1 M aqueous sodium hydroxide (2 mL) were added to the resulting crude reaction mixture, and the resulting mixture was extracted with chloroform. The resulting crude product was purified by using SCX and HPLC to obtain N-(6-(2-((((1S,2S)-2-hydroxycyclopentyl)oxy)methyl)pyrimidin-5-yl)benzo[d]thiazol-2-yl)-3-((S)-2-methyl-4-(2,2,2-trifluoroethyl)piperazin-1-yl)cyclobutane-1-carboxamide (22 mg, yield 19%).

LCMS (LC-1): RT=1.33, m/z 605 $[M+H]^+$

1H-NMR ($DMSOd_6$): δ (ppm) 9.14 (2H, s), 8.29 (1H, m), 7.75-7.65 (2H, m), 4.71-4.67 (3H, m), 4.02 (1H, brm), 3.83-3.80 (1H, m), 3.17-3.07 (2H, m), 2.95-2.82 (2H, m), 2.67-2.62 (3H, m), 2.30-2.23 (2H, m), 2.54-2.43 (2H, m), 2.19-2.02 (4H, m), 1.92-1.76 (2H, m), 1.65-1.55 (3H, m), 1.47-1.40 (1H, m), 0.95 (3H, d, J=6.4 Hz)

Intermediate B-8-1: tert-Butyl (S)-4-cyclopropyl-2-methylpiperazine-1-carboxylate

[Formula 106]

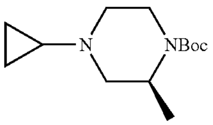

tert-Butyl (2S)-2-methylpiperazine-1-carboxylate (1 g, 5.0 mmol), and (1-ethoxycyclopropoxy)trimethylsilane (1 mL, 5.0 mmol) were dissolved in methanol (10 mL) and tetrahydrofuran (10 mL), acetic acid (0.57 mL, 10 mmol), and sodium cyanoborohydride (627 mg, 10 mmol) were added to the solution, and the resulting mixture was stirred at 60° C. for 6 hours. The resulting crude reaction mixture was cooled to room temperature, water (1 mL) and 1 M aqueous sodium hydroxide (6 mL) were added to the reaction mixture, and the organic solvent was removed under reduced pressure. The resulting aqueous layer was extracted with chloroform (20 mL), and the organic layer was washed with 1 M aqueous sodium hydroxide. The combined aqueous layer was extracted with chloroform (6 mL). The combined organic layer was washed with saturated brine (20 mL), dried over anhydrous sodium sulfate, filtered, and concentrated under reduced pressure to obtain tert-butyl (S)-4-cyclopropyl-2-methylpiperazine-1-carboxylate (1.21 g) as a crude product.

1H-NMR ($CDCl_3$): δ (ppm) 4.18-4.16 (1H, m), 3.79-3.76 (1H, m), 2.99-2.92 (1H, m), 2.86-2.83 (1H, m), 2.71-2.68 (1H, m), 2.36-2.33 (1H, m), 2.19-2.12 (1H, m), 1.57-1.52 (1H, m), 1.46 (9H, s), 1.13 (3H, d, J=6.7 Hz), 0.44-0.28 (4H, m)

Intermediate B-8-2: (S)-1-Cyclopropyl-3-methylpiperazine hydrochloride

[Formula 107]

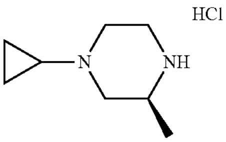

The aforementioned crude product, tert-butyl (S)-4-cyclopropyl-2-methylpiperazine-1-carboxylate (Intermediate B-8-1, 1.2 g), was dissolved in a 4 M solution of hydrochloric acid in 1,4-dioxane, and the resulting solution was stirred at room temperature for 30 minutes. The resulting crude reaction mixture was azeotroped 3 times with ethyl acetate to obtain (S)-1-cyclopropyl-3-methylpiperazine hydrochloride (1.2 g) as a crude product.

1H-NMR ($CD_3OD$): δ (ppm) 3.90-3.77 (3H, m), 3.74-3.70 (1H, m), 3.61-3.47 (2H, m), 3.36-3.30 (1H, m), 2.98-2.92 (1H, m), 1.44 (3H, d, J=6.5 Hz), 1.23-1.19 (2H, m), 1.02-0.96 (2H, m)

Example b-08-01: 3-((S)-4-Cyclopropyl-2-methylpiperazin-1-yl)-N-(6-(2-((((1S,2S)-2-hydroxycyclopentyl)oxy)methyl)pyrimidin-5-yl)benzo[d]thiazol-2-yl)cyclobutane-1-carboxamide

[Formula 108]

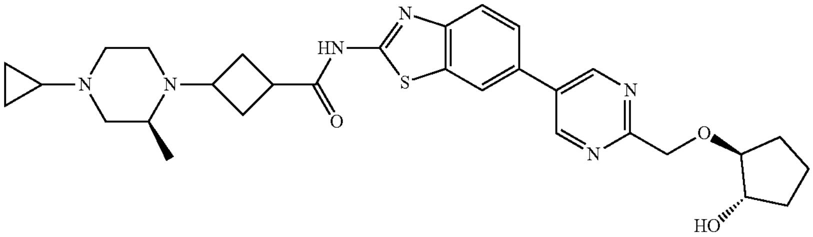

To N-(6-(2-((((1S,2S)-2-hydroxycyclopentyl)oxy)methyl)pyrimidin-5-yl)benzo[d]thiazol-2-yl)-3-oxocyclobutane-1-carboxamide (Intermediate B-2-2, 40.2 mg, 0.09 mmol), dichloromethane (1.5 mL) and THF (1.3 mL) were added to dissolve the compound, (S)-1-cyclopropyl-3-methylpiperazine hydrochloride (Intermediate B-8-2, 25.7 mg, 0.18 mml) was added to the solution, the resulting mixture was stirred, sodium triacetoxyborohydride (29.14 mg, 0.14 mmol) was further added to the reaction mixture, and the resulting mixture was stirred overnight at room temperature. (S)-1-Cyclopropyl-3-methylpiperazine hydrochloride (25.7 mg, 0.18 mml), acetic acid (200 μL), and sodium triacetoxyborohydride (29.14 mg, 0.14 mmol) were added to the reaction mixture, and the resulting mixture was stirred for further 5 hours. After completion of the reaction, aqueous sodium hydrogencarbonate was added to the reaction mixture, the resulting mixture was extracted with chloroform, the organic layer was concentrated by nitrogen blow, and the residue was purified by using HPLC to obtain 3-((S)-4-cyclopentyl-2-methylpiperazin-1-yl)-N-(6-(2-((((1S,2S)-2-hydroxycyclopentyl)oxy)methyl)pyrimidin-5-yl)benzo[d]thiazol-2-yl)cyclobutane-1-carboxamide (4.3 mg, yield 8%).

LCMS (LC-1): RT=1.13, m/z 563 $[M+H]^+$

1H-NMR ($CDCl_3$): δ (ppm) 8.92 (2H, s), 7.93-7.88 (1H, m), 7.78-7.70 (1H, m), 7.55-7.48 (1H, m), 4.92-4.81 (1H, m), 4.80-4.67 (1H, m), 4.18-4.09 (1H, m), 3.84-3.76 (1H, m), 3.36-3.30 (1H, m), 2.97-2.88 (11H, m), 2.78-2.70 (2H, m), 2.59 (4H, s), 2.49-2.37 (4H, m), 2.35-2.25 (2H, m), 2.23-2.11 (2H, m), 2.08-1.92 (31H, m), 1.74-1.62 (3H, m), 1.61-1.48 (3H, m), 1.01 (3H, brd, J=6.1 Hz), 0.45-0.33 (4H, m)

Intermediate C-1-1: N-(7-Oxo-4,5,6,7-tetrahydrobenzo[d]thiazol-2-yl)acetamide

[Formula 109]

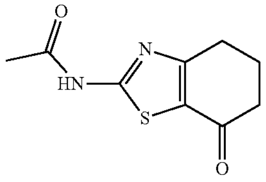

2-Amino-5,6-dihydro-4H-benzothiazol-7-one (60 g, 357 mmol) was suspended in acetic anhydride (300 mL), and the suspension was stirred for 4 hours under reflux by heating. The resulting crude reaction mixture was cooled to room temperature, and the precipitates were taken by filtration, washed with water, and vacuum-dried to obtain N-(7-oxo-4,5,6,7-tetrahydrobenzo[d]thiazol-2-yl)acetamide (69.6 g, yield 93%).

LCMS (LC-1): RT=0.75, m/z 211 $[M+H]^+$

1H-NMR ($DMSOd_6$): δ (ppm) 12.52 (1H, s), 2.85 (2H, t, J=6.2 Hz), 2.51-2.47 (2H, m), 2.18 (3H, s), 2.11-2.05 (2H, m)

Intermediate C-1-2: N-(6,6-Dibromo-7-oxo-4,5,6,7-tetrahydrobenzo[d]thiazol-2-yl)acetamide

[Formula 110]

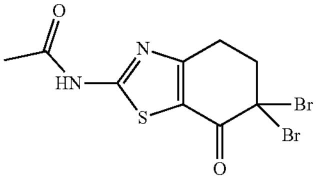

N-(7-Oxo-4,5,6,7-tetrahydrobenzo[d]thiazol-2-yl)acetamide (Intermediate C-1-1, 30 g, 143 mmol) was suspended in acetic acid (300 mL), 48% hydrobromic acid (3.2 mL, 29 mmol), and bromine (29 mL, 571 mmol) were added to the suspension, and the resulting mixture was stirred at 60° C. for 24 hours. Water (300 mL) was added to the resulting crude reaction mixture. The same operation was performed for 2 batches, the resulting precipitates were combined, taken by filtration, washed with water, and vacuum-dried to obtain N-(6,6-dibromo-7-oxo-4,5,6,7-tetrahydrobenzo[d]thiazol-2-yl)acetamide (75.3 g, 72%).

LCMS (LC-1): RT=1.21, m/z 366 $[M+H]^+$

1H-NMR ($DMSOd_6$): δ (ppm) 12.88 (1H, s), 3.15 (2H, t, J=5.8 Hz), 2.97 (2H, t, J=5.8 Hz), 2.22 (31H, s)

Intermediate C-1-3: N-(6-Bromo-7-hydroxybenzo[d]thiazol-2-yl)acetamide

[Formula 111]

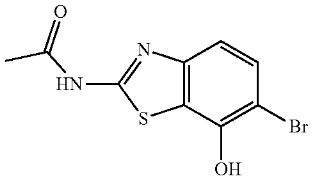

N-(6,6-Dibromo-7-oxo-4,5,6,7-tetrahydrobenzo[d]thiazol-2-yl)acetamide (Intermediate C-1-2, 37.6 g, 102 mmol) was suspended in tetrahydrofuran (300 mL), diazabicycloundecene (46 mL, 307 mmol) was added dropwise to the suspension, and the resulting mixture was stirred at room temperature for 1 hour. Water (300 mL) was added to the resulting crude reaction mixture, the resulting mixture was stirred at room temperature for 30 minutes, saturated aqueous ammonium chloride (300 mL) was added to the reaction mixture, stirring was terminated, and the reaction mixture was left standing for 30 minutes. The same operation was performed for 2 batches, and the resulting precipitates were taken by filtration, washed with water, and vacuum-dried to obtain N-(6-bromo-7-hydroxybenzo[d]thiazol-2-yl)acetamide (68.4 g) as a crude product.

LCMS (LC-1): RT=0.90, m/z 286 $[M+H]^+$

1H-NMR ($DMSOd_6$): δ (ppm) 7.37 (1H, d, J=8.4 Hz), 6.86 (1H, d, J=8.4 Hz), 2.17 (3H, s)

The following compound mentioned in the following table was synthesized by similar methods. In the following table, the preparation methods should be referred to are mentioned in the column of "Reference Methods".

TABLE 11

| Intermediate | Structure | Reference Methods | LCMS Data |
| --- | --- | --- | --- |
| C-1-10 | 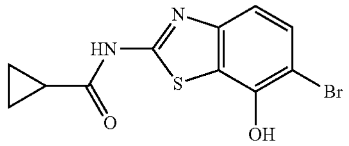 [SMILES: O=C(Nc1nc2ccc(Br)c(O)c2s1)C1CC1] | Intermediates C-1-1, 2, 3 | (LC-1): RT =1.14, m/z 312 [M + H]$^+$ |

Intermediate C-1-4: 2-Amino-6-bromobenzo[d]thiazol-7-ol

[Formula 112]

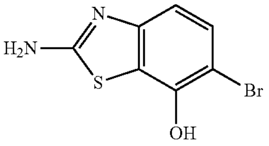

The aforementioned crude product, N-(6-bromo-7-hydroxybenzo[d]thiazol-2-yl)acetamide (Intermediate C-1-3, 68.4 g), was suspended in methanol (240 mL) and 5 M aqueous hydrochloric acid (360 mL), and the resulting suspension was stirred at 75° C. for 14 hours. Methanol was removed from the resulting crude reaction mixture under reduced pressure, and 5 M aqueous sodium hydroxide was added dropwise to the reaction mixture with ice cooling for neutralization. The resulting solid was taken by filtration, and vacuum-dried to obtain 2-amino-6-bromobenzo[d]thiazol-7-ol as a crude product.

LCMS (LC-1): RT=0.84, m/z 244 [M+H]$^+$ (detected as boronic acid)

1H-NMR ($DMSOd_6$): δ (ppm) 9.92 (1H, s, br), 7.52 (2H, s), 7.28 (1H, d, J=8.4 Hz), 6.81 (1H, d, J=8.4 Hz)

Intermediate C-1-5: 2-(6-Bromo-7-hydroxybenzo[d]thiazol-2-yl)isoindoline-1,3-dione

[Formula 113]

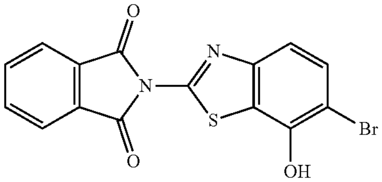

The aforementioned crude product, 2-amino-6-bromobenzo[d]thiazol-7-ol (Intermediate C-1-4, 163 mmol), was suspended in N,N-dimethylformamide (137 mL) and acetic acid (137 mL), phthalic acid anhydride (48 g, 326 mmol) was added to the suspension, and the resulting mixture was stirred at 120° C. for 5 hours. The resulting crude reaction mixture was cooled to room temperature, and the precipitates were taken by filtration, washed with water, and vacuum-dried to obtain 2-(6-bromo-7-hydroxybenzo[d]thiazol-2-yl)isoindoline-1,3-dione (54.7 g, yield for 3 steps 89%).

LCMS (LC-1): RT=1.23, m/z 374 [M+H]$^+$

1H-NMR ($DMSOd_6$): δ (ppm) 10.76 (1H, s), 8.08-8.04 (2H, m), 7.99-7.96 (2H, m), 7.65 (1H, d, J=8.6), 7.49 (1H, d, J=8.6)

Intermediate C-1-6: 2-(6-Bromo-7-methoxybenzo[d]thiazol-2-yl)isoindoline-1,3-dione

[Formula 114]

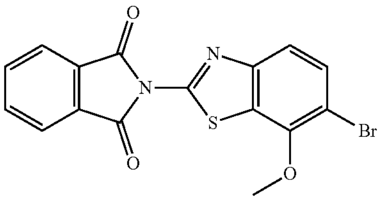

2-(6-Bromo-7-hydroxybenzo[d]thiazol-2-yl)isoindoline-1,3-dione (Intermediate C-1-5, 54.7 g, 146 mmol) was dissolved in N,N-dimethylformamide (547 mL), iodomethane (27 mL, 437 mmol), and N-ethyldiisopropylamine (102 mL, 583 mmol) were added to the solution, and the resulting mixture was stirred at room temperature for 9 hours. Water (110 mL) was added to the resulting crude reaction mixture, and the precipitates were taken by filtration, and vacuum-dried to obtain 2-(6-bromo-7-methoxybenzo[d]thiazol-2-yl)isoindoline-1,3-dione (52.0 g, 92%).

LCMS (LC-1): RT=1.74, m/z 388 [M+H]$^+$

1H-NMR ($DMSOd_6$): δ (ppm) 8.09-8.06 (2H, m), 8.01-7.96 (2H, m), 7.76 (2H, m), 4.03 (3H, s)

Intermediate C-1-7: 6-Bromo-7-methoxybenzo[d]thiazol-2-amine

[Formula 115]

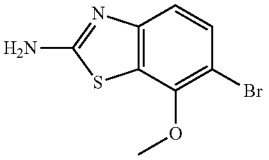

2-(6-Bromo-7-methoxybenzo[d]thiazol-2-yl)isoindoline-1,3-dione (Intermediate C-1-6, 52.0 g, 134 mmol) was suspended in ethanol, hydrazine monohydrate (7.1 mL, 147 mmol) was added to the suspension, and the resulting mixture was stirred for 1 hour under reflux by heating. The resulting crude reaction mixture was cooled to 50° C., the precipitates were removed by filtration, and the reaction mixture was washed with tetrahydrofuran. The resulting filtrate was concentrated under reduced pressure to obtain 6-bromo-7-methoxybenzo[d]thiazol-2-amine (41.6 g) as a crude product.

LCMS (LC-1): RT=1.23, m/z 258 [M+H]$^+$

1H-NMR (DMSOd$_6$): δ (ppm) 7.69 (2H, s), 7.40 (1H, d, J=8.4 Hz), 7.05 (1H, d, J=8.4 Hz), 3.85 (3H, s)

Intermediate C-1-8: (1S,2S)-2-((5-(2-Amino-7-methoxybenzo[d]thiazol-6-yl)pyrimidin-2-yl) methoxy)cyclopentyl acetate

[Formula 116]

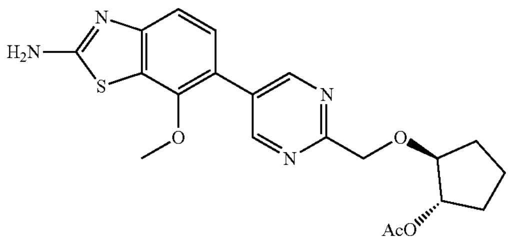

The aforementioned crude product, 6-bromo-7-methoxybenzo[d]thiazol-2-amine (Intermediate C-1-7, 12.35 g, 38.6 mmol), was suspended in 1,4-dioxane, the aforementioned crude product, (1S,2S)-2-((5-(4,4,5,5-tetramethyl-1,3,2-dioxaboran-2-yl)pyrimidin-2-yl)methoxy)cyclopentyl acetate (Intermediate B-4-2, 46.6 g, 77.2 mmol), [1,1'-bis(diphenylphosphino)ferrocene]dichloropalladium(II) (5.7 g, 7.7 mmol), cesium carbonate (37.7 g, 116 mmol), and water (25 mL) were added to the suspension, and the resulting mixture was stirred at 130° C. for 1 hours. The crude reaction mixture was diluted with ethyl acetate (200 mL), and washed with water (200 mL). The aqueous layer was extracted again with ethyl acetate (200 mL), and the combined organic layer was dried over anhydrous sodium sulfate, then filtered, and concentrated under reduced pressure. The resulting crude product was purified by using automatic silica gel column chromatography (eluent, chloroform: methanol=100:0 to 95:5) to obtain (1S,2S)-2-((5-(2-amino-7-methoxybenzo[d]thiazol-6-yl)pyrimidin-2-yl)methoxy) cyclopentyl acetate (19.3 g) as a crude product.

LCMS (LC-1): RT=1.22, m/z 415 [M+H]$^+$

Intermediate C-1-9: (1S,2S)-2-((5-(2-Amino-7-methoxybenzo[d]thiazol-6-yl)pyrimidin-2-yl) methoxy)cyclopentan-1-ol

[Formula 117]

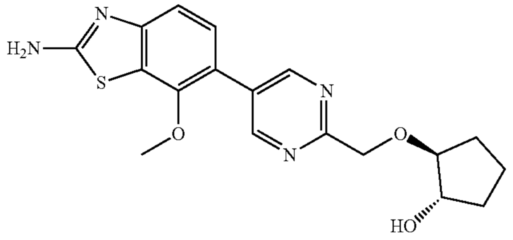

The aforementioned crude product, (1S,2S)-2-((5-(2-Amino-7-methoxybenzo[d]thiazol-6-yl)pyrimidin-2-yl) methoxy)cyclopentyl acetate (Intermediate C-1-8, 20 g), was dissolved in methanol (100 mL), 5 M aqueous sodium hydroxide (100 mL) was added to the solution, and the resulting mixture was stirred at room temperature for 5 minutes. Water (100 mL), saturated aqueous ammonium chloride (100 mL), and chloroform (400 mL) were added to the resulting crude reaction mixture, and the organic layer was separated. The aqueous layer was extracted twice with chloroform, and the combined organic layer was dried over anhydrous sodium sulfate, filtered, and concentrated under reduced pressure. The resulting crude product was purified by using automatic silica gel column chromatography (eluent, chloroform:methanol=99:1 to 92:8) to obtain (1S,2S)-2-((5-(2-amino-7-methoxybenzo[d]thiazol-6-yl)pyrimidin-2-yl)methoxy)cyclopentan-1-ol (8.1 g, yield for 2 steps 54%).

LCMS (LC-1): RT=0.93, m/z 373 [M+H]$^+$

1H-NMR (DMSOd$_6$): δ (ppm) 8.93 (2H, s), 7.73 (2H, s), 7.36 (1H, d, J=8.3 Hz), 7.24 (1H, d, J=8.3 Hz), 4.72 (1H, d, J=4.0 Hz), 4.68 (1H, m), 4.05-4.01 (1H, m), 3.84-3.81 (1H, m), 3.70 (3H, s), 1.92-1.77 (2H, m), 1.69-1.53 (3H, m), 1.48-1.41 (1H, m)

Example c-01-01: N-(6-(2-((((1S,2S)-2-Hydroxycyclopentyl)oxy)methyl)pyrimidin-5-yl)-7-methoxybenzo[d]thiazol-2-yl)cyclopropanecarboxamide

[Formula 118]

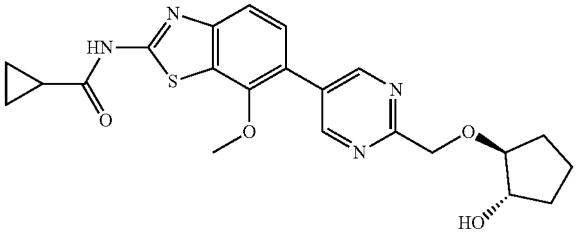

(1S,2S)-2-((5-(2-Amino-7-methoxybenzo[d]thiazol-6-yl) pyrimidin-2-yl)methoxy)cyclopentan-1-ol (Intermediate C-1-9, 5.7 g, 15.3 mmol) was dissolved in tetrahydrofuran (31 mL), N-ethyldiisopropylamine (8 mL, 46 mmol), and cyclopropanecarbonyl chloride (2.1 mL, 23 mmol) were added to the solution, and the resulting mixture was stirred at room temperature for 5 minutes. Cyclopropanecarbonyl chloride (700 μL, 7.7 mmol) was added to the reaction mixture, and the resulting mixture was stirred at room temperature for 1 minute. N-ethyldiisopropylamine (1.66 mL, 7.7 mmol), and cyclopropanecarbonyl chloride (700 μL, 7.7 mmol) were added to the reaction mixture, and the resulting mixture was stirred at room temperature for 15 minutes. Methanol (122 mL) was added to the obtained crude reaction mixture, and the resulting mixture was stirred at room temperature for 3 hours. Water (30 mL) was added to the reaction mixture, and the resulting mixture was concentrated under reduced pressure. Water (30 mL) was added to the obtained reaction mixture, and the resulting mixture was extracted 3 times with chloroform:methanol (9:1, v/v). The combined organic layer was concentrated, and the resulting crude product was purified by using automatic silica gel column chromatography (eluent, hexane:ethyl acetate=75:25 to 0:100, and ethyl acetate:methanol=100:0 to 90:10) to obtain N-(6-(2-((((1S,2S)-2-hydroxycyclopentyl)oxy)methyl)pyrimidin-5-yl)-7-methoxybenzo[d]thiazol-2-yl)cyclopropanecarboxamide (6.6 g, yield 98%).

LCMS (LC-1): RT=1.19, m/z 441 [M+H]$^+$

1H-NMR ($CD_3OD$): δ (ppm) 9.01 (2H, s), 7.64 (1H, d, J=8.3 Hz), 7.53 (1H, d, J=8.3 Hz), 4.81 (2H, m), 4.20-4.17 (1H, m), 3.91-3.88 (1H, m), 3.83 (3H, s), 2.06-1.93 (3H, m), 1.78-1.67 (3H, m), 1.60-1.52 (1H, m), 1.12-1.08 (2H, m), 1.07-1.01 (2H, m)

Example c-02-01: (1R,2R)—N-(6-(2-((((1S,2S)-2-Hydroxycyclopentyl)oxy)methyl)pyrimidin-5-yl)-7-methoxybenzo[d]thiazol-2-yl)-2-methoxycyclopropane-1-carboxamide

[Formula 119]

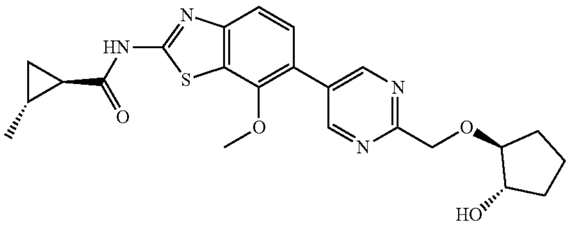

(1S,2S)-2-((5-(2-Amino-7-methoxybenzo[d]thiazol-6-yl)pyrimidin-2-yl)methoxy)cyclopentan-1-ol (Intermediate C-9-9, 540 mg, 110 μmol), and (1R,2R)-2-methylcyclopropane-1-carboxylic acid (16 mg, 160 μmol) were dissolved in N,N-dimethylformamide (537 μL), 1-hydroxybenzotriazole monohydrate (33 mg, 210 μmol), and 1-(3-dimethylaminopropyl)-3-ethylcarbodiimide hydrochloride (41 mg, 210 μmol) were added to the solution, and the resulting mixture was stirred at 70° C. for 5 hours. The resulting crude reaction mixture was purified by using HPLC to obtain (1R,2R)—N-(6-(2-((((1S,2S)-2-hydroxycyclopentyl)oxy)methyl)pyrimidin-5-yl)-7-methoxybenzo[d]thiazol-2-yl)-2-methoxycyclopropane-1-carboxamide (33 mg, yield 67%).

LCMS (LC-1): RT=1.31, m/z 455 $[M+H]^+$

1H-NMR ($CD_3OD$): δ (ppm) 9.01 (2H, s), 7.63 (1H, d, J=8, 4 Hz), 7.53 (11H, d, J=8.4 Hz), 4.81 (2H, m), 4.20-4.17 (1H, m), 3.91-3.88 (1H, m), 3.83 (3H, s), 2.06-1.94 (2H, m), 1.78-1.67 (4H, m), 1.60-1.48 (2H, m), 1.33-1.29 (1H, m), 1.20 (3H, d, J=6.0 Hz), 0.90-0.85 (1H, m)

The following compounds mentioned in the following table were synthesized by similar methods. In the following table, the examples of which preparation methods should be referred to are mentioned in the column of "Reference Methods".

TABLE 12

| Example | Structure | Reference Methods | LCMS Data |
|---|---|---|---|
| c-02-02 | 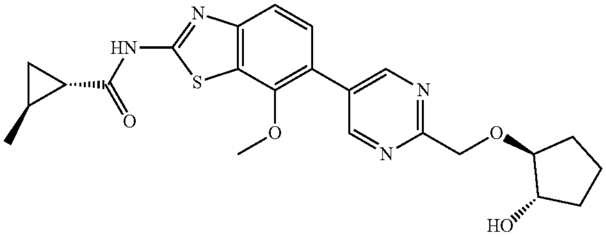 [SMILES: COc1c(-c2cnc(CO[C@H]3CCC[C@@H]3O)nc2)ccc2nc(NC(=O)[C@H]3C[C@@H]3C)sc12] | Example c-02-01 | (LC-1): RT = 1.31, m/z 455 $[M + H]^+$ |
| c-02-03 | 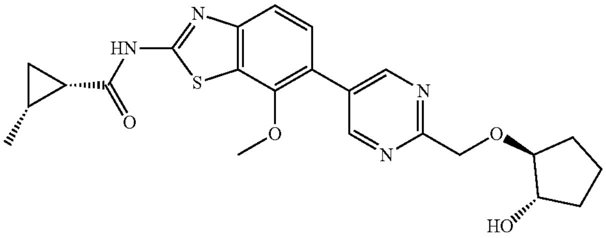 [SMILES: COc1c(-c2cnc(CO[C@H]3CCC[C@@H]3O)nc2)ccc2nc(NC(=O)[C@H]3C[C@H]3C)sc12] | Example c-02-01 | (LC-1): RT = 1.31, m/z 455 $[M + H]^+$ |
| c-02-04 | 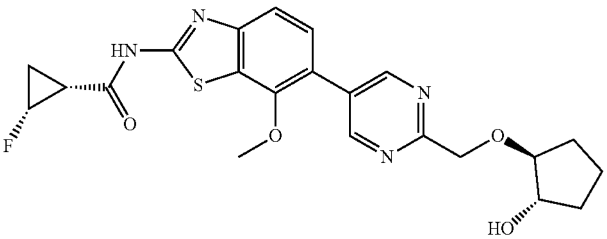 [SMILES: COc1c(-c2cnc(CO[C@H]3CCC[C@@H]3O)nc2)ccc2nc(NC(=O)[C@H]3C[C@H]3F)sc12] | Example c-02-01 | (LC-1): RT = 1.14, m/z 459 $[M + H]^+$ |
| c-02-05 | 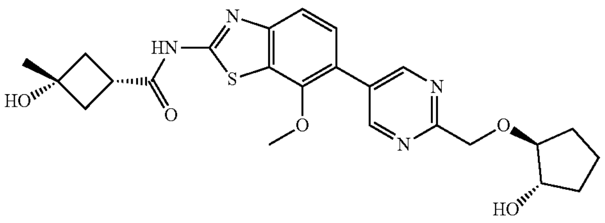 [SMILES: COc1c(-c2cnc(CO[C@H]3CCC[C@@H]3O)nc2)ccc2nc(NC(=O)[C@H]3C[C@@](C)(O)C3)sc12] | Example c-02-01 | (LC-1): RT = 1.02, m/z 485 $[M + H]^+$ |

TABLE 12-continued

| Example | Structure | Reference Methods | LCMS Data |
|---|---|---|---|
| c-02-06 | 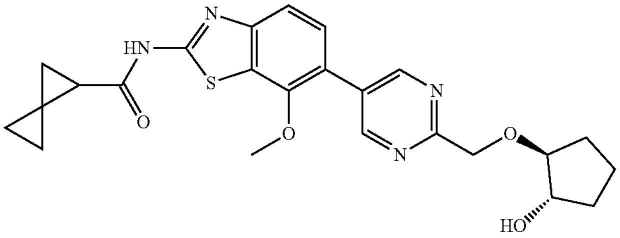 [SMILES: COc1c(-c2cnc(CO[C@H]3CCC[C@@H]3O)nc2)ccc2nc(NC(=O)C3CC34CC4)sc12] | Example c-02-01 | (LC-1): RT = 1.31, m/z 467 $[M + H]^+$ |
| c-02-07 | 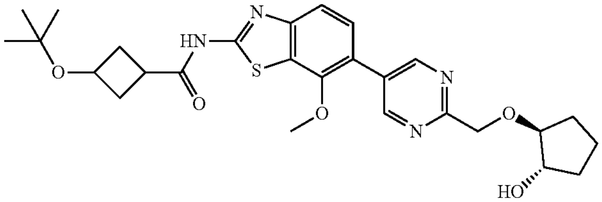 [SMILES: COc1c(-c2cnc(CO[C@H]3CCC[C@@H]3O)nc2)ccc2nc(NC(=O)C3CC(OC(C)(C)C)C3)sc12] | Example c-02-01 | (LC-1): RT = 1.46, m/z 527 $[M + H]^+$ |
| c-02-08 | 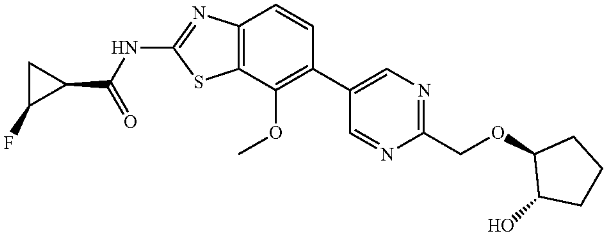 [SMILES: COc1c(-c2cnc(CO[C@H]3CCC[C@@H]3O)nc2)ccc2nc(NC(=O)[C@@H]3C[C@@H]3F)sc12] | Example c-02-01 | (LC-1): RT = 1.14, m/z 459 $[M + H]^+$ |

Intermediate C-3-1: N-(6-(2-((((1S,2S)-2-Hydroxycyclopentyl)oxy)methyl)pyrimidin-5-yl)-7-methoxybenzo[d] thiazol-2-yl)-3-oxocyclobutane-1-carboxamide

[Formula 120]

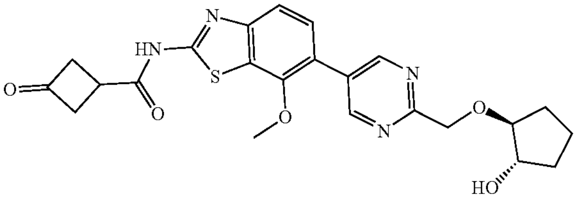

(1S,2S)-2-((5-(2-Amino-7-methoxybenzo[d]thiazol-6-yl) pyrimidin-2-yl)methoxy)cyclopentan-1-ol (Intermediate C-9-9, 805 mg, 2.2 mmol), and (3-oxocyclobutyl)carboxylic acid (370 mg, 3.2 mmol) were dissolved in N,N-dimethylformamide (7.7 mL), 1-hydroxybenzotriazole monohydrate (662 mg, 4.3 mmol), and 1-(3-dimethylaminopropyl)-3-ethylcarbodiimide hydrochloride (829 mg, 4.3 mmol) were added to the solution, and the resulting mixture was stirred at 60° C. for 20 minutes. Chloroform and saturated aqueous sodium hydrogencarbonate were added to the resulting crude reaction mixture, and the organic layer was separated. The aqueous layer was extracted again with chloroform, the combined organic layer was concentrated under reduced pressure, and the resulting crude product was purified by using automatic silica gel column chromatography (eluent, chloroform:methanol=98:2 to 80:20) to obtain N-(6-(2-((((1S,2S)-2-hydroxycyclopentyl)oxy)methyl)pyrimidin-5-yl)-7-methoxybenzo[d]thiazol-2-yl)-3-oxocyclobutane-1-carboxamide (990 mg, yield 98%).

LCMS (LC-1): RT=1.11, m/z 469 $[M+H]^+$

1H-NMR ($CD_3OD$): δ (ppm) 0.92 (2H, m), 7.66-7.61 (1H, m), 7.54-7.51 (11H, m), 4.81 (2H, s), 4.21-4.17 (1H, m), 3.91-3.88 (1H, m), 3.85 (3H, s), 3.58-3.35 (5H, m), 2.62-2.41 (1H, m), 2.06-1.94 (2H, m), 1.78-1.67 (3H, m), 1.60-1.52 (1H, m)

Example c-03-01: tert-Butyl (S)-4-((1s,3R)-3-((6-(2-((((1S,2S)-2-hydroxycyclopentyl)oxy)methyl) pyrimidin-5-yl)-7-methoxybenzo[d]thiazol-2-yl) carbamoyl)cyclobutyl)-3-methylpiperazine-1-carboxylate

[Formula 121]

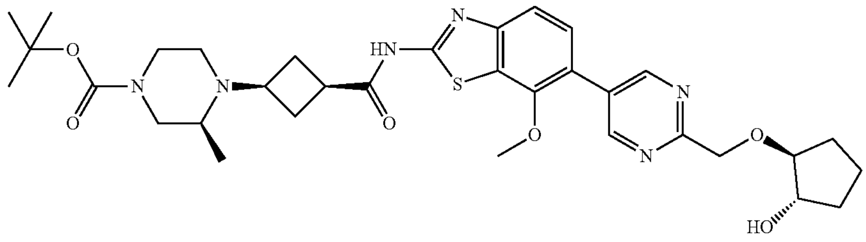

N-(6-(2-((((1S,2S)-2-Hydroxycyclopentyl)oxy)methyl) pyrimidin-5-yl)-7-methoxybenzo[d]thiazol-2-yl)-3-oxocyclobutane-1-carboxamide (Intermediate C-3-1, 967 mg, 2.1 mmol) was dissolved in dichloromethane (19 mL) and tetrahydrofuran (3.8 mL), (3S)-1-Boc-3-methylpiperazine (827 mg, 4.1 mmol), and sodium triacetoxyborohydride (656 mg, 3.1 mmol) were added to the solution, and the resulting mixture was stirred at room temperature for 14 hours. Saturated aqueous sodium hydrogencarbonate was added to the resulting crude reaction mixture, and the obtained mixture was extracted with chloroform. The resulting organic layer was concentrated under reduced pressure, and the obtained crude product was purified by using automatic silica gel column chromatography (eluent, chloroform:methanol=98:2 to 80:20) to obtain tert-butyl (S)-4-((1s,3R)-3-((6-(2-((((1S,2S)-2-hydroxycyclopentyl)oxy) methyl)pyrimidin-5-yl)-7-methoxybenzo[d]thiazol-2-yl) carbamoyl)cyclobutyl)-3-methylpiperazine-1-carboxylate (1.18 g, yield 88%).

LCMS (LC-1): RT=1.48, m/z 653 $[M+H]^+$

1H-NMR ($CD_3OD$): δ (ppm) 9.01 (2H, s), 7.63 (11H, d, J=8.3 Hz), 7.52 (11H, d, J=8.3 Hz), 4.81 (2H, s), 4.20-4.17 (1H, m), 3.91-3.88 (1H, m), 3.85 (3H, s), 3.51-3.35 (4H, m), 2.73-2.68 (1H, m), 2.60 (11H, m), 2.52-2.17 (5H, m), 2.06-1.94 (2H, m), 1.78-1.67 (3H, m), 1.61-1.52 (1H, m), 1.46 (9H, s), 1.03 (3H, d, J=6.5 Hz)

Intermediate C-3-2: (1R,3s)-N-(6-(2-((((1S,2S)-2-Hydroxycyclopentyl)oxy)methyl)pyridin-5-yl)-7-methoxybenzo[d]thiazol-2-yl)-3-((S)-2-methylpiperazin-1-yl)cyclobutane-1-carboxamide tert-Butyl (S)-4-((1s,3R)-3-((6-(2-((((1S,2S)-2-hydroxycyclopentyl)oxy)methyl)pyrimidin-5-yl)-7-methoxybenzo [d]thiazol-2-yl)carbamoyl)cyclobutyl)-3-methylpiperazine-1-carboxylate (Example c-03-01, 1.16 g, 1.8 mmol) was dissolved in dichloromethane (10 mL), concentrated hydrochloric acid (2.5 mL) was added to the solution, and the resulting mixture was stirred at room temperature for 15 minutes. Water (2 mL) and 28% aqueous ammonia (8 mL) were added to the obtained crude reaction mixture, and the resulting mixture was extracted with chloroform. The organic layer was dried over anhydrous sodium sulfate, filtered, and concentrated under reduced pressure to obtain (1R,3s)-N-(6-(2-((((1S,2S)-2-hydroxycyclopentyl)oxy) methyl)pyridin-5-yl)-7-methoxybenzo[d]thiazol-2-yl)-3-((S)-2-methylpiperazin-1-yl)cyclobutane-1-carboxamide (1.0 g, quant.).

LCMS (LC-1): RT=0.92, m/z 553 $[M+H]^+$

1H-NMR ($CD_3OD$): δ (ppm) 9.01 (2H, s), 7.62 (1H, d, J=8.3 Hz), 7.52 (1H, d, J=8.3 Hz), 4.81 (2H, s), 4.20-4.17 (1H, m), 3.91-3.88 (1H, m), 3.84 (3H, s), 3.19-3.02 (2H, m), 2.95-2.91 (1H, m), 2.85-2.73 (3H, m), 2.55-2.27 (6H, m), 2.18-2.11 (1H, m), 2.06-1.94 (2H, m), 1.78-1.67 (31H, m), 1.60-1.52 (1H, m), 1.06 (3H, d, J=6.4 Hz)

[Formula 122]

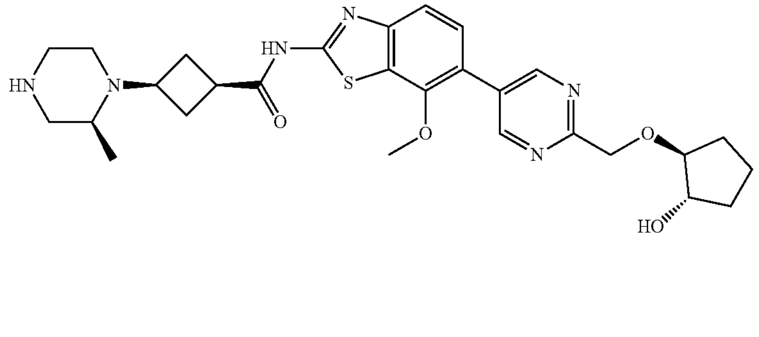

Example c-03-02: (1R,3s)-N-(6-(2-((((1S,2S)-2-Hydroxycyclopentyl)oxy)methyl)pyrimidin-5-yl)-7-methoxybenzo[d]thiazol-2-yl)-3-((S)-2-methyl-4-(2-methylisonicotinoyl)piperazin-1-yl)cyclobutane-1-carboxamide

[Formula 123]

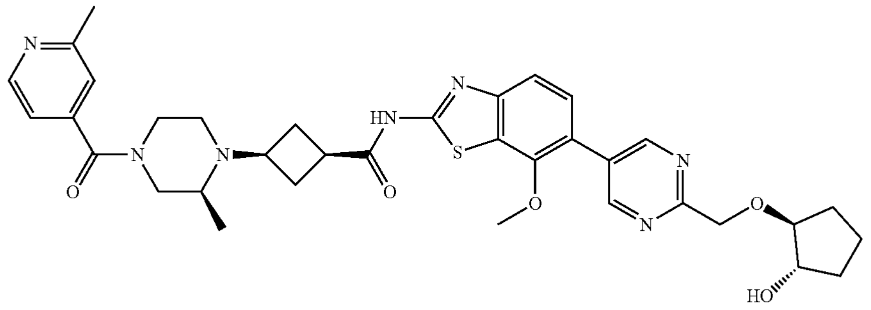

(1R,3s)-N-(6-(2-((((1S,2S)-2-Hydroxycyclopentyl)oxy)methyl)pyridin-5-yl)-7-methoxybenzo[d]thiazol-2-yl)-3-((S)-2-methylpiperazin-1-yl)cyclobutane-1-carboxamide (Intermediate C-3-2, 50 mg, 90 μmol) was dissolved in dichloromethane, 2-methylisonicotinic acid (15 mg, 110 μmol), N-ethyldiisopropylamine (47 μL, 270 mmol), and propylphosphonic acid anhydride (1.7 M solution in ethyl acetate, 80 μL, 140 mmol) were added to the solution, and the resulting mixture was stirred at room temperature for 10 minutes. Saturated aqueous sodium hydrogencarbonate (1 mL) and chloroform were added to the resulting crude reaction mixture for extraction. The organic layer was concentrated by $N_2$ blow, and the residue was purified by using HPLC to obtain (1R,3s)-N-(6-(2-((((1S,2S)-2-hydroxycyclopentyl)oxy)methyl)pyrimidin-5-yl)-7-methoxybenzo[d]thiazol-2-yl)-3-((S)-2-methyl-4-(2-methylisonicotinoyl)piperazin-1-yl)cyclobutane-1-carboxamide (38 mg, yield 62%).

LCMS (LC-1): RT=1.11, m/z 672 $[M+H]^+$

1H-NMR ($DMSOd_6$): δ (ppm) 12.52 (11-H, brs), 8.99 (21H, s), 8.52 (1H, d, J=5.0 Hz), 7.63 (11H, d, J=8.4 Hz), 7.57 (1H, d, J=8.4), 7.24-7.21 (11H, m), 7.17-7.13 (11H, m), 4.73-4.72 (1H, m), 4.70 (2H, m), 3.85-3.83 (1H, m), 3.81 (3H, s), 3.70-3.52 (2H, m), 3.25 (2H, m), 3.10-2.94 (3H, m), 2.68-2.63 (1H, m), 2.38-2.32 (1H, m), 2.28-2.21 (2H, m), 2.18-2.06 (3H, m), 1.92-1.77 (2H, m), 1.66-1.55 (3H, m), 1.48-1.41 (1H, m), 1.25-1.24 (1H, m), 1.01-0.99 (2H, m), 0.88-0.82 (2H, m)

The following compounds mentioned in the following table were synthesized by similar methods. In the following table, the examples of which preparation methods should be referred to are mentioned in the column of “Reference Methods”.

TABLE 13

| Example | Structure | Reference Methods | LCMS Data |
|---|---|---|---|
| b-03-03 | 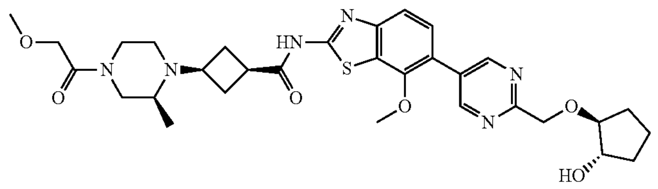 [SMILES: COCC(=O)N1CCN([C@H]2C[C@@H](C(=O)Nc3nc4ccc(-c5cnc(CO[C@H]6CCC[C@@H]6O)nc5)c(OC)c4s3)C2)[C@@H](C)C1] | Example c-03-02 | (LC-1): RT = 1.06, m/z 625 $[M + H]^+$ |
| b-03-04 | 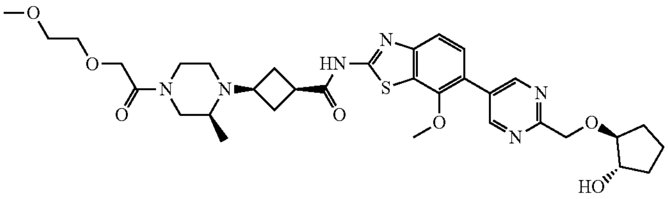 [SMILES: COCCOCC(=O)N1CCN([C@H]2C[C@@H](C(=O)Nc3nc4ccc(-c5cnc(CO[C@H]6CCC[C@@H]6O)nc5)c(OC)c4s3)C2)[C@@H](C)C1] | Example c-03-02 | (LC-1): RT = 1.08, m/z 669 $[M + H]^+$ |

TABLE 13-continued

| Example | Structure | Reference Methods | LCMS Data |
|---|---|---|---|
| b-03-05 | 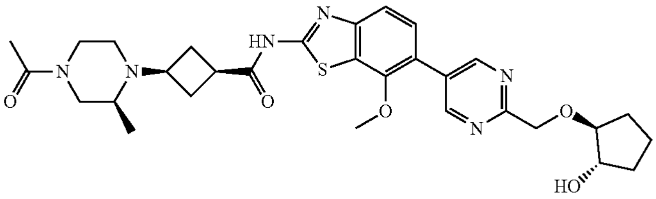 | Example c-03-01 | (LC-1): RT = 1.42, m/z 544 [M + H]$^+$ |
| b-03-06 | 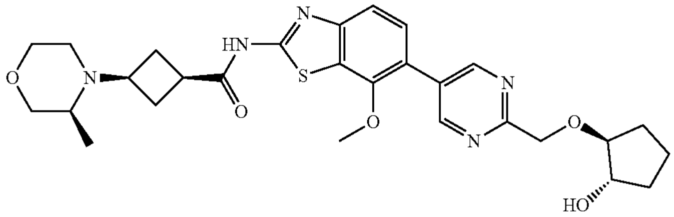 | Example c-03-01 | (LC-1): RT = 1.21, m/z 545 [M + H]$^+$ |
| b-03-07 | 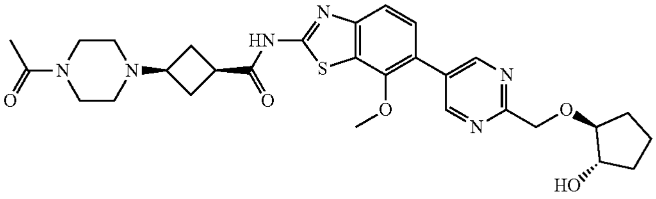 | Example c-03-01 | (LC-1): RT = 1.43, m/z 562 [M + H]$^+$ |
| b-03-08 | 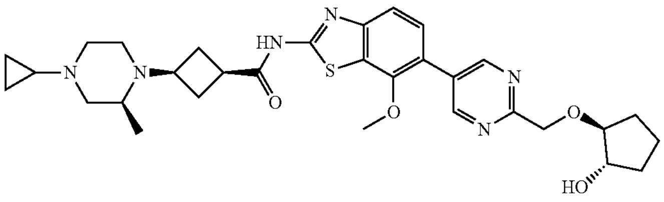 | Example c-03-02, Intermediate B-8-2 | (LC-1): RT = 1.27, m/z 544 [M + H]$^+$ |
| b-03-09 | 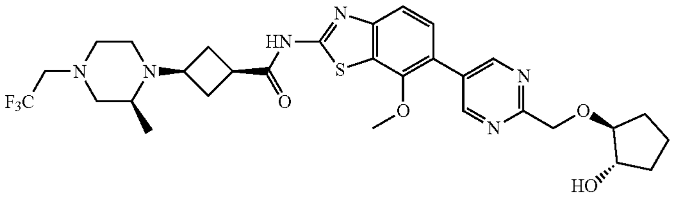 | Examples c-03-02, b-07-01 | (LC-1): RT = 1.07, m/z 534 [M + H]$^+$ |

Intermediate C-4-1: N-(6-Bromo-7-methoxybenzo[d]thiazol-2-yl)cyclopropanecarboxamide

[Formula 124]

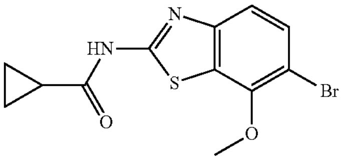

N-(6-Bromo-7-hydroxybenzo[d]thiazol-2-yl)cyclopropanecarboxamide (Intermediate C-9-10, 1.5 g, 4.8 mmol) was dissolved in N,N-dimethylformamide (10 mL), iodomethane (813 mg, 5.7 mmol), potassium iodide (79 mg, 478 μmol), and potassium carbonate (1.32 g, 9.6 mmol) were added to the solution, and the resulting mixture was stirred overnight at room temperature. The resulting crude reaction mixture was concentrated under reduced pressure, and the residue was purified by using silica gel column chromatography (eluent, petroleum ether:ethyl acetate=3:1) to obtain N-(6-bromo-7-methoxybenzo[d]thiazol-2-yl)cyclopropanecarboxamide (400 mg, yield 26%).

LCMS (LC-1): RT=1.56, m/z 326 [M+H]$^+$

1H-NMR ($DMSOd_6$): δ (ppm) 12.79 (1H, brs), 7.64 (1H, d, J=8.4 Hz), 7.46 (1H, d, J=8.4 Hz), 3.95 (3H, s), 2.01-1.99 (1H, m), 0.99-0.96 (4H, m)

Example c-04-01: N-(6-(2-((((1S,2S)-4,4-Difluoro-2-hydroxycyclopentyl)oxy)methyl)pyrimidin-5-yl)-7-methoxybenzo[d]thiazol-2-yl)cyclopropanecarboxamide

[Formula 125]

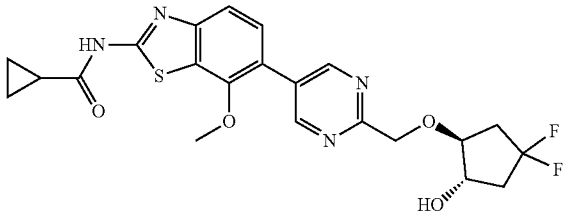

Trans-2-((5-bromopyrimidin-2-yl)methoxy)-4,4-difluorocyclopropan-1-ol (Intermediate A-4-2, 1 g, 3.2 mmol) was dissolved in 1,4-dioxane (15 mL), bis(pinacolato)diboron (1.1 g, 4.8 mmol), [1,1'-bis(diphenylphosphino)ferrocene] dichloropalladium(II) (0.24 g, 0.32 mmol), and potassium acetate (0.95 g, 9.7 mmol) were added to the solution, and the resulting mixture was stirred overnight at 80° C. The resulting crude reaction mixture was concentrated under reduced pressure to obtain 1.50 g of a crude reaction intermediate. The resulting reaction intermediate was dissolved in acetonitrile (8 mL) and water (1 mL), N-(6-bromo-7-methoxybenzo[d]thiazol-2-yl)cyclopropanecarboxamide (Intermediate $C_{1-4}$-1, 400 mg, 1.22 mmol), cesium fluoride (0.37 g, 2.4 mmol), and bis(di-tert-butyl(4-dimethylaminophenyl)phosphine)dichloropalladium(II) (43 mg, 61 μmol) were added to the solution, and the resulting mixture was stirred at 130° C. for 2 hours under microwave irradiation. The resulting crude reaction mixture was concentrated, and the residue was purified by using silica gel column chromatography (eluent, chloroform:methanol=30:1) and HPLC to obtain N-(6-(2-(((trans-4,4-difluoro-2-hydroxycyclopentyl)oxy)methyl)pyrimidin-5-yl)-7-methoxybenzo[d]thiazol-2-yl)cyclopropanecarboxamide (160 mg, yield 28%). The resulting stereoisomer mixture was resolved by using HPLC (CHIRALPAK IC (DAICEL); mobile phase, normal hexane:ethanol=50:50) to obtain the desired N-(6-(2-((((1S,2S)-4,4-difluoro-2-hydroxycyclopentyl)oxy)methyl)pyrimidin-5-yl)-7-methoxybenzo[d]thiazol-2-yl)cyclopropanecarboxamide (42.5 mg).

LCMS (LC-1): RT=1.30, m/z 477 $[M+H]^+$

1H-NMR ($DMSOd_6$): δ (ppm) 9.00 (2H, s), 7.62 (1H, d, J=8.4 Hz), 7.56 (1H, d, J=8.4 Hz), 5.37-5.36 (11H, m), 4.77 (2H, s), 4.20 (1H, m), 4.05 (1H, m), 3.80 (3H, s), 2.58-2.44 (2H, m), 2.26-2.15 (1H, m), 2.09-1.97 (2H, m), 0.98-0.96 (4H, m)

The following compounds mentioned in the following table were synthesized by similar methods. In the following table, the examples of which preparation methods should be referred to are mentioned in the column of "Reference Methods".

TABLE 14

| Example | Structure | Reference Methods | LCMS Data |
|---|---|---|---|
| c-04-02 | 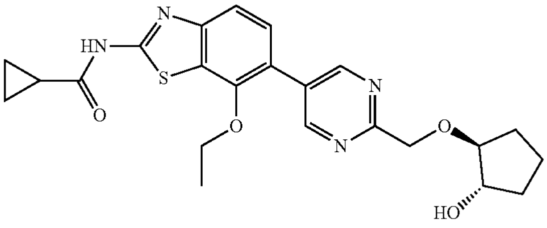 [SMILES: CCOc1c(-c2cnc(CO[C@H]3CCC[C@@H]3O)nc2)ccc2nc(NC(=O)C3CC3)sc12] | Examples c-04-01, a-01-01 Intermediates C-4-1, A-1-3 | (LC-1): RT = 1.25, m/z 455 $[M + H]^+$ |
| c-04-03 | 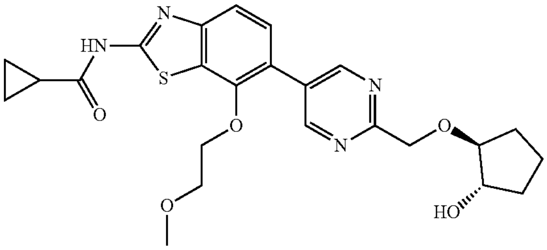 [SMILES: COCCOc1c(-c2cnc(CO[C@H]3CCC[C@@H]3O)nc2)ccc2nc(NC(=O)C3CC3)sc12] | Examples c-04-01, a-01-01 Intermediates C-4-1, A-1-3 | (LC-1): RT = 1.17, m/z 485 $[M + H]^+$ |

Intermediate C-5-1: tert-Butyl 3-(((6-bromo-2-(cyclopropanecarboxamido)benzo[d]thiazol-7-yl)oxy)methyl)-3-fluoroazetidine-1-carboxylate

[Formula 126]

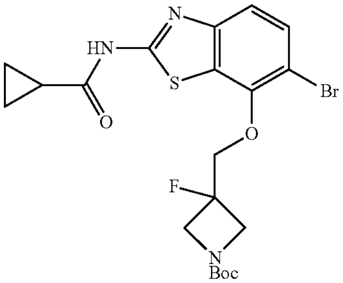

N-(6-Bromo-7-methoxybenzo[d]thiazol-2-yl)cyclopropanecarboxamide (Intermediate $C_{1-4}$-1, 0.2 g, 0.64 mmol), 1-Boc-3-fluoroazetidine-3-methanol (0.26 mg, 1.3 mmol), and triphenylphosphine (0.50 g, 1.9 mmol) were suspended in tetrahydrofuran (3.2 mL), a solution of diethyl azodicarboxylate (0.35 mL, 1.9 mmol) in tetrahydrofuran and toluene (6.4 mL, 1:1, v/v) was added dropwise to the suspension, and the resulting mixture was stirred at room temperature for 15 minutes. The resulting crude reaction mixture was purified by using automatic silica gel column chromatography (eluent, hexane:ethyl acetate=88:12 to 0:100) to obtain tert-butyl 3-(((6-bromo-2-(cyclopropanecarboxamido)benzo[d]thiazol-7-yl)oxy)methyl)-3-fluoroazetidine-1-carboxylate (629 mg) as a crude product.

LCMS (LC-1): RT=1.86, m/z 500 $[M+H]^+$

Intermediate C-5-2: tert-Butyl 3-(((6-(2-((((1S,2S)-2-((tert-butyldimethylsilyl)oxy)cyclopentyl)oxy)methyl)pyrimidin-5-yl)-2-(cyclopropanecarboxamido)benzo[d]thiazol-7-yl)oxy)methyl)-3-fluoroazetidine-1-carboxylate

[Formula 127]

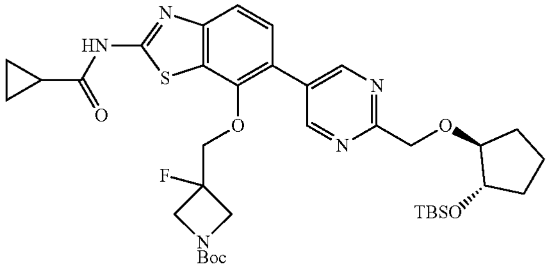

The aforementioned crude product, tert-butyl 3-(((6-bromo-2-(cyclopropanecarboxamido)benzo[d]thiazol-7-yl)oxy)methyl)-3-fluoroazetidine-1-carboxylate (Intermediate C-5-1, 344 mg), was suspended in acetonitrile (3.5 mL) and water (0.35 mL), 2-((((1S,2S)-2-((tert-butyldimethylsilyl)oxy)cyclopentyl)oxy)methyl)-5-(4,4,5,5-tetramethyl-1,3,2-dioxaboran-2-yl)pyrimidine (Intermediate A-1-3, 0.38 g, 0.70 mmol), cesium fluoride (106 mg, 0.70 mmol), and bis(di-tert-butyl(4-dimethylaminophenyl)phosphine)dichloropalladium(II) (50 mg, 70 μmol) were added to the suspension, and the resulting mixture was stirred at 130° C. for 4 hours under microwave irradiation. Ethyl acetate (12 mL) and water (3 mL) were added to the resulting crude reaction mixture, and the organic layer was separated and concentrated under reduced pressure. The resulting crude product was purified by using automatic silica gel column chromatography (eluent, hexane:ethyl acetate=88:12 to 0:100) to obtain tert-butyl 3-(((6-(2-((((1S,2S)-2-((tert-butyldimethylsilyl)oxy)cyclopentyl)oxy)methyl)pyrimidin-5-yl)-2-(cyclopropanecarboxamido)benzo[d]thiazol-7-yl)oxy)methyl)-3-fluoroazetidine-1-carboxylate (116 mg, yield for 2 steps 46%).

LCMS (LC-6), RT=1.57, m/z 728 $[M+H]^+$

Intermediate C-5-3: N-(7-((3-Fluoroazetidin-3-yl)methoxy)-6-(2-((((1S,2S)-2-hydroxycyclopentyl)oxy)methyl)pyrimidin-5-yl)benzo[d]thiazol-2-yl)cyclopropanecarboxamide

[Formula 128]

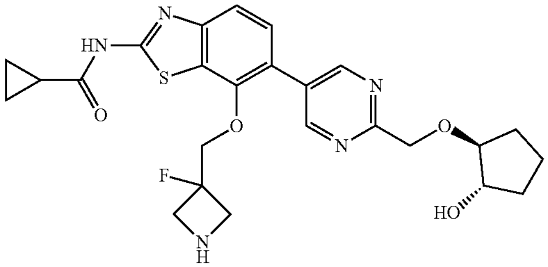

tert-Butyl 3-(((6-(2-((((1 S,2S)-2-((tert-butyldimethylsilyl)oxy)cyclopentyl)oxy)methyl)pyrimidin-5-yl)-2-(cyclopropanecarboxamido)benzo[d]thiazol-7-yl)oxy)methyl)-3-fluoroazetidine-1-carboxylate (Intermediate C-5-2, 112 mg, 0.15 mmol) was dissolved in dichloromethane (1.6 mL), trifluoroacetic acid (0.40 mL) was added to the solution, and the resulting mixture was stirred at room temperature for 3 hours. The resulting crude reaction mixture was purified with SCX to obtain N-(7-((3-fluoroazetidin-3-yl)methoxy)-6-(2-((((1S,2S)-2-hydroxycyclopentyl)oxy)methyl)pyrimidin-5-yl)benzo[d]thiazol-2-yl)cyclopropanecarboxamide as a crude product.

LCMS (LC-1): RT=0.98, m/z 514 $[M+H]^+$

Example c-05-01: N-(7-((3-Fluoro-1-methylazetidin-3-yl)methoxy)-6-(2-((((1S,2S)-2-hydroxycyclopentyl)oxy)methyl)pyrimidin-5-yl)benzo[d]thiazol-2-yl)cyclopropanecarboxamide

[Formula 129]

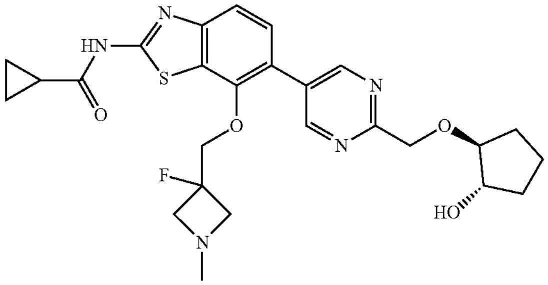

⅓ Amount of the aforementioned crude product, N-(7-((3-fluoroazetidin-3-yl)methoxy)-6-(2-((((1 S,2S)-2-hydroxycyclopentyl)oxy)methyl)pyrimidin-5-yl)benzo[d]thiazol-2-yl)cyclopropanecarboxamide (Intermediate C-5-3), was dissolved in methanol and dichloromethane (2 mL, 1:1, v/v), formaldehyde (37% aqueous solution, 12 μL, 0.16 mmol), and sodium triacetoxyborohydride (34 mg, 0.16 mol) were added to the solution, and the resulting mixture was stirred at room temperature for 15 minutes. The resulting crude reaction mixture was purified by using SCX and HPLC to obtain N-(7-((3-fluoro-1-methylazetidin-3-yl)methoxy)-6-(2-((((1S,2S)-2-hydroxycyclopentyl)oxy)methyl)pyrimidin-5-yl)benzo[d]thiazol-2-yl)cyclopropanecarboxamide (13.9 mg, yield for 2 steps 50%).

LCMS (LC-1): RT=1.16, m/z 528 $[M+H]^+$

1H-NMR ($CD_3OD$): d (ppm) 9.02 (2H, s), 7.67 (1H, d, J=8.3 Hz), 7.55 (1H, d, J=8.3 Hz), 4.81 (2H, s), 4.23 (1H, s), 4.20-4.16 (2H, m), 3.90-3.87 (1H, m), 3.50-3.44 (2H, m), 3.21-3.13 (2H, m), 2.37 (31H, s), 2.05-1.93 (3H, m), 1.78-1.67 (3H, m), 1.60-1.52 (111, m), 1.12-1.01 (4H, m)

Intermediate C-6-1: N-(6-Bromo-7-(methoxymethoxy)benzo[d]thiazol-2-yl)-N-(methoxymethoxy)cyclopropanecarboxamide

[Formula 130]

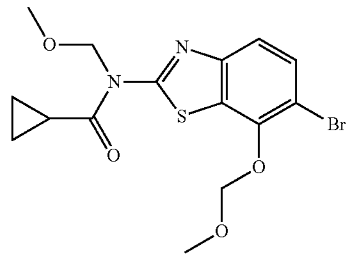

To N-(6-bromo-7-hydroxy-1,3-benzothiazol-2-yl)cyclopropanecarboxamide (Intermediate C-1-10, 5.41 g, 17.27 mmol), dichloromethane (173 mL) was added, and the resulting mixture was stirred at 0° C. with cooling. N,N-Diisopropylamine (15.04 mL, 86.37 mmol), and chloromethyl methyl ether (3.94 mL, 51.82 mmol) were slowly added 1 mL-portion-wise to the reaction mixture. The reaction mixture was stirred at 0° C. with cooling for a while, and then stirred at room temperature for 1 hour. The reagents, N,N-diisopropylamine (3.01 mL, 17.27 mmol), and chloromethyl methyl ether (0.66 mL, 8.63 mmol), were further added to the reaction mixture, and the resulting mixture was stirred for 30 minutes. Saturated aqueous sodium hydrogencarbonate and brine were added to the reaction mixture, and dichloromethane was further added for extraction. The aqueous layer was extracted again with dichloromethane. The organic layers were combined, washed again with brine, dried over sodium sulfate, then filtered, and concentrated, and the residue was purified by using silica gel column chromatography (eluent, hexane: ethyl acetate=80:20 to 70:30) to obtain N-(6-bromo-7-(methoxymethoxy)benzo[d]thiazol-2-yl)-N-(methoxymethoxy)cyclopropanecarboxamide (4.3 g, white solid, yield 63%).

LCMS (LC-1): RT=1.91, m/z 401 $[M+H]^+$

1H-NMR ($CDCl_3$): δ (ppm) 7.59-7.56 (1H, m), 7.49-7.43 (1H, m), 5.94-5.91 (2H, s), 5.32-5.30 (2H, s), 3.72-3.69 (3H, s), 3.57-3.52 (3H, s), 1.30-1.25 (2H, m), 1.17-1.14 (1H, m), 1.11-1.05 (2H, m)

Intermediate C-6-2: N-(6-(2-((((1S,2S)-2-((tert-Butyldimethylsilyl)oxy)cyclopentyl)oxy)methyl)pyrimidin-5-yl)-7-(methoxymethoxy)benzo[d]thiazol-2-yl)-N-(methoxymethyl)cyclopropanecarboxamide

[Formula 131]

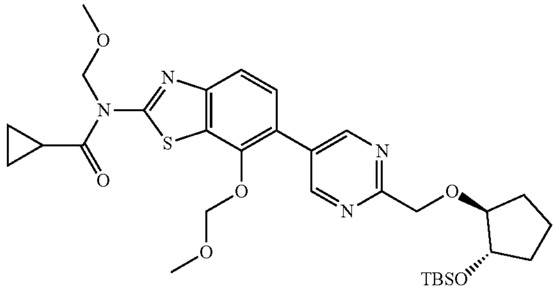

To N-(6-bromo-7-(methoxymethoxy)benzo[d]thiazol-2-yl)-N-(methoxymethoxy)cyclopropanecarboxamide (Intermediate C-6-1, 4.2 g, 10.47 mmol), and 2-((((1S,2S)-2-((tert-butyldimethylsilyl)oxy)cyclopentyl)oxy)methyl)-5-(4,4,5,5-tetramethyl-1,3,2-dioxaboran-2-yl)pyrimidine (Intermediate A-1-3, 6.82 g, 15.71 mmol), 1,4-dioxane (43 mL) was added, cesium carbonate (10.24 g, 31.42 mmol), [1,1'-bis(diphenylphosphino)ferrocene]dichloropalladium (II) (766.3 mg, 1.05 mmol), and water (10.64 mL) were added to the mixture, and the resulting mixture was stirred at 80° C. for 30 minutes with heating. The resulting reaction mixture was filtered through a Celite layer, and the filtrate was extracted with ethyl acetate. The organic layer was dried over sodium sulfate, filtered, and concentrated, and the resulting crude product was purified by using silica gel column chromatography (eluent, hexane:ethyl acetate=60:40) to obtain N-(6-(2-((((1S,2S)-2-((tert-butyldimethylsilyl)oxy)cyclopentyl)oxy)methyl)pyrimidin-5-yl)-7-(methoxymethoxy)benzo[d]thiazol-2-yl)-N-(methoxymethyl)cyclopropanecarboxamide (5.13 g, yield 78%).

LCMS (LC-1): RT=2.16, 2.27, m/z 629 $[M+H]^+$

1H-NMR ($CDCl_3$): δ (ppm) 8.97 (2H, s), 7.71 (1H, d, J=8.0 Hz), 7.38 (1H, d, J=8.0 Hz), 5.97 (2H, s), 5.04 (2H, s), 4.96 (1H, s), 4.36-4.24 (1H, m), 3.95-3.85 (2H, m), 3.57 (3H, s), 3.29 (3H, s), 2.31 (11H, s), 2.04-1.95 (2H, m), 1.76-1.73 (2H, m), 1.59-1.51 (2H, m), 1.32-1.28 (2H, m), 1.19-1.16 (1H, m), 1.13-1.06 (2H, m), 0.99-0.94 (11H, m), 0.88 (9H, s), 0.08 (6H, s)

Intermediate C-6-3: N-(7-Hydroxy-6-(2-((((1S,2S)-2-hydroxycyclopentyl)oxy)methyl)pyrimidin-5-yl)benzo[d]thiazol-2-yl)cyclopropanecarboxamide

[Formula 132]

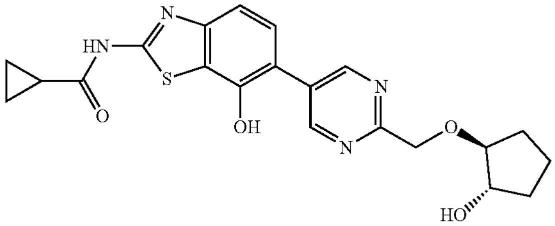

N-(6-(2-((((1S,2S)-2-((tert-Butyldimethylsilyl)oxy)cyclopentyl)oxy)methyl)pyrimidin-5-yl)-7-(methoxymethoxy)benzo[d]thiazol-2-yl)-N-(methoxymethyl)cyclopropanecarboxamide (Intermediate C-6-2, 5 g, 7.95 mmol) was dissolved in THF (8 mL), 5 N aqueous hydrochloric acid (80 mL) was added to the solution, and the resulting mixture was stirred overnight at 40° C. 5 N Aqueous hydrochloric acid (8 mL) was further added to the reaction mixture, and the resulting mixture was stirred for further 5 hours, and then subjected to a post-treatment. The reaction mixture was cooled to 0° C., neutralized by addition of 5 N aqueous sodium hydroxide (88 mL), and filtered to obtain N-(7-hydroxy-6-(2-((((1S,2S)-2-hydroxycyclopentyl)oxy)methyl)pyrimidin-5-yl)benzo[d]thiazol-2-yl)cyclopropancarboxamide (3.48 g, quant.).

LCMS (LC-1): RT=0.98, m/z 427 $[M+H]^+$

1H-NMR (DMSO): δ (ppm) 12.7 (1H, s), 10.35-10.1 (1H, m), 8.96 (21H, s), 7.50-7.35 (2H, m), 4.78-4.70 (1H, m), 4.70-4.63 (2H, m), 4.08-3.96 (1H, m), 3.92-3.76 (1H, m), 2.10-1.98 (1H, m), 1.97-1.76 (2H, m), 1.70-1.52 (3H, m), 1.52-1.38 (11H, m), 1.00-0.96 (2H, m)

Intermediate C-6-4: N-(7-((tert-Butyldimethylsilyl)oxy)-6-(2-((((1S,2S)-2-((tert-butyldimethylsilyl)oxy)cyclopentyl)oxy)methyl)pyrimidin-5-yl)benzo[d]thiazol-2-yl)cyclopropanecarboxamide

[Formula 133]

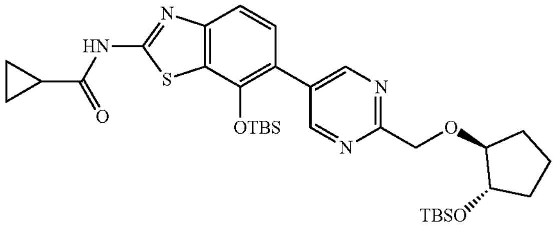

N-(7-Hydroxy-6-(2-((((1 S,2S)-2-hydroxycyclopentyl)oxy)methyl)pyrimidin-5-yl)benzo[d]thiazol-2-yl)cyclopropanecarboxamide (Intermediate C-6-3, 3 g, 7.0 mmol) was dissolved in dichloromethane (30 mL), 2,6-dimethylpyridine (6.0 g, 56 mmol), and trifluoromethanesulfonic acid tert-butyldimethylsilyl ester (11 g, 42 mmol) were added to the solution, and the resulting mixture was stirred at room temperature for 1 hour. The resulting crude reaction mixture was washed twice with water (50 mL), and the organic layer was concentrated under reduced pressure. The resulting crude product was purified by using silica gel column chromatography (eluent, petroleum ether:ethyl acetate=5:1) to obtain N-(7-((tert-butyldimethylsilyl)oxy)-6-(2-((((1S,2S)-2-((tert-butyldimethylsilyl)oxy)cyclopentyl)oxy)methyl)pyrimidin-5-yl)benzo[d]thiazol-2-yl)cyclopropanecarboxamide (3.0 g, yield 65%).

LCMS (LC-6), RT=2.46, m/z 655 $[M+H]^+$

1H-NMR ($CDCl_3$): δ (ppm) 10.19 (1H, m), 8.93 (2H, m), 7.55 (1H, d, J=8.2 Hz), 7.34 (1H, d, J=8.2 Hz), 4.88-4.80 (2H, m), 4.29-4.26 (1H, m), 3.89-3.85 (1H, m), 3.77-3.73 (1H, m), 2.05-1.89 (2H, m), 1.87-1.84 (1H, m), 1.76-1.68 (2H, m), 1.56-1.50 (1H, m), 1.30-1.26 (2H, m), 1.07-1.02 (2H, m), 0.96 (9H, s), 0.88 (9H, s), 0.07 (6H, s), 0.19 (d, J=6.1 Hz)

Intermediate C-6-5: N-(7-((tert-Butyldimethylsilyl)oxy)-6-(2-((((1S,2S)-2-((tert-butyldimethylsilyl)oxy)cyclopentyl)oxy)methyl)pyrimidin-5-yl)benzo[d]thiazol-2-yl)-N-(methoxymethyl)cyclopropanecarboxamide

[Formula 134]

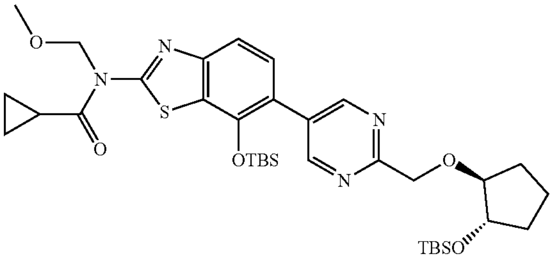

N-(7-((tert-Butyldimethylsilyl)oxy)-6-(2-((((1S,2S)-2-((tert-butyldimethylsilyl)oxy)cyclopentyl)oxy)methyl)pyrimidin-5-yl)benzo[d]thiazol-2-yl)cyclopropanecarboxamide (Intermediate C-6-4, 4.5 g, 6.87 mmol) was dissolved in dichloromethane (50 mL), N-ethyldiisopropylamine (3.6 mL, 21 mmol), and chloromethyl methyl ether (1.0 mL, 14 mmol) were added to the solution, and the resulting mixture was stirred overnight at room temperature. The resulting crude reaction mixture was washed twice with water (50 mL), and the organic layer was concentrated under reduced pressure to obtain N-(7-((tert-butyldimethylsilyl)oxy)-6-(2-((((1S,2S)-2-((tert-butyldimethylsilyl)oxy)cyclopentyl)oxy)methyl)pyrimidin-5-yl)benzo[d]thiazol-2-yl)-N-(methoxymethyl)cyclopropanecarboxamide (4.0 g, yield 83%).

LCMS (LC-6): RT=2.72, m/z 699 $[M+H]^+$

Intermediate C-6-6: N-(6-(2-((((1S,2S)-2-((tert-Butyldimethylsilyl)oxy)cyclopentyl)oxy)methyl)pyrimidin-5-yl)benzo[d]thiazol-2-yl)-N-(methoxymethyl)cyclopropanecarboxamide

[Formula 135]

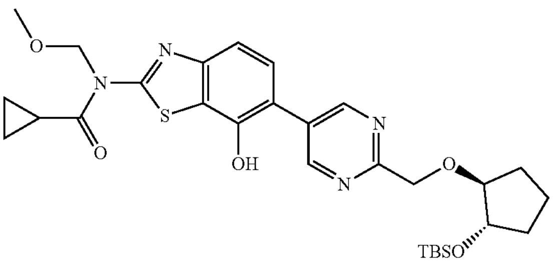

N-(7-((tert-Butyldimethylsilyl)oxy)-6-(2-((((1S,2S)-2-((tert-butyldimethylsilyl)oxy)cyclopentyl)oxy)methyl)pyrimidin-5-yl)benzo[d]thiazol-2-yl)-N-(methoxymethyl)cyclopropanecarboxamide (Intermediate C-6-5, 4.0 g, 5.7 mmol) was dissolved in N,N-dimethylformamide (40 mL), water (4 mL) and cesium carbonate (0.93 g, 2.9 mmol) were added to the solution, and the resulting mixture was stirred at room temperature for 1 hour. Water (300 mL) and dichloromethane (200 mL) were added to the resulting crude reaction mixture, and the organic layer was concentrated under reduced pressure. The resulting crude product was purified by using silica gel column chromatography (eluent, petroleum ether:ethyl acetate=2:1) to obtain N-(6-(2-((((1S,2S)-2-((tert-butyldimethylsilyl)oxy)cyclopentyl)oxy)methyl)pyrimidin-5-yl)benzo[d]thiazol-2-yl)-N-(methoxymethyl)cyclopropanecarboxamide (2.0 g, yield 60%).

LCMS (LC-1): RT=2.26 and 2.35 (2 peaks, mixture of positional isomers generated by methoxymethyl protection), m/z 585 $[M+H]^+$

Example c-06-01: N-(6-(2-((((1S,2S)-2-Hydroxycyclopentyl)oxy)methyl)pyrimidin-5-yl)-7-(2-hydroxyethoxy)benzo[d]thiazol-2-yl)cyclopropanecarboxamide

[Formula 136]

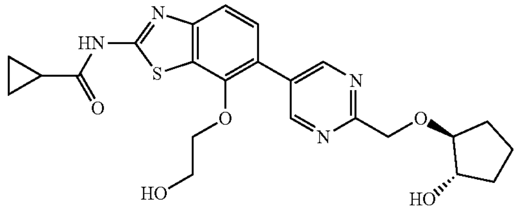

N-(6-(2-((((1S,2S)-2-((tert-Butyldimethylsilyl)oxy)cyclopentyl)oxy)methyl)pyrimidin-5-yl)benzo[d]thiazol-2-yl)-N-(methoxymethyl)cyclopropanecarboxamide (Intermediate C-6-6, 60 mg, 0.10 mmol), and 2-bromomethan-1-ol (25 mg, 0.20 mmol) were dissolved in N,N-dimethylformamide (2 mL), cesium carbonate (99 mg, 0.31 mmol) was added to the solution, and the resulting mixture was stirred at 80° C. for 3 hours. Dichloromethane and water were added to the resulting crude reaction mixture, and the organic layer was concentrated under reduced pressure. The resulting crude reaction mixture was purified by using silica gel column chromatography to obtain a crude reaction intermediate (3 mg). The resulting crude reaction intermediate (30 mg) was dissolved in 3 M hydrochloric acid in methanol (3 mL), and the solution was stirred at room temperature for 3 hours. The resulting crude reaction mixture was concentrated under reduced pressure, dichloromethane and aqueous sodium hydrogencarbonate were added to the residue, and the organic layer was concentrated under reduced pressure. The resulting crude product was purified by using preparative thin layer chromatography (eluent, dichloromethane:methanol=10:1) to obtain N-(6-(2-((((1S,2S)-2-hydroxycyclopentyl)oxy)methyl)pyrimidin-5-yl)-7-(2-hydroxyethoxy)benzo[d]thiazol-2-yl)cyclopropanecarboxamide (11.5 mg, yield 24%).

LCMS (LC-1): RT=1.00, m/z 471 $[M+H]^+$

1H-NMR ($CDCl_3$): δ (ppm) 9.04 (2H, s), 7.62 (1H, d, J=8.4 Hz), 7.56 (1H, d, J=8.4 Hz), 4.86-4.84 (1H, m), 4.73-4.72 (1H, m), 4.69 (2H, m), 4.05-4.01 (1H, m), 3.98-3.96 (2H, m), 3.85-3.82 (1H, m), 3.58-3.55 (2H, m), 2.04-1.98 (1H, m), 1.92-1.77 (2H, m), 1.66-1.56 (3H, m), 1.48-1.41 (1H, m), 0.99-0.96 (4H, m)

The following compounds mentioned in the following table were synthesized by similar methods. In the following table, the examples of which preparation methods should be referred to are mentioned in the column of "Reference Methods".

TABLE 15

| Example | Structure | Reference Methods | LCMS Data |
|---|---|---|---|
| c-06-02 | 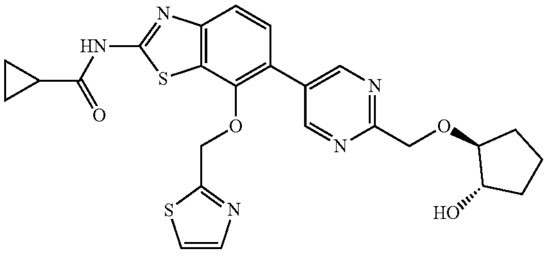 [SMILES: O=C(Nc1nc2ccc(-c3cnc(CO[C@H]4CCC[C@@H]4O)nc3)c(OCc3nccs3)c2s1)C1CC1] | Example c-06-01 | (LC-1): RT = 1.18, m/z 524 $[M + H]^+$ |

TABLE 15-continued

| Example | Structure | Reference Methods | LCMS Data |
|---|---|---|---|
| c-06-03 | 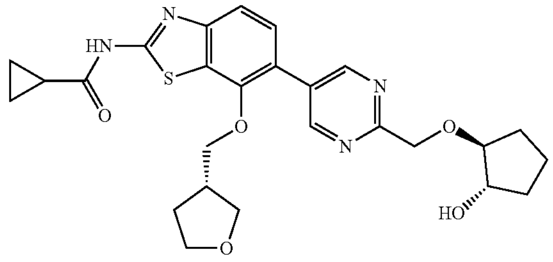 [SMILES: O=C(Nc1nc2ccc(-c3cnc(CO[C@H]4CCC[C@@H]4O)nc3)c(OC[C@H]3CCOC3)c2s1)C1CC1] | Example c-06-01 Intermediate C-5-1 | (LC-1): RT = 1.20, m/z 511 $[M + H]^+$ |

Intermediate C-7-1: 2-(Cyclopropanecarboxamido)-6-(2-((((1S,2S)-2-hydroxycyclopentyl)oxy)methyl) pyrimidin-5-yl)benzo[d]thiazol-7-yl trifluoromethanesulfonate

[Formula 137]

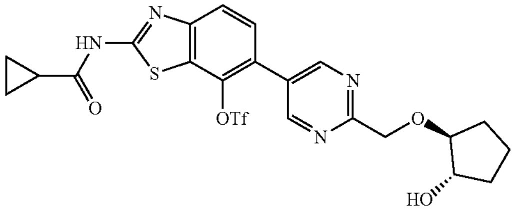

To N-(7-hydroxy-6-(2-((((1S,2S)-2-hydroxycyclopentyl) oxy)methyl)pyrimidin-5-yl)benzo[d]thiazol-2-yl)cyclopropanecarboxamide (Intermediate C-6-3, 500 mg, 1.17 mmol), THF (6 mL) and DMF (6 mL) were added to dissolve the compound, N-ethyldiisopropylamine (613 μL, 3.52 mmol), and 1,1,1-trifluoro-N-phenyl-N-(trifluoromethylsulfonyl) methanesulfonamide (629 mg, 1.76 mmol) were added to the solution, and the resulting mixture was stirred at room temperature for 5.5 hours. Water was added to the reaction mixture, the resulting mixture was extracted with ethyl acetate, the aqueous layer was extracted again with ethyl acetate, and the organic layers were combined, washed with saturated brine, dried over sodium sulfate, then filtered, and concentrated under reduced pressure. The resulting crude product was purified by using silica gel column chromatography (eluent, chloroform:methanol=98:2) to obtain 2-(cyclopropanecarboxamido)-6-(2-((((1S,2S)-2-hydroxycyclopentyl)oxy)methyl)pyrimidin-5-yl)benzo[d]thiazol-7-yl trifluoromethanesulfonate (531.2 mg, yield 81%).

LCMS (LC-1): RT=1.46, n/z 559 $[M+H]^+$

Example c-07-01: N-[6-[2-[[(1S,2S)-2-Hydroxycyclopentoxy]pyrimidin-5-yl]-7-methyl-1,3-benzothiazol-2-yl]cyclopropanecarboxamide

[Formula 138]

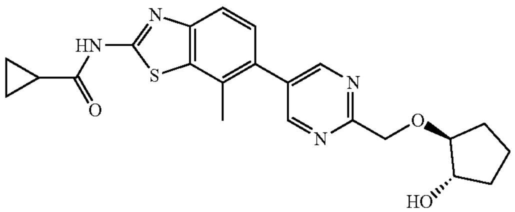

[2-(Cyclopropanecarbonylamino)-6-[2-[[(1S,2S)-2-hydroxycyclopentoxy]methyl]pyrimidin-5-yl]-1,3-benzothiazol-7-yl]trifluoromethanesulfonate (Intermediate C-7-1, 30 mg, 50 μmol) was dissolved in dimethylacetamide (0.5 mL), tetraethyltin (48 mg, 270 μmol), and tetrakis(triphenylphosphine)palladium(0) (12 mg, 10 μmol) were added to the solution, and the resulting mixture was irradiated with microwaves at 120° C. for 1 hour. The resulting reaction mixture was diluted with saturated brine, and extracted with ethyl acetate, the organic layer was dried over anhydrous magnesium sulfate, and then concentrated under reduced pressure, and the residue was purified by using HPLC to obtain N-[6-[2-[[(1S,2S)-2-hydroxycyclopentoxy]pyrimidin-5-yl]-7-methyl-1,3-benzothiazol-2-yl]cyclopropanecarboxamide (14.8 mg, yield 65%).

LCMS (LC-1): RT=1.20, m/z 425 $[M+H]^+$

1H-NMR ($CDCl_3$): δ (ppm) 8.78 (2H, s), 7.72 (1H, d, J=8.3 Hz), 7.31 (1H, d, J=8.3 Hz), 5.02 (1H, d, J=15.0 Hz), 4.85 (1H, d, J=15.0 Hz), 4.29-4.23 (1H, m), 3.93-3.88 (1H, m), 2.53 (3H, s), 2.13-2.03 (1H, m), 1.64-1.53 (1H, m), 1.30-1.26 (2H, m), 1.09-1.05 (2H, m)

Example d-01-01: (1R,2R)—N-(6-(2-((((1S,2S)-2-Hydroxycyclopentyl)oxy)methyl)pyrimidin-5-yl) benzo[d]thiazol-2-yl)-2-methylcyclopropane-1-carboxamide

[Formula 139]

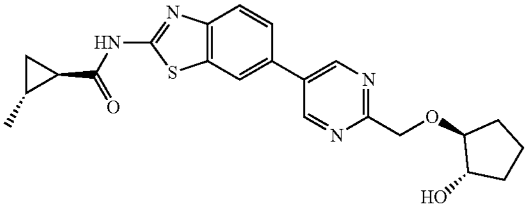

(1S,2S)-2-((5-(2-Aminobenzo[d]thiazol-6-yl)pyrimidin-2-yl)methoxy)cyclopentan-1-ol (Intermediate B-2-1, 40 mg, 120 μmol), and (1R,2R)-2-methylcyclopropane-1-carboxylic acid (18 mg, 180 μmol) were dissolved in N,N-dimethylformamide (0.58 mL), 1-hydroxybenzotriazole monohydrate (36 mg, 0.23 mmol), and 1-(3-dimethylaminopropyl)-3-ethylcarbodiimide hydrochloride (45 mg, 0.23 mmol) were added to the solution, and the resulting mixture was stirred at 70° C. for 5 hours. The resulting crude reaction mixture was purified by using HPLC to obtain (1R,2R)—N-(6-(2-((((1S,2S)-2-hydroxycyclopentyl)oxy)methyl)pyrimidin-5-yl)benzo[d]thiazol-2-yl)-2-methylcyclopropane-1-carboxamide (24 mg, yield 48%).

LCMS (LC-1): RT=1.24, m/z 425 $[M+H]^+$

1H-NMR ($DMSOd_6$): δ (ppm) 12.68 (1H, s), 9.17 (2H, s), 8.45 (1H, s), 7.86 (2H, s), 4.71-4.70 (1H, m), 4.69 (2H, s), 4.04-4.00 (1H, m), 3.83-3.81 (1H, m), 1.91-1.75 (3H, m), 1.65-1.56 (3H, m), 1.47-1.37 (2H, m), 1.22-1.16 (1H, m), 1.13 (3H, d, J=6.0 Hz)

The following compounds mentioned in the following table were synthesized by similar methods. In the following table, the examples of which preparation methods should be referred to are mentioned in the column of "Reference Methods".

TABLE 16

| Example | Structure | Reference Methods | LCMS Data |
|---|---|---|---|
| d-01-02 | 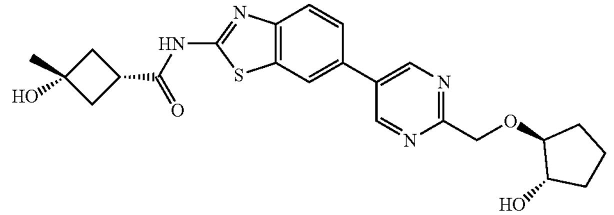 [SMILES: C[C@]1(O)C[C@@H](C(=O)Nc2nc3ccc(-c4cnc(CO[C@H]5CCC[C@@H]5O)nc4)cc3s2)C1] | Example d-01-01 | (LC-1): RT = 0.98, m/z 455 $[M + H]^+$ |
| d-01-03 | 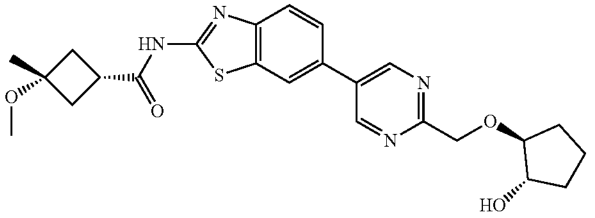 [SMILES: CO[C@]1(C)C[C@H](C(=O)Nc2nc3ccc(-c4cnc(CO[C@H]5CCC[C@@H]5O)nc4)cc3s2)C1] | Example d-01-01 | (LC-1): RT = 1.16, m/z 469 $[M + H]^+$ |
| d-01-04 | 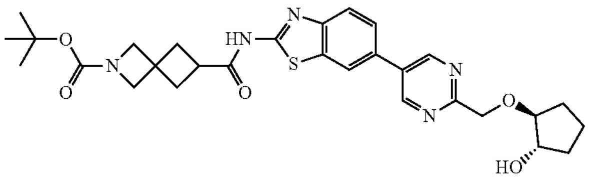 [SMILES: CC(C)(C)OC(=O)N1CC2(CC(C(=O)Nc3nc4ccc(-c5cnc(CO[C@H]6CCC[C@@H]6O)nc5)cc4s3)C2)C1] | Example d-01-01 | (LC-1): RT = 1.43, m/z 566 $[M + H]^+$ |
| d-01-05 | 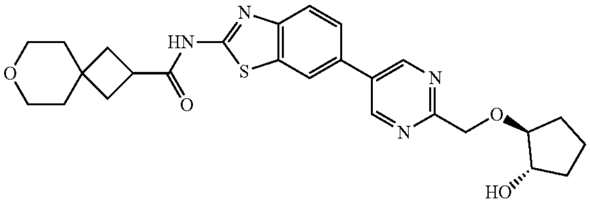 [SMILES: O=C(Nc1nc2ccc(-c3cnc(CO[C@H]4CCC[C@@H]4O)nc3)cc2s1)C1CC2(CCOCC2)C1] | Example d-01-01 | (LC-1): RT = 1.18, m/z 495 $[M + H]^+$ |
| d-01-06 | 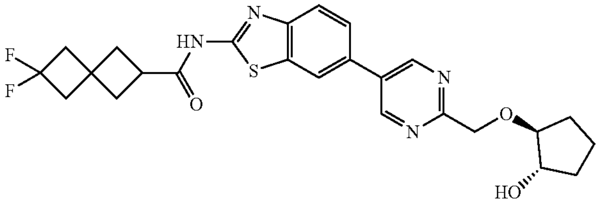 [SMILES: O=C(Nc1nc2ccc(-c3cnc(CO[C@H]4CCC[C@@H]4O)nc3)cc2s1)C1CC2(C1)CC(F)(F)C2] | Example d-01-01 | (LC-1): RT = 1.40, m/z 501 $[M + H]^+$ |
| d-01-07 | 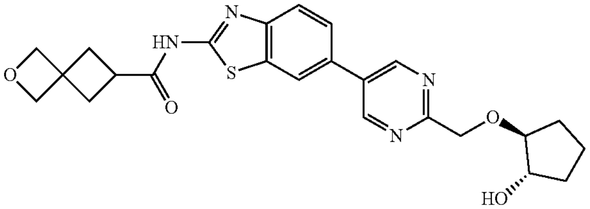 [SMILES: O=C(Nc1nc2ccc(-c3cnc(CO[C@H]4CCC[C@@H]4O)nc3)cc2s1)C1CC2(COC2)C1] | Example d-01-01 | (LC-1): RT = 1.04, m/z 467 $[M + H]^+$ |

TABLE 16-continued

| Example | Structure | Reference Methods | LCMS Data |
| --- | --- | --- | --- |
| d-01-08 | 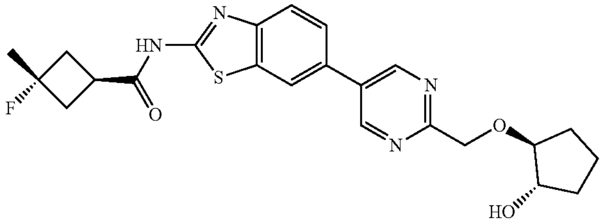 [SMILES: C[C@]1(F)C[C@H](C(=O)Nc2nc3ccc(-c4cnc(CO[C@H]5CCC[C@@H]5O)nc4)cc3s2)C1] | Example d-01-01 | (LC-1): RT = 1.25, m/z 457 [M + H]$^+$ |

Intermediate D-2-1: (1S,2S)-2-((5-(2-((1s,3s)-3-Hydroxycyclobutane-1-carboxamido)benzo[d]thiazol-6-yl)pyrimidin-2-yl)methoxy)cyclopentyl acetate

[Formula 140]

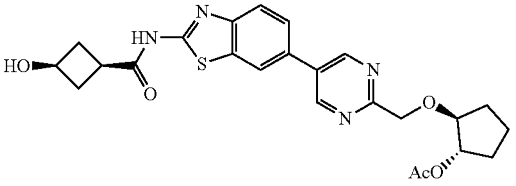

(1S,2S)-2--((5-(2-Aminobenzo[d]thiazol-6-yl)pyrimidin-2-yl)methoxy)cyclopentyl acetate (Intermediate B-4-3, 0.24 g, 0.61 mmol), and cis-3-hydroxycyclobutanearboxylic acid (72 mg, 0.62 mmol) were dissolved in N,N-dimethylformamide (3.1 mL), 1-hydroxybenzotriazole monohydrate (0.15 g, 0.99 mmol), and 1-(3-dimethylaminopropyl)-3-ethylcarbodiimide hydrochloride (0.18 g, 0.95 mmol) were added to the solution, and the resulting mixture was stirred at 60° C. for 15 minutes. The resulting crude reaction mixture was purified by using HPLC. Ethyl acetate and saturated aqueous sodium hydrogencarbonate were added to the resulting crude product, the organic layer was concentrated under reduced pressure, and the residue was purified by using automatic silica gel column chromatography (eluent, chloroform:methanol) to obtain (1S,2S)-2-((5-(2-((1s,3s)-3-hydroxycyclobutane-1-carboxamido)benzo[d]thiazol-6-yl)pyrimidin-2-yl)methoxy)cyclopentyl acetate (124 mg) as a crude product.

LCMS (LC-1): RT=1.19, m/z 483 [M+H]$^+$

Intermediate D-2-2: (1S,2S)-2-((5-(2-((1s,3s)-3-(tert-Butoxy)cyclobutane-1-carboxamido)benzo[d]thiazol-6-yl)pyrimidin-2-yl)methoxy)cyclopentyl acetate

[Formula 141]

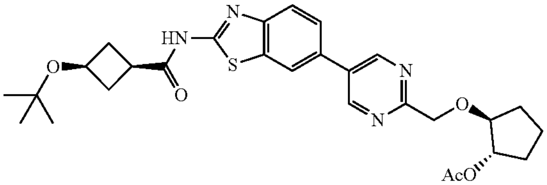

(1S,2S)-2-((5-(2-((1s,3s)-3-Hydroxycyclobutane-1-carboxamido)benzo[d]thiazol-6-yl)pyrimidin-2-yl)methoxy)cyclopentyl acetate (Intermediate D-2-1, 78 mg, 0.16 mmol) was dissolved in dichloromethane (1.6 mL), tert-butyl acetate (1.5 mL, 11 mmol), and 70% perchloric acid (42 μL, 0.49 mmol) were added to the solution, and the resulting mixture was stirred at room temperature for 30 minutes. Saturated aqueous sodium hydrogencarbonate was added to the reaction mixture under ice cooling until the reaction mixture became basic to terminate the reaction. The same operation was performed for another batch by using (1S,2S)-2-((5-(2-((1s,3s)-3-hydroxycyclobutane-1-carboxamido)benzo[d]thiazol-6-yl)pyrimidin-2-yl)methoxy)cyclopentyl acetate (Intermediate D-2-1, 19 mg, 39 μmol). The combined crude reaction mixture was washed with saturated aqueous sodium hydrogencarbonate and saturated brine, and the organic layer was dried over anhydrous sodium sulfate, filtered, and concentrated under reduced pressure. The resulting crude product was purified by using automatic silica gel column chromatography (eluent, chloroform:methanol) to obtain (1S,2S)-2-((5-(2-((1s,3s)-3-hydroxycyclobutane-1-carboxamido)benzo[d]thiazol-6-yl)pyrimidin-2-yl)methoxy)cyclopentyl acetate (152 mg) as a crude product.

LCMS (LC-1): RT=1.64, m/z 539 [M+H]$^+$

Example d-02-01: (1s,3s)-3-(tert-Butoxy)-N-(6-(2-((((1S,2S)-2-hydroxycyclopentyl)oxy)methyl)pyrimidin-5-yl)benzo[d]thiazol-2-yl)cyclobutane-1-carboxamide

[Formula 142]

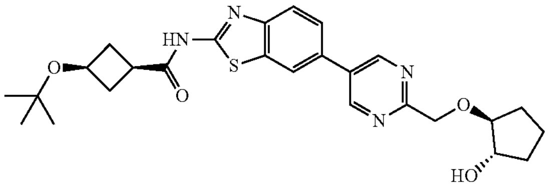

The aforementioned crude product, (1S,2S)-2-((5-(2-((1s,3s)-3-(tert-butoxy)cyclobutane-1-carboxamido)benzo[d]thiazol-6-yl)pyrimidin-2-yl)methoxy)cyclopentyl acetate (Intermediate D-2-2, 152 mg) was dissolved in methanol (1.6 mL) and tetrahydrofuran (0.8 mL), potassium carbonate (22 mg, 0.16 mmol) was added to the solution, and the resulting mixture was stirred at room temperature for 30 minutes. Ethyl acetate and water were added to the resulting crude reaction mixture, and the organic layer was dried over anhydrous sodium sulfate, filtered, and concentrated under reduced pressure. The resulting roughly purified product was purified by using HPLC to obtain (1s,3s)-3-(tert-butoxy)-N-(6-(2-((((1S,2S)-2-hydroxycyclopentyl)oxy)methyl)pyrimidin-5-yl)benzo[d]thiazol-2-yl)cyclobutane-1-carboxamide (31.5 mg).

LCMS (LC-1): RT=1.36, m/z 497 [M+H]$^+$

1H-NMR ($DMSOd_6$): δ (ppm) 12.42 (1H, m), 9.17 (2H, s), 8.45 (1H, s), 7.87-7.81 (2H, m), 4.72-4.70 (1H, m), 4.69 (2H, s), 4.14-4.07 (1H, m), 4.04-4.00 (1H, m), 3.83-3.81 (1H, m), 2.94-2.84 (1H, m), 2.46-2.40 (2H, m), 2.13-2.06 (2H, m), 1.91-1.77 (2H, m), 1.66-1.56 (3H, m), 1.48-1.40 (1H, m), 1.13 (9H, s)

Intermediate D-3-1: tert-Butyl 2-((6-2-((((1S,2S)-2-hydroxycyclopentyl)oxy)methyl)pyrimidin-5-yl)benzo[d]thiazol-2-yl)carbamoyl)-7-azaspiro[3,5]nonane-7-carboxylate

[Formula 143]

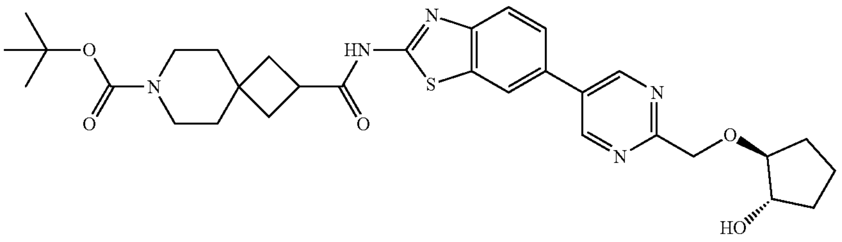

To (1S,2S)-2-((5-(2-aminobenzo[d]thiazol-6-yl)pyrimidin-2-yl)methoxy)cyclopentan-1-ol (Intermediate B-2-1, 604 mg, 1.76 mmol), dichloromethane (35 mL) and THF (25 mL) were added to dissolve the compound, 7-[(tert-butoxy)carbonyl]-7-azaspiro[3,5]nonane-2-carboxylic acid (950 mg, 3.53 mmol), N-ethyldiisopropylamine (921.1 µL, 5.29 mmol), and 1-propanephosphonic acid anhydride (1.24 mL, 4.17 mmol) were added to the solution, and the resulting mixture was stirred at room temperature for 14 hours. 7-[(tert-Butoxy)carbonyl]-7-azaspiro[3,5]nonane-2-carboxylic acid (950 mg, 3.53 mmol), N-ethyldiisopropylamine (921.1 µL, 5.29 mmol), and 1-propanephosphonic acid anhydride (1.24 mL, 4.17 mmol) were added to the reaction mixture, and the resulting mixture was stirred for further 2 hours. Aqueous sodium hydrogencarbonate was added to the reaction mixture, and the resulting mixture was extracted with chloroform. The aqueous layer was further extracted twice with chloroform, and the organic layers were combined, dried over sodium sulfate, filtered, and concentrated. The resulting crude product was purified by using silica gel column chromatography (eluent, chloroform:methanol=98:2) to obtain tert-butyl 2-((6-2-((((1S,2S)-2-hydroxycyclopentyl)oxy)methyl)pyrimidin-5-yl)benzo[d]thiazol-2-yl)carbamoyl)-7-azaspiro[3,5]nonane-7-carboxylate (712 mg, yield 68%).

LCMS (LC-1): RT=1.58, m/z 594 $[M+H]^+$

Intermediate D-3-2: N-(6-2-((((1 S,2S)-2-Hydroxycyclopentyl)oxy)methyl)pyrimidin-5-yl)benzo[d]thiazol-2-yl)carbamoyl) 7-azaspiro[3,5]nonane-2-carboxylate

[Formula 144]

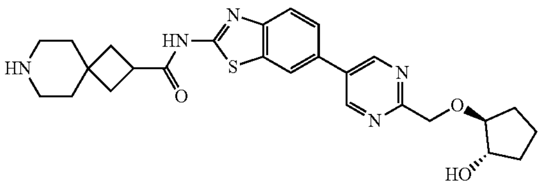

To tert-butyl 2-((6-2-((((1S,2S)-2-hydroxycyclopentyl)oxy)methyl)pyrimidin-5-yl)benzo[d]thiazol-2-yl)carbamoyl)-7-azaspiro[3,5]nonane-7-carboxylate (Intermediate D-3-1, 709.1 mg, 1.19 mmol), dichloromethane (27 mL) and THF (10 mL) were added to dissolve the compound, trifluoroacetic acid (500 µL) was added to the solution, and the resulting mixture was stirred at room temperature. Trifluoroacetic acid (12.5 ml) was further added 5 times to the reaction mixture as divided portions, and the resulting mixture was stirred at room temperature for 13 hours. The reaction mixture was made basic with 2 N aqueous sodium hydroxide, and extracted with chloroform. The aqueous layer was further extracted twice with chloroform, and the organic layer was dried over sodium sulfate, filtered, and concentrated under reduced pressure to obtain N-(6-2-((((1S,2S)-2-hydroxycyclopentyl)oxy)methyl)pyrimidin-5-yl)benzo[d]thiazol-2-yl)carbamoyl) 7-azaspiro[3,5]nonane-2-carboxylate (142.2 mg, yield 24%).

LCMS (LC-1): RT=0.89, m/z 494 $[M+H]^+$

1H-NMR ($CDCl_3$): δ (ppm) 8.93 (2H, s), 8.00-7.95 (1H, m), 7.81-7.74 (1H, m), 7.59-7.52 (1H, m), 4.87-4.66 (2H, m), 4.16-4.04 (1H, m), 3.80-3.74 (1H, m), 3.25-3.16 (1H, m), 3.25-3.16 (1H, m), 2.76-2.66 (2H, m), 2.16-2.06 (4H, m), 2.06-1.94 (4H, m), 1.72-1.52 (4H, m), 1.52-1.43 (2H, m)

Example d-03-01: 7-Acetyl-N-(6-(2-((((1S,2S)-2-hydroxycyclopentyl)oxy)methyl)pyrimidin-5-yl)benzo[d]thiazol-2-yl)-7-azaspiro[3,5]nonane-2-carboxamide

[Formula 145]

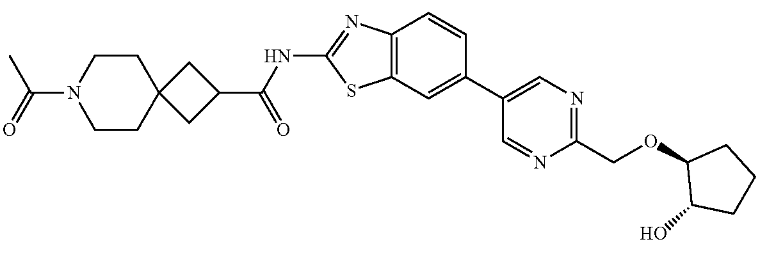

To N-(6-2-((((1S,2S)-2-hydroxycyclopentyl)oxy)methyl) pyrimidin-5-yl)benzo[d]thiazol-2-yl)carbamoyl) 7-azaspiro [3,5]nonane-2-carboxylate (Intermediate D-3-2, 30 mg, 0.06 mmol), dichloromethane (1.8 mL) and THE (0.8 mL) were added to dissolve the compound, acetyl chloride (5.19 μL, 0.07 mmol) and triethylamine (16.9 μL, 0.12 mmol) were added to the solution, and the resulting mixture was stirred at room temperature for 20 minutes. Aqueous sodium hydrogencarbonate was added to the reaction mixture, and the resulting mixture was extracted with chloroform. The organic layer was concentrated by nitrogen blow, and the residue was purified by using HPLC to obtain 7-acetyl-N-(6-(2-((((1S,2S)-2-hydroxycyclopentyl)oxy)methyl)pyrimidin-5-yl)benzo[d]thiazol-2-yl)carbamoyl)-7-azaspiro[3,5] nonane-2-carboxamide (8.5 mg, yield 26%).

LCMS (LC-1): RT=1.08, m/z 536 $[M+H]^+$

1H-NMR ($CDCl_3$): δ (ppm) 8.98 (2H, s), 8.01 (1H, s), 7.90-7.73 (1H, m), 7.65-7.58 (1H, m), 4.97-4.87 (1H, m), 4.80-4.72 (1H, m), 4.21-4.13 (1H, m), 3.86-3.78 (1H, m), 3.58-3.43 (2H, m), 3.43-3.26 (3H, m), 2.27-1.96 (7H, m), 2.06 (3H, s), 1.77-1.51 (7H, m)

The following compounds mentioned in the following table were synthesized by similar methods. In the following table, the examples of which preparation methods should be referred to are mentioned in the column of "Reference Methods".

TABLE 17

| Example | Structure | Reference Methods | LCMS Data |
|---|---|---|---|
| d-03-02 | 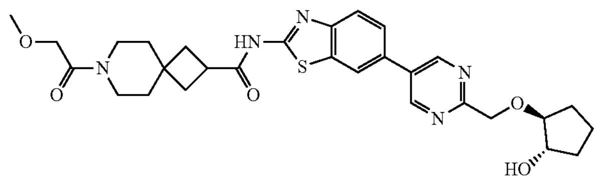 [SMILES: COCC(=O)N1CCC2(CC1)CC(C(=O)Nc1nc3ccc(-c4cnc(CO[C@H]5CCC[C@@H]5O)nc4)cc3s1)C2] | Example d-03-01 | (LC-1): RT = 1.09, m/z 566 $[M + H]^+$ |
| d-03-03 | 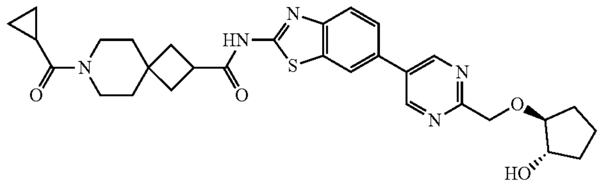 [SMILES: O=C(Nc1nc2ccc(-c3cnc(CO[C@H]4CCC[C@@H]4O)nc3)cc2s1)C1CC2(CCN(C(=O)C3CC3)CC2)C1] | Example d-03-01 | (LC-1): RT = 1.22, m/z 562 $[M + H]^+$ |
| d-03-04 | 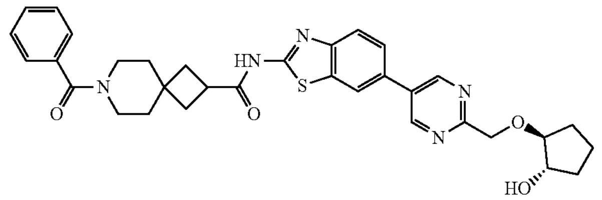 [SMILES: O=C(Nc1nc2ccc(-c3cnc(CO[C@H]4CCC[C@@H]4O)nc3)cc2s1)C1CC2(CCN(C(=O)c3ccccc3)CC2)C1] | Example d-03-01 | (LC-1): RT = 1.32, m/z 598 $[M + H]^+$ |
| d-03-05 | 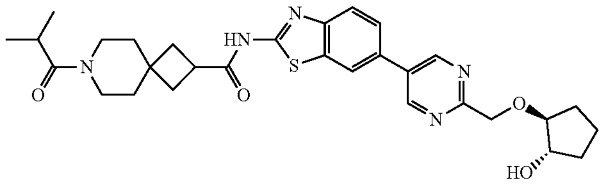 [SMILES: CC(C)C(=O)N1CCC2(CC1)CC(C(=O)Nc1nc3ccc(-c4cnc(CO[C@H]5CCC[C@@H]5O)nc4)cc3s1)C2] | Example d-03-01 | (LC-1): RT = 1.26, m/z 564 $[M + H]^+$ |
| d-03-06 | 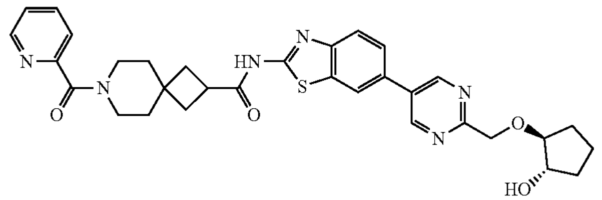 [SMILES: O=C(Nc1nc2ccc(-c3cnc(CO[C@H]4CCC[C@@H]4O)nc3)cc2s1)C1CC2(CCN(C(=O)c3ccccn3)CC2)C1] | Example d-03-01, b-04-02 | (LC-1): RT = 1.13, m/z 599 $[M + H]^+$ |
| d-03-07 | 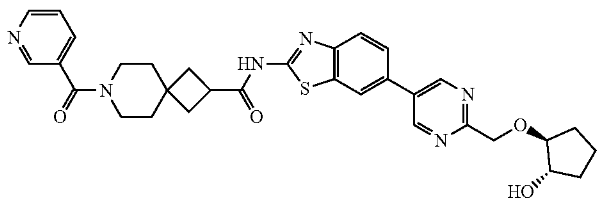 [SMILES: O=C(Nc1nc2ccc(-c3cnc(CO[C@H]4CCC[C@@H]4O)nc3)cc2s1)C1CC2(CCN(C(=O)c3cccnc3)CC2)C1] | Example d-03-01, b-04-02 | (LC-1): RT = 1.10, m/z 599 $[M + H]^+$ |

TABLE 17-continued

| Example | Structure | Reference Methods | LCMS Data |
|---|---|---|---|
| d-03-08 | 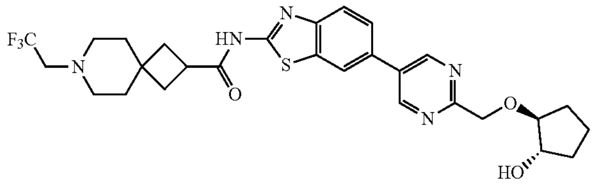 [SMILES: O=C(Nc1nc2ccc(-c3cnc(CO[C@H]4CCC[C@@H]4O)nc3)cc2s1)C1CC2(CCN(CC(F)(F)F)CC2)C1] | Example d-03-01, b-07-01 | (LC-1): RT = 1.51, m/z 576 [M + H]$^+$ |
| d-03-09 | 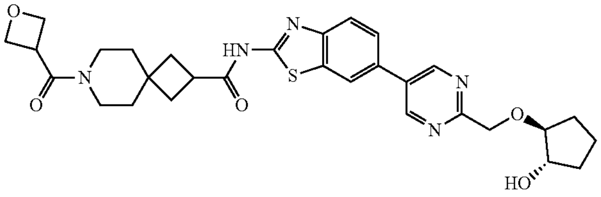 [SMILES: O=C(Nc1nc2ccc(-c3cnc(CO[C@H]4CCC[C@@H]4O)nc3)cc2s1)C1CC2(CCN(C(=O)C3COC3)CC2)C1] | Example d-03-01, b-04-02 | (LC-1): RT = 1.07, m/z 578 [M + H]$^+$ |

Intermediate D-4-1: tert-Butyl (1s,3s)-3-ethoxycyclobutane-1l-carboxylate

[Formula 146]

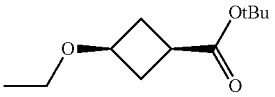

tert-Butyl 3-hydroxycyclobutanearboxylate (0.30 g, 1.7 mmol) was dissolved in N,N-dimethylformamide (3.5 mL), sodium hydride (55% in oil, 5 mg, 2.1 mmol) was added to the solution under ice cooling, and the resulting mixture was stirred for 10 minutes. Iodoethane (0.28 mL, 3.5 mmol) was added to the reaction mixture, and the resulting mixture was stirred overnight at room temperature. Saturated aqueous ammonium chloride was added to the reaction mixture to terminate the reaction, and the reaction mixture was extracted with ethyl acetate. The organic layer was concentrated under reduced pressure, and the resulting crude product was purified by using automatic silica gel column chromatography (eluent, hexane:ethyl acetate=98:2 to 50:50) to obtain tert-butyl (1s,3s)-3-ethoxycyclobutane-1-carboxylate (203 mg, yield 8%). 1H-NMR ($CDCl_3$): δ (ppm) 3.87-3.80 (1H, m), 3.40 (2H, q, J=7.0 Hz), 2.57-2.42 (3H, in), 2.22-2.10 (2H, m), 1.44 (9H, s), 1.19 (3H, t, J=7.0 Hz)

Intermediate D-4-2: (1s,3s)-3-Ethoxycyclobutane-1-carboxylic acid

[Formula 147]

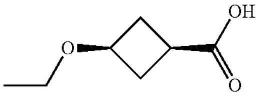

tert-Butyl (1s,3s)-3-ethoxycyclobutane-1-carboxylate (Intermediate D-4-1, 40 mg, 0.20 mmol) was dissolved in formic acid (0.40 mL), and the solution was stirred at room temperature for 2 hours. The resulting crude reaction mixture was concentrated under reduced pressure, and the residue was azeotroped 3 times with toluene to obtain (1s,3s)-3-ethoxycyclobutane-1-carboxylic acid as a crude product.

1H-NMR ($CDCl_3$): δ (ppm) 3.93-3.86 (11H, m), 3.41 (2H, q, J=7.0 Hz), 2.73-2.74 (1H, m), 2.58-2.50 (2H, m), 2.28-2.20 (2H, m), 1.19 (3H, t, J=7.0 Hz)

Example d-04-01: (1s,3s)-3-Ethoxy-N-(6-(2-((((1S,2S)-2-hydroxycyclopentyl)oxy)methyl)pyrimidin-5-yl)benzo[d]thiazol-2-yl)cyclobutane-1-carboxamide

[Formula 148]

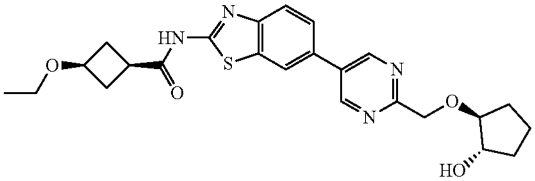

The aforementioned crude product, (1s,3s)-3-ethoxycyclobutane-1-carboxylic acid (Intermediate D-4-2), and (1S,2S)-2-((5-(2-aminobenzo[d]thiazol-6-yl)pyrimidin-2-yl)methoxy)cyclopentan-1-ol (Intermediate B-2-1, 30 mg, 90 μmol) were dissolved in N,N-dimethylformamide (0.44 mL), 1-hydroxybenzotriazole monohydrate (27 mg, 0.18 mmol), and 1-(3-dimethylaminopropyl)-3-ethylcarbodiimide hydrochloride (34 mg, 0.18 mmol) were added to the solution, and the resulting mixture was stirred at 60° C. for 15 minutes. The resulting crude reaction mixture was purified by using HPLC to obtain (1s,3s)-3-ethoxy-N-(6-(2-((((1S,2S)-2-hydroxycyclopentyl)oxy)methyl)pyrimidin-5-yl)benzo[d]thiazol-2-yl)cyclobutane-1-carboxamide (21 mg, yield 510%).

LCMS (LC-1): RT=1.19, m/z 469 [M+H]$^+$

1H-NMR ($DMSOd_6$): δ (ppm) 12.45 (1H, s), 9.18 (2H, s), 8.48 (1H, m), 7.89-7.84 (2H, m), 4.72-4.71 (1H, m), 4.69 (2H, s), 4.04-4.00 (1H, m), 3.95-3.88 (1H, m), 3.84-3.81 (1H, m), 3.36 (2H, q, J=7.0 Hz), 2.99-2.90 (1H, m), 2.48-2.44 (2H, m), 2.13-2.05 (2H, in), 1.91-1.77 (2H, m), 1.67-1.54 (3H, m), 1.48-1.40 (1H, m), 1.10 (31H, t, J=7.0 Hz)

The following compounds mentioned in the following table were synthesized by similar methods. In the following table, the examples of which preparation methods should be referred to are mentioned in the column of “Reference Methods”.

TABLE 18

| Example | Structure | Reference Methods | LCMS Data |
|---|---|---|---|
| d-04-02 | 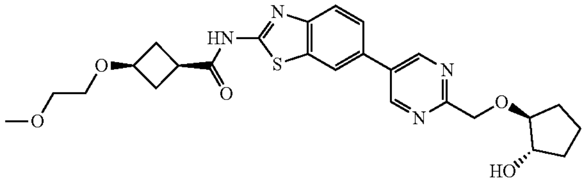 [SMILES: COCCO[C@H]1C[C@@H](C(=O)Nc2nc3ccc(-c4cnc(CO[C@H]5CCC[C@@H]5O)nc4)cc3s2)C1] | Example d-04-01 Intermediates D-4-1, 2 | (LC-1): RT = 1.10, m/z 499 [M + H]$^+$ |
| d-04-03 | 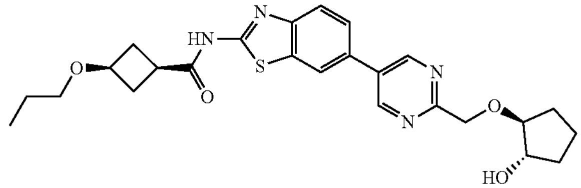 [SMILES: CCCO[C@H]1C[C@@H](C(=O)Nc2nc3ccc(-c4cnc(CO[C@H]5CCC[C@@H]5O)nc4)cc3s2)C1] | Example d-04-01 Intermediates D-4-1, 2 | (LC-1): RT = 1.33, m/z 483 [M + H]$^+$ |
| d-04-04 | 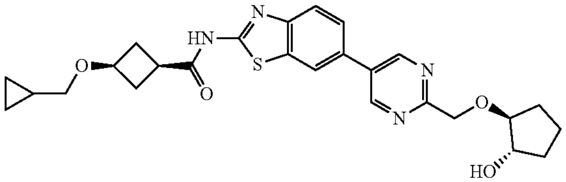 [SMILES: O=C(Nc1nc2ccc(-c3cnc(CO[C@H]4CCC[C@@H]4O)nc3)cc2s1)[C@H]1C[C@@H](OCC2CC2)C1] | Example d-04-01 Intermediates D-4-1, 2 | (LC-1): RT = 1.31, m/z 495 [M + H]$^+$ |
| d-04-05 | 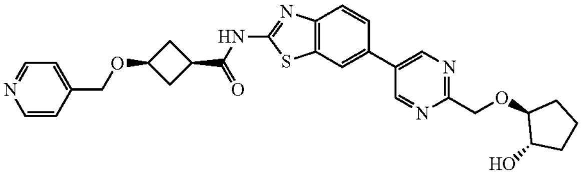 [SMILES: O=C(Nc1nc2ccc(-c3cnc(CO[C@H]4CCC[C@@H]4O)nc3)cc2s1)[C@H]1C[C@@H](OCc2ccncc2)C1] | Example d-04-01 Intermediates D-4-1, 2 | (LC-1): RT = 1.13, m/z 532 [M + H]$^+$ |

Intermediate D-5-1: N-(6-(2-((((1S,2S)-2-((tert-Butyldimethylsilyl)oxy)cyclopentyl)oxy)methyl)pyrimidin-5-yl)benzo[d]thiazol-2-yl)-3-(methoxymethylene)cyclobutane-1-carboxamide

[Formula 149]

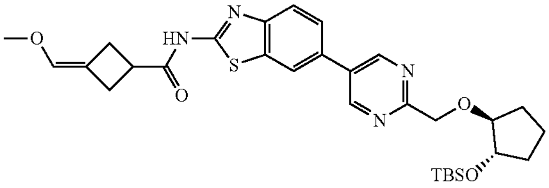

To methoxymethyl(triphenyl)phosphonium chloride (254.2 mg, 0.74 mmol), THF (1.5 mL) was added, and the resulting mixture was cooled to 0° C. tert-Butoxypotassium (83.2 mg, 0.74 mmol) was added to the reaction mixture, and the resulting mixture was stirred for 30 minutes. Then, N-(6-(2-((((1S,2S)-2-((tert-butyldimethylsilyl)oxy)cyclopentyl)oxy)methyl)pyrimidin-5-yl)benzo[d]thiazol-2-yl)-3-oxocyclobutane-1-carboxamide (Intermediate B-1-1, 292.8 mg, 0.53 mmol) was dissolved in THF (1.5 mL), and the solution was added dropwise to the reaction mixture with a syringe. The resulting mixture was stirred at 0° C. at 10 minutes, and then stirred at room temperature for 3.5 hours. Water was added to the reaction mixture, and the resulting mixture was extracted with ethyl acetate. The organic layer was dried over sodium sulfate, filtered, and concentrated under reduced pressure. The resulting crude product was purified by using silica gel column chromatography (eluent, chloroform:methanol=98:2) to obtain N-(6-(2-((((1 S,2S)-2-((tert-butyldimethylsilyl)oxy)cyclopentyl)oxy)methyl)pyrimidin-5-yl)benzo[d]thiazol-2-yl)-3-(methoxymethylene)cyclobutane-1-carboxamide (130.7 mg, yield 43%).

LCMS (LC-1): RT=2.31, n/z 581 [M+H]$^+$

Intermediate D-5-2: 3-Formyl-N-(6-(2-((((1S,2S)-2-hydroxycyclopentyl)oxy)methyl)pyrimidin-5-yl)benzo[d]thiazol-2-yl)cyclobutane-1-carboxamide

[Formula 150]

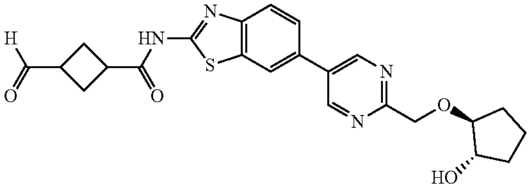

To N-(6-(2-((((1S,2S)-2-((tert-butyldimethylsilyl)oxy)cyclopentyl)oxy)methyl)pyrimidin-5-yl)benzo[d]thiazol-2-yl)-3-(methoxymethylene)cyclobutane-1-carboxamide (Intermediate D-5-1, 111.3 mg, 0.19 mmol), THF (1 mL) was added to dissolve the compound, 2 N aqueous hydrochloric acid (2 mL) was added to the solution, and the resulting mixture was stirred for 40 minutes. Aqueous sodium hydrogencarbonate was added to the reaction mixture, and the resulting mixture was extracted with chloroform. The aqueous layer was extracted again with chloroform, and the organic layer was dried over sodium sulfate, filtered, and concentrated under reduced pressure to obtain 3-formyl-N-(6-(2-((((1S,2S)-2-hydroxycyclopentyl)oxy)methyl)pyrimidin-5-yl)benzo[d]thiazol-2-yl)cyclobutane-1-carboxamide (95 mg) as a crude product.

LCMS (LC-1): RT=1.09, m/z 453 $[M+H]^+$

Example d-05-01: 3-((Dimethylamino)methyl)-N-(6-(2-((((1S,2S)-2-hydroxycyclopentyl)oxy)methyl)pyrimidin-5-yl)benzo[d]thiazol-2-yl)cyclobutane-1-carboxamide

[Formula 151]

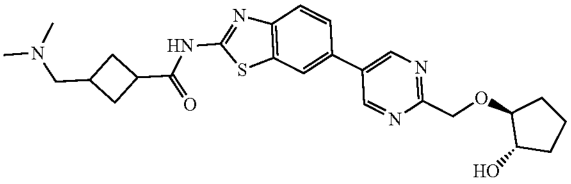

3-Formyl-N-(6-(2-((((1S,2S)-2-hydroxycyclopentyl)oxy)methyl)pyrimidin-5-yl)benzo[d]thiazol-2-yl)cyclobutane-1-carboxamide (Intermediate D-5-2, 32 mg, 0.07 mmol) was dissolved in dichloromethane (1 mL), dimethylamine (71 μL, 1.4 mmol), and sodium triacetoxyborohydride (22.5 mg, 0.11 mmol) were added to the solution, and the resulting mixture was stirred at room temperature for 5 hours. Saturated aqueous sodium hydrogencarbonate was added to the reaction mixture, the resulting mixture was extracted with chloroform, the organic layer was concentrated by nitrogen blow, and the residue was purified by using HPLC to obtain 3-((dimethylamino)methyl)-N-(6-(2-((((1S,2S)-2-hydroxycyclopentyl)oxy)methyl)pyrimidin-5-yl)benzo[d]thiazol-2-yl)cyclobutane-1-carboxamide (4.8 mg, 14%).

LCMS (LC-1): RT=0.88, m/z 482 $[M+H]^+$

1H-NMR ($CDCl_3$): δ (ppm) 8.98 (2H, d, J=1.2 Hz), 8.00 (1H, t, J=1.8 Hz), 7.86-7.78 (1H, m), 7.62-7.53 (1H, m), 4.96-4.88 (1H, m), 4.79-4.71 (1H, m), 4.21-4.12 (1H, m), 3.86-3.77 (1H, m), 3.40-3.35 (1H, m), 3.33-3.24 (1H, m), 3.25-3.14 (1H, m), 2.23-2.21 (3H, s), 2.21-2.20 (3H, s), 2.13-1.97 (4H, m), 1.77-1.62 (3H, m), 1.60-1.50 (1H, m)

The following compound mentioned in the following table was synthesized by similar methods. In the following table, the example of which preparation methods should be referred to is mentioned in the column of "Reference Methods".

Intermediate E-1-1: 5-(2-((((1S,2S)-2-((tert-Butyldimethylsilyl)oxy)cyclopentyl)oxy)methyl)pyrimidin-5-yl)pyrazolo[1,5-a]pyridin-2-amine

[Formula 152]

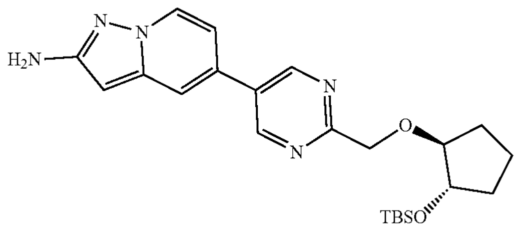

5-Chloropyrazolo[1,5-a]pyridin-2-amine (1.0 g, 5.97 mmol) was dissolved in 1,4-dioxane (12 mL), the aforementioned crude product, 2-((((1S,2S)-2-((tert-butyldimethylsilyl)oxy)cyclopentyl)oxy)methyl)-5-(4,4,5,5-tetramethyl-1,3,2-dioxaboran-2-yl)pyrimidine (Intermediate A-1-3, 8.96 mmol), [1,1'-bis(diphenylphosphino)ferrocene]dichloropalladium(II) (0.44 g, 0.60 mmol), cesium carbonate (5.8 g, 27.9 mmol), and water (1.2 mL) were added to the solution, and the resulting mixture was irradiated with microwaves at 100° C. for 5 hours. The crude reaction mixture was filtered through a Celite layer, and concentrated under reduced pressure. The resulting crude product was purified by using automatic silica gel column chromatography (eluent, ethyl acetate:methanol) to obtain 5-(2-((((1S,2S)-2-((tert-butyldimethylsilyl)oxy)cyclopentyl)oxy)methyl)pyrimidin-5-yl)pyrazolo[1,5-a]pyridin-2-amine (1.3 g, yield 50%).

LCMS (LC-1): RT=2.00, m/z 439 $[M+H]^+$

Example e-01-01: N-(5-(2-((((1S,2S)-2-Hydroxycyclopentyl)oxy)methyl)pyrimidin-5-yl)pyrazolo[1,5-a]pyridin-2-yl)cyclopropanecarboxamide

[Formula 153]

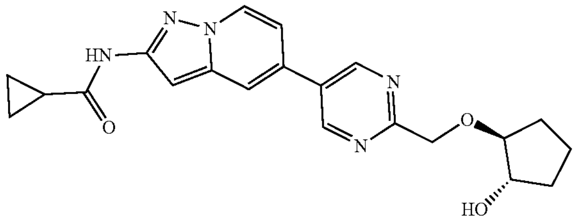

TABLE 19

| Example | Structure | Reference Methods | LCMS Data |
|---|---|---|---|
| d-05-02 | 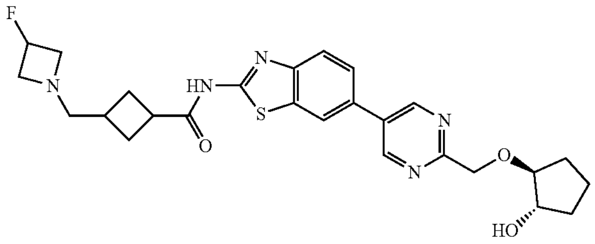 [SMILES: O=C(Nc1nc2ccc(-c3cnc(CO[C@H]4CCC[C@@H]4O)nc3)cc2s1)C1CC(CN2CC(F)C2)C1] | Example d-05-01 | (LC-1): RT = 1.06, m/z 512 $[M + H]^+$ |

Butyldimethylsilyl)oxy)cyclopentyl)oxy)methyl)pyrimidin-5-yl)pyrazolo[1,5-a]pyridin-2-amine (Intermediate E-1-1, 20 mg, 46 μmol) was dissolved in dichloromethane (455 μL), cyclopropanecarboxylic acid (12 μL, 0.15 mmol), N,N-diisopropylethylamine (70 μL, 0.41 mmol), and 1-propanephosphonic acid anhydride (50 weight % solution in ethyl acetate, 88 μL, 0.15 mmol) were added to the solution, and the resulting mixture was stirred at room temperature for 4 hours. Water was added to the resulting crude reaction mixture, and the resulting mixture was extracted with dichloromethane. A hydrochloric acid solution in methanol (2 mol/L) was added to the resulting crude reaction intermediate, and the resulting mixture was stirred at room temperature for 5 minutes. The resulting crude reaction mixture was purified by using SCX and HPLC to obtain N-(5-(2-((((1S,2S)-2-hydroxycyclopentyl)oxy)methyl)pyrimidin-5-yl)pyrazolo[1,5-a]pyridin-2-yl)cyclopropanecarboxamide (4.2 mg, yield 24%).

LCMS (LC-1): RT=0.99, m/z 394 $[M+H]^+$

1H-NMR ($CD_3OD$): δ (ppm) 9.15 (2H, s), 8.51 (1H, d, J=7.3 Hz), 7.95 (1H, d, J=1.2 Hz), 7.18 (1H, dd, J=7.2 Hz, 2.1 Hz), 6.96 (1H, s), 4.81 (2H, s), 4.19-4.15 (1H, m), 3.90-3.86 (11H, m), 2.05-1.94 (2H, m), 1.90-1.84 (1H, m), 1.77-1.66 (3H, m), 1.59-1.51 (1H, m), 1.02-0.98 (2H, m), 0.93-0.88 (2H, m)

The following compounds mentioned in the following table were synthesized by similar methods. In the following table, the examples of which preparation methods should be referred to are mentioned in the column of "Reference Methods".

Intermediate E-2-1: (1S,2S)-2-((5-(2-Aminopyrazolo[1,5-a]pyridin-5-yl)pyrimidin-2-yl)methoxy) cyclopentyl acetate

[Formula 154]

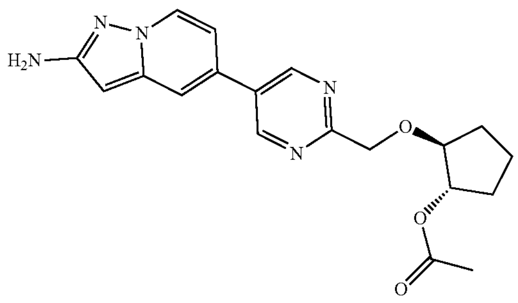

5-Chloropyrazolo[1,5-a]pyridin-2-amine (6.00 g, 35.8 mmol) was dissolved in 1,4-dioxane (358 mL), [(1S,2S)-2-[[5-(4,4,5,5-tetramethyl-1,3,2-dioxaborolan-2-yl)pyrimidin-2-yl]methoxy]cyclopentyl] acetate (43.2 g, 71.6 mmol), cesium carbonate (34.9 g, 107 mmol), dichloro(1,1'-bis (diphenylphosphino)ferrocene)palladium (2.62 g, 3.58 mmol), and water (36 mL) were added to the solution, and the resulting mixture was stirred at 100° C. for 15 hours. After completion of the reaction, methanol (30 mL) was added to the reaction mixture, and the resulting product was purified by using silica gel column chromatography (eluent, chloroform:methanol=90:10) to obtain (1S,2S)-2-((5-(2-aminopyrazolo[1,5-a]pyridin-5-yl)pyrimidin-2-yl)methoxy) cyclopentyl acetate (9.82 g, 74%).

LCMS (LC-1): RT=1.09, m/z 368 $[M+H]^+$

1H-NMR ($CDCl_3$): δ (ppm) 9.03-8.91 (2H, m), 8.48-8.09 (1H, m), 7.52-7.28 (2H, m), 6.97-6.47 (1H, m), 5.05-4.78 (3H, m), 4.21-4.01 (3H, m), 2.19-1.95 (9H, m)

TABLE 20

| Example | Structure | Reference Methods | LCMS Data |
|---|---|---|---|
| e-01-02 | 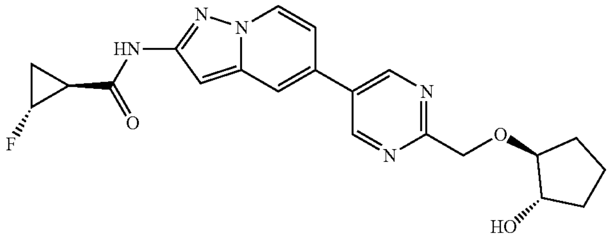 | Example e-01-01 | (LC-1): RT = 1.03, m/z 412 $[M + H]^+$ |
| e-01-03 | 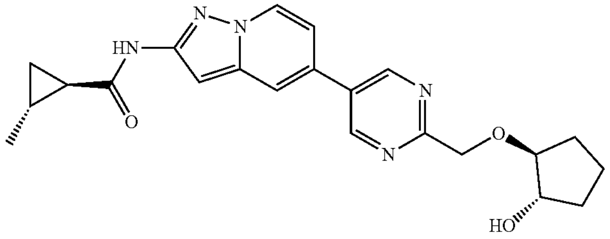 [SMILES: C[C@@H]1C[C@H]1C(=O)Nc1cc2cc(-c3cnc(CO[C@H]4CCC[C@@H]4O)nc3)ccn2n1] | Example e-01-01 | (LC-1): RT = 1.10, m/z 408 $[M + H]^+$ |

Intermediate E-2-2: (1S,2S)-2-((5-(2-Aminopyrazolo[1,5-a]pyridin-5-yl)pyrimidin-2-yl)methoxy)cyclopentan-1-ol

[Formula 155]

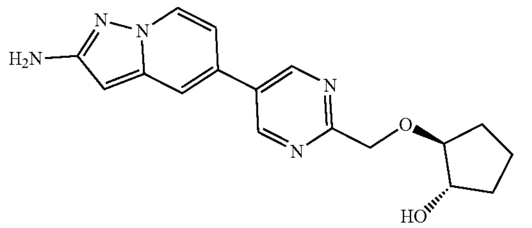

(1S,2S)-2-((5-(2-Aminopyrazolo[1,5-a]pyridin-5-yl)pyrimidin-2-yl)methoxy)cyclopentyl acetate (17.9 g, 48.7 mmol) was dissolved in methanol (487 mL), potassium carbonate (33.7 g, 243 mmol) was added to the solution, and the resulting mixture was stirred at room temperature for 3 hours. After completion of the reaction, water was added to the reaction mixture, the resulting mixture was extracted with chloroform, the organic layer was concentrated under reduced pressure, and then the crude product was purified by using silica gel column chromatography (eluent, chloroform:methanol=90:10 to 80:20) to obtain (1S,2S)-2-((5-(2-aminopyrazolo[1,5-a]pyridin-5-yl)pyrimidin-2-yl)methoxy)cyclopentan-1-ol (12.2 g, 77%).

LCMS (LC-1): RT=0.81, m/z 326 $[M+H]^+$

1H-NMR ($CD_3OD$): δ (ppm) 9.23-9.05 (3H, m), 8.27 (11H, d, J=7.1 Hz), 7.67-7.63 (1H, m), 6.91 (1H, dd, J=7.2, 2.0 Hz), 5.88 (1H, s), 4.83-4.66 (2H, m), 4.22-4.12 (2H, m), 4.11-3.83 (2H, m), 2.10-1.82 (2H, m), 1.77-1.48 (4H, m)

Intermediate E-2-3: N-(5-(2-((((1S,2S)-2-Hydroxycyclopentyl)oxy)methyl)pyrimidin-5-yl)pyrazolo[1,5-a]pyridin-2-yl)-3-oxocyclobutane-1-carboxamide

[Formula 156]

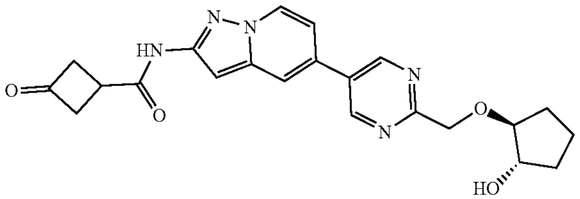

(1S,2S)-2-((5-(2-Aminopyrazolo[1,5-a]pyridin-5-yl)pyrimidin-2-yl)methoxy)cyclopentan-1-ol (Intermediate E-2-2, 3.22 g, 9.9 mmol) was dissolved in dichloromethane (50 mL), and the resulting solution was stirred with cooling at 0° C. N-Ethyldiisopropylamine (5.17 mL, 29.7 mmol), 3-oxocyclobutane-1-carboxylic acid (1.36 g, 11.88 mmol), and 1-propanephosphonic acid anhydride (8.74 mL, 14.85 mmol) were added to the solution, and then the resulting mixture was stirred at room temperature for 5 hours. Saturated aqueous sodium hydrogencarbonate and chloroform were added to the reaction mixture for extraction. The aqueous layer was extracted again with chloroform, and the organic layers were combined, and washed with saturated brine. The organic layer was dried over anhydrous sodium sulfate, then filtered, and concentrated under reduced pressure. The resulting residue was purified by using silica gel column chromatography (eluent, chloroform:methanol=98:2 to 95:5) to obtain N-(5-(2-((((1S,2S)-2-hydroxycyclopentyl)oxy)methyl)pyrimidin-5-yl)pyrazolo[1,5-a]pyridin-2-yl)-3-oxocyclobutane-1-carboxamide (2.26 g, yield: 54.3%).

LCMS (LC-1): RT=0.92, m/z 422 $[M+H]^+$

1H-NMR ($CDCl_3$): δ (ppm) 9.00 (2H, s), 8.36 (1H, d, J=7 Hz), 8.30 (1H, s), 7.66 (1H, d, J=1.3 Hz), 7.13 (11H, s), 6.91 (1H, dd, J=7, 1.8 Hz), 5.02-4.82 (2H, m), 4.27-4.22 (1H, m), 3.90-3.85 (2H, m), 3.66-3.60 (2H, m), 3.37-3.25 (3H, m), 2.13-2.02 (2H, m), 1.79-1.53 (4H, m)

Intermediate E-2-4: tert-Butyl (S)-2-methyl-4-(2-methylisonicotinoyl)piperazine-1-carboxylate

[Formula 157]

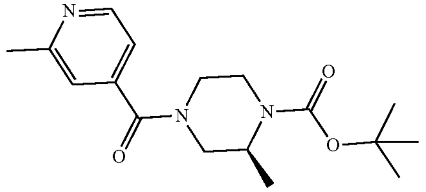

tert-Butyl (S)-2-methylpiperazine-1-carboxylate (600 mg, 3.00 mmol) was dissolved in dichloromethane (30.0 mL), 2-methylisonicotinic acid (821 mg, 6.00 mmol), N-ethyldiisopropylamine (3.2 mL, 18.0 mmol), and propanephosphonic acid anhydride (6.0 mL, 1.7 M solution in ethyl acetate) were added to the solution, and the resulting mixture was stirred at room temperature for 1 hour. Saturated aqueous sodium hydrogencarbonate was added to the reaction mixture, the resulting mixture was extracted with chloroform, and the organic layer was concentrated under reduced pressure. The resulting crude product was purified by using silica gel column chromatography (eluent, hexane:ethyl acetate=100:0 to 0:100) to obtain tert-butyl (S)-2-methyl-4-(2-methylisonicotinoyl)piperazine-1-carboxylate (1.025 g, quant.).

LCMS (LC-1): RT=1.21, m/z 320 $[M+H]^+$

1H-NMR ($CDCl_3$): δ (ppm) 8.58 (1H, d, J=4.9 Hz), 7.14 (11H, brs), 7.07 (1H, brd, J=4.2 Hz), 4.58 (0.5H, brd, J=13.1 Hz), 4.46 (1H, brd, J=13.1 Hz), 4.22 (0.51H, brs), 3.96 (0.5H, brd, J=13.7 Hz), 3.62-3.41 (0.5H, m), 3.34 (1H, brs), 3.21-2.96 (2H, m), 2.96-2.83 (1H, m), 2.60 (3H, s), 1.47 (91H, s), 1.33-1.03 (3H, m)

Intermediate E-2-5: (S)-(3-Methylpiperazin-1-yl)(2-methylpyridin-4-yl)methanone

[Formula 158]

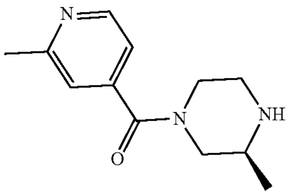

tert-Butyl (S)-2-methyl-4-(2-methylisonicotinoyl)piperazine-1-carboxylate (1.56 g, 4.88 mmol) was dissolved in dichloromethane (25 mL), trifluoroacetic acid (7.5 mL, 97.6 mmol) was added to the solution, and the resulting mixture was stirred at room temperature for 1 hour. After completion of the reaction, the reaction mixture was purified with SCX to obtain (S)-(3-methylpiperazin-1-yl)(2-methylpyridine-4-yl)methanone (896 mg, 83%).

LCMS (LC-1): RT=0.29, m/z 220 $[M+H]^+$

1H-NMR ($CD_3OD$): δ (ppm) 8.51 (1H, d, J=5.1 Hz), 7.31 (1H, s), 7.23 (11H, d, J=5.1 Hz), 4.49 (1H, brd, J=12.8 Hz), 3.56-3.39 (1H, m), 3.28-3.05 (1H, m), 2.95 (1H, brd, J=12.8 Hz), 2.90-2.73 (3H, m), 2.65-2.56 (4H, m), 1.22-0.95 (3H, m)

Example e-02-01: (1R,3s)-N-(5-(2-((((1S,2S)-2-Hydroxycyclopentyl)oxy)methyl)pyrimidin-5-yl)pyrazolo[1,5-a]pyridin-2-yl)-3-((S)-2-methyl-4-(2-methylisonicotinoyl)piperazin-1-yl)cyclobutane-1-carboxamide

[Formula 159]

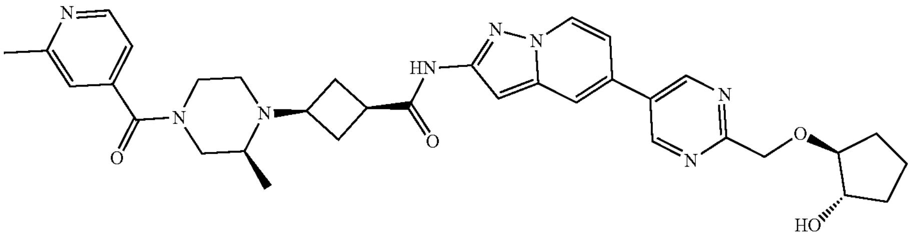

N-(5-(2-((((1S,2S)-2-Hydroxycyclopentyl)oxy)methyl)pyrimidin-5-yl)pyrazolo[1,5-a]pyridin-2-yl)-3-oxocyclobutane-1-carboxamide (Intermediate E-2-3, 60 mg, 0.14 mmol) was dissolved in dichloromethane (2.8 mL), [(3S)-3-methylpiperazin-1-yl]-(2-methyl-4-pyridyl)methanone (62 mg, 0.28 mmol), and sodium triacetoxyborohydride (90 mg, 0.43 mmol) were added to the solution, and the resulting mixture was stirred at room temperature for 1 hour. Then, saturated aqueous sodium hydrogencarbonate was added to the reaction mixture, the resulting mixture was extracted with chloroform, and the organic layer was concentrated under reduced pressure. The crude product was purified by using HPLC to obtain (1R,3s)-N-(5-(2-((((1S,2S)-2-hydroxycyclopentyl)oxy)methyl)pyrimidin-5-yl)pyrazolo[1,5-a]pyridin-2-yl)-3-((S)-2-methyl-4-(2-methylisonicotinoyl)piperazin-1-yl)cyclobutane-1-carboxamide (13.7 mg, 15%).

LCMS (LC-1): RT=0.96, m/z 625 $[M+H]^+$

1H-NMR ($DMSOd_6$): δ (ppm) 10.78 (1H, s), 9.23 (2H, s), 8.66 (1H, d, J=7.2 Hz), 8.52 (11H, d, J=5.0 Hz), 8.12 (11H, s), 7.30-7.12 (3H, m), 6.97 (11H, s), 5.76 (1H, s), 4.74-4.67 (3H, m), 4.02 (11H, brd, J=3.11 Hz), 3.84-3.79 (11H, m), 3.62 (11H, m), 3.28-3.21 (1H, m), 3.10-2.89 (3H, m), 2.77-2.59 (2H, m), 2.27 (1H, brs), 2.24-2.00 (5H, m), 1.96-1.73 (3H, m), 1.68-1.51 (4H, m), 1.49-1.35 (1H, m), 0.99 (1.5H, brd, J=6.2 Hz), 0.82 (1.5H, brd, J=6.2 Hz)

The following compounds mentioned in the following tables were synthesized by similar methods. In the following tables, the examples of which preparation methods should be referred to are mentioned in the column of "Reference Methods".

TABLE 21-1

| Example | Structure | Reference Methods | LCMS Data |
|---|---|---|---|
| e-02-02 | 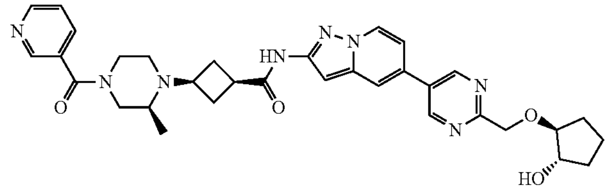 [SMILES: C[C@H]1CN(C(=O)c2cccnc2)CCN1[C@H]1C[C@@H](C(=O)Nc2cc3cc(-c4cnc(CO[C@H]5CCC[C@@H]5O)nc4)ccn3n2)C1] | Example e-02-01 | (LC-1): RT = 0.96, m/z 611 $[M + H]^+$ |
| e-02-03 | 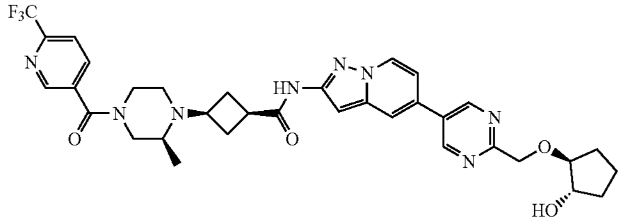 [SMILES: C[C@H]1CN(C(=O)c2ccc(C(F)(F)F)nc2)CCN1[C@H]1C[C@@H](C(=O)Nc2cc3cc(-c4cnc(CO[C@H]5CCC[C@@H]5O)nc4)ccn3n2)C1] | Example e-02-01 | (LC-1): RT = 1.20, m/z 679 $[M + H]^+$ |

TABLE 21-1-continued
| Example | Structure | Reference Methods | LCMS Data |
|---|---|---|---|
| e-02-04 | 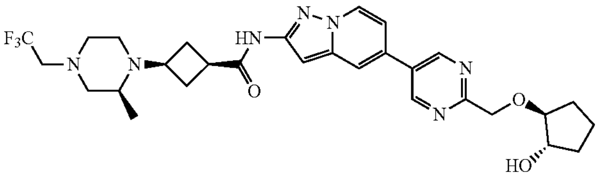 [SMILES: C[C@H]1CN(CC(F)(F)F)CCN1[C@H]1C[C@@H](C(=O)Nc2cc3cc(-c4cnc(CO[C@H]5CCC[C@@H]5O)nc4)ccn3n2)C1] | Example e-02-01 | (LC-1): RT = 1.18, m/z 588 $[M + H]^+$ |
| e-02-05 | 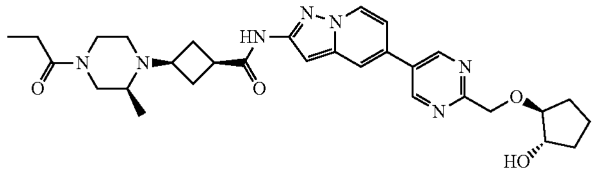 [SMILES: CCC(=O)N1CCN([C@H]2C[C@@H](C(=O)Nc3cc4cc(-c5cnc(CO[C@H]6CCC[C@@H]6O)nc5)ccn4n3)C2)[C@@H](C)C1] | Example e-02-01 | (LC-1): RT = 0.97, m/z 562 $[M + H]^+$ |
| e-02-06 | 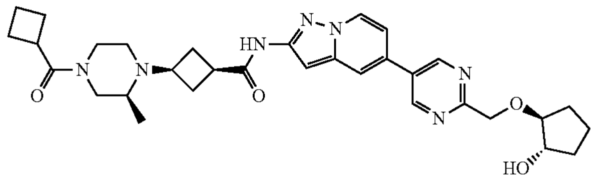 [SMILES: C[C@H]1CN(C(=O)C2CCC2)CCN1[C@H]1C[C@@H](C(=O)Nc2cc3cc(-c4cnc(CO[C@H]5CCC[C@@H]5O)nc4)ccn3n2)C1] | Example e-02-01 | (LC-1): RT = 1.08, m/z 588 $[M + H]^+$ |
| e-02-07 | 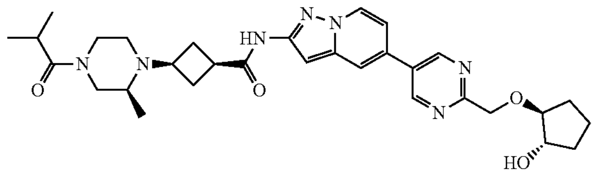 [SMILES: CC(C)C(=O)N1CCN([C@H]2C[C@@H](C(=O)Nc3cc4cc(-c5cnc(CO[C@H]6CCC[C@@H]6O)nc5)ccn4n3)C2)[C@@H](C)C1] | Example e-02-01 | (LC-1): RT = 1.04, m/z 576 $[M + H]^+$ |
| e-02-08 | 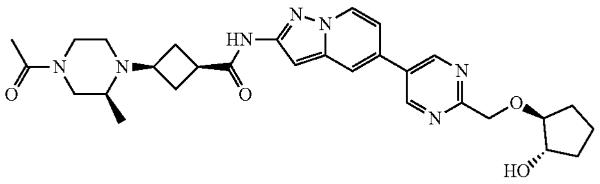 [SMILES: CC(=O)N1CCN([C@H]2C[C@@H](C(=O)Nc3cc4cc(-c5cnc(CO[C@H]6CCC[C@@H]6O)nc5)ccn4n3)C2)[C@@H](C)C1] | Example e-02-01 | (LC-1): RT = 0.90, m/z 548 $[M + H]^+$ |
| e-02-09 | 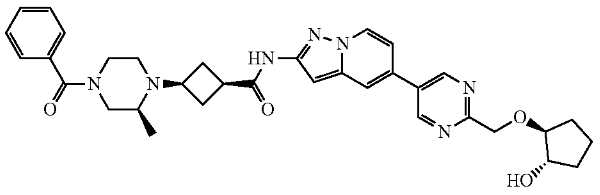 [SMILES: C[C@H]1CN(C(=O)c2ccccc2)CCN1[C@H]1C[C@@H](C(=O)Nc2cc3cc(-c4cnc(CO[C@H]5CCC[C@@H]5O)nc4)ccn3n2)C1] | Example e-02-01 | (LC-1): RT = 1.11, m/z 610 $[M + H]^+$ |
| e-02-10 | 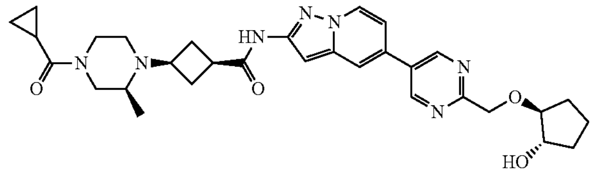 [SMILES: C[C@H]1CN(C(=O)C2CC2)CCN1[C@H]1C[C@@H](C(=O)Nc2cc3cc(-c4cnc(CO[C@H]5CCC[C@@H]5O)nc4)ccn3n2)C1] | Example e-02-01 | (LC-1): RT = 1.00, m/z 574 $[M + H]^+$ |
| e-02-11 | 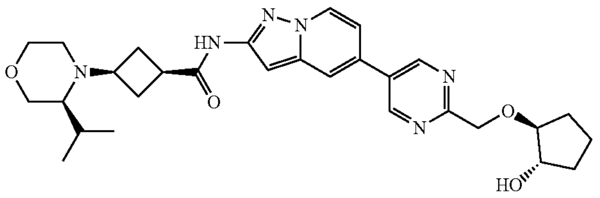 [SMILES: CC(C)[C@H]1COCCN1[C@H]1C[C@@H](C(=O)Nc2cc3cc(-c4cnc(CO[C@H]5CCC[C@@H]5O)nc4)ccn3n2)C1] | Example e-02-01 | (LC-1): RT = 1.12, m/z 535 $[M + H]^+$ |

TABLE 21-2
| | | | |
|---|---|---|---|
| e-02-12 | 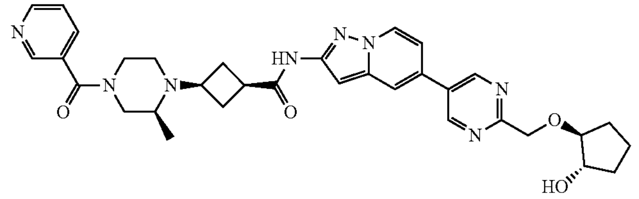 [SMILES: C[C@H]1CN(C(=O)c2cccnc2)CCN1[C@H]1C[C@@H](C(=O)Nc2cc3cc(-c4cnc(CO[C@H]5CCC[C@@H]5O)nc4)ccn3n2)C1] | Example e-02-01 | (LC-1): RT = 0.94, m/z 611 [M + H]$^+$ |
| e-02-13 | 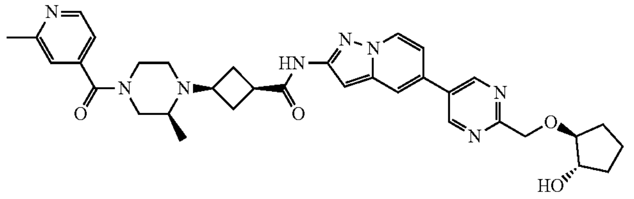 [SMILES: Cc1cc(C(=O)N2CCN([C@H]3C[C@@H](C(=O)Nc4cc5cc(-c6cnc(CO[C@H]7CCC[C@@H]7O)nc6)ccn5n4)C3)[C@@H](C)C2)ccn1] | Example e-02-01 | (LC-1): RT = 0.96, m/z 625 [M + H]$^+$ |
| e-02-14 | 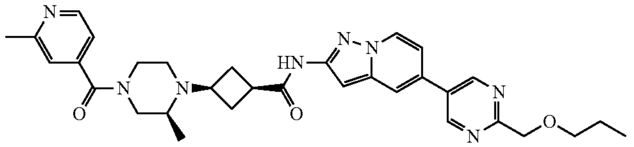 [SMILES: CCCOCc1ncc(-c2ccn3nc(NC(=O)[C@H]4C[C@@H](N5CCN(C(=O)c6ccnc(C)c6)C[C@@H]5C)C4)cc3c2)cn1] | Example e-02-01 | (LC-1): RT = 1.12, m/z 583 [M + H]$^+$ |
| e-02-15 | 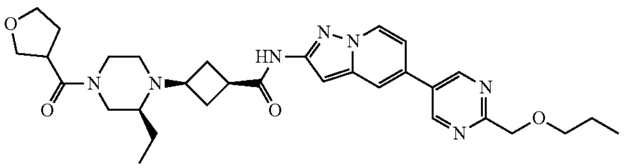 [SMILES: CCCOCc1ncc(-c2ccn3nc(NC(=O)[C@H]4C[C@@H](N5CCN(C(=O)C6CCOC6)C[C@@H]5CC)C4)cc3c2)cn1] | Example e-02-01 | (LC-1): RT = 1.16, m/z 576 [M + H]$^+$ |
| e-02-16 | 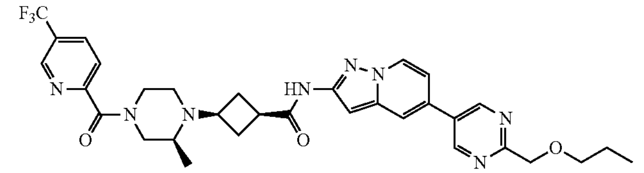 [SMILES: CCCOCc1ncc(-c2ccn3nc(NC(=O)[C@H]4C[C@@H](N5CCN(C(=O)c6ccc(C(F)(F)F)cn6)C[C@@H]5C)C4)cc3c2)cn1] | Example e-02-01 | (LC-1): RT = 1.37, m/z 637 [M + H]$^+$ |
| e-02-17 | 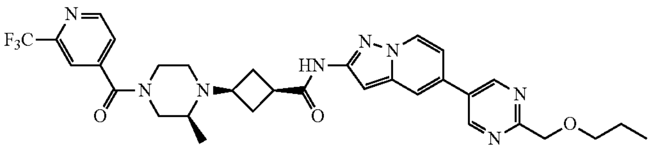 [SMILES: CCCOCc1ncc(-c2ccn3nc(NC(=O)[C@H]4C[C@@H](N5CCN(C(=O)c6ccnc(C(F)(F)F)c6)C[C@@H]5C)C4)cc3c2)cn1] | Example e-02-01 | (LC-1): RT = 1.34, m/z 637 [M + H]$^+$ |
| e-02-18 | 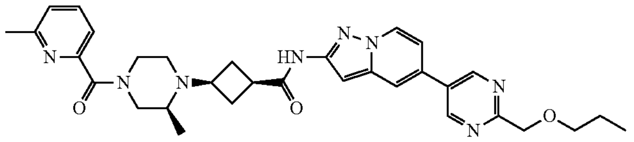 [SMILES: CCCOCc1ncc(-c2ccn3nc(NC(=O)[C@H]4C[C@@H](N5CCN(C(=O)c6cccc(C)n6)C[C@@H]5C)C4)cc3c2)cn1] | Example e-02-01 | (LC-1): RT = 1.17, m/z 583 [M + H]$^+$ |
| e-02-19 | 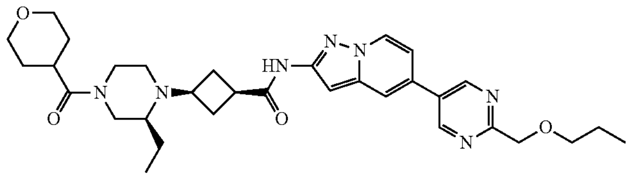 [SMILES: CCCOCc1ncc(-c2ccn3nc(NC(=O)[C@H]4C[C@@H](N5CCN(C(=O)C6CCOCC6)C[C@@H]5CC)C4)cc3c2)cn1] | Example e-02-01 | (LC-1): RT = 1.17, m/z 590 [M + H]$^+$ |
| e-02-20 | 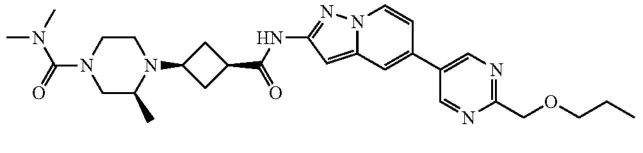 [SMILES: CCCOCc1ncc(-c2ccn3nc(NC(=O)[C@H]4C[C@@H](N5CCN(C(=O)N(C)C)C[C@@H]5C)C4)cc3c2)cn1] | Example e-02-01 | (LC-1): RT = 1.11, m/z 535 [M + H]$^+$ |

TABLE 21-2-continued
| | | | |
|---|---|---|---|
| e-02-21 | 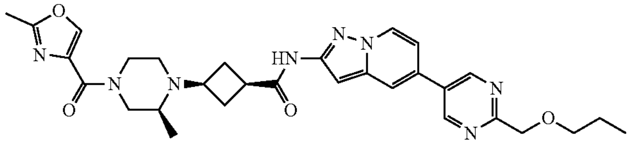 [SMILES: CCCOCc1ncc(-c2ccn3nc(NC(=O)[C@H]4C[C@@H](N5CCN(C(=O)c6coc(C)n6)C[C@@H]5C)C4)cc3c2)cn1] | Example e-02-01 | (LC-1): RT = 1.14, m/z 573 $[M + H]^+$ |
TABLE 21-3
| | | | |
|---|---|---|---|
| e-02-22 | 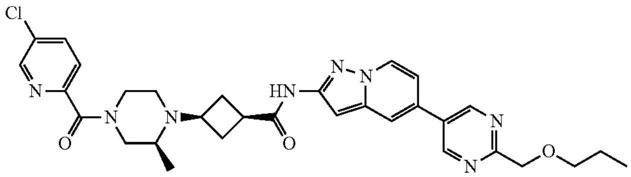 [SMILES: CCCOCc1ncc(-c2ccn3nc(NC(=O)[C@H]4C[C@@H](N5CCN(C(=O)c6ccc(Cl)cn6)C[C@@H]5C)C4)cc3c2)cn1] | Example e-02-01 | (LC-1): RT = 1.27, m/z 603 $[M + H]^+$ |
| e-02-23 | 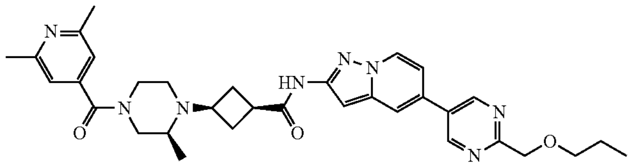 [SMILES: CCCOCc1ncc(-c2ccn3nc(NC(=O)[C@H]4C[C@@H](N5CCN(C(=O)c6cc(C)nc(C)c6)C[C@@H]5C)C4)cc3c2)cn1] | Example e-02-01 | (LC-1): RT = 1.15, m/z 597 $[M + H]^+$ |
| e-02-24 | 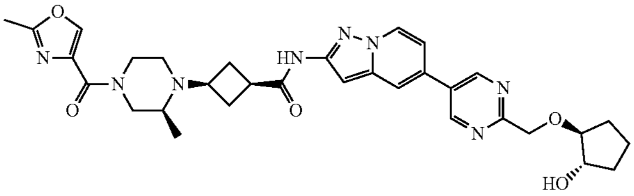 [SMILES: Cc1nc(C(=O)N2CCN([C@H]3C[C@@H](C(=O)Nc4cc5cc(-c6cnc(CO[C@H]7CCC[C@@H]7O)nc6)ccn5n4)C3)[C@@H](C)C2)co1] | Example e-02-01 | (LC-1): RT = 0.98, m/z 615 $[M + H]^+$ |
| e-02-25 | 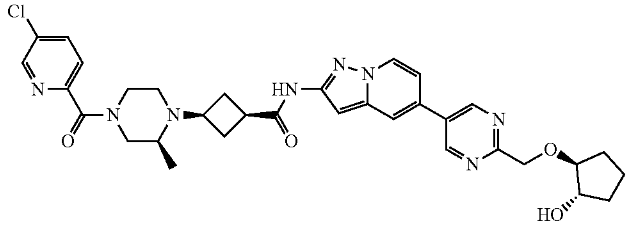 [SMILES: C[C@H]1CN(C(=O)c2ccc(Cl)cn2)CCN1[C@H]1C[C@@H](C(=O)Nc2cc3cc(-c4cnc(CO[C@H]5CCC[C@@H]5O)nc4)ccn3n2)C1] | Example e-02-01 | (LC-1): RT = 1.11, m/z 645 $[M + H]^+$ |
| e-02-26 | 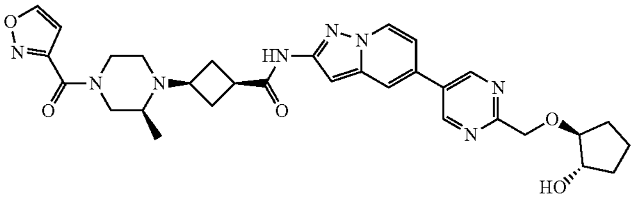 [SMILES: C[C@H]1CN(C(=O)c2ccon2)CCN1[C@H]1C[C@@H](C(=O)Nc2cc3cc(-c4cnc(CO[C@H]5CCC[C@@H]5O)nc4)ccn3n2)C1] | Example e-02-01 | (LC-1): RT = 1.01, m/z 601 $[M + H]^+$ |
| e-02-27 | 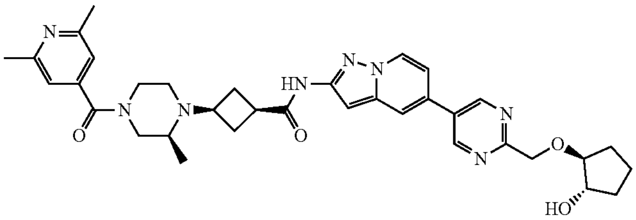 [SMILES: Cc1cc(C(=O)N2CCN([C@H]3C[C@@H](C(=O)Nc4cc5cc(-c6cnc(CO[C@H]7CCC[C@@H]7O)nc6)ccn5n4)C3)[C@@H](C)C2)cc(C)n1] | Example e-02-01 | (LC-1): RT = 1.00, m/z 639 $[M + H]^+$ |

Intermediate E-3-1: 3-(tert-Butoxy)cyclobutane-1-carboxylic acid anhydride

[Formula 160]

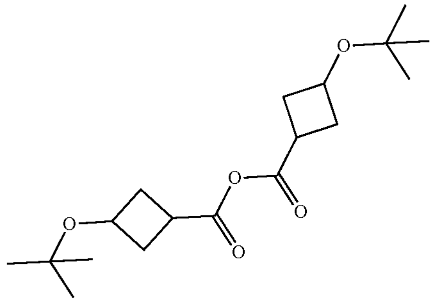

3-tert-Butoxycyclobutanecarboxylic acid (60 mg, 0.35 mmol) was dissolved in dichloromethane (3.5 mL), trimethylamine (145 μL, 1.0 mmol), and 2-chloro-1-methylpyridinium iodide (134 mg, 0.52 mmol) were added to the solution, and the resulting mixture was stirred for 3 hours under reflux by heating. The solvent of the reaction mixture was evaporated to obtain 3-(tert-butoxy)cyclobutane-1-carboxylic acid anhydride (55 mg, 96%).

LCMS (LC-1): RT=2.09, m/z 327 $[M+H]^+$

1H-NMR ($CDCl_3$): δ (ppm) 4.09-3.94 (m, 2H), 2.70-2.61 (m, 2H), 2.55-2.46 (m, 4H), 2.30-2.21 (m, 4H), 2.05 (s, 2H), 1.19 (s, 18H)

Example e-03-01: 3-(tert-Butoxy)-N-(5-(2-((((1S, 2S)-2-hydroxycyclopentyl)oxy)methyl)pyrimidin-5-yl)pyrazolo[1,5-a]pyridin-2-yl)cyclobutane-1-carboxamide

[Formula 161]

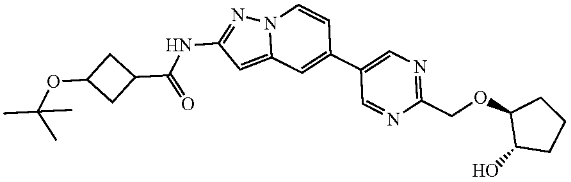

[(1S,2S)-2-[[5-(2-Aminopyrazolo[1,5-a]pyridin-5-yl)pyrimidin-2-yl]methoxy]cyclopentyl] acetate (Intermediate E-2-2, 60 mg, 0.16 mmol) was dissolved in pyridine (0.8 mL), 3-(tert-butoxy)cyclobutane-1-carboxylic acid anhydride (53 mg, 0.16 mmol), and dimethylaminopyridine (10 mg, 82 μmol) were added to the solution, and the resulting mixture was stirred at 120° C. at 14 hours. The reaction mixture was cooled to room temperature, and then methanol (0.8 mL) and 2 M aqueous sodium hydroxide (400 μL, 0.82 mmol) were added, and the resulting mixture was stirred at room temperature for 1 hour. The reaction mixture was diluted with water, and extracted with chloroform, the solvent was evaporated, and the residue was purified by using HPLC to obtain 3-(tert-butoxy)-N-(5-(2-((((1S,2S)-2-hydroxycyclopentyl)oxy)methyl)pyrimidin-5-yl)pyrazolo [1,5-a]pyridin-2-yl)cyclobutane-1-carboxamide (5.1 mg, 78%).

LCMS (LC-1): RT=1.51, m/z 522 $[M+H]^+$

1H-NMR ($CD_3OD$): δ (ppm) 9.15 (s, 2H), 8.49 (d, J=7.5 Hz, 1H), 7.99-7.93 (m, 1H), 7.17 (dd, J=7.5, 2.0 Hz, 1H), 7.01 (s, 1H), 4.83-4.76 (m, 2H), 4.28-4.01 (m, 2H), 3.90-3.87 (m, 1H), 2.94-2.72 (m, 1H), 2.57-2.38 (m, 2H), 2.35-2.13 (m, 2H), 2.07-1.91 (m, 3H), 1.81-1.63 (m, 4H), 1.60-1.51 (m, 2H), 1.20 (s, 9H)

Intermediate E-4-1: 2-(Bromomethyl)-4-chloro-3-methoxypyridine

[Formula 162]

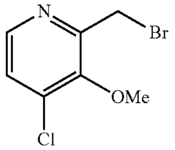

4-Chloro-3-methoxy-2-methylpyridine (3.15 g, 20 mmol) was dissolved in carbon tetrachloride (40 mL), N-bromosuccinimide (3.56 g, 20 mmol), and benzoyl peroxide (0.42 mL, 2 mmol) were added to the solution, and the resulting mixture was stirred for 7 hours under reflux by heating. The resulting reaction mixture was cooled to room temperature, solid was separated by filtration, and the obtained filtrate was concentrated under reduced pressure. The resulting crude product was purified by using automatic silica gel column chromatography (eluent, hexane:ethyl acetate=96:4 to 66:34) to obtain 2-(bromomethyl)-4-chloro-3-methoxypyridine (1.5 g, yield 32%).

LCMS (LC-1): RT=1.35, m/z 235 $[M+H]^+$

1H-NMR ($CDCl_3$): δ (ppm) 8.25 (11H, d, J=5.1 Hz), 7.30 (1H, d, J=5.1 Hz), 4.63 (2H, s), 4.04 (3H, s)

Intermediate E-4-2: 2-(4-Chloro-3-methoxypyridin-2-yl)acetonitrile

[Formula 163]

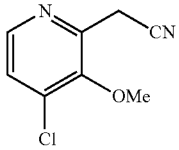

2-(Bromomethyl)-4-chloro-3-methoxypyridine (1.5 g, 6.34 mmol), and sodium cyanide (1.55 g, 32 mmol) were added to a mixed solvent of water (3.2 mL) and ethanol (3.1714 mL), and the resulting mixture was stirred at 60° C. for 1 hour. Saturated aqueous sodium hydrogencarbonate and chloroform were added to the resulting crude reaction mixture for extraction. The obtained organic layer was dried over anhydrous sodium sulfate, filtered, and concentrated under reduced pressure. The resulting crude product was purified by using automatic silica gel column chromatography (eluent, hexane:ethyl acetate=94:6 to 50:50) to obtain 2-(4-chloro-3-methoxypyridin-2-yl)acetonitrile (691 mg, yield 60%).

LCMS (LC-1): RT=1.05, m/z 183 $[M+H]^+$

1H-NMR ($CDCl_3$): δ (ppm) 8.25 (1H, d, J=5.2 Hz), 7.35 (1H, d, J=5.2 Hz), 4.01 (3H, s), 3.96 (2H, s)

Intermediate E-4-3: 5-Chloro-4-methoxypyrazolo[1,5-a]pyridin-2-amine

[Formula 164]

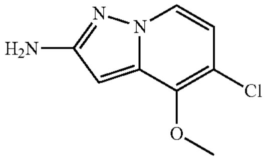

To a solution of ethyl O-mesitylsulfonylacetohydroxamate (467 mg, 1.64 mmol, 1.1 eq.) in 1,4-dioxane (1 mL), 70% aqueous perchloric acid (140 μL, 1.64 mmol, 1.1 eq.) was added, and the resulting mixture was stirred at 0° C. for 30 minutes. The reaction mixture was diluted with cold water and hexane, and the precipitates were separated by filtration to obtain solid. The solid was added to a solution of 2-(4-chloro-3-methoxy-2-pyridyl)acetonitrile (Intermediate E-4-2, 272 mg, 1.49 mmol) in dichloromethane (1 mL), and the resulting mixture was stirred at 0° C. for 1 hour. The reaction mixture was concentrated, a solution of potassium carbonate (103 mg, 74 mmol) in dimethylformamide (1 mL) was added to the concentrated reaction mixture, and the resulting mixture was stirred at 120° C. with heating. The reaction mixture was cooled to room temperature, then saturated brine was added to the reaction mixture, the resulting mixture was extracted with ethyl acetate, the organic layer was dried over magnesium sulfate, then the solvent was evaporated, and the resulting crude product was purified by using automatic silica gel column chromatography (eluent, hexane:ethyl acetate=1:1) to obtain 5-chloro-4-methoxypyrazolo[1,5-a]pyridin-2-amine (112 mg, 38%).

LCMS (LC-1): RT=1.03, m/z 198 $[M+H]^+$

1H-NMR ($CDCl_3$): δ (ppm) 8.02 (s, 2H), 7.91 (d, J=7.3 Hz, 2H), 6.50 (d, J=7.3 Hz, 2H), 5.86 (s, 2H), 3.98 (s, 31H)

Intermediate E-4-4: (1S,2S)-2-((5-(2-Amino-4-methoxypyrazolo[1,5-a]pyridin-5-yl)pyrimidin-2-yl)methoxy)cyclopentyl acetate

[Formula 165]

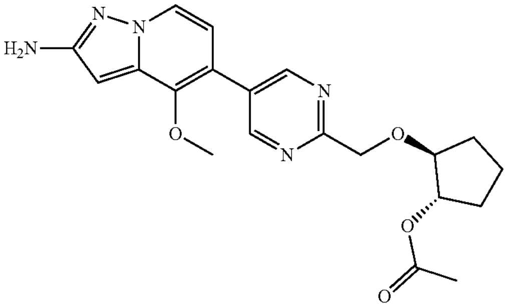

5-Chloro-4-methoxypyrazolo[1,5-a]pyridin-2-amine (Intermediate E-4-3, 40 mg, 0.2 mmol) was dissolved in dimethylacetoamide (1 mL), the aforementioned crude product, (1S,2S)-2-((5-(4,4,5,5-tetramethyl-1,3,2-dioxaboran-2-yl)pyrimidin-2-yl)methoxy)cyclopentyl acetate (Intermediate B-4-2, 4.4 mmol), tetrakis(triphenylphosphine)palladium(0) (23 mg, 0.02 mmol), sodium carbonate (42 mg, 0.4 mmol), and water (0.1 mL) were added to the solution, and the resulting mixture was irradiated with microwaves at 185° C. for 1 hour. The crude reaction mixture was concentrated under reduced pressure, and the resulting crude product was purified by using automatic silica gel column chromatography (eluent, chloroform:methanol=95:5) to obtain (1S,2S)-2-((5-(2-amino-4-methoxypyrazolo[1,5-a]pyridin-5-yl)pyrimidin-2-yl)methoxy)cyclopentyl acetate (46.9 g, yield 58%).

LCMS (LC-1): RT=1.11, m/z 398 $[M+H]^+$

1H-NMR ($CDCl_3$): δ (ppm) 9.01-8.96 (m, 2H), 8.12-8.05 (m, 11H), 6.56-6.48 (m, 1H), 6.01-5.93 (m, 1H), 5.21-5.19 (m, 2H), 4.95-4.82 (m, 4H), 4.12-4.09 (m, 3H), 3.86-3.77 (m, 3H), 2.28-2.14 (m, 2H), 2.04 (s, 3H), 1.89-1.79 (m, 4H), 1.32-1.22 (m, 2H)

Intermediate E-4-5: (1S,2S)-2-((5-(2-(Cyclopropanecarboxamido)-4-methoxypyrazolo[1,5-a]pyridin-5-yl)pyrimidin-2-yl)methoxy)cyclopentyl acetate

[Formula 166]

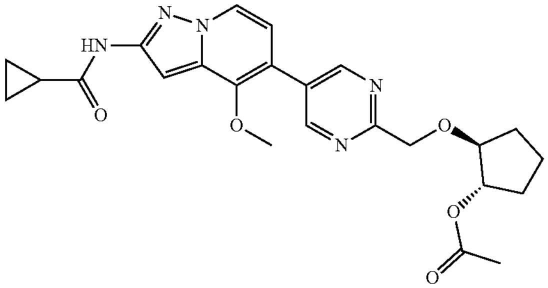

(1S,2S)-2-((5-(2-Amino-4-methoxypyrazolo[1,5-a]pyridin-5-yl)pyrimidin-2-yl)methoxy)cyclopentyl acetate (Intermediate E-4-4, 32 mg, 0.07 mmol) was dissolved in dichloromethane (1 mL), a solution of dimethylamine (71 μL, 1.4 mmol) in dichloromethane (1.2 mL), cyclopropanecarbonyl chloride (16 μL, 0.18 mmol), and N-ethylisopropylamine (41 μL, 0.24 mmol) were added to the solution, and the resulting mixture was stirred at room temperature for 30 minutes. The solvent of the reaction mixture was evaporated to obtain (1S,2S)-2-((5-(2-(cyclopropanecarboxamido)-4-methoxypyrazolo[1,5-a]pyridin-5-yl)pyrimidin-2-yl)methoxy)cyclopentyl acetate (54.9 mg, 99%) as a crude product.

LCMS (LC-1): RT=1.32, m/z 466 $[M+H]^+$

Example e-04-01: N-(5-(2-((((1S,2S)-2-Hydroxycyclopentyl)oxy)methyl)pyrimidin-5-yl)-4-methoxypyrazolo[1,5-a]pyridin-2-yl)cyclopropanecarboxamide

[Formula 167]

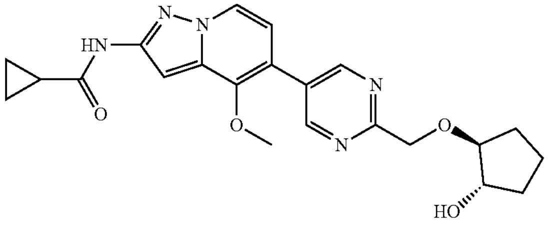

(1S,2S)-2-((5-(2-(Cyclopropanecarboxamido)-4-methoxypyrazolo[1,5-a]pyridin-5-yl)pyrimidin-2-yl)methoxy)cyclopentyl acetate (Intermediate E-4-5, 54.9 mg, 0.12 mmol) was dissolved in methanol (1.2 mL), 2 M aqueous sodium hydroxide (500 μL) was added to the solution, and the resulting mixture was stirred at room temperature for 30 minutes. Saturated brine was added to the reaction mixture, the resulting mixture was extracted with chloroform, the organic layer was dried over magnesium sulfate, the solvent was evaporated, and then the residue was purified by using HPLC to obtain N-(5-(2-((((1S,2S)-2-hydroxycyclopentyl)oxy)methyl)pyrimidin-5-yl)-4-methoxypyrazolo[1,5-a]pyridin-2-yl)cyclopropanecarboxamide (5.6 mg, 11%).

LCMS (LC-1): RT=1.06, m/z 424 $[M+H]^+$

1H-NMR ($CDCl_3$): δ (ppm) 8.99 (s, 2H), 8.19 (brs, 1H), 8.18-8.13 (m, 1H), 7.25-7.19 (m, 1H), 6.69 (d, J=7.1 Hz, 1H), 5.00 (d, J=15 Hz, 1H), 4.83 (d, J=15 Hz, 1H), 4.28-4.20 (m, 1H), 3.93 (s, 3H), 3.91-3.84 (m, 1H), 2.17-2.00 (m, 3H), 1.77-1.71 (m, 4H), 1.19-1.12 (m, 2H), 0.98-0.90 (m, 2H)

Test Example 1: Measurement of Human IRAK-4 Inhibitory Activity (1) Measurement Method For the measurement of the activity of the human IRAK-4 (Invitrogen, Cat. PV3362), phosphorylation of the IRAK-4 peptide substrate (biotin-KKKKRFSFKKSFKC) by the enzyme in the presence of 10 μM ATP (Sigma-Aldrich, Cat. A7699) was measured by the TR-FRET method. The enzymatic reaction was performed in a reaction buffer containing 50 mM HEPES (pH 7.2), 1 mM DTT, 0.1 mM $Na_3VO_4$, 5 mM $MgCl_2$, 1 mM $MnCl_2$, and 0.1% bovine serum albumin. For the measurement of the IRAK-4 inhibitory activity, a test compound was added to the reaction buffer containing 1 nM IRAK-4, 0.5 μM peptide substrate, and 10 μM ATP, and the mixture was incubated at 23° C. for 30 minutes. Then, a detection solution containing an antibody labeled with europium cryptate (0.3 μg/mL, the antibody was prepared by using the IRAK-4 peptide substrate as the antigen), streptavidin-XL665 (2 μg/mL, CisBio, Cat. 610SAXLB), 50 mM HEPES (pH 7.2), 0.1% BSA, 120 mM KF, and 66.7 mM EDTA (all the concentrations of the reagents are final concentrations) was added to terminate the reaction, and then the mixture was further incubated at 23° C. for 60 minutes. Fluorescence intensity was measured at wavelengths of 665 nm and 620 nm with a microplate reader, and the enzymatic activity was calculated as the ratio of fluorescence intensities at 665 nm and 620 nm (665 nm/620 nm). The IRAK-4 suppression ratio observed with addition of 12.5 μM staurosporine (LC Laboratories, Cat. S-9300) was defined to be 100%, the IRAK-4 suppression ratio observed with no addition of test compound was defined to be 0%, and $IC_{50}$ of the test compound was calculated by using the 4-parameter logistic model of the data analysis software XLfit (ID Business Solutions Ltd.).

The operations and conditions used for the measurement may be appropriately changed within such a range that those skilled in the art can understand them, and the measurement is not significantly affected.

(2) Measurement Results

As shown below, the compounds of the present invention according to a certain embodiment showed outstanding IRAK-4 inhibitory activities.

When the measurement was performed in multiplicate, the results are represented with average values.

TABLE 22

| Example | $IC_{50}$ (nM) |
|---|---|
| a-01-01 | 1.89 |
| a-01-02 | 1.98 |
| a-01-03 | 2.69 |
| a-01-04 | 1.73 |
| a-01-05 | 2.08 |
| a-01-06 | 3.29 |
| a-01-07 | 1.73 |
| a-01-08 | 2.66 |
| a-01-09 | 1.81 |
| a-01-10 | 12.11 |
| a-01-11 | 7.89 |
| a-01-12 | 7.75 |
| a-02-01 | 16.05 |
| a-03-01 | 1.41 |
| a-04-01 | 1.38 |
| a-04-02 | 1.26 |
| a-04-03 | 2.32 |
| a-04-04 | 2.32 |
| a-05-01 | 7.81 |
| b-01-01 | 3.39 |
| b-01-02 | 3.33 |
| b-02-01 | 3.16 |
| b-02-02 | 2.79 |
| b-02-03 | 2.53 |
| b-02-04 | 3.64 |
| b-02-05 | 2.12 |
| b-02-06 | 1.34 |
| b-02-07 | 2.28 |
| b-02-08 | 2.76 |
| b-02-09 | 2.42 |
| b-02-10 | 3.94 |
| b-02-11 | 2.87 |
| b-02-12 | 3.37 |
| b-02-13 | 3.77 |
| b-02-14 | 2.41 |
| b-02-15 | 2.25 |
| b-02-16 | 2.01 |
| b-02-17 | 1.59 |
| b-02-18 | 2.92 |
| b-02-19 | 2.54 |
| b-02-20 | 4.28 |
| b-02-21 | 2.12 |
| b-02-22 | 1.89 |
| b-02-23 | 2.52 |
| b-02-24 | 1.91 |
| b-02-25 | 1.98 |
| b-02-26 | 1.75 |
| b-02-27 | 1.48 |
| b-02-28 | 2.17 |
| b-02-29 | 2.43 |
| b-02-30 | 4.12 |
| b-02-31 | 2.36 |
| b-02-32 | 2.37 |
| b-02-33 | 1.63 |
| b-02-34 | 2.52 |
| b-02-35 | 2.52 |
| b-02-36 | 1.82 |
| b-02-37 | 2.22 |
| b-02-38 | 2.98 |
| b-02-39 | 1.90 |

TABLE 23

| Example | $IC_{50}$ (nM) |
|---|---|
| b-02-40 | 1.62 |
| b-02-41 | 2.86 |
| b-02-42 | 1.93 |
| b-02-43 | 3.10 |
| b-02-44 | 3.93 |
| b-02-46 | 3.55 |
| b-02-47 | 1.75 |
| b-02-48 | 2.03 |
| b-02-49 | 2.52 |
| b-02-50 | 1.93 |

TABLE 23-continued

| Example | $IC_{50}$ (nM) |
|---|---|
| b-02-51 | 2.17 |
| b-02-52 | 2.60 |
| b-02-53 | 2.59 |
| b-02-54 | 3.46 |
| b-02-55 | 2.97 |
| b-02-56 | 1.76 |
| b-02-57 | 2.62 |
| b-02-58 | 2.70 |
| b-02-59 | 1.51 |
| b-02-60 | 4.27 |
| b-02-61 | 3.87 |
| b-02-62 | 1.38 |
| b-02-63 | 2.39 |
| b-02-65 | 2.38 |
| b-02-66 | 5.00 |
| b-02-67 | 2.36 |
| b-02-68 | 2.18 |
| b-02-69 | 1.81 |
| b-02-70 | 2.94 |
| b-02-71 | 2.36 |
| b-02-72 | 1.47 |
| b-02-74 | 1.57 |
| b-02-76 | 1.55 |
| b-02-77 | 2.60 |
| b-02-78 | 2.29 |
| b-02-79 | 3.39 |
| b-02-80 | 6.86 |
| b-02-81 | 3.64 |
| b-02-82 | 4.02 |
| b-02-83 | 1.93 |
| b-02-84 | 1.04 |
| b-02-85 | 1.88 |
| b-02-86 | 0.803 |
| b-02-87 | 0.95 |
| b-03-01 | 1.30 |
| b-03-02 | 10.98 |
| b-03-03 | 1.43 |
| b-03-04 | 1.67 |
| b-03-05 | 2.93 |
| b-03-06 | 2.80 |
| b-03-07 | 5.26 |
| b-03-08 | 2.68 |
| b-03-09 | 2.21 |
| b-04-01 | 5.49 |
| b-04-02 | 1.40 |
| b-04-03 | 3.21 |
| b-04-04 | 2.69 |
| b-04-05 | 2.85 |
| b-04-06 | 2.37 |
| b-04-07 | 2.60 |

TABLE 24

| Example | $IC_{50}$ (nM) |
|---|---|
| b-04-08 | 2.48 |
| b-04-09 | 2.58 |
| b-04-10 | 3.94 |
| b-04-11 | 1.89 |
| b-04-12 | 1.93 |
| b-04-13 | 1.70 |
| b-04-14 | 1.50 |
| b-04-15 | 1.61 |
| b-04-16 | 1.51 |
| b-04-17 | 1.58 |
| b-04-18 | 1.11 |
| b-04-19 | 1.38 |
| b-04-20 | 1.12 |
| b-04-21 | 1.15 |
| b-04-22 | 1.30 |
| b-04-23 | 1.41 |
| b-04-24 | 0.76 |
| b-04-25 | 0.88 |
| b-04-26 | 1.22 |
| b-04-27 | 1.60 |

TABLE 24-continued

| Example | $IC_{50}$ (nM) |
|---|---|
| b-04-28 | 1.58 |
| b-04-29 | 1.60 |
| b-04-30 | 1.49 |
| b-04-31 | 1.73 |
| b-04-32 | 1.57 |
| b-04-33 | 1.99 |
| b-04-34 | 1.65 |
| b-04-35 | 2.08 |
| b-04-36 | 0.90 |
| b-04-37 | 0.81 |
| b-04-38 | 0.85 |
| b-04-39 | 0.66 |
| b-04-40 | 0.89 |
| b-04-41 | 0.69 |
| b-04-42 | 0.49 |
| b-04-43 | 0.65 |
| b-04-44 | 0.46 |
| b-04-45 | 0.66 |
| b-04-46 | 0.58 |
| b-04-47 | 0.54 |
| b-04-48 | 0.52 |
| b-05-01 | 1.90 |
| b-05-02 | 2.47 |
| b-05-03 | 1.81 |
| b-05-04 | 4.38 |
| b-05-05 | 1.95 |
| b-05-06 | 2.25 |
| b-05-07 | 2.51 |
| b-05-09 | 2.13 |
| b-06-02 | 4.19 |
| b-07-01 | 2.34 |
| b-08-01 | 1.97 |
| c-01-01 | 3.92 |
| c-02-01 | 3.70 |
| c-02-04 | 3.35 |
| c-02-05 | 4.64 |
| c-02-06 | 2.13 |
| c-02-07 | 1.56 |
| c-02-08 | 2.44 |
| c-03-01 | 16.59 |

TABLE 25

| Example | $IC_{50}$ (nM) |
|---|---|
| c-03-02 | 2.36 |
| c-03-03 | 2.54 |
| c-03-04 | 2.69 |
| c-03-05 | 4.16 |
| c-03-06 | 4.97 |
| c-03-07 | 5.35 |
| c-03-08 | 4.62 |
| c-03-09 | 5.43 |
| c-04-01 | 4.04 |
| c-04-02 | 6.33 |
| c-04-03 | 12.44 |
| c-05-01 | 5.48 |
| c-06-01 | 5.45 |
| c-06-02 | 10.74 |
| c-06-03 | 17.15 |
| c-07-01 | 6.48 |
| d-01-01 | 1.31 |
| d-01-02 | 2.75 |
| d-01-03 | 2.16 |
| d-01-04 | 6.39 |
| d-01-05 | 2.07 |
| d-01-06 | 3.62 |
| d-01-07 | 1.75 |
| d-01-08 | 2.89 |
| d-02-01 | 1.83 |
| d-03-01 | 1.38 |
| d-03-05 | 2.52 |
| d-03-06 | 0.849 |
| d-03-07 | 0.852 |
| d-03-08 | 1.28 |

TABLE 25-continued

| Example | $IC_{50}$ (nM) |
|---|---|
| d-03-09 | 1.47 |
| d-04-01 | 2.10 |
| d-04-02 | 2.48 |
| d-04-03 | 2.22 |
| d-04-05 | 2.05 |
| d-05-01 | 1.51 |
| d-05-02 | 2.10 |
| e-01-01 | 2.89 |
| e-01-02 | 2.48 |
| e-01-03 | 1.03 |
| e-02-01 | 1.43 |
| e-02-02 | 1.38 |
| e-02-03 | 2.23 |
| e-02-04 | 1.05 |
| e-02-05 | 1.14 |
| e-02-06 | 1.30 |
| e-02-07 | 1.33 |
| e-02-08 | 1.32 |
| e-02-09 | 1.09 |
| e-02-10 | 1.09 |
| e-02-11 | 1.04 |
| e-02-12 | 1.90 |
| e-02-13 | 1.43 |
| e-02-14 | 1.64 |
| e-02-15 | 1.81 |
| e-02-16 | 1.85 |
| e-02-17 | 1.36 |
| e-02-18 | 1.84 |
| e-02-19 | 1.19 |
| e-02-20 | 2.22 |

TABLE 26

| Example | $IC_{50}$ (nM) |
|---|---|
| e-02-21 | 1.73 |
| e-02-22 | 1.29 |
| e-02-23 | 0.88 |
| e-02-24 | 1.27 |
| e-02-25 | 1.58 |
| e-02-26 | 1.86 |
| e-02-27 | 1.38 |
| e-03-01 | 1.75 |
| e-04-01 | 3.74 |
| e-04-02 | 1.07 |

Test Example 2: LPS-Stimulated TNFα Production Inhibition Test Using Human Acute Monocytic Leukemia Cell Strain THP-1

(1) Measurement Method

By the THP-1 assay, influence of a test compound on the TNFα production induced by LPS stimulation can be evaluated. The THP-1 cells (ATCC, Cat. TIB-202) were inoculated on a 96-well plate at a density of $1\times10^5$ cells/160 μL/well, a test compound was added in a volume of 20 μL, and the plate was incubated at 37° C. for 1 hour in a 5% $CO_2$ incubator. Then, LPS in a volume of 20 μL (final concentration 2.5 ng/mL, Sigma, Cat. L2630) was added, and the plate was further incubated for 4 hours. After the incubation, the plate was centrifuged, and 100 μL of the supernatant was taken from each well, and used for evaluation of the amount of TNFα using HTRF (Cisbio, Cat. 62TNFPEB). In the measurement of the amount of TNFα, the supernatant was diluted twice with the medium, and then added to wells of a 384-well plate in a volume of 10 μL, then anti-TNFα-cryptate (5 μL), and anti-TNFα-XL665 (5 μL) were added, and the plate was left standing overnight. The fluorescence intensity ratio for the wavelengths of 620 and 665 nm (620 nm/665 nm) was measured with a microplate reader, and the amount of TNFα in the supernatant was calculated by using a calibration curve. The TNFα production suppression ratio observed with no addition of LPS was defined to be 100%, the TNFα production suppression ratio observed with no addition of the test compound was defined to be 0%, and $IC_{50}$ of the test compound was calculated by using the 4-parameter logistic model of the data analysis software XLfit (ID Business Solutions Ltd.).

By using the 96-well plate from which 100 μL of the supernatant was removed, cell survival ratio was measured, and influence of the off-target effect of the test compound was evaluated. CCK-8 (Dojindo, Cat. CK04-10) was added in a volume of 5 μL, the plate was incubated at 37° C. for 1 hour, and then absorbance was measured at 450 nm with a microplate reader. The cell survival ratio observed with no addition of LPS was defined to be 100%, and $IC_{50}$ of the test compound was calculated by using XLfit.

The operations and conditions used for the measurement may be appropriately changed within such a range that those skilled in the art can understand them, and the measurement is not significantly affected.

(2) Measurement Results

As shown below, the compounds of the present invention according to a certain embodiment showed outstanding TNFα production inhibitory activity.

When the measurement was performed in multiplicate, the results are represented with average values. The values were rounded to three decimal places.

TABLE 27

| Example | $IC_{50}$ (μM) |
|---|---|
| a-01-01 | 0.121 |
| a-01-02 | 0.180 |
| a-01-03 | 0.141 |
| a-01-04 | 0.151 |
| a-01-05 | 0.121 |
| a-01-06 | 0.17 |
| a-01-07 | 0.148 |
| a-01-08 | 0.161 |
| a-01-09 | 0.14 |
| a-01-10 | 0.678 |
| a-01-11 | 0.437 |
| a-01-12 | 0.361 |
| a-02-01 | 0.33 |
| a-03-01 | 0.057 |
| a-04-01 | 0.261 |
| a-04-02 | 0.241 |
| a-04-03 | 0.355 |
| a-04-04 | 0.444 |
| a-05-01 | 0.304 |
| b-01-01 | 0.154 |
| b-01-02 | 0.177 |
| b-02-01 | 0.195 |
| b-02-02 | 0.195 |
| b-02-03 | 0.166 |
| b-02-04 | 0.146 |
| b-02-05 | 0.131 |
| b-02-06 | 0.066 |
| b-02-07 | 0.164 |
| b-02-08 | 0.113 |
| b-02-09 | 0.142 |
| b-02-10 | 0.141 |
| b-02-11 | 0.152 |
| b-02-12 | 0.17 |
| b-02-13 | 0.175 |
| b-02-14 | 0.164 |
| b-02-15 | 0.157 |
| b-02-16 | 0.107 |
| b-02-17 | 0.12 |
| b-02-18 | 0.164 |
| b-02-19 | 0.144 |

TABLE 27-continued

| Example | $IC_{50}$ (μM) |
|---|---|
| b-02-20 | 0.078 |
| b-02-21 | 0.066 |
| b-02-22 | 0.208 |
| b-02-23 | 0.166 |
| b-02-24 | 0.18 |
| b-02-25 | 0.199 |
| b-02-26 | 0.126 |
| b-02-27 | 0.159 |
| b-02-28 | 0.103 |
| b-02-29 | 0.124 |
| b-02-30 | 0.137 |
| b-02-31 | 0.194 |
| b-02-32 | 0.041 |
| b-02-33 | 0.051 |
| b-02-34 | 0.116 |
| b-02-35 | 0.14 |
| b-02-36 | 0.145 |
| b-02-37 | 0.094 |
| b-02-38 | 0.15 |
| b-02-39 | 0.182 |

TABLE 28

| Example | $IC_{50}$ (μM) |
|---|---|
| b-02-40 | 0.139 |
| b-02-41 | 0.16 |
| b-02-42 | 0.123 |
| b-02-43 | 0.123 |
| b-02-44 | 0.143 |
| b-02-45 | 0.2 |
| b-02-46 | 0.171 |
| b-02-47 | 0.11 |
| b-02-48 | 0.143 |
| b-02-49 | 0.119 |
| b-02-50 | 0.144 |
| b-02-51 | 0.146 |
| b-02-52 | 0.176 |
| b-02-53 | 0.172 |
| b-02-54 | 0.135 |
| b-02-55 | 0.15 |
| b-02-56 | 0.109 |
| b-02-57 | 0.119 |
| b-02-58 | 0.133 |
| b-02-59 | 0.105 |
| b-02-60 | 0.158 |
| b-02-61 | 0.109 |
| b-02-62 | 0.141 |
| b-02-63 | 0.159 |
| b-02-64 | 0.164 |
| b-02-65 | 0.163 |
| b-02-66 | 0.227 |
| b-02-67 | 0.091 |
| b-02-68 | 0.16 |
| b-02-69 | 0.08 |
| b-02-70 | 0.09 |
| b-02-71 | 0.105 |
| b-02-72 | 0.162 |
| b-02-73 | 0.113 |
| b-02-74 | 0.189 |
| b-02-75 | 0.186 |
| b-02-76 | 0.099 |
| b-02-77 | 0.187 |
| b-02-78 | 0.111 |
| b-02-79 | 0.138 |
| b-02-80 | 0.176 |
| b-02-81 | 0.202 |
| b-02-82 | 0.131 |
| b-02-83 | 0.149 |
| b-02-84 | 0.101 |
| b-02-85 | 0.127 |
| b-02-86 | 0.132 |
| b-02-87 | 0.182 |
| b-03-01 | 0.071 |
| b-03-02 | 0.145 |

TABLE 28-continued

| Example | $IC_{50}$ (μM) |
|---|---|
| b-03-03 | 0.126 |
| b-03-04 | 0.117 |
| b-03-05 | 0.108 |
| b-03-06 | 0.116 |
| b-03-07 | 0.183 |
| b-03-08 | 0.127 |
| b-03-09 | 0.143 |
| b-04-01 | 0.051 |
| b-04-02 | 0.021 |
| b-04-03 | 0.046 |

TABLE 29

| Example | $IC_{50}$ (μM) |
|---|---|
| b-04-04 | 0.049 |
| b-04-05 | 0.054 |
| b-04-06 | 0.064 |
| b-04-07 | 0.06 |
| b-04-08 | 0.053 |
| b-04-09 | 0.055 |
| b-04-10 | 0.03 |
| b-04-11 | 0.038 |
| b-04-12 | 0.039 |
| b-04-13 | 0.027 |
| b-04-14 | 0.025 |
| b-04-15 | 0.028 |
| b-04-16 | 0.023 |
| b-04-17 | 0.022 |
| b-04-18 | 0.03 |
| b-04-19 | 0.039 |
| b-04-20 | 0.039 |
| b-04-21 | 0.033 |
| b-04-22 | 0.05 |
| b-04-23 | 0.054 |
| b-04-24 | 0.095 |
| b-04-25 | 0.071 |
| b-04-26 | 0.086 |
| b-04-27 | 0.108 |
| b-04-28 | 0.072 |
| b-04-29 | 0.055 |
| b-04-30 | 0.062 |
| b-04-31 | 0.055 |
| b-04-32 | 0.05 |
| b-04-33 | 0.055 |
| b-04-34 | 0.066 |
| b-04-35 | 0.037 |
| b-04-36 | 0.048 |
| b-04-37 | 0.035 |
| b-04-38 | 0.087 |
| b-04-39 | 0.044 |
| b-04-40 | 0.025 |
| b-04-41 | 0.076 |
| b-04-42 | 0.064 |
| b-04-43 | 0.096 |
| b-04-44 | 0.023 |
| b-04-45 | 0.015 |
| b-04-46 | 0.022 |
| b-04-47 | 0.026 |
| b-04-48 | 0.035 |
| b-05-01 | 0.048 |
| b-05-02 | 0.056 |
| b-05-03 | 0.05 |
| b-05-04 | 0.024 |
| b-05-05 | 0.05 |
| b-05-06 | 0.046 |
| b-05-07 | 0.044 |
| b-05-08 | 0.081 |
| b-05-09 | 0.044 |

TABLE 29-continued

| Example | $IC_{50}$ (μM) |
|---|---|
| b-06-01 | 0.093 |
| b-06-02 | 0.046 |
| b-07-01 | 0.058 |
| b-08-01 | 0.056 |
| c-01-01 | 0.143 |
| c-02-01 | 0.11 |

TABLE 30

| Example | $IC_{50}$ (μM) |
|---|---|
| c-02-02 | 0.186 |
| c-02-03 | 0.229 |
| c-02-04 | 0.261 |
| c-02-05 | 0.175 |
| c-02-06 | 0.194 |
| c-02-07 | 0.076 |
| c-02-08 | 0.196 |
| c-03-01 | 0.049 |
| c-03-02 | 0.013 |
| c-03-03 | 0.230 |
| c-03-04 | 0.320 |
| c-03-05 | 0.038 |
| c-03-06 | 0.046 |
| c-03-07 | 0.184 |
| c-03-08 | 0.037 |
| c-03-09 | 0.054 |
| c-04-01 | 0.115 |
| c-04-02 | 0.207 |
| c-04-03 | 0.184 |
| c-05-01 | 0.233 |
| c-06-01 | 0.358 |
| c-06-02 | 0.317 |
| c-06-03 | 0.277 |
| c-07-01 | 0.347 |
| d-01-01 | 0.085 |
| d-01-02 | 0.165 |
| d-01-03 | 0.175 |
| d-01-04 | 0.178 |
| d-01-05 | 0.101 |
| d-01-06 | 0.174 |
| d-01-07 | 0.184 |
| d-01-08 | 0.202 |
| d-02-01 | 0.077 |
| d-03-01 | 0.067 |
| d-03-02 | 0.111 |
| d-03-03 | 0.087 |
| d-03-04 | 0.194 |
| d-03-05 | 0.093 |
| d-03-06 | 0.125 |
| d-03-07 | 0.139 |
| d-03-08 | 0.137 |
| d-03-09 | 0.158 |
| d-04-01 | 0.182 |
| d-04-02 | 0.207 |
| d-04-03 | 0.162 |
| d-04-04 | 0.169 |
| d-04-05 | 0.145 |
| d-05-01 | 0.182 |
| d-05-02 | 0.223 |
| e-01-01 | 0.279 |
| e-01-02 | 0.225 |
| e-01-03 | 0.171 |
| e-02-01 | 0.077 |
| e-02-02 | 0.123 |
| e-02-03 | 0.067 |
| e-02-04 | 0.116 |
| e-02-05 | 0.123 |
| e-02-06 | 0.113 |
| e-02-07 | 0.152 |
| e-02-08 | 0.165 |

TABLE 31

| Example | $IC_{50}$ (μM) |
|---|---|
| e-02-09 | 0.065 |
| e-02-10 | 0.131 |
| e-02-11 | 0.095 |
| e-02-12 | 0.129 |
| e-02-13 | 0.077 |
| e-02-14 | 0.139 |
| e-02-15 | 0.167 |
| e-02-16 | 0.175 |
| e-02-17 | 0.2 |
| e-02-18 | 0.2 |
| e-02-19 | 0.191 |
| e-02-20 | 0.244 |
| e-02-21 | 0.188 |
| e-02-22 | 0.106 |
| e-02-23 | 0.111 |
| e-02-24 | 0.117 |
| e-02-25 | 0.053 |
| e-02-26 | 0.08 |
| e-02-27 | 0.054 |
| e-03-01 | 0.168 |
| e-04-01 | 0.431 |
| e-04-02 | 0.314 |

Test Example 3: Rat Collagen-Induced Arthritis Model (1) Measurement Method

Eight weeks old female Lewis rats (SLC Inc.) were immunized with bovine type II collagen (CII, Collagen Technical Study Session, product number K41) to induce arthritis. A 1:1 mixed emulsion of the incomplete Freund's adjuvant (Difco, Cat. 263910) and a 3 mg/mL solution of CII was prepared, and 0.7 mL of the emulsion was injected to each rat at seven sites in the tale base part and skins of both fore and hind legs in a volume of 0.1 mL per site. Booster immunization was performed after 7 days by injecting 0.2 mL of the same 1:1 mixed emulsion of the incomplete Freund's adjuvant and CII as that used in the first day at two sites in the tale base part in a volume of 0.1 mL per site. After 12 days, footpad volumes of the both hind feet of the animals were measured by using Plethysmometer (UGO BASILE, Cat. 37140), and the individual animals were divided into groups according to the footpad volume ratio based on that of the normal group and body weight. After they were divided into groups, administration of a test compound or a solvent (vehicle, 0.5% methylcellulose) was started, and it was orally administered twice a day for 7 days (provided that, on the day of grouping, the administration was performed only once after grouping). After the start of the administration, the footpad volumes of both hind feet of the animals were measured every other day or every 3 days by using Plethysmometer, and influence of the test compound was evaluated.

Average value of the footpad volumes was calculated for each individual on each measurement day by using Excel 2010 (Microsoft), and plotted as a graph by using GraphPadPrism 7.03 (GraphPad Software, Inc.). The normal group was defined to be a 100% suppression group, and the solvent administration group was defined to be a 0% suppression group. The suppression ratios based on these controls were calculated for each concentration of the test compound by using Excel 2010 (Microsoft).

The operations and conditions used for the measurement may be appropriately changed within such a range that those skilled in the art can understand them, and the measurement is not significantly affected.

(2) Measurement Results

The results for change of the footpad volume for the groups are shown in FIG. 1. The vertical axis indicates the footpad volume, and the horizontal axis indicates number of days after the first immunization with bovine type II collagen. "n" represents the number of rats used.

The suppression ratios observed after 19 days from the first immunization for the groups that received twice a day administration of 20, 60, and 120 mg/kg of the compound of Example c-01-01 were 45%, 65%, and 77%, respectively.

As described above, the compound of the present invention according to a certain embodiment (Example c-01-01) showed superior swelling-suppressing effect in rat arthritis.

INDUSTRIAL APPLICABILITY

The compounds of the general formula (1) and salts thereof have a superior IRAK-4 inhibitory activity, and thus they are useful as active ingredients of medicaments for prophylactic treatment and/or therapeutic treatment of diseases relating to IRAK-4 inhibition.

The invention claimed is:

1. A compound represented by the following general formula (1):

[Formula 1]

(1)

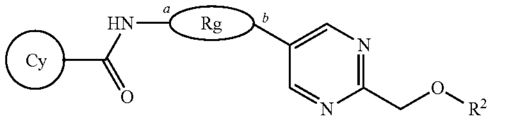

[in the formula (1),

Rg is a group represented by the following general formula (1-1):

[Formula 2]

(1-1)

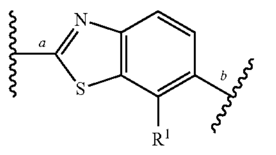

or the following general formula (1-2):

[Formula 3]

(1-2)

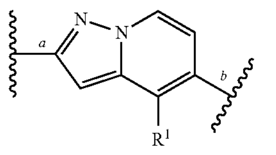

(a and b represent direction of bonding), $R^1$ is —H, —F, —Cl, methyl, or $C_{1-3}$ alkoxy, the $C_{1-3}$ alkoxy may be substituted with the same or different 1 to 3 substituents selected from the group $G^1$;

the group $G^1$ is a group consisting of —F, hydroxy, cyano, halogeno-$C_{1-6}$ alkyl, $C_{1-4}$ alkoxy, phenyl, 5- or 6-membered heteroaryl, and a 3- to 7-membered saturated ring group, the phenyl and 5- or 6-membered heteroaryl included in the group $G^1$ may be substituted with the same or different 1 to 3 substituents selected from the group GM;

the group $G^{Ar}$ is a group consisting of —F, —Cl, hydroxy, cyano, $C_{1-6}$ alkyl, halogeno-$C_{1-6}$ alkyl, and —$NH_2$;

$R^2$ is $C_{1-6}$ alkyl, halogeno-$C_{1-6}$ alkyl, or a 3- to 7-membered saturated ring group, $R^2$ may be substituted with the same or different 1 to 3 substituents selected from the group $G^2$;

the group $G^2$ is a group consisting of —F, hydroxy, halogeno-$C_{1-3}$ alkyl, and $C_{1-4}$ alkoxy;

Cy is a group represented by the following general formula (2-1):

[Formula 4]

(2-1)

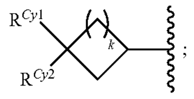

in the formula (2-1), k is an integer of 0 or 1;

$R^{Cy1}$ and $R^{Cy2}$ are independently —H, —F, hydroxy, cyano, $C_{1-6}$ alkyl, halogeno-$C_{1-6}$ alkyl, $C_{1-6}$ alkoxy, —$NR^{11}R^{12}$, phenyl, 5- or 6-membered heteroaryl, or a 3- to 7-membered saturated ring group, the phenyl and 5- or 6-membered heteroaryl as $R^{Cy1}$ and $R^{Cy2}$ may be substituted with the same or different 1 to 3 substituents selected from the group $G^{Ar}$, $R^{Cy1}$ and $R^{Cy2}$ may be substituted with the same or different 1 to 3 substituents selected from the group $G^1$;

$R^{11}$ and $R^{12}$ are independently —H, $C_{1-6}$ alkyl, halogeno-$C_{1-6}$ alkyl, hydroxy-$C_{1-6}$ alkyl, $C_{1-6}$ alkoxy-$C_{1-6}$ alkyl, a 3- to 7-membered saturated ring group, phenyl, or 5- or 6-membered heteroaryl, and $R^{11}$ and $R^{12}$ may be substituted with the same or different 1 to 3 substituents selected from the group $G^1$; or $R^{11}$ and $R^{12}$ combine to form a 4- to 10-membered saturated ring or a 7- to 11-membered spiro ring, the 4- to 10-membered saturated ring and 7- to 11-membered spiro ring may contain the same or different 1 or 2 heteroatoms selected from the group consisting of O and N, or —$S(O_2)$—, in addition to N, the 4- to 10-membered saturated ring and 7- to 11-membered spiro ring may be substituted with the same or different 1 to 3 substituents selected from the group $G^3$;

the group $G^3$ is a group consisting of —F, hydroxy, $C_{1-6}$ alkyl, halogeno-$C_{1-6}$ alkyl, hydroxy-$C_{1-6}$ alkyl, $C_{1-6}$ alkoxy, $C_{1-6}$ alkoxy-$C_{1-6}$ alkyl, halogeno-$C_{1-6}$ alkoxy, —$C(O)R^{14}$, —$NR^{13}C(O)R^{14}$, —$C(O)NR^{13}R^{14}$, —$C(O)NH_2$, —$NR^{13}S(O_2)R^{14}$, —$S(O_2)NR^{13}R^{14}$, —$S(O_2)NH_2$, —$S(O_2)R^{14}$, phenyl, 5- or 6-membered heteroaryl, and a 3- to 7-membered saturated ring group, the phenyl and 5- or 6-membered heteroaryl included in the group $G^3$ may be substituted with the same or different 1 to 3 substituents selected from the group $G^A$;

$R^{13}$ is —H, $C_{1-6}$ alkyl, halogeno-$C_{1-6}$ alkyl, $C_{1-6}$ alkoxy-$C_{1-6}$ alkyl, halogeno-$C_{1-6}$ alkoxy-$C_{1-6}$ alkyl, phenyl, 5- or 6-membered heteroaryl, or a 3- to 7-membered saturated ring group, the phenyl and 5- or 6-membered heteroaryl as $R^{13}$ may be substituted with the same or different 1 to 3 substituents selected from the group $G^{A}r$;

$R^{14}$ is $C_{1-6}$ alkyl, halogeno-$C_{1-6}$ alkyl, $C_{1-6}$ alkoxy-$C_{1-6}$ alkyl, halogeno-$C_{1-6}$ alkoxy-$C_{1-6}$ alkyl, phenyl, 5- or 6-membered heteroaryl, or a 3- to 7-membered saturated ring group, and the phenyl and 5- or 6-membered heteroaryl as $R^{14}$ may be substituted with the same or different 1 to 3 substituents selected from the group $G^{Ar}$; or $R^{13}$ and $R^{14}$ combine to form a 4- to 7-membered saturated ring or a 7- to 11-membered spiro ring, and the 4- to 7-membered saturated ring and 7- to 11-membered spiro ring may contain the same or different 1 or 2 heteroatoms selected from the group consisting of O and N, or —$S(O_2)$—, in addition to N; or $R^{Cy1}$ and $R^{Cy2}$ combine to form a 4- to 7-membered saturated ring, the 4- to 7-membered saturated ring may contain the same or different 1 or 2 heteroatoms selected from the group consisting of O and N, or —$S(O_2)$—, and the 4- to 7-membered saturated ring may be substituted with the same or different 1 to 3 substituents selected from the group $G^1$], or a salt thereof.

2. The compound or a salt thereof according to claim 1, wherein Rg is a group represented by the general formula (1-1).

3. The compound or a salt thereof according to claim 2, wherein $R^1$ is —F, —Cl, methyl, or $C_{1-3}$ alkoxy.

4. The compound or a salt thereof according to claim 2, wherein $R^1$ is $C_{1-3}$ alkoxy.

5. The compound or a salt thereof according to claim 2, wherein $R^1$ is methoxy.

6. The compound or a salt thereof according to claim 2, wherein:

$R^1$ is —H; and

Cy is a group represented by the following general formula (2-1-1):

[Formula 5]

(2-1-1)

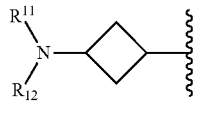

($R^{11}$ and $R^{12}$ have the same meanings as those defined above).

7. The compound or a salt thereof according to claim 2, wherein:

Cy is a group represented by the following general formula (2-1-2):

[Formula 6]

(2-1-2)

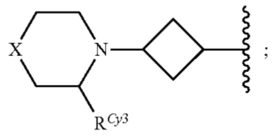

[in the formula (2-1-2), $R^{Cy3}$ is $C_{1-4}$ alkyl, or halogeno-$C_{1-4}$ alkyl;

X is O or $NR^{15}$;

$R^{15}$ is —H, $C_{1-6}$ alkyl, halogeno-$C_{1-6}$ alkyl, hydroxy-$C_{1-6}$ alkyl, $C_{1-6}$ alkoxy-$C_{1-6}$ alkyl, —$C(O)R^{16}$, —$S(O_2)R^{16}$, —$C(O)NR^{16}R^{17}$, —$C(O)OR^{16}$, or a 3- to 7-membered saturated ring group, $R^5$ may be substituted with the same or different 1 to 3 substituents selected from the group $G^1$;

$R^{16}$ is $C_{1-6}$ alkyl, halogeno-$C_{1-6}$ alkyl, $C_{1-6}$ alkoxy-$C_{1-6}$ alkyl, halogeno-$C_{1-6}$ alkoxy-$C_{1-6}$ alkyl, phenyl, 5- or 6-membered heteroaryl, or a 3- to 7-membered saturated ring group, the phenyl and 5- or 6-membered heteroaryl as $R^{16}$ may be substituted with the same or different 1 to 3 substituents selected from the group $G^{Ar}$;

$R^{17}$ is —H, $C_{1-6}$ alkyl, halogeno-$C_{1-6}$ alkyl, $C_{1-3}$ alkoxy-$C_{1-6}$ alkyl, halogeno-$C_{1-6}$ alkoxy-$C_{1-6}$ alkyl, phenyl, 5- or 6-membered heteroaryl, or a 3- to 7-membered saturated ring group, and the phenyl and 5- or 6-membered heteroaryl as $R^{17}$ may be substituted with the same or different 1 to 3 substituents selected from the group $G^{Ar}$; or $R^{16}$ and $R^{17}$ combine to form a 4- to 7-membered saturated ring or a 7- to 11-membered spiro ring, and the 4- to 7-membered saturated ring and 7- to 11-membered spiro ring may contain the same or different 1 or 2 heteroatoms selected from the group consisting of O and N, or —$S(O_2)$—, in addition to N].

8. The compound or a salt thereof according to claim 2, wherein X is $NR^{15}$ ($R^{15}$ has the same meaning as that defined above).

9. The compound or a salt thereof according to claim 2, wherein: Cy is a group represented by the following general formula (2-1-3):

[Formula 7]

(2-1-3)

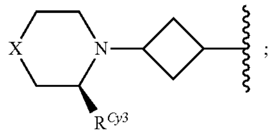

($R^{Cy3}$ and X have the same meanings as those defined above).

10. The compound or a salt thereof according to claim 2, wherein:

$R^2$ is a group represented by the following formula (3-1):

[Formula 8]

(3-1)

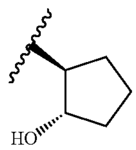

or normal propyl.

11. The compound or a salt thereof according to claim 2, wherein $R^2$ is a group represented by the following formula (3-1):

[Formula 9]

(3-1)

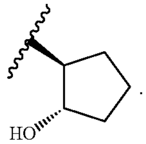

12. A compound represented by the following formula:

[Formula 10]

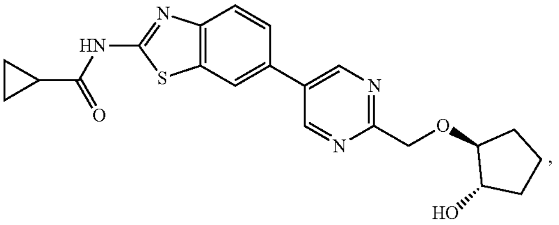

or a salt thereof.

13. A compound represented by the following formula:

[Formula 11]

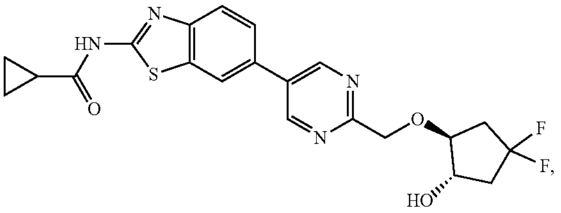

or a salt thereof.

14. A compound represented by the following formula:

[Formula 12]

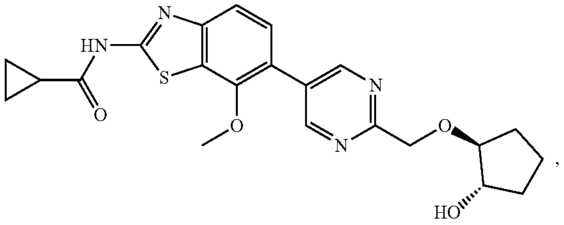

or a salt thereof.

15. A compound represented by the following formula:

[Formula 13]

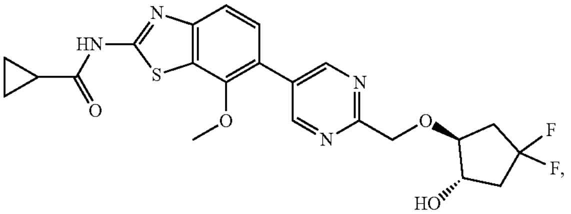

or a salt thereof.

16. A compound represented by the following formula:

[Formula 14]

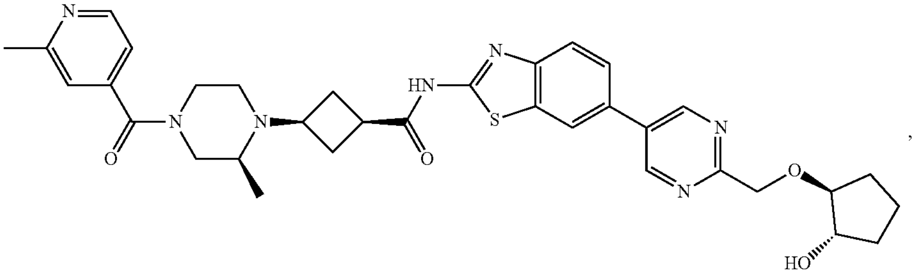

or a salt thereof.

17. A compound represented by the following formula:
[Formula 15]
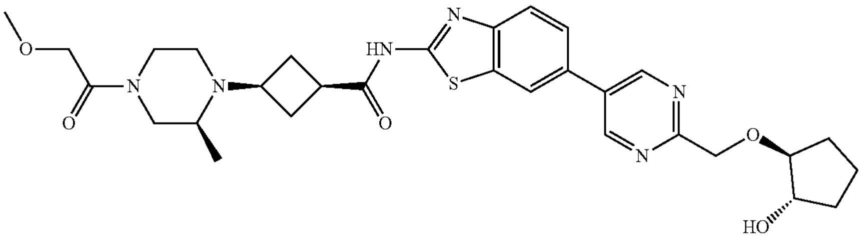
,
or a salt thereof.
18. A compound represented by the following formula:
[Formula 16]
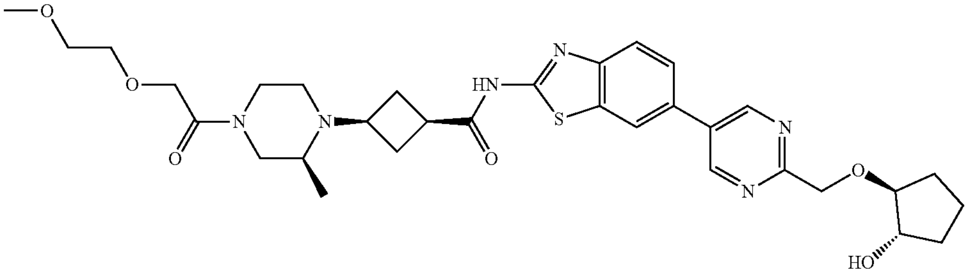
,
or a salt thereof.
19. A compound represented by the following formula:
[Formula 17]
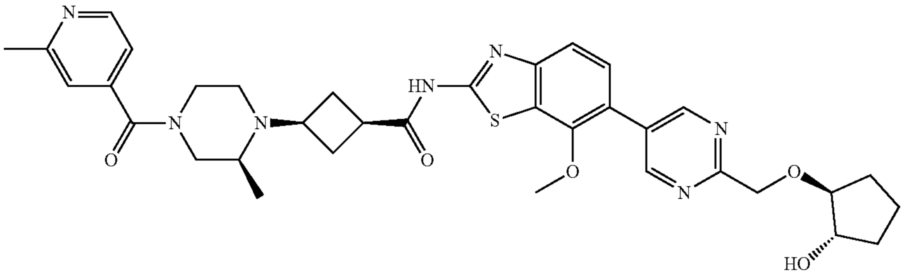
,
or a salt thereof.
20. A compound represented by the following formula:
[Formula 18]
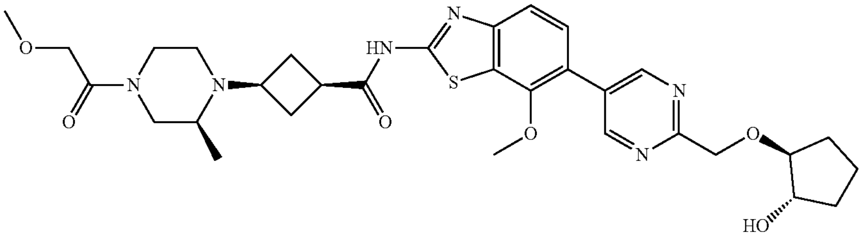
,
or a salt thereof.

21. A compound represented by the following formula:

[Formula 19]

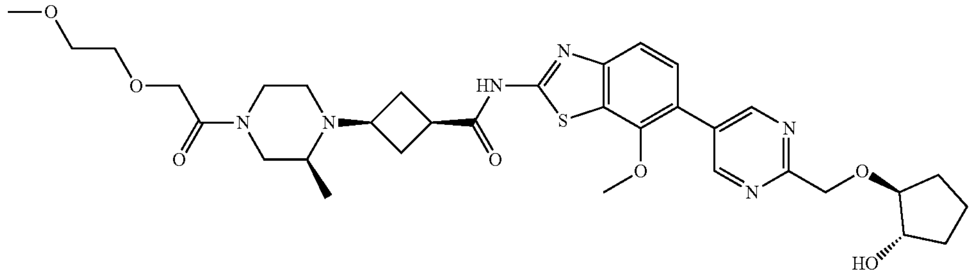

, or a salt thereof.

22. The compound or a salt thereof according to claim 1, wherein Rg is a group represented by the general formula (1-2).

23. The compound or a salt thereof according to claim 22, wherein $R^1$ is —H or methoxy.

24. The compound or a salt thereof according to claim 22, wherein $R^1$ is —H.

25. The compound or a salt thereof according to claim 22, wherein Cy is a group represented by the general formula (2-1):

[in the formula (2-1), k is an integer of 1;

$R^{Cy1}$ and $R^{Cy2}$ are independently —H, —F, hydroxy, cyano, $C_{1-6}$ alkyl, halogeno-$C_{1-6}$ alkyl, $C_{1-6}$ alkoxy, —$NR^{11}R^{12}$, phenyl, 5- or 6-membered heteroaryl, or a 3- to 7-membered saturated ring group, the phenyl and 5- or 6-membered heteroaryl as $R^{Cy1}$ and $R^{Cy2}$ may be substituted with the same or different 1 to 3 substituents selected from the group $G^{Ar}$, and $R^{Cy1}$ and $R^{Cy2}$ may be substituted with the same or different 1 to 3 substituents selected from the group $G^1$ ($R^{11}$ and $R^{12}$ have the same meanings as those defined above)].

26. The compound or a salt thereof according to claim 22, wherein Cy is a group represented by the following general formula (2-1-1):

[Formula 20]

(2-1-1)

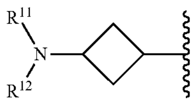

($R^{11}$ and $R^{12}$ have the same meanings as those defined above).

27. The compound or a salt thereof according to claim 22, wherein Cy is a group represented by the following general formula (2-1-2):

[Formula 21]

(2-1-2)

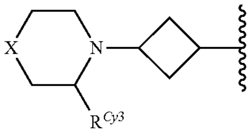

($R^{Cy3}$ has the same meaning as that defined above); and

X is O or $NR^{15}$ ($R^{15}$ has the same meaning as that defined above).

28. The compound or a salt thereof according to claim 22, wherein X is $NR^{15}$ ($R^{15}$ has the same meaning as that defined above).

29. The compound or a salt thereof according to claim 22, wherein Cy is a group represented by the following general formula (2-1-3):

[Formula 22]

(2-1-3)

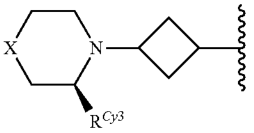

($R^{Cy3}$ and X have the same meanings as those defined above).

30. The compound or a salt thereof according to claim 22, wherein $R^2$ is a group represented by the following formula (3-1):

[Formula 23]

(3-1)

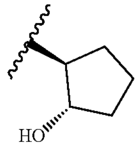

or normal propyl.

31. The compound or a salt thereof according to claim 22, wherein $R^2$ is a group represented by the following formula (3-1):

[Formula 24]

(3-1)

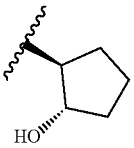

.

32. A compound represented by the following formula:
[Formula 25]
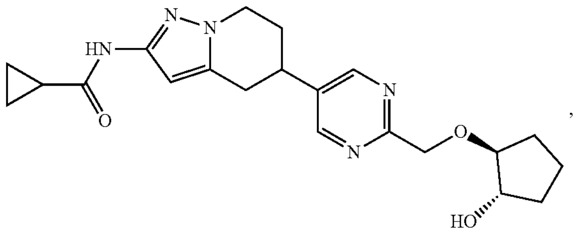
,
or a salt thereof.
33. A compound represented by the following formula:
[Formula 26]
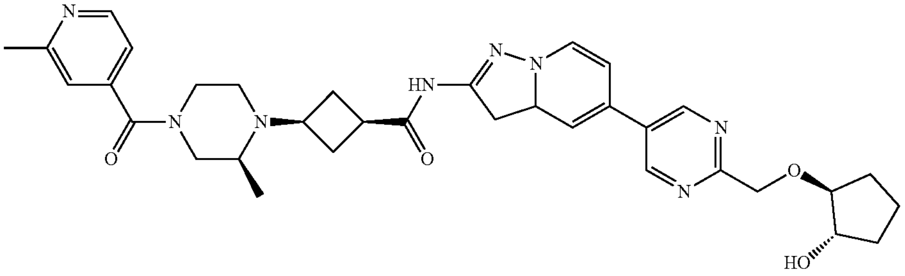
,
or a salt thereof.
34. A compound represented by the following formula:
[Formula 27]
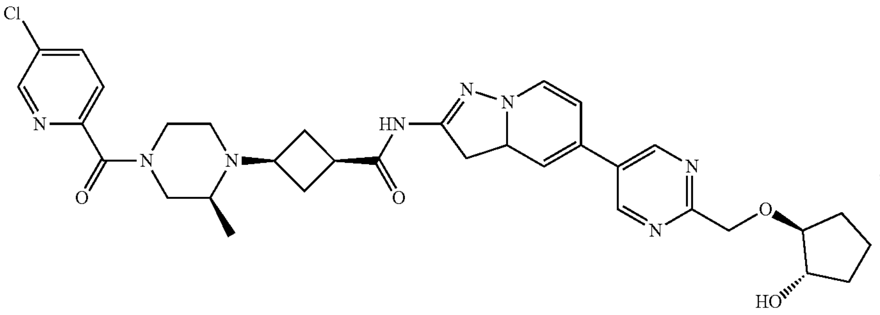
,
or a salt thereof.
35. A compound represented by the following formula:
[Formula 28]
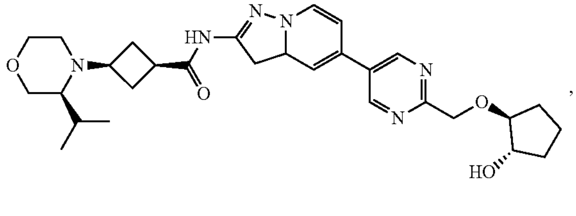
,
or a salt thereof.
* * * * *